US009808534B2

(12) United States Patent
Hershkovitz et al.

(10) Patent No.: US 9,808,534 B2
(45) Date of Patent: Nov. 7, 2017

(54) METHOD OF INCREASING THE HYDRODYNAMIC VOLUME OF POLYPEPTIDES BY ATTACHING TO GONADOTROPHIN CARBOXY TERMINAL PEPTIDES

(71) Applicant: Opko Biologics Ltd., Kiryat Gat (IL)

(72) Inventors: Oren Hershkovitz, Rishon Lezion (IL); Ahuva Bar-Ilan, Rehovot (IL)

(73) Assignee: OPKO Biologics Ltd., Kiryat Gat (IL)

( * ) Notice: Subject to any disclaimer, the term of this patent is extended or adjusted under 35 U.S.C. 154(b) by 0 days.

(21) Appl. No.: 14/085,221

(22) Filed: Nov. 20, 2013

(65) Prior Publication Data

US 2014/0316112 A1 Oct. 23, 2014

Related U.S. Application Data

(60) Provisional application No. 61/728,662, filed on Nov. 20, 2012.

(51) Int. Cl.
| | |
|---|---|
| *A61K 38/24* | (2006.01) |
| *C07K 14/59* | (2006.01) |
| *A61K 47/48* | (2006.01) |
| *A61K 38/17* | (2006.01) |
| *A61K 38/18* | (2006.01) |
| *A61K 38/26* | (2006.01) |
| *A61K 38/27* | (2006.01) |
| *A61K 38/48* | (2006.01) |

(52) U.S. Cl.
CPC .... *A61K 47/48246* (2013.01); *A61K 38/1709* (2013.01); *A61K 38/1816* (2013.01); *A61K 38/26* (2013.01); *A61K 38/27* (2013.01); *A61K 38/4846* (2013.01); *C07K 2319/00* (2013.01)

(58) Field of Classification Search
CPC ............ A61K 38/1709; A61K 38/3816; A61K 38/24; A61K 38/27; A61K 38/4846; C07K 14/59

See application file for complete search history.

(56) References Cited

U.S. PATENT DOCUMENTS

| | | |
|---|---|---|
| 3,791,932 A | 2/1974 | Schuurs |
| 3,839,153 A | 10/1974 | Schuurs |
| 3,850,578 A | 11/1974 | McConnell |
| 3,850,752 A | 11/1974 | Schuurs |
| 3,853,987 A | 12/1974 | Dreyer |
| 3,867,517 A | 2/1975 | Ling |
| 3,879,262 A | 4/1975 | Schuurs |
| 3,901,654 A | 8/1975 | Gross |
| 3,935,074 A | 1/1976 | Leute |
| 3,984,533 A | 10/1976 | Uzgiris |
| 3,996,345 A | 12/1976 | Schwarzberg |
| 4,034,074 A | 7/1977 | Miles |
| 4,098,876 A | 7/1978 | Piasio et al. |
| 4,400,316 A | 8/1983 | Katsuragi et al. |
| 4,666,828 A | 5/1987 | Gusella |
| 4,683,202 A | 7/1987 | Mullis |
| 4,801,531 A | 1/1989 | Frossard |
| 4,853,332 A | 8/1989 | Mark et al. |
| 4,873,316 A | 10/1989 | Meade |
| 4,879,219 A | 11/1989 | Schoemaker et al. |
| 4,911,691 A | 3/1990 | Aniuk et al. |
| 5,011,771 A | 4/1991 | Bellet |
| 5,118,666 A | 6/1992 | Habener |
| 5,177,193 A | 1/1993 | Boime et al. |
| 5,192,659 A | 3/1993 | Simons |
| 5,272,057 A | 12/1993 | Smulson et al. |
| 5,281,521 A | 1/1994 | Trojanowski |
| 5,338,835 A | 8/1994 | Boime |
| 5,405,945 A | 4/1995 | Boime et al. |
| 5,464,764 A | 11/1995 | Capecchi |
| 5,487,992 A | 1/1996 | Capecchi |
| 5,585,345 A | 12/1996 | Boime |
| 5,597,797 A | 1/1997 | Clark |
| 5,643,575 A | 7/1997 | Martinez |
| 5,681,567 A | 10/1997 | Martinez |
| 5,705,478 A | 1/1998 | Boime |
| 5,712,122 A | 1/1998 | Boime et al. |
| 5,759,818 A | 6/1998 | Boime |
| 5,792,460 A | 8/1998 | Boime |
| 5,919,455 A | 7/1999 | Greenwald |
| 5,929,028 A | 7/1999 | Skrabanja et al. |
| 5,932,447 A | 8/1999 | Siegall |
| 5,935,924 A | 8/1999 | Bunting et al. |
| 5,958,737 A | 9/1999 | Boime et al. |

(Continued)

FOREIGN PATENT DOCUMENTS

| | | |
|---|---|---|
| EP | 0264166 | 4/1988 |
| EP | 0167825 | 8/1990 |

(Continued)

OTHER PUBLICATIONS

Puett et al. 2005; Structure-Function relationships of the luteinizing hormone receptor. Ann. NY Acad. Sci. 1061: 41-54.*
Sugahara et al. 1996; Characterization of the O-glycosylation sites in the chorionic gonadotropin B subunit in vivo using site-directed mutagenesis and gene transfer. J. Biol. Chem. 271(34): 20797-20804.*
Fares et al. 1992; Design of a long-acting follitropin agonist by fusing the C-terminal sequence of chorionic gonadotropin B subunit to the follitropin B subunit. PNAS 89: 4304-4308.*
Fares et al. 2007; Development of a long-acting erythropoietin by fusing the carboxyl-terminal peptide of human chorionic gonadotropin B-subunit to the coding sequence of human erythropoietin. Endocrinology. 148(10): 5081-5087.*

(Continued)

*Primary Examiner* — Karen Cochrane Carlson
(74) *Attorney, Agent, or Firm* — Mark Cohen; Pearl Cohen Zedek Latzer Baratz LLP

(57) ABSTRACT

This invention is directed to the use of a chorionic gonadotrophin carboxy terminal peptide (CTP) or fragments thereof for modifying a polypeptide or a fragment thereof in order to increase the hydrodynamic volume of the polypeptide or fragment thereof.

8 Claims, 8 Drawing Sheets

(56) References Cited

U.S. PATENT DOCUMENTS

| | | |
|---|---|---|
| 6,028,177 A | 2/2000 | Boime |
| 6,083,725 A | 7/2000 | Selden et al. |
| 6,103,501 A | 8/2000 | Boime et al. |
| 6,113,906 A | 9/2000 | Greenwald |
| 6,225,449 B1 | 5/2001 | Boime |
| 6,238,890 B1 | 5/2001 | Boime |
| 6,242,580 B1 | 6/2001 | Boime et al. |
| 6,306,654 B1 | 10/2001 | Boime et al. |
| 6,310,183 B1 | 10/2001 | Johannessen et al. |
| 6,340,742 B1 | 1/2002 | Burg et al. |
| 6,514,729 B1 | 2/2003 | Bentzien |
| 6,897,039 B2 | 5/2005 | Graversen |
| 7,081,446 B2 | 7/2006 | Lustbader |
| 7,091,326 B2 | 8/2006 | Lee et al. |
| 7,094,566 B2 | 8/2006 | Medlock et al. |
| 7,141,547 B2 | 11/2006 | Rosen et al. |
| 7,202,215 B2 | 4/2007 | Lustbader |
| 7,217,689 B1 | 5/2007 | Elliot et al. |
| 7,371,372 B2 | 5/2008 | Chaturvedi et al. |
| 7,371,373 B2 | 5/2008 | Shirley et al. |
| 7,425,539 B2 | 9/2008 | Donovan et al. |
| 7,442,684 B2 | 10/2008 | Lustbader et al. |
| 7,459,429 B2 | 12/2008 | Klima et al. |
| 7,459,435 B2 | 12/2008 | Lehmann et al. |
| 7,459,436 B2 | 12/2008 | Lehmann et al. |
| 7,553,940 B2 | 6/2009 | Fares |
| 7,553,941 B2 | 6/2009 | Fares et al. |
| 7,585,837 B2 | 9/2009 | Shechter et al. |
| 7,649,084 B2 | 1/2010 | Ferguson |
| 7,666,835 B2 | 2/2010 | Bloom et al. |
| 7,795,210 B2 | 9/2010 | DeFrees et al. |
| 8,008,454 B2 | 8/2011 | Lee et al. |
| 8,048,846 B2 | 11/2011 | Chahal et al. |
| 8,048,848 B2 | 11/2011 | Fares et al. |
| 8,048,849 B2 | 11/2011 | Fares et al. |
| 8,063,015 B2 | 11/2011 | Defrees et al. |
| 8,097,435 B2 | 1/2012 | Fares et al. |
| 8,110,376 B2 | 2/2012 | Fares et al. |
| 8,114,836 B2 | 2/2012 | Fares et al. |
| 8,129,330 B2 | 3/2012 | Martinez et al. |
| 8,426,166 B2 | 4/2013 | Fares et al. |
| 8,450,269 B2 | 5/2013 | Fares et al. |
| 8,465,958 B2 | 6/2013 | Lopez De Leon et al. |
| 2001/0007757 A1 | 7/2001 | Boime et al. |
| 2001/0028895 A1* | 10/2001 | Bisgaier et al. ............ 424/450 |
| 2002/0127652 A1 | 9/2002 | Schambye |
| 2002/0160944 A1 | 10/2002 | Boime et al. |
| 2003/0113871 A1 | 6/2003 | Lee et al. |
| 2003/0143694 A1 | 7/2003 | Lustbader |
| 2003/0216313 A1 | 11/2003 | Lustbader et al. |
| 2004/0009902 A1 | 1/2004 | Boime et al. |
| 2004/0018240 A1 | 1/2004 | Ohmachi et al. |
| 2004/0053370 A1 | 3/2004 | Glaesner et al. |
| 2004/0057996 A1 | 3/2004 | Takada et al. |
| 2004/0115774 A1 | 6/2004 | Kochendoerfer |
| 2005/0234221 A1 | 10/2005 | Medlock et al. |
| 2006/0073571 A1 | 4/2006 | Saxena et al. |
| 2006/0088595 A1 | 4/2006 | Asakawa et al. |
| 2006/0160177 A1 | 7/2006 | Okkels et al. |
| 2006/0171920 A1 | 8/2006 | Shechter et al. |
| 2007/0184530 A1 | 8/2007 | Fares et al. |
| 2007/0190610 A1 | 8/2007 | Fares et al. |
| 2007/0190611 A1 | 8/2007 | Fares et al. |
| 2007/0298041 A1 | 12/2007 | Tomlinson |
| 2008/0064856 A1 | 3/2008 | Warne |
| 2008/0206270 A1 | 8/2008 | Minev |
| 2009/0053185 A1 | 2/2009 | Schulte et al. |
| 2009/0087411 A1 | 4/2009 | Fares et al. |
| 2009/0130060 A1 | 5/2009 | Weimer et al. |
| 2009/0221037 A1 | 9/2009 | Lee et al. |
| 2009/0221485 A1 | 9/2009 | James |
| 2009/0270489 A1 | 10/2009 | Fares et al. |
| 2009/0275084 A1 | 11/2009 | Fares et al. |
| 2009/0286733 A1 | 11/2009 | Fares et al. |
| 2009/0312254 A1 | 12/2009 | Fares et al. |
| 2010/0081614 A1 | 4/2010 | Fares et al. |
| 2010/0144617 A1 | 6/2010 | Sinha Roy et al. |
| 2010/0310546 A1 | 12/2010 | Schuster et al. |
| 2010/0317585 A1 | 12/2010 | Fima et al. |
| 2011/0004172 A1 | 1/2011 | Eckstein et al. |
| 2011/0034374 A1 | 2/2011 | Bloom et al. |
| 2011/0065660 A1 | 3/2011 | Baron et al. |
| 2011/0152182 A1 | 6/2011 | Alsina-Fernandez |
| 2011/0166063 A1 | 7/2011 | Bossard et al. |
| 2011/0223151 A1 | 9/2011 | Behrens et al. |
| 2011/0286967 A1 | 11/2011 | Fares et al. |
| 2012/0004286 A1 | 1/2012 | Fares et al. |
| 2012/0015437 A1 | 1/2012 | Fares et al. |
| 2012/0035101 A1 | 2/2012 | Fares et al. |
| 2012/0114651 A1 | 5/2012 | De Wildt et al. |
| 2012/0208759 A1 | 8/2012 | Fima et al. |
| 2013/0184207 A1 | 7/2013 | Fares et al. |
| 2013/0243747 A1 | 9/2013 | Fima et al. |
| 2014/0113860 A1 | 4/2014 | Fima et al. |
| 2014/0316112 A1 | 10/2014 | Hershkovitz et al. |
| 2014/0371144 A1 | 12/2014 | Fares et al. |
| 2015/0038413 A1 | 2/2015 | Fares et al. |
| 2015/0158926 A1 | 6/2015 | Fares et al. |

FOREIGN PATENT DOCUMENTS

| | | |
|---|---|---|
| EP | 2532674 | 12/2012 |
| EP | 2420251 | 3/2013 |
| JP | H8-509218 | 10/1996 |
| JP | 2002/226365 A | 8/2002 |
| JP | 2002/255857 A | 9/2002 |
| JP | 2004/269516 A | 9/2004 |
| WO | WO 89/10756 | 11/1989 |
| WO | WO 93/06844 A1 | 4/1993 |
| WO | WO 94/24148 | 10/1994 |
| WO | WO 00/23472 | 4/2000 |
| WO | WO 02/36169 A2 | 5/2002 |
| WO | WO 02/48194 | 6/2002 |
| WO | WO 03/038100 A1 | 5/2003 |
| WO | WO 02/085311 A2 | 10/2003 |
| WO | WO 2004/006756 | 1/2004 |
| WO | WO 2005/035761 | 4/2005 |
| WO | WO 2005/080544 | 9/2005 |
| WO | WO 2006/134340 | 12/2006 |
| WO | WO 2007/094985 | 8/2007 |
| WO | WO 2007/149406 A2 | 12/2007 |
| WO | WO 2010/007622 | 1/2010 |
| WO | WO 2010/097077 | 9/2010 |
| WO | WO 2011/004361 | 1/2011 |
| WO | WO 2011/087672 | 7/2011 |
| WO | WO 2012/011752 | 5/2012 |
| WO | WO 2012/167251 | 12/2012 |
| WO | WO 2013/157002 | 10/2013 |
| WO | WO 2013/183052 | 12/2013 |
| WO | WO 2014/080401 | 5/2014 |

OTHER PUBLICATIONS

Tape et al. 1990; Apolipoprotein A—I and apolipoprotein SAA half-lives during acute inflammation and amyloidogenesis. Biochimica et Biophysica Acta (lipid and lipid metabolism) 1043: 295-300.*
U.S. Appl. No. 60/764,761, filed Feb. 3, 2006, Fares et al.
U.S. Appl. No. 61/224,366, filed Jul. 9, 2009, Fima et al.
U.S. Appl. No. 11/700,910, filed Feb. 1, 2007, Fares et al.
U.S. Appl. No. 11/700,911, filed Feb. 1, 2007, Fares et al.
U.S. Appl. No. 11/702,156, filed Feb. 5, 2007, Fares et al.
U.S. Appl. No. 12/216,989, filed Jul. 14, 2008, Fares et al.
U.S. Appl. No. 12/401,746, filed Mar. 11, 2009, Fares et al.
U.S. Appl. No. 12/401,755, filed Mar. 11, 2009, Fares et al.
U.S. Appl. No. 12/476,916, filed Jun. 2, 2009, Fares et al.
Ameredes et al. "Growth Hormone Improves Body Mass Recovery with Refeeding after Chronic Undernutrition-Induced Muscle Atrophy in Aging Male Rats" Journal of Nutrition. 129:2264-2270 (1999).
Amirizahdeh et al. "Expression of biologically active recombinant B-domain-deleted human VIII in mammalian cells" Journal of Science, Islamic Republic of Iran. Abstract. 16(2):103-112, (2005).

(56) References Cited

OTHER PUBLICATIONS

Anson et al. "The gene structure of human anti-haemophilic factor IX", The EMBO Journal (1984) 3(5):1053-1060.
Askoy et al., "A study of the intracellular and secreted forms of the MUC2 mucin from the PC/AA intestinal cell line." Glycobiology 9.7: 739-746 (1999).
Banerji et al., "A lymphocyte-specific cellular enhancer is located downstream of the joining region in immunoglobulin heavy chain genes." Cell 33.3: 729-740 (1983).
Barker et al. "An immunomagnetic-base method for the purification of ovarian cancer cells from patient-derived ascites"(Gynecologic Oncology 82, 57-63, 2001).
Bengtsson et al. "Treatment of adults with growth hormone (GH) deficiency with recombinant human GH" J Clin Endocrinol Metab. Feb. 1993;76(2):309-17.
Berntorp et al. "The pharmacokinetics of clotting factor therapy"; Haemophilia (2003) 9:353-359.
Bitter et al. "Expression and secretion vectors for yeast." Methods in enzymology 153: 516-544 (1987).
Bohl et al. "Improvement of erythropoiesis in b-thalassemic mice by continuous erythropoietin delivery from muscle" Blood 95:2793-2798 (2000).
Boissel et al. "Erythropoietin structure-function relationships" The Journal of Biological Chemistry 268(21):15983-15993 (1993).
Booth et al., "The use of a 'universal'yeast expression vector to produce an antigenic protein of< i> Mycobacterium leprae</i>." Immunology Letters 19.1: 65-69 (1988).
Brisson et al., "Expression of a bacterial gene in plants by using a viral vector." Nature 310.5977: 511-514 (1984).
Broglie et al., "Light-regulated expression of a pea ribulose-1,5-bisphosphate carboxylase small subunit gene in transformed plant cells." Science 224.4651: 838-843 (1984).
Buchwald et al., "Long-term, continuous intravenous heparin administration by an implantable infusion pump in ambulatory patients with recurrent venous thrombosis." Surgery 88.4: 507-516 (1980).
Butler et al., "The beta-subunit of human chorionic gonadotrophin exists as a homodimer." Journal of Molecular Endocrinology 22.2: 185-192 (1999).
Byrne et al., "Multiplex gene regulation: a two-tiered approach to transgene regulation in transgenic mice." Proc. Natl. Acad. Sci. USA 86.14: 5473-5477 (1989).
Calame et al., "Transcriptional Controlling Elements in the Immunoglobulin and T Cell Receptor Loci." Adv. Immunol. 43: 235-275 (1988).
Chen and Bahl, "Recombinant carbohydrate variant of human choriogonadotropin beta-subunit (hCG beta) descarboxyl terminus (115-145). Expression and characterization of carboxyl-terminal deletion mutant of hCG beta in the baculovirus system." Journal of Biological Chemistry 266.10: 6246-6251 (1991).
Chen et al., "Glycoengineering Approach to Half-Life Extension of Recombinant Biotherapeutics." Bioconjugate Chemistry 23.8: 1524-1533 (2012).
Chen et al., "Modulating antibody pharmacokinetics using hydrophilic polymers." Expert Opinion on Drug Delivery 8.9: 1221-1236 (2011).
Coruzzi et al., "Tissue-specific and light-regulated expression of a pea nuclear gene encoding the small subunit of ribulose-1, 5-bisphosphate carboxylase." The EMBO Journal 3.8: 1671-1679 (1984).
Database Geneseq [Online] Apr. 7, 2005, "Human interferon beta (without signal peptide)." XP002664024 retrieved from EBI accession No. GSP: ADW02285, Database accession No. ADW02285.
Davis CG et al. "Deletion of clustered O-linked carbohydrates does not impair function of low density lipoprotein receptor in transfected fibroblasts" J Biol Chem. 261(6):2828-38, Feb. 25, 1986.
Dong et al. "The prolonged half-lives of new erythropoietin derivatives via peptide addition" Biochemical Research Communications, 339(1):380-385 (Jan. 6, 2006).

Drake et al. "Optimizing GH therapy in adults and children" Endocr Rev. Aug. 2001;22(4):425-50. Review.
Edlund et al., "Cell-specific expression of the rat insulin gene: evidence for role of two distinct 5' flanking elements." Science 230.4728: 912-916 (1985).
Eldem et al., "Optimization of spray-dried and-congealed lipid micropellets and characterization of their surface morphology by scanning electron microscopy." Pharmaceutical research 8.1: 47-54 (1991).
European Search Report Application No. EP 10796803 dated Feb. 28, 2013.
European Search Report for Application No. 12150722.2 Dated Jun. 4, 2012.
European Search Report for Application No. 07749922 dated Oct. 8, 2009.
European Search Report for European Patent Application No. 12179805.2.
European Search Report for European Patent Application No. 12179821.
Extended European Search Report for EP patent application No. 09797630.2, dated Dec. 5, 2011.
Fares et al. "Design of a long-acting follitropin agonist by fusing the C-terminal sequence of the chorionic gonadotropin beta subunit to the follitropin beta subunit" Proc Natl Acad Sci U S A., 89(10): 4304-4308, May 15, 1992.
Fares et al. "Growth hormone (GH) retardation of muscle damage due to immobilization in old rats. Possible intervention with a new long-acting recombinant GH" Ann N Y Acad Sci. 786:430-43 (Jun. 15, 1996).
Fares et al., "Designing a Long Acting Erythropoietin by Fusing Three Carboxyl-Terminal Peptides of Human Chorionic Gonadotropin Subunit to the N-Terminal and C-Terminal Coding Sequence." International Journal of Cell Biology 2011 (2011).
Fares et al., "Designing a long-acting human growth hormone (hGH) by fusing the carboxyl-terminal peptide of human chorionic gonadotropin β-subunit to the coding sequence of hGH." Endocrinology 151.9: 4410-4417 (2010).
Fares et al., "Development of a long-acting erythropoietin by fusing the carboxyl-terminal peptide of human chorionic gonadotropin β-subunit to the coding sequence of human erythropoietin." Endocrinology 148.10: 5081-5087 (2007).
Fares, "The role of< i> O</i>-linked and< i> N</i>-linked oligosaccharides on the structure—function of glycoprotein hormones: Development of agonists and antagonists." Biochimica et Biophysica Acta (BBA)—General Subjects 1760.4: 560-567 (2006).
Fayad et al. "Update of the M. D. Anderson Cancer Center experience with hyper-CVAD and rituximab for the treatment of mantle cell and Burkitt-type lymphomas" Clin Lymphoma Myeloma. Dec. 2007;8 Suppl 2:S57-62.
Fingl et al., "General Principles." The Pharmacological Basis of Therapeutics (ed. Goodman, LS & Gilman, A,): 1-46 (1975).
Freshney "Culture of animal cells: A manual of basic technique" (Culture of Animal Cells, A Manual of Basic Technique, Alan R. Liss, Inc., 1983, New York, p. 4).
Fuentes-Prior et al. "Structural basis for the anticoagulant activity of the thrombin-thrombomodulin complex" Nature. Mar. 30, 2000; 404 (6777):518-25.
Furuhashi and Suganuma, "Processing of O-linked glycosylation in the chimera consisting of alpha-subunit and carboxyl-terminal peptide of the human chorionic gonadotropin beta-subunit is affected by dimer formation with follicle-stimulating hormone beta-subunit." Endocrine Journal 51.1: 53-59 (2004).
Furuhashi et al., "Fusing the carboxy-terminal peptide of the chorionic gonadotropin (CG) β-subunit to the common alpha-subunit: retention of O-linked glycosylation and enhanced in vivo bioactivity of chimeric human CG." Molecular Endocrinology (Baltimore, Md.) 9.1: 54-63 (1995).
Gao et al., "Erythropoietin gene therapy leads to autoimmune anemia in macaques" Blood 103(9):3300-3302 (2004).

(56) References Cited

OTHER PUBLICATIONS

Garcia-Campayo et al., "Unmasking a new recognition signal for *O*-linked glycosylation in the chorionic gonadotropin β subunit." Molecular and Cellular Endocrinology 194.1: 63-70 (2002).
Gardella et al., "Expression of human parathyroid hormone-(1-84) in *Escherichia coli* as a factor X-cleavable fusion protein." J. Biol. Chem. 265: 15854-15859 (1990).
Gellerfors et al. "Characterisation of a secreted form of recombinant derived human growth hormone, expressed in *Escherichia coli* cells", J Pharm Biomed Anal 7(2):173-83 (1989).
Gilboa et al., "Transfer and expression of cloned genes using retrovial vectors." BioTechniques 4.6: 504-512 (1986).
Goodson, "Dental applications." Medical Applications of Controlled Release 2: 115-138 (1984).
Guitton et al., "Influence of in vitro non-enzymatic glycosylation on the physicochemical parameters of type I collagen." Collagen and Related Research 4.4:253-264 (1984).
Gurley et al., "Upstream sequences required for efficient expression of a soybean heat shock gene." Mol. Cell. Biol. 6.2: 559-565 (1986).
Hacke et al. "Intravenous thrombolysis with recombinant tissue plasminogen activator for acute hemispheric stroke. The European Cooperative Acute Stroke Study (ECASS)" JAMA. 1995;274(13):1017-1025.
Hammerling et al. "In vitro bioassay for human erythropoietin based on proliferative stimulation of an erythroid cell line and analysis of carbohydrate-dependent microheterogeneity" Journal of Pharm. Biomed. Analysis 14(11):1455-1469 (1996).
Heffernan et al. "Effects of oral administration of a synthetic fragment of human growth hormone on lipid metabolism" Am J Physiol Endocrinol Metab 279: E501-E507, (2000).
Houdebine, L., "The methods to generate transgenic animals and to control transgene expression" Journal of Biotechnology 98:145-160 (2002).
Huston et al. "Protein engineering of antibody binding sites: Recovery of specific activity in an anti-digoxin single-chain Fv analogue produced in *Escherichia coli*" Proc. Natl. Acad. Sci. USA vol. 85, pp. 5879-5883, Biochemistry, Aug. 1988.
International Preliminary Report on Patentability for Application No. PCT/IL09/00700 dated Feb. 4, 2010.
International Preliminary Report on Patentability for Application No. PCT/US07/02767 dated Feb. 15, 2008.
International Preliminary Report on Patentability for Application No. PCT/IL2010/000532 dated Jan, 19, 2012.
International Preliminary Report on Patentability for Application No. PCT/US07/03014 dated Apr. 2, 2009.
International Search Report and Written Opinion for PCT Application No. PCT/IL09/00700 dated Feb. 4, 2010.
International Search Report and Written Opinion for PCT Application No. PCT/IL10/00532 dated Apr. 11, 2011.
International Search Report and Written Opinion for PCT Application No. PCT/US07/02767 dated Feb. 15, 2008.
International Search Report and Written Opinion for PCT Application No. PCT/US07/03014 dated Sep. 22, 2008.
International Search Report Application No. PCT/IL13/50107 dated Jul. 10, 2013.
International Search Report for PCT Application No. PCT/IL 12/50288 dated Jan. 28, 2013.
Isgaard et al. "Effects of local administration of GH and IGF-1 on longitudinal bone growth in rats" Am J Physiol. Apr. 1986;250(4 Pt 1):E367-72.
Joshi et al. "Recombinant thyrotropin containing a beta-subunit chimera with the human chorionic gonadotropin-beta carboxy-terminus is biologically active, with a prolonged plasma half-life: role of carbohydrate in bioactivity and metabolic clearance" Endocrinology. Sep. 1995;136(9):3839-48.
Kelly et al. "Outcomes of patients with Burkitt lymphoma older than age 40 treated with intensive chemotherapeutic regimens." Clin Lymphoma Myeloma. Aug. 2009;9(4):307-10.
Kessler et al. "Structure and location of the O-glycosidic carbohydrate units of human chorionic gonadotropin" J Biol Chem. 25;254(16):7909-14 , Aug. 1979.
Kessler et al., "Structures of N-Glycosidic Carbohydrate Units of Human Chorionic Gonadotropin" J Biol Chem. Aug. 25, 1979;254(16):7901-8.
Kicman et al., "Human chorionic gonadotrophin and sport." British Journal of Sports Medicine 25.2 : 73-80 (1991).
Kontermann, "Half-Life Modulating Strategies—An Introduction." Therapeutic Proteins: Strategies to Modulate Their Plasma Half-Lives : 1-21 (2012).
Kontos and Hubbell, "Improving protein pharmacokinetics by engineering erythrocyte affinity." Molecular Pharmaceutics 7.6: 2141-2147 (2010).
Kotler et al. "Effects of growth hormone on abnormal visceral adipose tissue accumulation and dyslipidemia in HIV-infected patients." J Acquir Immune Defic Syndr. Mar. 1, 2004;35(3):239-52. Erratum in: J Acquir Immune Defic Syndr. Nov. 1, 2006;43(3):381.
Langer, "New methods of drug delivery." Science 249.4976: 1527-1533 (1990).
Larsen et al., "Accumulation of magnetic iron oxide nanoparticles coated with variably sized polyethylene glycol in murine tumors." Nanoscale 4.7: 2352-2361 (2012).
Lentz et al., "Posttranslational modification of the carboxy-terminal region of the. beta. subunit of human chorionic gonadotropin." Biochemistry 23.22: 5330-5337 (1984).
Li et al. "Bioassay of hGH .I. Weight gain of hypophysectomized rats". Abstract, Yaowu Fenxi Zazhi 15(2), 3-7 (1995).
Lippin et al. "Human erythropoietin gene therapy for patients with chronic renal failure" Blood 106(7):2280-2286 (2005).
Lo et al. "The effects of recombinant human growth hormone on body composition andglucose metabolism in HIV-infected patients with fat accumulation" J Clin Endocrinol Metab. Aug. 2001;86(8):3480-7. PubMed PMID: 11502767.
Lopez-Berenstein, Liposomes in the Therapy of Infectious Disease and Cancer, Lopez- Berestein and Fidler (eds.), Liss, New York, pp. 317-327 (1989).
Maheshwari et al., "Manipulation of Electrostatic and Saccharide Linker Interactions in the Design of Efficient Glycopolypeptide-Based Cholera Toxin Inhibitors." Macromolecular bioscience 10.1: 68-81 (2010).
Matsuo et al. "Thrombolysis by human tissue plasminogen activator and urokinase in rabbits with experimental pulmonary embolus" Nature. Jun. 18, 1981;291(5816):590-1.
McAlister et al. "NMR analysis of the N-terminal SRCR domain of human CD5: engineering of a glycoprotein for superior characteristics in NMR experiments." Protein Engineering 11.10: 847-853 (1998).
Milton et al. The delineation of a decapeptide gonadotropin-releasing sequence in the carboxyl-terminal extension of the human gonadotropin-releasing hormone precursor J Biol Chem. Dec. 25, 1986; 261(36):16990-7.
Ngo et al. "Computational Complexity, Protein Structure Protein Prediction and the Levinthal Paradox" in Birkhauser The Protein Folding Problem And Tertiary Structure Prediction, pp. 433-440 and 492-495 (1994).
Oosterhof et al. Regulation of whole body energy homeostasis with growth hormone replacement therapy and endurance exercise Physiol Genomics. Jun. 28, 2011;43(12):739-48. doi: 10.1152/physiolgenomics.00034.2010. Epub Mar. 29, 2011.
Pedrosa et al., "Selective neoglycosylation increases the structural stability of vicilin, the 7S storage globulin from pea seeds." Archives of Biochemistry and Biophysics 382.2: 203-210 (2000).
Persson et al. "Recombinant coagulation factor VIIa—from molecular to clinical aspects of a versatile haemostatic agent", Thrombosis Research (2010) 125:483-489.
Philips A. "The challenge of gene therapy and DNA delivery" J Pharm. Pharmacology 53:1169-1174 (2001).
Pierce and Parsons, "Glycoprotein hormones: structure and function." Annual review of biochemistry 50.1: 465-495 (1981).

(56) References Cited

OTHER PUBLICATIONS

Pinkert et al., "An albumin enhancer located 10 kb upstream functions along with its promoter to direct efficient, liver-specific expression in transgenic mice." Genes Dev. 1.3: 268-277 (1987).
Polizzotti et al., "Effects of saccharide spacing and chain extension on toxin inhibition by glycopolypeptides of well-defined architecture." Macromolecules 40.20: 7103-7110 (2007).
Poreddy et al., "Exogenous fluorescent tracer agents based on pegylated pyrazine dyes for real-time point-of-care measurement of glomerular filtration rate." Bioorganic & Medicinal Chemistry 20.8: 2490-2497 (2012).
Rebois et al., "Hydrodynamic properties of the gonadotropin receptor from a murine Leydig tumor cell line are altered by desensitization." Biochemistry 26.20: 6422-6428 (1987).
Reiter et al. "A multicenter study of the efficacy and safety of sustained release GH in the treatment of naive pediatric patients with GH deficiency" J Clin Endocrinol Metab. 86(10):4700-6 (Oct. 2001).
Rudman et al. "Effects of human growth hormone in men over 60 years old" N Engl J Med. Jul. 5, 1990;323(1):1-6.
Russell et al. "Local injections of human or rat growth hormone or of purified human somatomedin-C stimulate unilateral tibial epiphyseal growth in hypophysectomized rats" Endocrinology. Jun. 1985;116(6):2563-7.
Saudek et al "A preliminary trial of the programmable implantable medication system for insulin delivery." N. Engl. J. Med. 321.9: 574-579 (1989).
Schein, Catherine H. "The shape of the messenger: Using protein structure information to design novel cytokine-based therapeutics" Abstract; Current Pharmaceutical Design 8(24):2113-2129 (2002).
Schulte "Half-life extension through albumin fusion technologies", Thrombosis Research (2009) 124 Suppl. 2;S6-S8.
Sefton, "Implantable Pumps." CRC Critical Reviews in Miomedical Engineering 14.3:201-240 (1987).
Sheffield et al. "Effects of genetic fusion of factor IX to albumin on in vivo clearance in mice and rabbits", Blackwell Publishing Ltd, British Journal of Haematology (2004) 126:565-573.
Silverman et al. "A long-acting human growth hormone (Nutropin Depot): Efficacy and safety following two years of treatment in children with growth hormone deficiency" J Pediatr Endocrinol Metab.15 Suppl 2:715-22. (May 2002).
Smeland et al. "Treatment of Burkitt's/Burkitt-like lymphoma in adolescents and adults: a 20-year experience from the Norwegian Radium Hospital with the use of three successive regimens."Ann Oncol. Jul. 2004;15(7):1072-8.
Srour et al., "Regulation of human factor IX expression using doxycycline-inducible gene expression system." Thrombosis and Haemostasis 90.3: 398-405 (2003).
Studier et al., "Use of T7 RNA polymerase to direct expression of cloned genes." Methods in Enzymology 185: 60-89 (1990).
Su et al., "Curcumin Inhibits Human Lung Cell Carcinoma Cancer Tumour Growth in a Murine Xenograft Model" (Phytother. Res. 24:189-191, 2010).
Sugahara et al., "Characterization of the O-glycosylation sites in the chorionic gonadotropin β subunit in vivo using site-directed mutagenesis and gene transfer." Journal of Biological Chemistry 271.34: 20797-20804 (1996).
Takamatsu et al., "Expression of bacterial chloramphenicol acetyltransferase gene in tobacco plants mediated by TMV-RNA." The EMBO Journal 6.2: 307-311 (1987).
Treat, in "Liposomes in the Therapy of Infectious Disease and Cancer." Lopez-Berestein and Fidler eds., Liss, New York 353-365 (1989).
Uenalp et al. "Factor VII deficiency associated with valproate treatment" Pediatrics International 50(3):403-405 Abstract (2008).
Venn and Mason, "Biosynthesis and metabolism in vivo of intervertebral-disc proteoglycans in the mouse." Biochem. J 215: 217-225 (1983).
Weiss et al. "Noncompliance in Neurologic Patients" Current Treatment Options in Neurology 7:419-425 (2005).
Wells, J.A, "Additivity of Mutational Effects in Proteins" Biochemistry 29:8509-8517 (1990).
White et al. "Mammalian Recombinant Coagulation Proteins: Structure and Function", Transfus. Sci. (1998) 19(2):177-189.
Wildt et al., "The humanization of N-glycosylation pathways in yeast." Nature Reviews Microbiology 3.2: 119-128 (2005).
Wilken and Bedows, "A novel four-amino acid determinant defines conformational freedom within chorionic gonadotropin β-subunits." Biochemistry 46.14: 4417-4424 (2007).
Winoto and Baltimor, "A novel, inducible and T cell-specific enhancer located at the 3'end of the T cell receptor alpha locus." The EMBO Journal 8.3: 729 (1989).
Yefenof & McConnell "Interferon amplifies complement activation by Burkitt's lymphoma cells" Nature. Feb. 21-27, 1985;313(6004):68.
Yin et al. "Recombinant human growth hormone replacement therapy in HIV-associated wasting and visceral adiposity". Exper. Rev. Anti-Infect. Ther. 3(5):727-736 (2005).
Zheng et al., "The impact of glycosylation on monoclonal antibody conformation and stability." MAbs. vol. 3. No. 6. Landes Bioscience (Nov.-Dec. 2011).
Zhong et al. "The N-terminal epidermal growth factor-like domain in factor IX and factor X represents an important recognition motif for binding to tissue factor" J. Biol. Chem. (2002) 277(5):3622-31.
"Epogen signal peptide"; XP002685292, retrieved from EBI accession No. GSP:ADS64918, Database accession No. ADW64918.
Beeley, Glycoprotein and proteoglycan techniques. Elsevier: 69-72 (1985).
Diederichs and Muller, "Liposomes in cosmetics and pharmaceutical products." Pharmazeutische Industrie 56.3: 267-275 (1994).
Kontermann, "Strategies for extended serum half-life of protein therapeutics." Current opinion in Biotechnology 22.6: 868-876 (2011).
Reichel, "Sarcosyl-Page: a new electrophoretic method for the separation and immunological detection of PEGylated proteins." Protein Electrophoresis. Humana Press 65-79 (2012).
Weissbach and Weissbach, "Methods for Plant Molecular Biology." Selected Methods in Enzymology (USA) Section VIII: 421-463 (1988).
Bjorkman et al. "Pharmacokinetics of coagulation factors: clinical relevance for patients with haemophilia", Clin Pharmacokinet. 2001;40(11):815-32.
Brunetti-Pierri et al. "Bioengineered factor IX molecules with increased catalytic activity improve the therapeutic index of gene therapy vectors for hemophilia B", Hum Gene Ther. May 2009;20(5):479-85.
Cawley et al. "Developing long-acting growth hormone formulations", Clin Endocrinol (Oxf). Sep. 2013;79(3):305-9. Epub Jun. 13, 2013.
Chan et al. "Plasma Insulin-Like Growth Factor-I and Prostate Cancer Risk: A Prospective Study", Science. Jan. 23, 1998;279(5350):563-6.
Claxton et al. "A systematic review of the associations between dose regimens and medication compliance", Clin Ther. Aug. 2001;23(8):1296-310.
Coleman et al. "Dosing frequency and medication adherence in chronic disease." Journal of managed care pharmacy, J Manag Care Pharm. Sep. 2012;18(7):527-39.
Cutfield et al. "Non-compliance with growth hormone treatment in children is common and impairs linear growth", PLoS One. Jan. 31, 2011;6(1):e16223.
Diness et al. "Effect of recombinant human FVIIA on warfarin-induced bleeding in rats", Thromb Res. Sep. 15, 1990;59(6):921-9.
Eldem et al. "Optimization of spray-dried and -congealed lipid micropellets and characterization of their surface morphology", Pharm Res. Jan. 1991;8(1):47-54.
Eschbach et al. "Correction of the Anemia of End-Stage Renal Disease with Recombinant Human Erythropoietin", N Engl J Med. Jan. 8, 1987;316(2):73-8.
Ghosh et al. "Activity and regulation of factor VIIa analogs with increased potency at the endothelial cell surface", J Thromb Haemost. Feb. 2007;5(2):336-46. Epub Nov. 9, 2006.

(56) References Cited

OTHER PUBLICATIONS

International Search Report for PCT Application No. PCT/IL2013/050960 dated Jul. 21, 2014.
Kanda et al. "Genetic fusion of an alpha-subunit gene to the follicle-stimulating hormone and chorionic gonadotropin-beta subunit genes: production of a bifunctional protein", Mol Endocrinol. Nov. 1999;13(11):1873-81.
Le et al. "Improved vancomycin dosing in children using area under the curve exposure", Pediatr Infect Dis J. Apr. 2013;32(4):e155-63.
Lopez-Berestein et al. "Treatment of systemic fungal infections with liposomal amphotericin B", Arch Intern Med. Nov. 1989;149(11):2533-6.
Maston et al. "Chorionic gonadotropin beta subunit [*Homo sapiens*]", NCBI Accession No. AAL69705.1 (Apr. 3, 2002).
Matsumoto et al. "The measurement of low levels of factor VIII or factor IX in hemophilia A and hemophilia B plasma by clot waveform analysis and thrombin generation assay", J Thromb Haemost. Feb. 2006;4(2):377-84.
Maun et al. "Disulfide locked variants of factor VIIa with a restricted beta-strand conformation have enhanced enzymatic activity", Protein Sci. May 2005;14(5):1171-80.
McShane et al. "MHC class I antigen, partial [Bos taurus]", NCBI GenBank Accession No. AAL69702 (Apr. 3, 2002).
Meulien et al. "Increased biological activity of a recombinant factor IX variant carrying alanine at position +1", Protein Eng. Jul. 1990;3(7):629-33.
Muleo et al. "Small doses of recombinant factor VIIa in acquired deficiencies of vitamin K dependent factors", Blood Coagul Fibrinolysis. Dec. 1999;10(8):521-2.
Murray et al. "Dose titration and patient selection increases the efficacy of GH replacement in severely GH deficient adults", Clin Endocrinol (Oxf). Jun. 1999;50(6):749-57.
Mutter et al. "A new base-labile anchoring group for polymer-supported peptide synthesis", Helvetica Chimica Acta 1984 67(7):2009-16.
Mutter et al. "Evolution versus design: template-directed self-assembly of peptides to artificial proteins (TASP)", Chimia Int J Chem 2000 54(10):552-557.
Ogle et al. "Renal effects of growth hormone. I. Renal function and kidney growth", Pediatr Nephrol. Jul. 1992;6(4):394-8.
Persson et al. "Rational design of coagulation factor VIIa variants with substantially increased intrinsic activity", Proc Natl Acad Sci U S A. Nov. 20, 2001;98(24):13583-8. Epub Nov. 6, 2001.
Ronzi et al. "Optimisation of a freeze-drying process of high purity Factor VIII and Factor IX concentrates", Chemical Engineering and Processing 2003 42:751-757.
Scheuttrumpf et al. "Factor IX variants improve gene therapy efficacy for hemophilia B", Blood. Mar. 15, 2005;105(6):2316-23. Epub Nov. 18, 2004.
Wynne et al. "Subcutaneous oxyntomodulin reduces body weight in overweight and obese subjects: a double-blind, randomized, controlled trial", Diabetes. Aug. 2005;54(8):2390-5.
Morgan et al. "The amino acid sequence of human chorionic gonadotropin. The alpha subunit and beta subunit", J Biol Chem. Jul. 10, 1975;250(13):5247-58.
Biller et al. "Effects of once-weekly sustained-release growth hormone: a double-blind, placebo-controlled study in adult growth hormone deficiency", J Clin Endocrinol Metab. Jun. 2011;96(6):1718-26.
Bouloux et al. "First human exposure to FSH-CTP in hypogonadotrophic hypogonadal males." Human Reproduction 16.8 (2001): 1592-1597.
Carles-Bonnet et al. "H-Lys-Arg-Asn-Lys-Asn-Asn-OH is the minimal active structure of oxyntomodulin." Peptides 17.3 (1996): 557-561.
Chihara et al. "Clinical aspect of growth hormone deficiency in adults", Nihon Naika Gakkai Zasshi. Sep. 10, 2000:89(9):2010-8; with English Abstract.
Dalton et al. "Over-expression of secreted proteins from mammalian cell lines", Protein Sci. May 2014;23(5):517-25.
Edmunds et al. "Plasma erythropoietin levels and acquired cystic disease of the kidney in patients receiving regular haemodialysis treatment" Br J Haematol. Jun. 1991:78(2):275-7.
Jarrousse et al. "Oxyntomodulin (glucagon-37) and its C-terminal octapeptide inhibit gastric acid secretion", FEBS Lett. Aug. 19, 1985; 188(1): 81-4.
Krantz et al. "Specific binding of erythropoietin to spleen cells infected with the anemia strain of Friend virus" Proc Natl Acad Sci U S A. Dec. 1984;81(23):7574-8.
Littlewoord, T.J. "Erythropoietin for the treatment of anemia associated with hematological malignancy" Hematol Oncol, Mar. 2001;19(1):19-30.
Musto "The role of recombinant erythropoietin for the treatment of anemia in multiple myeloma" Leuk Lymphoma. Apr. 1998;29(3-4):283-91.
Nezu et al. "Treatment of idiopathic pituitary dwarfism with human growth hormone", Journal of Nara Medical Association 1989, vol. 40, No. 1, p. 16-22; with English Abstract.
Office Action for Japanese Application No. 2014-523441 dated May 24, 2016.
Stuart et al, "Polycythemia vera" Am Fam Physician. May 1, 2004;69(9):2139-44.
Supplementary Search Report for European Application No. 13856398.6 dated Jul. 5, 2016.
Tharakan et al. "Emerging therapies in the treatment of 'diabesity': beyond GLP-1" Trends Pharmacol Sci. Jan. 2011;32(1):8-15.
Verhoef et al, "Recombinant human erythropoietin for the treatment of anemia in the myelodysplastic syndromes: a clinical and erythrokinetic assessment" Ann Hematol. Jan. 1992;64(1):16-21.
Alberts et al. "Molecular biology of the cell"; 5th ed.(Garland Science, 2008), 2002, p. 367.
Schneider KH "GMP Requirements for master and working cell bank" Pharmazeutische Industrie, Jan. 1, 2005;67(11):1366-9.
Takeya et al. "Bovine factor VII, Its purification and complete amino acid sequence", Journal of Biological Chemistry, Oct. 15, 1988;263(29):14868-77.

\* cited by examiner

METHOD OF INCREASING THE HYDRODYNAMIC VOLUME OF POLYPEPTIDES BY ATTACHING TO GONADOTROPHIN CARBOXY TERMINAL PEPTIDES

CROSS REFERENCE TO RELATED APPLICATIONS

This application claims the benefit of U.S. Provisional Patent Application No. 61/728,662, filed on Nov. 20, 2012, which is incorporated herein by reference in its entirety.

FIELD OF INVENTION

This invention is directed to the use of a chorionic gonadotrophin carboxy terminal peptide (CTP) for increasing the hydrodynamic volume of a polypeptide or a fragment thereof.

BACKGROUND OF THE INVENTION

Biotechnology products cover an increased proportion of all therapeutic drugs, including monoclonal antibodies, vaccines, growth factors, hormones, cytokines, coagulation factors, fusion proteins, enzymes and other proteins. Other than monoclonal antibodies and vaccines, many on this list possess a molecular mass below 50 kDa and a short terminal half-life that is in the range of minutes to hours.

The efficacy of protein therapeutics is strongly determined by their pharmacokinetic properties, including their plasma half-lives, which influence distribution and excretion. Although a small size facilitates tissue penetration, these molecules are often rapidly cleared from circulation. Thus, to maintain a therapeutically effective concentration over a prolonged period of time, infusions or frequent administrations are performed, or the drug is applied loco—regional or subcutaneously utilizing a slow adsorption into the blood stream. These limitations of small size protein drugs have led to the development and implementation of half-life extension strategies to prolong circulation of these recombinant antibodies in the blood and thus improve administration and pharmacokinetic as well as pharmacodynamic properties.

The present invention employs such a strategy in order to increase the hydrodynamic size or volume of proteins of interest or fragments thereof, including peptides, by a particular factor and thereby improve administration, pharmacokinetics as well as pharmacodynamic properties of the same. This increase in hydrodynamic volume is achieved by making use of a peptide-based technology for extending serum half-life of proteins and peptides. This technology is based on using a natural peptide, the C-terminal peptide (CTP) of the beta chain of human chorionic gonadotropin (hCG), which provides hCG with the required longevity to maintain pregnancy. The beta chain of luteinizing hormone (LH), a fertility hormone that triggers ovulation, is almost identical to hCG but does not include the CTP. As a result, LH has a significantly shorter half-life in blood. Attaching a predetermined number of CTPs to a protein or peptide of interest increases the hydrodynamic volume of the same by a specific factor and results in improved properties that include an enhanced serum half-life and potency of the protein or peptide of interest.

SUMMARY OF THE INVENTION

In one embodiment, the invention relates to a method of increasing the hydrodynamic size or hydrodynamic volume of a polypeptide of interest or a fragment thereof, the method comprising attaching one to ten chorionic gonadotrophin carboxy terminal peptide (CTP) to said polypeptide or a fragment thereof, wherein attaching said one to ten CTP peptides to said polypeptide or fragment thereof results in increasing the hydrodynamic size or hydrodynamic volume of said polypeptide or fragment thereof by about 28-53 kDa per each CTP attached, thereby increasing the hydrodynamic size of hydrodynamic volume of said polypeptide or fragment thereof.

In another embodiment, the invention relates to a method of increasing the hydrodynamic size or hydrodynamic volume of a polypeptide or a fragment thereof, the method comprising attaching between one to ten chorionic gonadotrophin carboxy terminal peptide (CTP) said polypeptide or fragment thereof, wherein attaching said one to ten CTP to said polypeptide or fragment thereof results in increasing the hydrodynamic size or hydrodynamic volume of said polypeptide or fragment thereof by an amount that is dependent on the particular polypeptide or fragment thereof to which the CTP is attached to, thereby increasing the hydrodynamic size of hydrodynamic volume of said polypeptide or fragment thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Figure 1:
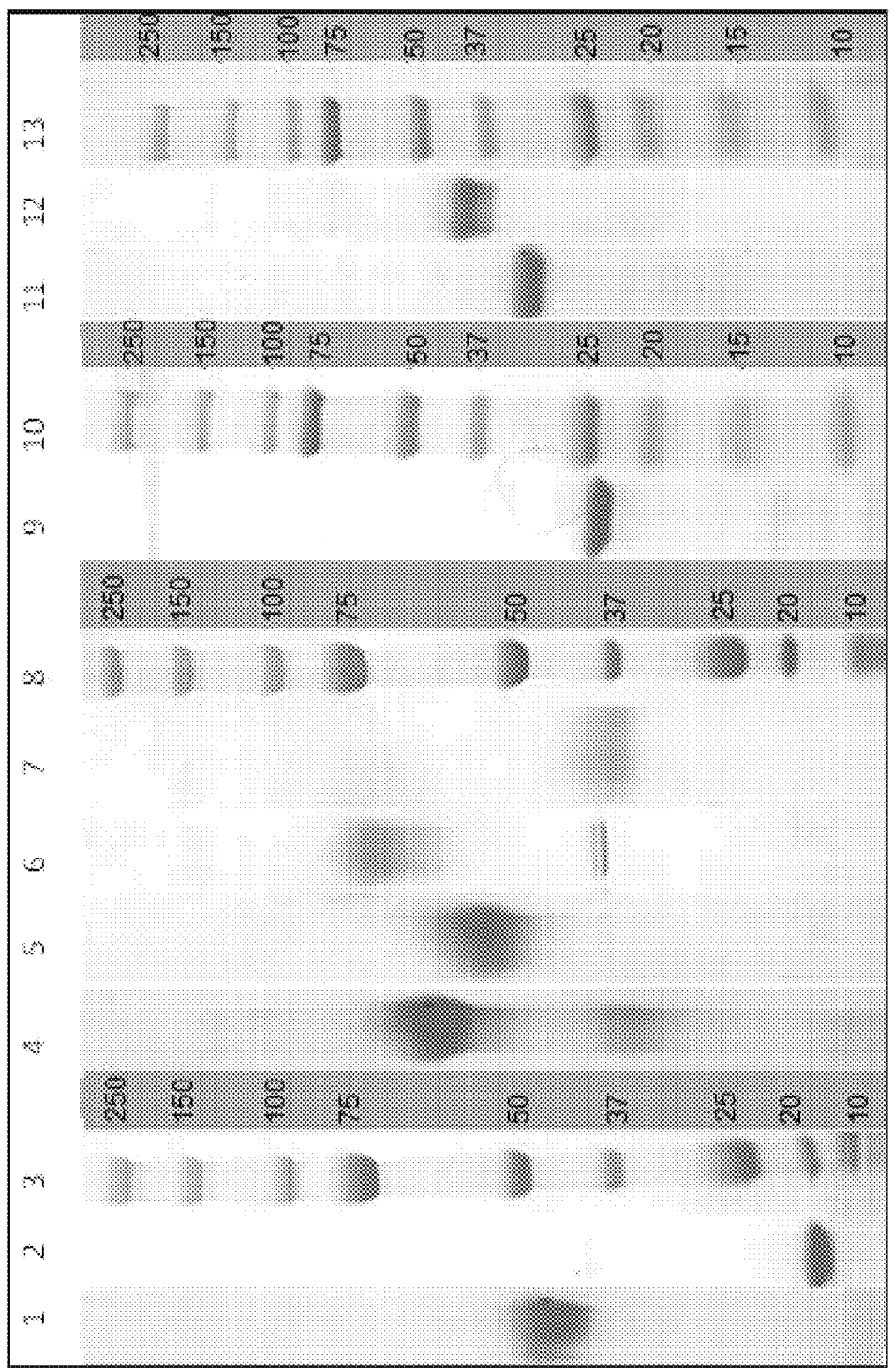
FIG. 1 shows an SDS-PAGE analysis of six different purified CTP-modified proteins and their corresponding native proteins. 1. CTP-hGH-CTP-CTP (MOD-4023), 2. Biotropin (rhGH), 3. Size marker, 4. CTP-EPO-CTP-CTP, 5. CTP-CTP-EPO, 6. CTP-CTP-EPO-CTP-CTP, 7. EPREX® (rEPO), 8. Size marker, 9. APO-A1, 10. Size marker, 11. Apo-CTP, 12. Apo-CTP-CTP, 13. Size marker.

In one embodiment, provided herein is a method of increasing the hydrodynamic volume or hydrodynamic size of a polypeptide of interest or fragment thereof, the method comprising the step of fusing the polypeptide or fragment thereof to at least one chorionic gonadotropin C-terminal peptide (CTP) on either the N-terminus or C-terminus of the polypeptide or fragment thereof.

In one embodiment, the terms "protein" and "polypeptide" are used interchangeably herein. In another embodiment, the terms "polypeptide of interest or fragment thereof", or "protein of interest or fragment thereof" encompass native polypeptides (either degradation to products, synthetically synthesized polypeptides or recombinant polypeptides) and peptidomimetics (typically, synthetically synthesized polypeptides), as well as peptoids and semipeptoids which are polypeptide analogs, which have, in another embodiment, modifications rendering the modified polypeptides provided herein even more stable while in a body or more capable of penetrating into cells. Moreover, the terms include peptides of interest as well. In another embodiment, at least one CTP peptide provided herein is attached to the polypeptides of interest or fragments thereof, or peptides of interest provided herein. In another embodiment, the term "fragment thereof" when in reference to a protein or polypeptide encompasses truncated versions of the protein or polypeptide of interest, including peptides of interest.

In another embodiment, the term "fragment thereof" of a protein or polypeptide refers to a functional fragment (e.g., a fragment that has biological activity as the parent polypeptide does or enhanced activity as compared to the parent polypeptide). Examples of fragments thereof can include variants of the polypeptide, or peptides derived from the parent polypeptide. Hence, it is to be understood that the terms "fragment thereof" of a protein or polypeptide, and the term "peptide" can be used interchangeably herein.

In one embodiment, provided herein is a method of increasing the hydrodynamic size or volume of a polypeptide of interest or a fragment thereof by at least about 28 kDa the method comprising the step of fusing the polypeptide or fragment thereof to at least one chorionic gonadotropin C-terminal peptide (CTP) on either the N-terminus or the C-terminus of the polypeptide or fragment thereof.

In one embodiment, provided herein is a method of increasing the hydrodynamic size or hydrodynamic volume of a polypeptide of interest or a fragment thereof, the method comprising attaching one to ten chorionic gonadotrophin carboxy terminal peptide (CTP) to said polypeptide or a fragment thereof, wherein attaching said one to ten CTP peptides to said polypeptide or fragment thereof results in increasing the hydrodynamic size or hydrodynamic volume of said polypeptide or fragment thereof. In another embodiment, the hydrodynamic size or hydrodynamic volume of said polypeptide or fragment thereof is increased by about 28-53 kDa per each glycosylated CTP attached to said polypeptide or fragment thereof, thereby increasing the hydrodynamic size of hydrodynamic volume of said polypeptide or fragment thereof. In another embodiment, the hydrodynamic size or hydrodynamic volume of said polypeptide or fragment thereof is increased by about 8.0-22 kDa per each non-glycosylated CTP attached to said polypeptide or fragment thereof, thereby increasing the hydrodynamic size of hydrodynamic volume of said polypeptide or fragment thereof. In another embodiment, the hydrodynamic size or hydrodynamic volume of said polypeptide or fragment thereof is increased by about 8.1-21.6 kDa per each non-glycosylated CTP attached to said polypeptide or fragment thereof, thereby increasing the hydrodynamic size of hydrodynamic volume of said polypeptide or fragment thereof.

In another embodiment, provided herein is a method of increasing the hydrodynamic size or hydrodynamic volume of a polypeptide or a fragment thereof, the method comprising attaching between one to ten chorionic gonadotrophin carboxy terminal peptide (CTP) said polypeptide or fragment thereof, wherein attaching said one to ten CTP to said polypeptide or fragment thereof results in increasing the hydrodynamic size or hydrodynamic volume of said polypeptide or fragment thereof by an amount that is dependent on the particular polypeptide or fragment thereof to which the CTP is attached to, thereby increasing the hydrodynamic size of hydrodynamic volume of said polypeptide or fragment thereof.

In one embodiment, said one to ten CTPs are attached to the N-terminus of said polypeptide. In another embodiment, said one to ten CTPs are attached to the C-terminus of said polypeptide. In another embodiment, said one to ten CTPs are attached to both, the N-terminus and the C-terminus of said polypeptide. In another embodiment, one CTP is attached to the N-terminus of said polypeptide and two CTPs are attached to said C-terminus of said polypeptide. In another embodiment, two CTPs are attached to the N-terminus of said polypeptide and two CTPs are attached to said C-terminus of said polypeptide.

In one embodiment, the terms "hydrodynamic size" or "hydrodynamic volume" are used interchangeably herein and each refers to the apparent size of a molecule (e.g., a protein molecule) based on the diffusion of the molecule through an aqueous solution. The diffusion, or motion of a protein through solution can be processed to derive an apparent size of the protein, where the size is given by the "stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein.

In another embodiment, the type of glycosylation is O-glycosylation. In another embodiment, the type of O-glycosylation is the GalNAc attachment to serine (Ser) or threonine (Thr) in the protein chain by an a-glycosidic linkage. In another embodiment, the type of O-glycosylation is the N-acetylglycosamine (GlcNac) attachement to Ser or Thr residues in the protein chain. In another embodiment, the type of O-glycosylation is O-fucosylation, O-mannosylation, core 1 O-glycosylation, core 2 O-glycosylation or O-glucosylation. In another embodiment, the O-glycosylation is mucin-type O-glycosylation. In another embodiment, the O-glycosylation comprises O-linked glycans attached to the hydroxy oxygen of serine, threonine, tyrosine, hydroxylysine, or hydroxyproline side-chains. In another embodiment, the O-glycosylation is followed by the addition of galactose and/or sialic acid, where in other embodiments at least one molecule of galactose is added, and/or at least one molecule of sialic acid is added to the protein of interest following O-glycosylation. In another embodiment, about 1 to 3 galactose molecules are added. In another embodiment, about 1 to 3 sialic acid molecules are added. In another embodiment, about 1 to 5 galactose molecules are added. In another embodiment, about 1 to 5 sialic acid molecules are added. In another embodiment, about 1 to 10 galactose molecules are added. In another embodiment, about 1 to 20 galactose molecules are added. In another embodiment, about 21 to 30 galactose molecules are added. In another embodiment, about 31 to 40 galactose molecules are added. I In another embodiment, about 41 to 50 galactose molecules are added. In another embodiment, about 51 to 60 galactose molecules are added. In another embodiment, about 61 to 70 galactose molecules are added. In another embodiment, about 1 to 10 sialic acid molecules are added. In another embodiment, 2 sialic acid molecules are added per each galactose molecule added. In another embodiment, about 1 to 5 galactose molecules are added per each CTP. In another embodiment, about 1 to 10 sialic acid molecules are added per each CTP. In another embodiment, about 1 to 60 galactose molecules are added and about 1 to 120 sialic acid molecules are added in total per each CTP-modified polypeptide or fragment thereof. In one embodiment, one to six galactose molecules are added per each CTP. In one embodiment, one to 12 sialic acid molecules are added per each CTP. In another embodiment, one to six galactose molecules and one to 12 sialic acid molecules are added per each CTP.

In another embodiment, the type of glycosylation provided herein is N-glycosylation. In another embodiment, N-linked glycans are attached to a nitrogen of asparagine or arginine side-chains. The N-linked amino acid consensus sequence is Asn-any Amino acid-Ser or Thr, where any amino acid cannot be proline.

In another embodiment, provided herein is a method of increasing the hydrodynamic size or hydrodynamic volume of a polypeptide or a fragment thereof, the method comprising attaching at least one non-glycosylated chorionic gonadotrophin carboxy terminal peptide (CTP) to the N-terminus or C-terminus of the polypeptide of interest or fragment thereof, wherein attaching at least one CTP to the polypeptide or fragment thereof results in increasing the hydrodynamic size or hydrodynamic volume of the polypeptide or fragment thereof by an amount that is dependent on the particular polypeptide or fragment thereof to which the CTP is attached to, thereby increasing the hydrodynamic size or hydrodynamic volume of said polypeptide or fragment thereof.

In one embodiment, glycosylated CTP increase the hydrodynamic volume of a protein to which it is attached or fused to. In another embodiment, non-glycosylated CTP increase the hydrodynamic volume of a protein to which it is attached or fused to.

In one embodiment, CTP modified proteins that contain glycans in the native portion of the protein contribute a higher increment to the hydrodynamic volume of one copy of glycosylated CTP, for instance, Example 3/Table 5 herein demonstrate that FIX and FVIIa-CTP modified proteins that contain glycans in the native portion of the protein contribute a higher increment to the hydrodynamic volume of one copy of glycosylated CTP.

It will be appreciated by the skilled artisan, when guided by the present invention's specification, that combinations of glycosylated and non-glycosylated CTPs may be employed for use to increase the hydrodynamic size or volume of polypeptides or fragments thereof provided herein. Such manipulations can be carried out in order to increase the hydrodynamic volume of the polypeptides or fragments thereof to an optimal or desired level. In one embodiment, such optimal or desired level of increase in the hydrodynamic volume is associated with an enhanced retention time in a subject, a low clearance rate from the subject, and an enhanced biological activity of the polypeptide of interest or fragment thereof. In one embodiment, 1 to 5 glycosylated CTPs and 1 to 5 non-glycosylated CTPs are concurrently attached to a polypeptide or fragment thereof provided herein. In another embodiment, the glycosylated or non-glycosylated CTP peptides are tandemly attached on either the N- or C-terminus or are randomly attached to both N- and C-termini. It will also be appreciated by the skilled artisan that additional combinations of glycosylated and non-glycosylated CTP peptides may be used and are hence encompassed by the present invention.

In one embodiment, the term "attached" and grammatical variants thereof refers to binding of one protein, polypeptide or peptide to another protein, polypeptide or peptide. In another embodiment, such binding refers to the binding of a protein, polypeptide or peptide of interest to at least one CTP peptide provided herein. In another embodiment, such binding refers to the binding of a protein, polypeptide or peptide of interest to one to ten CTP peptides provided herein. Such binding can be accomplished through numerous means which include but are not limited to covalent binding, hydrogen binding, ionic binding, metallic binding, polar covalent binding, non-covalent binding (van der waals interactions, hydrophobic interactions, hydrogen bonding, etc.), binding through the use of linkers, and the like.

In one embodiment, provided herein is a method of increasing the hydrodynamic size or hydrodynamic volume of a polypeptide of interest or a fragment thereof, the method comprising attaching at least one non-glycosylated chorionic gonadotrophin carboxy terminal peptide (CTP) to the N-terminus or C-terminus of the polypeptide or fragment thereof, wherein attaching at least one CTP to said polypeptide or fragment thereof results in increasing the hydrodynamic size or hydrodynamic volume of the polypeptide or fragment thereof by an amount that is dependent on the particular polypeptide or fragment thereof to which the CTP is attached to, thereby increasing the hydrodynamic size or hydrodynamic volume of said polypeptide or fragment thereof.

In another embodiment, the CTP provided herein is deglycosylated using methods known in the art that include, but are not limited to, enzyme-based deglycosylation.

It will be appreciated by the skilled artisan that the terms "non-glycosylation" and "deglycosylation" and grammatical variants thereof are used interchangeably herein.

In another embodiment, provided herein is a method of increasing the in-vivo biological activity, increasing the serum half-life, increasing the bioavailability, increasing the potency, or extending the area under the curve (AUC), etc., as further provided herein, of a polypeptide of interest or fragment thereof, the method comprising the step of fusing at least one glycosylated CTP peptide to the polypeptide or fragment thereof, wherein fusing the glycosylated CTP peptide to the polypeptide or fragment thereof results in increasing the hydrodynamic volume of the polypeptide or fragment thereof by at least about 28 kDa as compared to the hydrodynamic volume of an unmodified polypeptide or fragment thereof.

In another embodiment, the CTP-modified polypeptide has lower in-vitro biological activity but this lower activity is compensated by an extended half-life. In another embodiment, the CTP-modified polypeptide has an increased in-vitro biological activity.

In another embodiment, increasing the hydrodynamic volume of the polypeptide or fragment thereof provided herein reduces the administration frequency of the polypeptide or fragment thereof. In another embodiment, increasing the hydrodynamic volume of the polypeptide or fragment thereof also increases the apparent molecular weight of the polypeptide or fragment thereof.

In one embodiment, the apparent molecular weight is determined using methods well known in the art, including, but not limited to, size-exclusion chromatography (SEC), dynamic light scattering methods (DLS), sedimentation velocity, sedimentation equilibrium centrifugation and spectrophotometric detection. In another embodiment, the theoretical molecular weight is determined using a proteomic software available in the art. Such softwares include but are not limited to, Expasy portal, ProteoIQ, Scaffold 3, and the like. In another embodiment, the actual molecular weight is determined using methods well known in the art, including, but not limited to MALDI-TOF.

In another embodiment, provided herein is a method of increasing the apparent molecular weight of a polypeptide of interest or fragment thereof by at least 28 kDa. In another embodiment, provided herein is a method of increasing the apparent molecular weight of a polypeptide or fragment thereof by about 1-14 kDa, the method comprising attaching to the polypeptide or fragment thereof at least one CTP. In another embodiment, provided herein is a method of increasing the apparent molecular weight of a polypeptide or fragment thereof by about 15-27 kDa, the method comprising attaching to the polypeptide or fragment thereof at least one CTP. In another embodiment, provided herein is a method of increasing the apparent molecular weight of a polypeptide or fragment thereof by about 28-40.0 kDa, the method comprising attaching to the polypeptide or fragment thereof at least one CTP. In another embodiment, provided herein is a method of increasing the apparent molecular weight of a polypeptide or fragment thereof by about 28-55.0 kDa, the method comprising attaching to the polypeptide or fragment thereof at least one CTP. In another embodiment, provided herein is a method of increasing the apparent molecular weight of a polypeptide or fragment thereof by about 28-70.0 kDa, the method comprising attaching to the polypeptide or fragment thereof at least one CTP. In another embodiment, provided herein is a method of increasing the apparent molecular weight of a polypeptide or fragment thereof by about 28-80.0 kDa, the method comprising attaching to the polypeptide or fragment thereof at least one CTP. In another embodiment, provided herein is a method of increasing the apparent molecular weight of a polypeptide or fragment thereof by about 28-90.0 kDa, the method comprising attaching to the polypeptide or fragment thereof at least one CTP. In another to embodiment, provided herein is a method of increasing the apparent molecular weight of a polypeptide or fragment thereof by about 28-100.0 kDa, the method comprising attaching to the polypeptide or fragment thereof at least one CTP. In another embodiment, provided herein is a method of increasing the apparent molecular weight of a polypeptide or fragment thereof by about 41.0-50 kDa, the method comprising attaching to the polypeptide or fragment thereof at least one CTP peptide. In another embodiment, provided herein is a method of increasing the apparent molecular weight of a polypeptide or fragment thereof by about 51.0-60 kDa, the method comprising attaching to the polypeptide or fragment thereof at least one CTP peptide. In another embodiment, provided herein is a method of increasing the apparent molecular weight of a polypeptide or fragment thereof by about 61.0-70 kDa, the method comprising attaching to the polypeptide or fragment thereof at least one CTP peptide. In another embodiment, the CTP is glycosylated. In another embodiment, the CTP is a non-glycosylated CTP.

In one embodiment, the methods provided herein unexpectedly demonstrate that subsequent additions of glycosylated CTP peptides to a polypeptide of interest or a fragment thereof linearly contribute about the same apparent molecular weight as a prior attachment of a CTP peptide to the polypeptide of interest or a fragment thereof (see Table 4).

In another embodiment, at least one glycosylated CTP contributes about 28 to 40 kDa per each glycosylated CTP to the protein of interest. In another embodiment, at least one glycosylated CTP contributes about 28 to 55 kDa per each glycosylated CTP to the protein of interest, regardless of the number of CTP attached.

In one embodiment, the provided herein is a method of increasing the apparent moleculear weight of a polypeptide of interest or fragment thereof by a factor of about 2 over the theoretical molecular weight of the polypeptide or fragment thereof, the method comprising the step of attaching one to ten CTP peptide to said polypeptide or fragment thereof. In another embodiment, provided herein is a method of increasing the apparent molecular weight of a polypeptide or fragment thereof by a factor of about 3-5 over the theoretical molecular weight of the polypeptide or fragment thereof, the method comprising the step of attaching at least one CTP peptide to said polypeptide or fragment thereof. In another embodiment, provided herein is a method of increasing the apparent molecular weight of a polypeptide or fragment thereof by a factor of about 6-10 over the theoretical molecular weight of the polypeptide or fragment thereof, the method comprising the step of attaching to one to ten CTP peptides to said polypeptide or fragment thereof. In another embodiment, provided herein is a method of increasing the apparent molecular weight of a polypeptide or fragment thereof by a factor of about 11-20 over the theoretical molecular weight of the polypeptide or fragment thereof, the method comprising the step of attaching one to ten CTP peptides to said polypeptide or fragment thereof. In another embodiment, provided herein is a method of increasing the apparent molecular weight of a polypeptide or fragment thereof by a factor of about 21-30 over the theoretical molecular weight of the polypeptide or fragment thereof, the method comprising the step of attaching one to ten CTP peptides to said polypeptide or fragment thereof, the method comprising the step of attaching at least one CTP peptide to said polypeptide or fragment thereof. In another embodiment, provided herein is a method of increasing the apparent molecular weight of a polypeptide or fragment thereof by a factor of about 31-40 over the theoretical molecular weight of the polypeptide or fragment thereof, the method comprising the step of attaching one to ten CTP peptides to said polypeptide or fragment thereof. In another embodiment, provided herein is a method of increasing the apparent molecular weight of a polypeptide or fragment thereof by a factor of about 41-50 over the theoretical molecular weight of the polypeptide or fragment thereof, the method comprising the step of attaching at least one CTP peptides to said polypeptide or fragment thereof. In another embodiment, provided herein is a method of increasing the apparent molecular weight of a polypeptide or fragment thereof by a factor of about 51-60 the theoretical molecular weight of the polypeptide or fragment thereof, the method comprising the step of attaching at one to ten CTP peptides to said polypeptide or fragment thereof. In another embodiment, provided herein is a method of increasing the apparent molecular weight of a polypeptide or fragment thereof by a factor of about 61-70 over the theoretical molecular weight of the polypeptide or fragment thereof, the method comprising the step of attaching one to ten CTP peptides to said polypeptide or fragment thereof. In another embodiment, provided herein is a method of increasing the apparent molecular weight of a polypeptide or fragment thereof a factor of about 71-80 over the theoretical molecular weight of the polypeptide or fragment thereof, the method comprising the step of attaching one to ten CTP peptides to said polypeptide or fragment thereof. In another embodiment, provided herein is a method of increasing the apparent molecular weight of a polypeptide or fragment thereof by a factor of about 81-90 over the theoretical molecular weight of the polypeptide or fragment thereof, the method comprising the step of attaching one to ten CTP peptides to said polypeptide or fragment thereof. In another embodiment, provided herein is a method of increasing the apparent molecular weight of a polypeptide or fragment thereof by a factor of about 91-100 over the theoretical molecular weight of the polypeptide or fragment thereof, the method comprising the step of attaching one to ten CTP peptides to said polypeptide or fragment thereof. In another embodiment, the at least one CTP peptide is attached to said polypeptide or fragment thereof. In another embodiment, one to five CTP peptides are attached to said polypeptide or fragment thereof. In another embodiment, one to fifteen CTP peptides are attached to said polypeptide or fragment thereof. In another embodiment, one to twenty CTP peptides are attached to said polypeptide or fragment thereof. In another embodiment, the at least one CTP peptide is glycosylated. In another embodiment, at least one CTP peptide is a non-glycosylated CTP peptide.

In another embodiment, the method of increasing the biological activity, serum half-life, bioavailability, potency, etc., of a polypeptide of interest or fragment thereof or a peptide of interest, comprises increasing the total hydrodynamic volume of the polypeptide of interest or fragment thereof by about 28 kDa, as compared to an unmodified polypeptide or fragment thereof, by attaching to said polypeptide or fragment thereof a glycosylated CTP. In another embodiment, the method of increasing the biological activity, serum half-life, bioavailability, etc., of a polypeptide of interest or fragment thereof comprises increasing the total hydrodynamic volume of the polypeptide or fragments thereof by about 1-10 kDa, 11-20 kDa, 21-30 kDa, 31-40 kDa, 41-50 kDa, 51-60 kDa, 61-70 kDa, 71-80 kDa, 81-90 kDa, 91-100 kDa, 100-150 kDa, 151-200 kDa, 201-400 kDa, 401-1000 kDa, or 1001-5000 kDa as compared to an unmodified polypeptide of interest or fragment thereof, by attaching to said polypeptide or fragment thereof a CTP provided herein.

In another embodiment, in the methods provided herein at least one CTP is glycosylated. In another embodiment, in the methods provided herein at least one CTP contributes to the hydrodynamic volume about 28.3 to 38.7 kDa per each CTP to the polypeptide or fragment thereof also provided herein. In another embodiment, the glycosylated CTP contributes 28.3 to 38.7 kDa per each CTP regardless of which polypeptide or fragment thereof it is bound to (see Example 3 herein). In another embodiment, the glycosylated CTP contributes 28.3 to 38.7 kDa per each CTP regardless of the number of CTP peptides attached to the polypeptide (see Example 3 herein). In another embodiment, the contribution of at least one CTP is at least 20 kDa. In another embodiment, the contribution of at least one CTP is at least about 20 kDa to 27.9 kDa. In another embodiment, the contribution of one CTP is at least 28 kDa. In another embodiment, the contribution of one CTP is about 28 kDa to 40 kDa. In another embodiment, the contribution of one CTP is about 41 kDa to 50 kDa. In another embodiment, the contribution of one CTP is about 51 kDa to 60 kDa.

In another embodiment, the method of increasing the serum half-life of or enhancing the potency of the polypeptide of interest or fragment thereof comprises increasing the hydrodynamic volume of the polypeptide or fragment thereof by about 84 kDa as compared to an unmodified polypeptide or fragment thereof. In another embodiment, increasing the hydrodynamic volume by about 84 kDa corresponds to the polypeptide or fragment thereof being modified by attaching it to 3 glycosylated CTP peptides, according to the methods provided herein. In another embodiment, out of the 3 glycosylated CTP peptides attached to the polypeptide or fragment thereof provided herein, one glycosylated CTP peptide is attached to the N-terminus of the polypeptide or fragment thereof, while 2 glycosylated CTP peptides are tandemly attached to the C-terminus of the polypeptide or fragment thereof.

In one embodiment, the method of increasing the serum half-life of or the biological activity of the polypeptide of interest or fragment thereof, comprises increasing the hydrodynamic size or volume of the polypeptide or fragment thereof by about 84-159 kDa as compared to an unmodified polypeptide or fragment thereof. In another embodiment, increasing the hydrodynamic size or volume by about 56-110 kDa is achieved by attaching 2 glycosylated CTP peptides to the polypeptide of interest or fragment thereof. In another embodiment, increasing the hydrodynamic size or volume by about 84-162 kDa is achieved by attaching 3 glycosylated CTP peptides to the polypeptide of interest or fragment thereof. In another embodiment, increasing the hydrodynamic size or volume by about 112-230 kDa is achieved by attaching 4 glycosylated CTP peptides to the polypeptide of interest or fragment thereof. In another embodiment, increasing the hydrodynamic size or volume by about 140-280 kDa is achieved by attaching 5 glycosylated CTP peptides to the polypeptide of interest or fragment thereof. In another embodiment, increasing the hydrodynamic size or volume by about 168-330 kDa is achieved by attaching 6 glycosylated CTP peptides to the polypeptide of interest or fragment thereof. In another embodiment, increasing the hydrodynamic size or volume by about 196-390 kDa is achieved by attaching 7 glycosylated CTP peptides to the polypeptide of interest or fragment thereof. In another embodiment, increasing the hydrodynamic size or volume by about 224-425 kDa is achieved by attaching 8 glycosylated CTP peptides to the polypeptide of interest or fragment thereof. In another embodiment, increasing the hydrodynamic size or volume by about 252-480 kDa is achieved by attaching 9 glycosylated CTP peptides to the polypeptide of interest or fragment thereof. In another embodiment, increasing the hydrodynamic size or volume by about 280-330 kDa is achieved by attaching 10 glycosylated CTP peptides to the polypeptide of interest or fragment thereof.

In one embodiment, the methods provided herein also comprise attaching a non-glycosylated CTP to a polypeptide of interest or fragment thereof. It is to be understood that various manners of modifying a polyptide of interest or fragment thereof, with a glycosylated and/or non-glycosylated CTP can be carried out. In one embodiment, a polypeptide of interest or a fragment thereof is modified with at least one glycosylated CTP alone, or at least one non-glycosylated CTP alone. In another embodiment, a polypeptide of interest or a fragment thereof is modified with at least one glycosylated CTP and at least one non-glycosylated CTP.

In another embodiment, truncated versions of both, glycosylated and/or non-glycosylated CTPs are employed for use in the methods provided herein.

In another embodiment, provided herein is a method of increasing the biological activity, serum half-life, bioavailability, potency, etc., of a polypeptide of interest or fragment thereof by increasing the hydrodynamic volume of the polypeptide of interest or fragment thereof by a specific amount, the method comprising attaching at least one chorionic gonadotrophin carboxy terminal peptide (CTP) to the N-terminus or C-terminus of the polypeptide, wherein attaching at least one non-glycosylated CTP peptide to the polypeptide of interest or fragment thereof results in increasing the hydrodynamic size or hydrodynamic volume of the polypeptide or fragment thereof, as compared to an unmodified form of the polypeptide or fragment thereof, and wherein the specific amount is dependent on the polypeptide of interest or fragment thereof to which the non-glycosylated CTP is attached to.

In another embodiment when at least one non-glycosylated CTP is attached to the polypeptide of interest or fragment thereof, the polypeptide of interest to which the non-glycosylated CTP is attached to dictates the amount of increase in the apparent molecular weight or hydrodynamic volume. In another embodiment, when one non-glycosylated CTP is attached to hGH, the non-glycosylated CTP contributes about 8 kDa to the hydrodynamic size or hydrodynamic volume of human growth hormone (hGH). In another embodiment, when one non-glycosylated CTP is attached to erythropoietin (EPO), the non-glycosylated CTP contributes about 16 kDa to the hydrodynamic size or hydrodynamic volume of EPO. In another embodiment, when one non-glycosylated CTP is attached to apolipoprotein-A1 (APO-A1), the non-glycosylated CTP contributes about 21 kDa to the hydrodynamic size or hydrodynamic volume of APO-A1. In another embodiment, when one non-glycosylated CTP is attached to Factor IX (FIX), the non-glycosylated CTP contributes about 20 kDa to the hydrodynamic size or hydrodynamic volume of FIX. In another embodiment, when one non-glycosylated CTP is attached to Factor VIIa (FVIIa), the non-glycosylated CTP contributes about 20 kDa to the hydrodynamic size or hydrodynamic volume of FIX.

In one embodiment, the method of increasing the hydrodynamic volume of a polypeptide of interest or fragment thereof provided herein enhances the polypeptide's or fragment thereof's bioavailability.

In another embodiment, the method of increasing the hydrodynamic volume of a polypeptide of interest or fragment thereof provided herein reduces the dosing frequency of the polypeptide of interest or fragment thereof.

In one embodiment, the polypeptide that is modified by the methods provided herein is a cytokine, a monoclonal antibody, a growth factor, a hormone, a cytokine, a coagulation factor, an enzyme and the like.

In another embodiment, the polypeptide to which at least one CTP peptide is attached is erythropoietin (EPO), human growth hormone (hGH), apolipoprotein A1 (APO-A1), Factor IIa (FVIIa), Factor IX (FIX) or oxyntomodulin (OXM).

In one embodiment, at least one non-glycosylated CTP contributes about 16 kDa to EPO. In another embodiment, at least one non-glycosylated CTP contributes about 16 kDA to the apparent molecular weight of EPO, when attached to the EPO. In another embodiment, at least one non-glycosylated CTP contributes about 8 kDa to hGH. In another embodiment, at least one non-glycosylated CTP contributes about 8 kDA to the apparent molecular weight of hGH, when attached to the hGH. In another embodiment, at least one non-glycosylated CTP contributes about 21 kDa to the APO-A1. In another embodiment, at least one non-glycosylated CTP contributes about 21 kDA to the apparent molecular weight of APO-A1, when attached to the APO-A1.

In one embodiment, the non-glycosylated CTP contributes a different hydrodynamic volume to each polypeptide to which the non-glycosylated CTP is linked with. In another embodiment, this difference depends on the polypeptide or fragment thereof to which the non-glycosylated CTP is bound to (see Example 3 herein). In another embodiment, the non-glycosylated CTP unexpectedly contributes the same hydrodynamic size per each CTP on each particular polypeptide regardless of the number of non-glycosylated CTP peptides attached to the polypeptide (see Example 3 herein).

In one embodiment, provided herein is a method of increasing the serum half-life of, or the biological activity of hGH, the method comprising the step of increasing the hydrodynamic size or volume of the polypeptide or fragment thereof by about 28-40 kDa as compared to an unmodified hGH. In another embodiment, increasing the hydrodynamic size or volume by about 56-80 kDa is achieved by attaching about 2 glycosylated CTP peptides to hGH. In another embodiment, increasing the hydrodynamic size or volume by about 84-120 kDa is achieved by attaching about 3 glycosylated CTP peptides to the hGH. In another embodiment, increasing the hydrodynamic size or volume by about 112-160 kDa is achieved by attaching about 4 glycosylated CTP peptides to hGH. In another embodiment, increasing the hydrodynamic size or volume by about 140-200 kDa is achieved by attaching about 5 glycosylated CTP peptides to hGH. In another embodiment, increasing the hydrodynamic size or volume by about 168-240 kDa is achieved by attaching about 6 glycosylated CTP peptides hGH. In another embodiment, increasing the hydrodynamic size or volume by about 196-280 kDa is achieved by attaching about 7 glycosylated CTP peptides to hGH. In another embodiment, increasing the hydrodynamic size or volume by about 224-320 kDa is achieved by attaching about 8 glycosylated CTP peptides to hGH. In another embodiment, increasing the hydrodynamic size or volume by about 252-360 kDa is achieved by attaching about 9 glycosylated CTP peptides to hGH. In another embodiment, increasing the hydrodynamic size or volume by about 280-400 kDa is achieved by attaching about 10 glycosylated CTP peptides to hGH. In another embodiment, one to ten truncated or partial CTP peptides are attached to the polypeptide of interest or fragment thereof.

In one embodiment, provided herein is a method of increasing the serum half-life of or the biological activity of EPO, the method comprising the step of increasing the hydrodynamic size or volume of the polypeptide or fragment thereof by about 28-40 kDa as compared to an unmodified EPO. In another embodiment, increasing the hydrodynamic size or volume by about 56-80 kDa is achieved by attaching 2 glycosylated CTP peptides to EPO. In another embodiment, increasing the hydrodynamic size or volume by about 84-120 kDa is achieved by attaching 3 glycosylated CTP peptides to EPO. In another embodiment, increasing the hydrodynamic size or volume by about 112-160 kDa is achieved by attaching 4 glycosylated CTP peptides to EPO. In another embodiment, increasing the hydrodynamic size or volume by about 140-200 kDa is achieved by attaching 5 glycosylated CTP peptides to EPO. In another embodiment, increasing the hydrodynamic size or volume by about 168-

240 kDa is achieved by attaching 6 glycosylated CTP peptides to EPO. In another embodiment, increasing the hydrodynamic size or volume by about 196-280 kDa is achieved by attaching 7 glycosylated CTP peptides to EPO. In another embodiment, increasing the hydrodynamic size or volume by about 224-320 kDa is achieved by attaching 8 glycosylated CTP peptides EPO. In another embodiment, increasing the hydrodynamic size or volume by about 252-360 kDa is achieved by attaching 9 glycosylated CTP peptides EPO. In another embodiment, increasing the hydrodynamic size or volume by about 280-400 kDa is achieved by attaching 10 glycosylated CTP peptides EPO.

In one embodiment, provided herein is a method of increasing the serum half-life of or the biological activity of APO-A1, the method comprising the step of increasing the hydrodynamic size or volume of the polypeptide or fragment thereof by about 28-40 kDa as compared to an unmodified APO-A1. In another embodiment, increasing the hydrodynamic size or volume by about 56-80 kDa is achieved by attaching 2 glycosylated CTP peptides to APO-A1. In another embodiment, increasing the hydrodynamic size or volume by about 84-120 kDa is achieved by attaching 3 glycosylated CTP peptides to the APO-A1. In another embodiment, increasing the hydrodynamic size or volume by about 112-160 kDa is achieved by attaching 4 glycosylated CTP peptides to APO-A1. In another embodiment, increasing the hydrodynamic size or volume by about 140-200 kDa is achieved by attaching 5 glycosylated CTP peptides to APO-A1. In another embodiment, increasing the hydrodynamic size or volume by about 168-240 kDa is achieved by attaching 6 glycosylated CTP peptides to APO-A1. In another embodiment, increasing the hydrodynamic size or volume by about 196-280 kDa is achieved by attaching 7 glycosylated CTP peptides to APO-A1. In another embodiment, increasing the hydrodynamic size or volume by about 224-320 kDa is achieved by attaching 8 glycosylated CTP peptides to APO-A1. In another embodiment, increasing the hydrodynamic size or volume by about 252-360 kDa is achieved by attaching 9 glycosylated CTP peptides to APO-A1. In another embodiment, increasing the hydrodynamic size or volume by about 280-400 kDa is achieved by attaching 10 glycosylated CTP peptides to APO-A1.

In one embodiment, provided herein is a method of increasing the serum half-life of, or the biological activity of FIX, the method comprising the step of increasing the hydrodynamic size or volume of the polypeptide or fragment thereof by about 48-53 kDa as compared to an unmodified FIX. In another embodiment, increasing the hydrodynamic size or volume by about 96-106 kDa is achieved by attaching 2 glycosylated CTP peptides to FIX. In another embodiment, increasing the hydrodynamic size or volume by about 144-159 kDa is achieved by attaching 3 glycosylated CTP peptides to the FIX. In another embodiment, increasing the hydrodynamic size or volume by about 192-212 kDa is achieved by attaching 4 glycosylated CTP peptides to FIX. In another embodiment, increasing the hydrodynamic size or volume by about 240-265 kDa is achieved by attaching 5 glycosylated CTP peptides to FIX. In another embodiment, increasing the hydrodynamic size or volume by about 288-318 kDa is achieved by attaching 6 glycosylated CTP peptides to FIX. In another embodiment, increasing the hydrodynamic size or volume by about 336-371 kDa is achieved by attaching 7 glycosylated CTP peptides to FIX. In another embodiment, increasing the hydrodynamic size or volume by about 384-424 kDa is achieved by attaching 8 glycosylated CTP peptides to FIX. In another embodiment, increasing the hydrodynamic size or volume by about 432-530 kDa is achieved by attaching 9 glycosylated CTP peptides to FIX. In another embodiment, increasing the hydrodynamic size or volume by about 480-530 kDa is achieved by attaching 10 glycosylated CTP peptides to FIX.

In one embodiment, provided herein is a method of increasing the serum half-life of, or the biological activity of FVIIa, the method comprising the step of increasing the hydrodynamic size or volume of the polypeptide or fragment thereof by about 43-50 kDa as compared to an unmodified FVIIA. In another embodiment, increasing the hydrodynamic size or volume by about 86-100 kDa is achieved by attaching 2 glycosylated CTP peptides to FVIIA. In another embodiment, increasing the hydrodynamic size or volume by about 129-150 kDa is achieved by attaching 3 glycosylated CTP peptides to the FVIIA. In another embodiment, increasing the hydrodynamic size or volume by about 172-200 kDa is achieved by attaching 4 glycosylated CTP peptides to FVIIA. In another embodiment, increasing the hydrodynamic size or volume by about 215-250 kDa is achieved by attaching 5 glycosylated CTP peptides to FVIIA. In another embodiment, increasing the hydrodynamic size or volume by about 258-300 kDa is achieved by attaching 6 glycosylated CTP peptides to FVIIA. In another embodiment, increasing the hydrodynamic size or volume by about 301-350 kDa is achieved by attaching 7 glycosylated CTP peptides to FVIIA. In another embodiment, increasing the hydrodynamic size or volume by about 344-400 kDa is achieved by attaching 8 glycosylated CTP peptides to FVIIA. In another embodiment, increasing the hydrodynamic size or volume by about 387-450 kDa is achieved by attaching 9 glycosylated CTP peptides to FVIIA. In another embodiment, increasing the hydrodynamic size or volume by about 430-500 kDa is achieved by attaching 10 glycosylated CTP peptides to FVIIA.

In one embodiment, provided herein is a method of increasing the serum half-life of, or the biological activity of hGH, the method comprising the step of increasing the hydrodynamic size or volume of the polypeptide or fragment thereof by about 8 kDa as compared to an unmodified hGH. In another embodiment, increasing the hydrodynamic size or volume by about 16 kDa is achieved by attaching 2 non-glycosylated CTP peptides to hGH. In another embodiment, increasing the hydrodynamic size or volume by about 24 kDa is achieved by attaching 3 non-glycosylated CTP peptides to the hGH. In another embodiment, increasing the hydrodynamic size or volume by about 32 kDa is achieved by attaching 4 non-glycosylated CTP peptides to hGH. In another embodiment, increasing the hydrodynamic size or volume by about 40 kDa is achieved by attaching 5 non-glycosylated CTP peptides to hGH. In another embodiment, increasing the hydrodynamic size or volume by about 48 kDa is achieved by attaching 6 non-glycosylated CTP peptides to hGH. In another embodiment, increasing the hydrodynamic size or volume by about 56 kDa is achieved by attaching 7 non-glycosylated CTP peptides to hGH. In another embodiment, increasing the hydrodynamic size or volume by about 64 kDa is achieved by attaching 8 non-glycosylated CTP peptides to hGH. In another embodiment, increasing the hydrodynamic size or volume by about 72 kDa is achieved by attaching 9 non-glycosylated CTP peptides to hGH. In another embodiment, increasing the hydrodynamic size or volume by about 80 kDa is achieved by attaching 10 non-glycosylated CTP peptides to hGH.

In one embodiment, provided herein is a method of increasing the serum half-life of or the biological activity of EPO, the method comprising the step of increasing the hydrodynamic size or volume of the polypeptide or fragment thereof by about 16 kDa as compared to an unmodified EPO. In another embodiment, increasing the hydrodynamic size or volume by about 32 kDa is achieved by attaching 2 non-glycosylated CTP peptides to EPO. In another embodiment, increasing the hydrodynamic size or volume by about 48 kDa is achieved by attaching 3 non-glycosylated CTP peptides to EPO. In another embodiment, increasing the hydrodynamic size or volume by about 16 kDa is achieved by attaching 4 non-glycosylated CTP peptides to EPO. In another embodiment, increasing the hydrodynamic size or volume by about 80 kDa is achieved by attaching 5 non-glycosylated CTP peptides to EPO. In another embodiment, increasing the hydrodynamic size or volume by about 96 kDa is achieved by attaching 6 non-glycosylated CTP peptides to EPO. In another embodiment, increasing the hydrodynamic size or volume by about 112 kDa is achieved by attaching 7 non-glycosylated CTP peptides to EPO. In another embodiment, increasing the hydrodynamic size or volume by about 128 kDa is achieved by attaching 8 non-glycosylated CTP peptides EPO. In another embodiment, increasing the hydrodynamic size or volume by about 144 kDa is achieved by attaching 9 non-glycosylated CTP peptides EPO. In another embodiment, increasing the hydrodynamic size or volume by about 160 kDa is achieved by attaching 10 non-glycosylated CTP peptides EPO.

In one embodiment, provided herein is a method of increasing the serum half-life of or the biological activity of APO-A1, the method comprising the step of increasing the hydrodynamic size or volume of the polypeptide or fragment thereof by about 21 kDa as compared to an unmodified APO-A1. In another embodiment, increasing the hydrodynamic size or volume by about 42 kDa is achieved by attaching 2 non-glycosylated CTP peptides to APO-A1. In another embodiment, increasing the hydrodynamic size or volume by about 63-120 kDa is achieved by attaching 3 non-glycosylated CTP peptides to the APO-A1. In another embodiment, increasing the hydrodynamic size or volume by about 84 kDa is achieved by attaching 4 non-glycosylated CTP peptides to APO-A1. In another embodiment, increasing the hydrodynamic size or volume by about 105 kDa is achieved by attaching 5 non-glycosylated CTP peptides to APO-A1. In another embodiment, increasing the hydrodynamic size or volume by about 126 kDa is achieved by attaching 6 non-glycosylated CTP peptides to APO-A1. In another embodiment, increasing the hydrodynamic size or volume by about 147 kDa is achieved by attaching 7 non-glycosylated CTP peptides to APO-A1. In another embodiment, increasing the hydrodynamic size or volume by about 168 kDa is achieved by attaching 8 non-glycosylated CTP peptides to APO-A1. In another embodiment, increasing the hydrodynamic size or volume by about 189 kDa is achieved by attaching 9 non-glycosylated CTP peptides to APO-A1. In another embodiment, increasing the hydrodynamic size or volume by about 210 kDa is achieved by attaching 10 non-glycosylated CTP peptides to APO-A1.

In one embodiment, provided herein is a method of increasing the serum half-life of, or the biological activity of FIX, the method comprising the step of increasing the hydrodynamic size or volume of the polypeptide or fragment thereof by about 20 kDa as compared to an unmodified FIX. In another embodiment, increasing the hydrodynamic size or volume by about 40 kDa is achieved by attaching 2 non-glycosylated CTP peptides to FIX. In another embodiment, increasing the hydrodynamic size or volume by about 60 kDa is achieved by attaching 3 non-glycosylated CTP peptides to the FIX. In another embodiment, increasing the hydrodynamic size or volume by about 80 kDa is achieved by attaching 4 non-glycosylated CTP peptides to FIX. In another embodiment, increasing the hydrodynamic size or volume by about 100 kDa is achieved by attaching 5 non-glycosylated CTP peptides to FIX. In another embodiment, increasing the hydrodynamic size or volume by about 120 kDa is achieved by attaching 6 non-glycosylated CTP peptides to FIX. In another embodiment, increasing the hydrodynamic size or volume by about 140 kDa is achieved by attaching 7 non-glycosylated CTP peptides to FIX. In another embodiment, increasing the hydrodynamic size or volume by about 160 kDa is achieved by attaching 8 non-glycosylated CTP peptides to FIX. In another embodiment, increasing the hydrodynamic size or volume by about 180 kDa is achieved by attaching 9 non-glycosylated CTP peptides to FIX. In another embodiment, increasing the hydrodynamic size or volume by about 200 kDa is achieved by attaching 10 non-glycosylated CTP peptides to FIX.

In one embodiment, provided herein is a method of increasing the serum half-life of, or the biological activity of FVIIa, the method comprising the step of increasing the hydrodynamic size or volume of the polypeptide or fragment thereof by about 20 kDa as compared to an unmodified FVIIA. In another embodiment, increasing the hydrodynamic size or volume by about 40 kDa is achieved by attaching 2 non-glycosylated CTP peptides to FVIIA. In another embodiment, increasing the hydrodynamic size or volume by about 60 kDa is achieved by attaching 3 non-glycosylated CTP peptides to the FVIIA. In another embodiment, increasing the hydrodynamic size or volume by about 80 kDa is achieved by attaching 4 non-glycosylated CTP peptides to FVIIA. In another embodiment, increasing the hydrodynamic size or volume by about 100 kDa is achieved by attaching 5 non-glycosylated CTP peptides to FVIIA. In another embodiment, increasing the hydrodynamic size or volume by about 120 kDa is achieved by attaching 6 non-glycosylated CTP peptides to FVIIA. In another embodiment, increasing the hydrodynamic size or volume by about 140 kDa is achieved by attaching 7 non-glycosylated CTP peptides to FVIIA. In another embodiment, increasing the hydrodynamic size or volume by about 160 kDa is achieved by attaching 8 non-glycosylated CTP peptides to FVIIA. In another embodiment, increasing the hydrodynamic size or volume by about 180 kDa is achieved by attaching 9 non-glycosylated CTP peptides to FVIIA. In another embodiment, increasing the hydrodynamic size or volume by about 200 kDa is achieved by attaching 10 non-glycosylated CTP peptides to FVIIA.

In one embodiment, the hydrodynamic volume increases the retention time of the protein of interest in a biological sample. In another embodiment, the hydrodynamic volume increases the area under the curve (AUC) of the protein of interest in a biological sample. In another embodiment, the biological sample is blood, target tissues (e.g., join, CNS), cerebro-spinal fluid (CSF), lymph, or sera.

In another embodiment, increasing the hydrodynamic volume increases the bioavailability of the polypeptide of interest or fragment thereof provided herein. In another embodiment, increasing the hydrodynamic volume of the polypeptide also extends the serum half-life of the polypeptide or fragment thereof.

In another embodiment, increasing the hydrodynamic volume increases the bioactivity of the polypeptide.

In another embodiment, the terms "CTP peptide," "carboxy terminal peptide" and "CTP sequence" are used interchangeably herein. In another embodiment, the carboxy terminal peptide is a full-length CTP. In another embodiment, the carboxy terminal peptide is a truncated CTP. Each possibility represents a separate embodiment of the present invention.

In another embodiment, a signal peptide is attached to the amino terminus of the CTP, as described in U.S. Pat. No. 7,553,940, which is incorporated by reference herein in its entirety.

In another embodiment, at least one CTP is attached to the polypeptide via a linker. In another embodiment, the linker is a peptide bond. In another embodiment, the fused protein forms a CTP-modified polypeptide. In one embodiment, the method of increasing a hydrodynamic volume of a polypeptides or fragments thereof comprises fusing the polypeptides or fragments thereof to at least one CTP peptide on the amino or carboxyl terminus of the polypeptides or fragments thereof. In another embodiment, the CTP is recombinantly fused to the polypeptides or fragments thereof. In another embodiment, the CTP is chemically conjugated to the polypeptides or fragments thereof.

In one embodiment, the CTP-modified polypeptide comprises a peptide that comprises fewer than 50 amino acids and at least one chorionic gonadotrophin carboxy terminal peptide, attached to an N-(amino) or a C-(carboxy) terminus of the peptide.

In one embodiment, engineered polypeptides of interest of the invention comprising at least a single CTP attached to their N-terminus and/or C-terminus are at least equivalent to the non CTP modified polypeptides of interest, in terms of biological activity. In other embodiments, engineered polypeptides of interest of the invention comprising at least one CTP attached to their N-terminus and/or C-terminus are at least equivalent to the non CTP modified polypeptides of interest, in terms of pharmacological measures such as pharmacokinetics and pharmacodynamics.

In one embodiment, the CTP sequence provided herein comprises: DPRFQDSSSSKAPPPSLPSPSRLPGPSDTPIL (SEQ ID NO: 1). In another embodiment, the CTP sequence comprises: SSSSKAPPPSLPSPSRLPGPSDTPILPQ (SEQ ID NO: 2). In another embodiment, the CTP sequence comprises an amino acid sequence selected from the sequences set forth in SEQ ID NO: 1 and SEQ ID NO: 2. In yet another embodiment, the CTP sequence is selected from the group consisting of SEQ ID NO: 1 and SEQ ID NO: 2.

In one embodiment, the carboxy terminal peptide (CTP) peptide of the present invention comprises the amino acid sequence from amino acid 112 to position 145 of human chorionic gonadotrophin. In another embodiment, the CTP sequence of the present invention comprises the amino acid sequence from amino acid 118 to position 145 of human chorionic gonadotropin, as set forth in SEQ ID NO: 2. In another embodiment, the CTP sequence also commences from any position between positions 112-118 and terminates at position 145 of human chorionic gonadotrophin. In another embodiment, the CTP sequence peptide is 28, 29, 30, 31, 32, 33 or 34 amino acids long and commences at position 112, 113, 114, 115, 116, 117 or 118 of the CTP amino acid sequence.

In one embodiment, the truncated CTP comprises the first 10 amino acids of SEQ ID NO: 3. In another embodiment, SEQ ID NO: 3 comprises the following amino acid (AA) sequence: SSSSKAPPPSLP.

In one embodiment, the truncated CTP comprises the first 11 amino acids of SEQ ID NO: 2. In one embodiment, the truncated CTP comprises the first 12 amino acids of SEQ ID NO: 2. In one embodiment, the truncated CTP comprises the first 8 amino acids of SEQ ID NO: 2 or SEQ ID NO: 3. In one embodiment, the truncated CTP comprises the first 13 amino acids of SEQ ID NO: 2. In one embodiment, the truncated CTP comprises the first 14 amino acids of SEQ ID NO: 2. In one embodiment, the truncated CTP comprises the first 6 amino acids of SEQ ID NO: 2 or SEQ ID NO: 3. In one embodiment, the truncated CTP comprises the first 5 amino acids of SEQ ID NO: 2 or SEQ ID NO: 3.

In another embodiment, the CTP peptide is a variant of chorionic gonadotrophin CTP which differs from the native CTP by 1-5 conservative amino acid substitutions as described in U.S. Pat. No. 5,712,122, which is incorporated herein by reference. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions.

In another embodiment, the CTP peptide amino acid sequence of the present invention is at least 40% homologous to the native CTP amino acid sequence or a peptide thereof. In another embodiment, the CTP peptide amino acid sequence of the present invention is at least 50% homologous to the native CTP amino acid sequence or a peptide thereof. In another embodiment, the CTP peptide amino acid sequence of the present invention is at least 60% homologous to the native CTP amino acid sequence or a peptide thereof. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof. In another embodiment, the CTP peptide amino acid sequence of the present invention is at least 98% homologous to the native CTP amino acid sequence or a peptide thereof.

In another embodiment, the polynucleotide encoding the CTP peptide of the present invention is at least 70% homologous to the native human CTP DNA sequence or a peptide thereof. In another embodiment, the polynucleotide encoding the CTP peptide of the present invention is at least 80% homologous to the native human CTP DNA sequence or a peptide thereof. In another embodiment, the polynucleotide encoding the CTP peptide of the present invention is at least 90% homologous to the native CTP DNA sequence or a peptide thereof. In another embodiment, the polynucleotide encoding the CTP peptide of the present invention is at least 95% homologous to the native CTP DNA sequence or a peptide thereof. In another embodiment, the polynucleotide encoding the CTP peptide of the present invention is at least 98% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, two of the chorionic gonadotrophin CTP amino acid sequences are truncated. In another embodiment, three of the chorionic gonadotrophin CTP amino acid sequences are truncated. In another embodiment, four of the chorionic gonadotrophin CTP amino acid sequences are truncated. In another embodiment, five of the chorionic gonadotrophin CTP amino acid sequences are truncated. In another embodiment, six of the chorionic gonadotrophin CTP amino acid sequences are truncated. In another embodiment, seven of the chorionic gonadotrophin CTP amino acid sequences are truncated. In another embodiment, eight of the chorionic gonadotrophin CTP amino acid sequences are truncated. In another embodiment, two or more of the chorionic gonadotrophin CTP amino acid sequences are truncated. In another embodiment, all of the chorionic gonadotrophin CTP amino acid sequences are truncated.

In one embodiment, the CTP peptides provided herein are attached to the polypeptides or fragments thereof provided herein via a linker. In one embodiment, one to ten CTP peptides are attached to the polypeptides or fragments thereof provided herein via a linker. In one embodiment, at least one CTP is attached to the polypeptides or fragments thereof provided herein via a linker. In another embodiment, the linker is a peptide bond.

In one embodiment, at least one of the chorionic gonadotrophin CTP amino acid sequences is glycosylated. In another embodiment, both of the chorionic gonadotrophin CTP amino acid sequences are glycosylated. In another embodiment, two of the chorionic gonadotrophin CTP amino acid sequences are glycosylated. In another embodiment, three of the chorionic gonadotrophin CTP amino acid sequences are glycosylated. In another embodiment, four of the chorionic gonadotrophin CTP amino acid sequences are glycosylated. In another embodiment, five of the chorionic gonadotrophin CTP amino acid sequences are glycosylated. In another embodiment, two or more of the chorionic gonadotrophin CTP amino acid sequences are glycosylated. In another embodiment, all of the chorionic gonadotrophin CTP amino acid sequences are glycosylated.

In one embodiment, at least one of the chorionic gonadotrophin CTP amino acid sequences is not glycosylated. In another embodiment, both of the chorionic gonadotrophin CTP amino acid sequences are not glycosylated. In another embodiment, two of the chorionic gonadotrophin CTP amino acid sequences are not glycosylated. In another embodiment, three of the chorionic gonadotrophin CTP amino acid sequences are not glycosylated. In another embodiment, four of the chorionic gonadotrophin CTP amino acid sequences are not glycosylated. In another embodiment, five of the chorionic gonadotrophin CTP amino acid sequences are not glycosylated. In another embodiment, two or more of the chorionic gonadotrophin CTP amino acid sequences are not glycosylated. In another embodiment, all of the chorionic gonadotrophin CTP amino acid sequences are not glycosylated.

In one embodiment, the glycosylated CTP sequence of the present invention comprises at least one glycosylation site. In another embodiment, the glycosylated CTP sequence of the present invention comprises two glycosylation sites. In another embodiment, the glycosylated CTP sequence of the present invention comprises three glycosylation sites. In another embodiment, the glycosylated CTP sequence of the present invention comprises four glycosylation sites. In another embodiment, the glycosylated CTP sequence of the present invention comprises five glycosylation sites. In another embodiment, the glycosylated CTP sequence of the present invention comprises six glycosylation sites. In another embodiment, the glycosylated CTP sequence of the present invention comprises seven glycosylation sites. In another embodiment, the glycosylated CTP sequence of the present invention comprises eight glycosylation sites. In another embodiment, the CTP sequence of the present invention comprises from one to four glycosylation sites. In another embodiment, the CTP sequence of the present invention comprises from four to nine glycosylation sites. In another embodiment, the CTP sequence of the present invention comprises from six to twelve glycosylation sites.

In one embodiment, at least one of the chorionic gonadotrophin CTP amino acid sequences is fully glycosylated. In another embodiment, at least one of the chorionic gonadotrophin CTP amino acid sequences is partially glycosylated. In one embodiment, partially glycosylated indicates that at least one of the CTP glycosylation sites is glycosylated. In another embodiment, the glycosylation sites are O-glycosylation sites. In another embodiment, the glycosylation sites are N-glycosylation sites.

In one embodiment, the CTP sequence modification is advantageous in permitting the usage of lower dosages when attached to a polypeptide, drug, or agent of interest. In another embodiment, the CTP sequences modification is advantageous in permitting fewer dosages of a polypeptide, drug, or agent of interest. In another embodiment, the CTP sequences modification is advantageous in permitting a safe, long-acting effect when administering a CTP-modified polypeptide, drug, or agent of interest.

In another embodiment, modifications to polypeptides of interest and CTP peptides herein include, but are not limited to C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In another embodiment, polypeptide bonds (—CO—NH—) within the polypeptide are substituted. In another embodiment, the polypeptide bonds are substituted by N-methylated bonds (—N(CH3)-CO—). In another embodiment, the polypeptide bonds are substituted by ester bonds (—C(R)H—C—O—O—C(R)—N—). In another embodiment, the polypeptide bonds are substituted by ketomethylen bonds (—CO—CH2-). In another embodiment, the polypeptide bonds are substituted by α-aza bonds (—NH—N(R)—CO—), wherein R is any alkyl, e.g., methyl, carba bonds (—CH2-NH—). In another embodiment, the polypeptide bonds are substituted by hydroxyethylene bonds (—CH(OH)—CH2-). In another embodiment, the polypeptide bonds are substituted by thioamide bonds (—CS—NH—). In another embodiment, the polypeptide bonds are substituted by olefinic double bonds (—CH═CH—). In another embodiment, the polypeptide bonds are substituted by retro amide bonds (—NH—CO—). In another embodiment, the to polypeptide bonds are substituted by polypeptide derivatives (—N(R)—CH2-CO—), wherein R is the "normal" side chain, naturally presented on the carbon atom. In another embodiment, these modifications occur at any of the bonds along the polypeptide chain and in one embodiment at several (2-3 bonds) at the same time.

In one embodiment, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In another embodiment, the polypeptides of the present invention include one or more modified amino acid or one or more non-amino acid monomers (e.g. fatty acid, complex carbohydrates etc).

In one embodiment, "amino acid" or "amino acid sequence" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acids.

In another embodiment, the engineered polypeptides or peptides of the present invention are biochemically synthesized such as by using standard solid phase techniques. In another embodiment, these biochemical methods include exclusive solid phase synthesis, partial solid phase synthesis, fragment condensation, or classical solution synthesis.

In one embodiment, recombinant protein techniques are used to generate the engineered polypeptides of interest or fragments thereof of the present invention. In another embodiment, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463, which are incorporated herein by reference in their entirety.

In another embodiment, the CTP-modified polypeptide of interest or fragment thereof comprises a peptide that comprises fewer than 50 amino acids and at least one glycosylated and/or non-glycosylated chorionic gonadotrophin carboxy terminal peptide, to attached to an N- or a C-terminus of the polypeptide. In one embodiment, the CTP-modified polypeptide of interest or fragment thereof provided herein comprises a peptide that comprises fewer than 40 amino acids and at least one chorionic gonadotrophin carboxy terminal peptide, attached to an N- or a C-terminus of the polypeptide. In another embodiment, the CTP-modified polypeptide of interest or fragment thereof provided herein comprises a peptide that comprises fewer than 30, 20, or 10 amino acids. In one embodiment, the polypeptide of interest or fragment thereof comprising fewer than 50 amino acids includes peptides provided herein. In another embodiment, the peptide comprising fewer than 50 amino acids is hGH, OXM, EPO, apolipoprotein A1 (APO-A1), an interferon, a cytokine or a coagulation factor.

In one embodiment the polypeptide of interest or fragment thereof provided herein is an EPO. In one embodiment the polypeptide of interest or fragment thereof provided herein is an APO. In one embodiment the polypeptide of interest or fragment thereof provided herein is an FVIIa. In one embodiment the polypeptide of interest or fragment thereof provided herein is an FIX. In one embodiment the polypeptide of interest or fragment thereof provided herein is an interferon. In another embodiment the polypeptide of interest or fragment thereof provided herein is an hGH. In another embodiment the polypeptide of interest or fragment thereof provided herein is a OXM. In another embodiment the polypeptide of interest or fragment thereof provided herein is a GLP-1. In another embodiment the polypeptide of interest or fragment thereof provided herein is insulin. In another embodiment the polypeptide of interest or fragment thereof provided herein is enkephalin. In another embodiment the polypeptide of interest or fragment thereof provided herein is an ACTH. In another embodiment the polypeptide of interest or fragment thereof provided herein is a glucagon. In another embodiment the polypeptide of interest or fragment thereof provided herein is an insulin-like growth factor. In another embodiment the polypeptide of interest or fragment thereof provided herein is an epidermal growth factor. In another embodiment the polypeptide of interest or fragment thereof provided herein is an acidic or basic fibroblast growth factor. In another embodiment the polypeptide of interest or fragment thereof provided herein is a platelet-derived growth factor. In another embodiment the polypeptide of interest or fragment thereof provided herein is a granulocyte-CSF. In another embodiment the polypeptide of interest or fragment thereof provided herein is a macrophage-CSF. In another embodiment the polypeptide of interest or fragment thereof provided herein is an IL-2. In another embodiment the polypeptide of interest or fragment thereof provided herein is an IL-3. In another embodiment the polypeptide of interest or fragment thereof provided herein is a tumor necrosis factor. In another embodiment the polypeptide of interest or fragment thereof provided herein is an LHRH. In another embodiment polypeptide of interest or fragment thereof provided herein is an LHRH analog. In another embodiment the polypeptide of interest or fragment thereof provided herein is a somatostatin. In another embodiment the polypeptide of interest or fragment thereof provided herein is a growth hormone releasing factor. In another embodiment the polypeptide of interest or fragment thereof provided herein is an endorphin. In another embodiment the polypeptide of interest or fragment thereof provided herein is an alveolar surfactant protein. In another embodiment the polypeptide of interest or fragment thereof provided herein is a natriuretic factor. In another embodiment the polypeptide of interest or fragment thereof provided herein is an adhesin. In another embodiment the polypeptide of interest or fragment thereof provided herein is an angiostatin. In another embodiment the polypeptide of interest or fragment thereof provided herein is an endostatin. In another embodiment the polypeptide of interest or fragment thereof provided herein is a receptor peptide. In another embodiment the polypeptide of interest or fragment thereof provided herein is a receptor binding ligand. In another embodiment the polypeptide of interest or fragment thereof provided herein is an antibody. In another embodiment the polypeptide of interest or fragment thereof provided herein is an antibody fragment. In another embodiment the polypeptide of interest or fragment thereof provided herein is a peptide or a protein including any modified form.

In another embodiment, the polypeptide of interest or fragment thereof comprises additionally at least one CTP amino acid peptide attached on the N-terminus and/or one CTP amino acid peptide attached on the C-terminus. In another embodiment, the polypeptide of interest or fragment thereof is selected from the following list: insulin, Albutein/albumin, Activase altiplase/tPA, adenosine deaminase, immune globulin, glucocerebrosidase, Leukine-sargramostim/GM-CSF, G-CSF, Venoglobulin-S/IgG, Proleukin aldesleukin, DNase, factor VIII, Helixate, L-asparaginase, WinRho SDF Rh I, Retavase retaplase/tPA, Factor IX, FSH, globulin, fibrin, interleukin-11, becaplermin/PDGF, lepirudin/herudin, TNF, Thymoglobulin, factor VIIa, interferon alpha-2a, interferon alfa n-1, interferon alfa-N3, interferon beta-1b, interferon gamma-1b, Interleukin-2, HGH, or monoclonal antibodies.

In one embodiment, the polypeptide of interest or fragment thereof provided herein further comprises a signal peptide. In another embodiment, the polypeptide of interest or fragment thereof is a growth hormone. In another embodiment, the growth hormone further comprises a signal peptide. In another embodiment, following expression and secretion, the signal peptide is cleaved from the precursor engineered peptides/polypeptides resulting in the mature engineered peptides/polypeptides. In another embodiment, signal sequences include, but are not limited to the endogenous signal sequences.

In another embodiment, the polypeptides and methods of the present invention provide a growth hormone having additionally a signal peptide comprising the following amino acid sequence: MATGSRTSLLLAFGLLCLP-WLQEGSA (SEQ ID NO: 4).

In another embodiment, CTP-modified or conjugated growth hormones of this invention are used in the same manner as unmodified growth hormones. In another embodiment, conjugated growth hormones of this invention have an increased circulating half-life and plasma residence time, decreased clearance, and increased clinical activity in vivo. In another embodiment, due to the improved properties of the conjugated growth hormones as described herein, these conjugates are administered less frequently than unmodified growth hormones. In another embodiment, conjugated growth hormones as described herein are administered once a week to once every two weeks. In another embodiment, conjugated growth hormones as described herein are administered once every two weeks to once every three weeks. In another embodiment, conjugated growth hormones as described herein are administered once a day to three times a week. In another embodiment, decreased frequency of administration will result in improved patient compliance leading to improved treatment outcomes, as well as improved patient quality of life. In another embodiment, compared to conventional conjugates of growth hormones linked to poly(ethylene glycol) it has been found that growth hormone CTP conjugates having the molecular weight and linker structure of the conjugates of this invention have an improved potency, improved stability, elevated area under the curve (AUC) levels, and enhanced circulating half-life. In another embodiment, compared to conventional conjugates of growth hormones linked to poly(ethylene glycol) it has been found that growth hormones having the molecular weight and linker structure of the conjugates of this invention have an improved potency, improved stability, elevated AUC levels, enhanced circulating half-life. In another embodiment, compared to conventional conjugates of growth hormones linked to poly(ethylene glycol) it has been found that growth hormones having the optimal hydrodynamic volume of the conjugates of this invention have an improved potency, improved stability, elevated AUC levels, enhanced circulating half-life. In another embodiment, a therapeutically effective amount of a conjugated growth hormone is the amount of conjugate necessary for the in vivo measurable expected biological activity. In another embodiment, a growth hormone utilized according to the teachings of the present invention exhibits increased potency. In another embodiment, the attachment of CTP sequences to both the N- and C-termini of a growth hormone results in prolonged in-vivo activity.

In another embodiment, the growth hormone is any growth hormone known to one of skill in the art. In another embodiment, the growth hormone is a human growth hormone. In another embodiment, the nucleotide sequence and/or the amino acid sequence of a growth hormone is available in a gene bank database. In another embodiment, the growth hormone is a homologue of a growth hormone provided herein and/or of a growth hormone provided in a gene bank database. In another embodiment, a homologue also refers to a deletion, insertion, or substitution variant, including an amino acid substitution, thereof and biologically active polypeptide fragments thereof.

In another embodiment, the growth hormone is variant of hGH missing exons 2, 3, 4, or any combination thereof. In another embodiment, the growth hormone comprises a signal peptide. In another embodiment, the growth hormone comprises a signal cleavage site. In another embodiment, polypeptides comprising GH modified by CTPs of the present invention comprise recombinant GH.

In another embodiment, a growth hormone as described herein is a member of the superfamily of growth hormone (GH)-like cytokines. In another embodiment, a growth hormone as described herein is human growth hormone (hGH). In another embodiment, a human growth hormone comprises the following amino acid sequence (Genbank Accession No. P01241):
MATGSRTSLLLAFGLLCLPWLQEGSAFPTIPLSRLFD-NAMLRAHRLHQLAFDTYQEFE EAYIPKEQKYS-FLQNPQTSLCFSESIPTPSNREETQQKSNLELLRIS-LLLIQSWLEPVQFL
RSVFANSLVYGASDSNVY-DLLKDLEEGIQTLMGRLEDGSPRTGQIFKQ-TYSKFDTNS HNDDALLKNYGLLYCFRKDMDKVET-FLRIVQCRSVEGSCGF (SEQ ID NO: 5).

In another embodiment, a human growth hormone comprises the following amino acid sequence:
MFPTIPLSRLFDNAMLRAHRLHQLAFDTYQEFEEAY-IPKEQKYSFLQNPQTSLCFSESI PTPSNREETQQKSN-LELLRISLLLIQSWLEPVQFLRSVFANSLVYGASDSN-VYDLLKDL
EEGIQTLMGRLEDGSPRTGQIFKQTYSKFDTNSHND-DALLKNYGLLYCFRKDMDKVE TFLRIVQCRSVEG-SCGF (SEQ ID NO: 6). In another embodiment, a human growth hormone comprises the following amino acid sequence:
MFPTIPLSRLFDNAMLRAHRLHQLA (SEQ ID NO: 7). In another embodiment, an hGH comprises the following amino acid sequence:
MATGSRTSLLLAFGLLCLPWLQEGSAFPTIPLSRLFD-NAMLRAHRLHQLAFDTYQEFE EAYIPKVQKYS-FLQNPQTSLCFSESIPTPSNREETQQKSNLELLRIS-LLLIQSWLEPVQFL
RSVFANSLVYGASDSNVY-DLLKDLEEGIQTLMGRLEDGSPRTGQIFKQ-TYSKFDTNS HNDDALLKNYGLLYCFRKDMDKVET-FLRIVQCRSVEGSCGF (SEQ ID NO: 8). In another embodiment, an hGH is a substitution variant in which glutamine in position 65 of hGH is substituted by a valine.

In another embodiment, a growth hormone of the invention comprises the gene bank amino acid deposited sequence under accession no. AAA72260. In another embodiment, a growth hormone of the invention comprises the gene bank amino acid deposited sequence under accession no. AAK69708. In another embodiment, a growth hormone of the invention comprises the gene bank amino acid deposited sequence under accession no. CAA01435. In another embodiment, a growth hormone of the invention comprises the gene bank amino acid deposited sequence under accession no. CAA01329. In another embodiment, a growth hormone of the invention comprises the gene bank amino acid deposited sequence under accession no. CAA00380. In another embodiment, a growth hormone of the invention comprises the gene bank amino acid deposited sequence under accession no. AAA72555. In another embodiment, a growth hormone of the invention comprises the gene bank amino acid deposited sequence under accession no. NP_000506.2. In another embodiment, a growth hormone of the invention comprises the gene bank amino acid deposited sequence under accession no. NP_072053.1. In another embodiment, a growth hormone of the invention comprises the gene bank amino acid deposited sequence under accession no. NP_072054.1. In another embodiment, a growth hormone of the invention comprises the gene bank amino acid deposited sequence under accession no. NP_072055.1. In another embodiment, a growth hormone of the invention comprises the gene bank amino acid deposited sequence under accession no. NP_072056.1.

In another embodiment, the nucleic acid molecule encoding a growth hormone as described herein encodes any amino acid sequence of a growth hormone known to one of skill in the art. In another embodiment, the nucleic acid molecule encoding a growth hormone as described herein encodes an hGH. In another embodiment, the nucleic acid molecule encoding a growth hormone comprises the gene bank nucleic acid deposited sequence under accession no. NM_000515.3. In another embodiment, the nucleic acid molecule encoding a growth hormone comprises the gene bank nucleic acid deposited sequence under accession no. NM_022559.2. In another embodiment, the nucleic acid molecule encoding a growth hormone comprises the gene bank nucleic acid deposited sequence under accession no. NM_022560.2. In another embodiment, the nucleic acid molecule encoding a growth hormone comprises the gene bank nucleic acid deposited sequence under accession no. NM_022561.2. In another embodiment, the nucleic acid molecule encoding a growth hormone comprises the gene bank nucleic acid deposited sequence under accession no. NM_022562.2.

In another embodiment, a polypeptide comprising a growth hormone of the invention comprises one CTP attached to a C-terminus of a growth hormone (hGH-CTP) and having the following amino acid sequence:
MATGSRTSLLLAFGLLCLPWLQEGSAFPTIPLSRLFDNAMLRAHRLHQLAFDTYQEFE EAYIPKEQKYSFLQNPQTSLCFSESIPTPSNREETQQKSNLELLRISLLLIQSWLEPVQFL RSVFANSLVYGASDSNVYDLLKDLEEGIQTLMGRLEDGSPRTGQIFKQTYSKFDTNS HNDDALLKNYGLLYCFRKDMDKVETFLRIVQCRSVEGSCGFSSSSKAPPPSLPSPSRL PGPSDTPILPQ (SEQ ID NO: 9).

In another embodiment, a polypeptide comprising a growth hormone of the invention comprises two CTPs in tandem attached to a C-terminus of a growth hormone (hGH-CTP-CTP) and having the following amino acid sequence:
MATGSRTSLLLAFGLLCLPWLQEGSAFPTIPLSRLFDNAMLRAHRLHQLAFDTYQEFE EAYIPKEQKYSFLQNPQTSLCFSESIPTPSNREETQQKSNLELLRISLLLIQSWLEPVQFL RSVFANSLVYGASDSNVYDLLKDLEEGIQTLMGRLEDGSPRTGQIFKQTYSKFDTNS HNDDALLKNYGLLYCFRKDMDKVETFLRIVQCRSVEGSCGFSSSSKAPPPSLPSPSRL PGPSDTPILPQSSSSKAPPPSLPSPSRLPGPSDTPILPQ (SEQ ID NO: 10).

In another embodiment, a polypeptide comprising a growth hormone of the invention comprises two CTPs attached in tandem to a C-terminus of a growth hormone and one CTP attached to an N-terminus of a growth hormone (CTP-hGH-CTP-CTP) and having the following amino acid sequence:
MATGSRTSLLLAFGLLCLPWLQEGSASSSSKAPPPSLPSPSRLPGPSDTPILPQFPTIPLS RLFDNAMLRAHRLHQLAFDTYQEFEEAYIPKEQKYSFLQNPQTSLCFSESIPTPSNREE TQQKSNLELLRISLLLIQSWLEPVQFLRSVFANSLVYGASDSNVYDLLKDLEEGIQTL MGRLEDGSPRTGQIFKQTYSKFDTNSHNDDALLKNYGLLYCFRKDMDKVETFLRIVQ CRSVEGSCGFSSSSKAPPPSLPSPSRLPGPSDTPILPQSSSSKAPPPSLPSPSRLPGPSDTPI LPQ (SEQ ID NO: 11).

In another embodiment, a polypeptide comprising a growth hormone of the invention comprises two CTPs in tandem attached to a C-terminus of a growth hormone, wherein one CTP of two CTPs is truncated, and one additional CTP attached to an N-terminus of a growth hormone (tCTP-hGH-CTP-CTP) and having the following amino acid sequence:
MATGSRTSLLLAFGLLCLPWLQEGSASSSSKAPPPSLPFPTIPLSRLFDNAMLRAHRLH QLAFDTYQEFEEAYIPKEQKYSFLQNPQTSLCFSESIPTPSNREETQQKSNLELLRISLL LIQSWLEPVQFLRSVFANSLVYGASDSNVYDLLKDLEEGIQTLMGRLEDGSPRTGQIF KQTYSKFDTNSHNDDALLKNYGLLYCFRKDMDKVETFLRIVQCRSVEGSCGFSSSSK APPPSLPSPSRLPGPSDTPILPQSSSSKAPPPSLPSPSRLPGPSDTPILPQ (SEQ ID NO: 12).

In another embodiment, a polypeptide comprising a growth hormone of the invention comprises one CTP attached to a C-terminus of a growth hormone and one CTP attached to an N-terminus of a growth hormone (CTP-hGH-CTP) and having the following amino acid sequence:
MATGSRTSLLLAFGLLCLPWLQEGSASSSSKAPPPSLPSPSRLPGPSDTPILPQFPTIPLS RLFDNAMLRAHRLHQLAFDTYQEFEEAYIPKEQKYSFLQNPQTSLCFSESIPTPSNREE TQQKSNLELLRISLLLIQSWLEPVQFLRSVFANSLVYGASDSNVYDLLKDLEEGIQTL MGRLEDGSPRTGQIFKQTYSKFDTNSHNDDALLKNYGLLYCFRKDMDKVETFLRIVQ CRSVEGSCGFSSSSKAPPPSLPSPSRLPGPSDTPILPQ (SEQ ID NO: 13).

In another embodiment, a polypeptide comprising a growth hormone and one CTP comprises the following amino acid sequence:
MATGSRTSLLLAFGLLCLPWLQEGSASSSSKAPPPSLPSPSRLPGPSDTPILPQFPTIPLS RLFDNAMLRAHRLHQLAFDTYQEFEEAYIPKEQKYSFLQNPQTSLCFSESIPTPSNREE TQQKSNLELLRISLLLIQSWLEPVQFLRSVFANSLVYGASDSNVYDLLKDLEEGIQTL MGRLEDGSPRTGQIFKQTYSKFDTNSHNDDALLKNYGLLYCFRKDMDKVETFLRIVQ CRSVEGSCGF (SEQ ID NO: 14).

In another embodiment, a polynucleotide molecule encoding a polypeptide having CTP-hGH-CTP comprises the following nucleic acid sequence:
tctagaggacatggccaccggcagcaggaccagcctgctgctggccttcggcct-gctgtgcctgccatggctgcaggagggcagcg ccagctcttcttctaaggctc-caccccatctctgcccagccccagcagactgccgggccccagcgacacac-ccattctgcccagttc
cccaccatcccctgagcaggctgttcgacaacgccatgctgagggctcacag-gctgcaccagctggcctttgacacctaccaggag ttcgaggaagcctacatc-cccaaggagcagaagtacagcttcctgcagaaccccagacctccctgtgcttca-gcgagagcatcccc
accccagcaacagagaggagacccagcagaagagcaacctggagctgct-gaggatctccctgctgctgatccagagctggctgg agcccgtgcagttcct-gagaagcgtgttcgccaacagcctggtgtacggcgccagcgacagcaacgtg-tacgacctgctgaaggac
ctggaggagggcatccagaccctgatgggccggctggaggacggcagcccca-ggaccggccagatcttcaagcagacctacagc aagttcgacaccaacagcca-caacgacgacgccctgctgaagaactacgggctgctgtactgcttcagaaagga-catggacaaggtg
gagaccttcctgaggatcgtgcagtgcagaagcgtggagggcagctgcggct-tcagctccagcagcaaggcccctcccccgagcct gccctccccaagcaggct-gcctgggccctccgacacaccaatcctgcctcagtgatgaaggtctggatgcggc-cgc (SEQ ID NO: 15).

In another embodiment, a polynucleotide molecule encoding a polypeptide having CTP-hGH-CTP-CTP comprises the following nucleic acid sequence:
tctagaggacatggccaccggcagcaggaccagcctgctgctggccttcggcct-gctgtgcctgccatggctgcaggagggcagcg ccagctcttcttctaaggctc-caccccatctctgcccagccccagcagactgccgggccccagcgacacac-ccattctgcccagttc
cccaccatcccctgagcaggctgttcgacaacgccatgctgagggctcacag-gctgcaccagctggcctttgacacctaccaggag ttcgaggaagcctacatc-cccaaggagcagaagtacagcttcctgcagaaccccagacctccctgtgcttca-gcgagagcatcccc
accccagcaacagagaggagacccagcagaagagcaacctggagctgct-gaggatctccctgctgctgatccagagctggctgg agcccgtgcagttcct-gagaagcgtgttcgccaacagcctggtgtacggcgccagcgacagcaacgtg-tacgacctgctgaaggac
ctggaggagggcatccagaccctgatgggccggctggaggacggcagcccca-ggaccggccagatcttcaagcagacctacagc aagttcgacaccaacagcca-caacgacgacgccctgctgaagaactacgggctgctgtactgcttcagaaagga-catggacaaggtg
gagaccttcctgaggatcgtgcagtgcagaagcgtggagggcagctgcggct-tcagctccagcagcaaggcccctcccccgagcct gccctccccaagcaggct-gcctgggccctccgacacaccaatcctgccacagagcagctcctctaaggc-cctcctccatccctgcc
atccccctcccggctgcctggcccctctgacacccctatcctgcctcagtgat-gaaggtctggatgcggccgc (SEQ ID NO: 16).

In another embodiment, a polynucleotide molecule encoding a polypeptide having CTP-hGH-CTP-CTP comprises the following nucleic acid sequence:
tctagaggacatggccaccggcagcaggaccagcctgctgctggccttcggcct-gctgtgcctgccatggctgcaggagggcagcg ccagctcttcttctaaggctc-caccccgagcctgcccttcccaccatcccctgagcaggctgttcgacaacgc-catgctgagggct
cacaggctgcaccagctggcctttgacacctaccaggagttcgaggaagccta-catccccaaggagcagaagtacagcttcctgcag aaccccagacctccctgt-gcttcagcgagagcatccccaccccagcaacagagaggagacccagca-gaagagcaacctggagc
tgctgaggatctccctgctgctgatccagagctggctggagcccgtgcagttcct-gagaagcgtgttcgccaacagcctggtgtacgg cgccagcgacagcaacgtg-tacgacctgctgaaggacctggaggagggcatccagaccctgatgggccg-gctggaggacggcag
ccccaggaccggccagatcttcaagcagacctacagcaagttcgacaccaaca-gccacaacgacgacgccctgctgaagaactacg ggctgctgtactgcttca-gaaaggacatggacaaggtggagaccttcctgaggatcgtgcagtgca-gaagcgtggagggcagctgc ggcttcagctccagcagcaaggcccctc-cccgagcctgccctccccaagcaggctgcctgggccctccgacacaccaatc-ctgcc
acagagcagctcctctaaggcccctcctccatccctgccatcccctcccggct-gcctggcccctctgacaccctatcctgcctcagt gatgaaggtctggatgcggc-cgc (SEQ ID NO: 17).

In another embodiment, a growth hormone of the invention is homologous to a known sequence of a growth hormone. In another embodiment, a growth hormone of the invention is homologous to a growth hormone sequence as disclosed herein. In another embodiment, homology according to the present invention also encompasses deletions, insertions, or substitution variants, including an amino acid substitution, thereof and biologically active polypeptide fragments thereof. In one embodiment the substitution variant is one, in which the glutamine in position 65 of hGH is substituted by a valine [Gellerfors et al., J Pharm Biomed Anal 1989, 7:173-83].

In one embodiment, the phrase "human growth hormone" (hGH) refers to a polypeptide, such as set forth in Genbank Accession No. P01241 exhibiting hGH activity (i.e., stimulation of growth).

In one embodiment, "human growth hormone" (hGH) refers to a polypeptide, such as set forth in Genbank Accession No. P01241, exhibiting hGH activity (i.e., stimulation of growth). In one embodiment, hGH of the present invention also refers to homologues. In one embodiment, hGH amino acid sequence of the present invention is at least 50% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 60% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 70% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 80% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 90% homologous to an hGH sequence set forth in GenBank Accession No. P01241 as determined using BlastP software of the National Center of Biotechnology Information (NCBI) using default parameters). In one embodiment, hGH amino acid sequence of the present invention is at least 95% homologous to an hGH sequence set forth in GenBank Accession No. P01241 as determined using BlastP software of the National Center of Biotechnology Information (NCBI) using default parameters).

In one embodiment, the peptide of interest provided herein is oxyntomodulin. In another embodiment, oxyntomodulin (OXM) comprises the following amino acid (AA) sequence: HSQGTFTSDYSKYLDSRRAQD-FVQWLMNTKRNRNNIA (SEQ ID NO: 18). In another embodiment, OXM consists of the amino acid sequence of SEQ ID NO: 18. In another embodiment, OXM comprises or consists of the amino acid sequence depicted in CAS No. 62340-29-8.

In one embodiment, the term oxyntomodulin further includes a homologue of a known oxyntomodulin. In one embodiment, the homologue is a functional homologue. In another embodiment, the term "functional" refers to the ability a homologue, polypeptides or fragments thereof provided herein has to suppress appetite. The term also refers to the ability a homologue, polypeptides or fragments thereof provided herein has to extend another protein's or peptide's biological half-life. In another embodiment, the biological half-life (T½) of a protein, peptide or homologue provided herein refers to the time it takes for half of the amount of the protein, peptide or homologue to be degraded or to not be present in a biological medium in a subject. In another embodiment, the biological medium is serum, cerebospinal fluid, tissue, mucosa, and the like.

In another embodiment, OXM is human OXM or any mammal OXM. In another embodiment, OXM is also referred to as glucagon-37 or bioactive enteroglucagon. In another embodiment, OXM is a dual Polypeptide or fragments thereof. In another embodiment, OXM is a biologically active fragment of OXM. In another embodiment, biologically active OXM extends from amino acid 30 to amino acid 37 of SEQ ID NO: 18. In another embodiment, biologically active OXM extends from amino acid 19 to amino acid 37 of SEQ ID NO: 18. In another embodiment, OXM of the invention corresponds to an octapeptide from which the two C-terminal amino acids are deleted. In another embodiment, OXM of the invention corresponds to any fragment of SEQ ID NO: 18 which retains OXM activity as described herein. In another embodiment, the invention also encompasses homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to an oxyntomodulin as determined using BlastP software of the National Center of Biotechnology Information (NCBI) using default parameters.

In other embodiments, the term engineered oxyntomodulin refers to the amino acid sequence of a matured oxyntomodulin. In other embodiments, the term engineered oxyntomodulin refers to the amino acid sequence of the oxyntomodulin including its signal sequence or signal peptide.

In another embodiment, the polypeptides or fragments thereof provided herein comprise a signal peptide or signal sequence.

In another embodiment, "signal sequence" and "signal peptide" are used interchangeably herein. In another embodiment, "sequence" when in reference to a polynucleotide molecule can refer to a coding portion. Each possibility represents a separate embodiment of the present invention.

In one embodiment, the polypeptide or peptide of interest provided herein is erythropoietin (EPO). In another embodiment, the term "erythropoietin" refers to mammalian erythropoietin. In one embodiment, "erythropoietin" refers to human erythropoietin, such as set forth in GenBank Accession No. AAA52400.

In one embodiment, an erythropoietin or EPO sequence of the present invention also refers to homologues. In one embodiment, the erythropoietin amino acid sequence of the present invention is at least 50% homologous to an erythropoietin sequence set forth in GenBank Accession No. AAA52400 as determined using BlastP software of the National Center of Biotechnology Information (NCBI) using default parameters). In one embodiment, the erythropoietin amino acid sequence of the present invention is at least 60% homologous to an erythropoietin sequence set forth in GenBank Accession No. AAA52400 as determined using BlastP software of the National Center of Biotechnology Information (NCBI) using default parameters). In one embodiment, the erythropoietin amino acid sequence of the present invention is at least 70% homologous to an erythropoietin sequence set forth in GenBank Accession No. AAA52400 as determined using BlastP software of the National Center of Biotechnology Information (NCBI) using default parameters). In one embodiment, the erythropoietin amino acid sequence of the present invention is at least 80% homologous to an erythropoietin sequence set forth in GenBank Accession No. AAA52400 as determined using BlastP software of the National Center of Biotechnology Information (NCBI) using default parameters). In one embodiment, the erythropoietin amino acid sequence of the present invention is at least 90% homologous to an erythropoietin sequence set forth in GenBank Accession No. AAA52400 as determined using BlastP software of the National Center of Biotechnology Information (NCBI) using default parameters). In one embodiment, the erythropoietin amino acid sequence of the present invention is at least 95% homologous to an erythropoietin sequence set forth in GenBank Accession No. AAA52400 as determined using BlastP software of the National Center of Biotechnology Information (NCBI) using default parameters).

In another embodiment, the methods of the present invention provide an EPO peptide set forth in SEQ ID NO: 19 having additionally at least one CTP amino acid peptide on the N-terminus and at least additional one CTP amino acid peptide on the C-terminus. In another embodiment, the methods of the present invention provide an EPO peptide set forth in SEQ ID NO: 19:
MGVHECPAWLWLLLSLLSLPLGLPVLGAPPRLICD-SRVLERYLLEAKEAENITTGCAE HCSLNENITVPDT-KVNFYAWKRMEVGQQAVEVWQGLALLSEAVL-RGQALLVNSSQ PWEPLQLHVDKAVSGLRSLTTLLRALGAQKEAISPP-DAASAAPLRTITADTFRKLFRV YSNFLRGKLKLYT-GEACRTGDRSSSSKAPPPSLPSPSRLPGPSDTPILPQ (SEQ ID NO: 19).

In another embodiment, the EPO peptide additionally has at least one CTP amino acid peptide on the N-terminus and at least one additional CTP amino acid peptide on the C-terminus for the treatment of anemia. In another embodiment, the methods of the present invention provide an EPO peptide set forth in SEQ ID NO: 20 having additionally at least one CTP amino acid peptide on the N-terminus and at least one CTP amino acid peptide on the C-terminus:
MGVHECPAWLWLLLSLLSLPLGLPVLGAPPRLICD-SRVLERYLLEAKEAENITTGCAE HCSLNENITVPDT-KVNFYAWKRMEVGQQAVEVWQGLALLSEAVL-RGQALLVNSSQ PWEPLQLHVDKAVSGLRSLTTLLRALGAQKEAISPP-DAASAAPLRTITADTFRKLFRV YSNFLRGKLKLYT-GEACRTGDRSSSSKAPPPSLPSPSRLPGPSDTPIL-PQSSSSKAPPPSL PSPSRLPGPSDTPILPQ (SEQ ID NO: 20).

In another embodiment, the methods of the present invention provide an EPO peptide set forth in SEQ ID NO: 21 having additionally at least one CTP amino acid peptide on the N-terminus and at least one CTP amino acid peptide on the C-terminus:
MGVHECPAWLWLLLSLLSLPLGLPVLGSSSSKAP-PPSLPSPSRLPGPSDTPILPQAPPRL ICDSRVLERYL-LEAKEAENITTGCAEHCSLNENITVPDTKVN-FYAWKRMEVGQQAVE VWQGLALLSEAVLRGQALLVNSSQPWEPLQLHVD-KAYSGLRSLTTLLRALGAQKEA ISPPDAASAAPLRTI- TADTFRKLFRVYSNFLRGKLKLYTGEACRTGDRSSSSKAPPPSL PSPSRLPGPSDTPILPQSSSSKAPPPSLPSPSRLPGPSDTPILPQ (SEQ ID NO: 21).

In another embodiment, the methods of the present invention provide an EPO peptide set forth in SEQ ID NO: 22 having additionally at least one CTP amino acid peptide on the N-terminus and at least one CTP amino acid peptide on the C-terminus:
MGVHECPAWLWLLLSLLSLPLGLPVLGAPPRLICDSRVLERYLLEAKEAENITTGCAE HCSLNENITVPDTKVNFYAWKRMEVGQQAVEVWQGLALLSEAVLRGQALLVNSSQ PWEPLQLHVDKAVSGLRSLTTLLRALGAQKEAISPPDAASAAPLRTITADTFRKLFRV YSNFLRGKLKLYTGEACRTGDRSSSSKAPPPSLPSPSRLPGPSDTPILPQAPPRLICDSR VLERYLLEAKEAENITTGCAEHCSLNENITVPDTKVNFYAWKRMEVGQQAVEVWQG LALLSEAVLRGQALLVNSSQPWEPLQLHVDKAVSGLRSLTTLLRALGAQKEAISPPD AASAAPLRTITADTFRKLFRVYSNFLRGKLKLYTGEACRTGDR (SEQ ID NO: 22).

In another embodiment, the methods of the present invention provide an EPO peptide set forth in SEQ ID NO: 23 having additionally at least one CTP amino acid peptide on the N-terminus and at least one CTP amino acid peptide on the C-terminus:
MGVHECPAWLWLLLSLLSLPLGLPVLGSSSSKAPPPSLPSPSRLPGPSDTPILPQAPPRL ICDSRVLERYLLEAKEAENITTGCAEHCSLNENITVPDTKVNFYAWKRMEVGQQAVE VWQGLALLSEAVLRGQALLVNSSQPWEPLQLHVDKAYSGLRSLTTLLRALGAQKEA ISPPDAASAAPLRTITADTFRKLFRVYSNFLRGKLKLYTGEACRTGDR (SEQ ID NO: to 23).

In another embodiment, the methods of the present invention provide an EPO peptide set forth in SEQ ID NO: 24 having additionally at least one CTP amino acid peptide on the N-terminus and at least one CTP amino acid peptide on the C-terminus:
MGVHECPAWLWLLLSLLSLPLGLPVLGSSSSKAPPPSLPSPSRLPGPSDTPILPQAPPRL ICDSRVLERYLLEAKEAENITTGCAEHCSLNENITVPDTKVNFYAWKRMEVGQQAVE VWQGLALLSEAVLRGQALLVNSSQPWEPLQLHVD KAYSGLRSLTTLLRALGAQKEA ISPPDAASAAPLRTITADTFRKLFRVYSNFLRGKLKLYTGEACRTGDRSSSSKAPPPSL PSPSRLPGPSDTPILPQ (SEQ ID NO: 24).

In another embodiment, the methods of the present invention provide an EPO peptide set forth in SEQ ID NO: 25:
MGVHECPAWLWLLLSLLSLPLGLPVLGAPPRLICDSRVLERYLLEAKEAENITTGCAE HCSLNENITVPDTKVNFYAWKRMEVGQQAVEVWQGLALLSEAVLRGQALLVNSSQ PWEPLQLHVDKAVSGLRSLTTLLRALGAQKEAISPPDAASAAPLRTITADTFRKLFRV YSNFLRGKLKLYTGEACRTGDR (SEQ ID NO: 25).

In another embodiment, the methods of the present invention provide a nucleic acid set forth in SEQ ID NO: 26 encoding an EPO peptide and one CTP amino acid peptide on the N-terminus and two CTP amino acid peptides on the C-terminus: tctagaggtc atcatggggg tgcacgaatg tcctgcctgg ctgtggcttc tcctgtcccttc tgtcgctc cctctgggcc tcccagtcct gggctc ctct tcctcaaagg cccctcccc gagccttcca agtccatccc gactcccggg gccctcggac acccaatat taccacaagc cccaccacgc ctcatctgtg aca gccgagt cctggagagg tacctcttgg aggccaagga ggccgagaat atcacgacgg gctgtgctga acactgcagc ttgaatgaga atatcactgt cccagacacc aaagttaatt tctatgcctg gaagaggatg gaggtcgggc agcaggccgt agaagtctgg cagggcctgg ccctgctgtc ggaagctgtc ctgcggggcc aggccctgtt ggtcaactct tcccagccgt gggagcccct gcagctgcat gtggataaag ccgtcagtgg ccttcgcagc ctcaccactc tgcttcgggc tctgggagcc cagaaggaag ccatctcccc tccagatgcg gcctcagctg ctccactccg aacaatcact gctgacactt tccgcaaact cttccgagtc tactccaatt tcctccgggg aaagctgaag ctgtacacag gggaggcctg caggacaggg gacagatcct cttcctcaaa ggcccctccc ccgagccttc caagtccatc ccgactcccg gggccctccg acacaccaat cctgccacag agcagctcct ctaaggcccctcctccatcc ctgccatccc cctccggct gcctggcccc tctgacaccc ctatcctgcc tcagtgatga aggtctctg gatccgcggc cgc (SEQ ID NO: 26). In another embodiment, the methods of the present invention the methods of the present invention provide an amino acid sequence comprising an EPO peptide set forth in SEQ ID NO: 66 having two CTP amino acid peptides on the N-terminus:
MGVHECPAWLWLLLSLLSLPLGLPVLGSSSSKAPPPSLPSPSRLPGPSDTPILPQSSSSK APPPSLPSPSRLPGPSDTPILPQAPPRLICDSRVLERYLLEAKEAENITTGCAEHCSLNEN ITVPDTKVNLYAWKRMEVGQQAVEVWQGLALLSEAVLRGQALLVNSSQPWEPLQL HVDKAVSGLRSLTTLLRALGAQKEAISPPDAASAAPLRTITADTFRKLFRVYSNFLRG KLKLYTGEACRTGDR (SEQ ID NO: 66).

In another embodiment, the methods of the present invention provide a nucleic acid sequence, set forth in SEQ ID NO: 67, encoding an EPO peptide and two CTP amino acid peptides on the N-terminus:
ATGGGCGTGCACGAGTGTCCTGCTTGGCTGTGGCTGCTGCTGAGCCTGCTGTCCCT GCCTCTGGGCCTGCCTGTGCTGGGCAGCAGCAGCTCTAAGGCCCCTCCACCCAGC CTGCCCAGCCCTTCTAGACTGCCTGGCCCCAGCGACACCCCCATCCTGCCTCAGA GCAGCAGCAGCAAGGCCCCACCACCATCCCTGCCTAGCCCCAGCAGACTGCCAG GCCCTTCCGATACCCCAATCCTGCCCCAGGCCCCTCCCAGACTGATCTGCGACAG CCGGGTGCTGGAAAGATACCTGCTGGAAGCCAAAGAGGCCGAGAACATCACCAC CGGCTGCGCCGAGCACTGCAGCCTGAACGAGAATATCACCGTGCCCGACACCAA AGTGAACTTCTACGCCTGGAAGCGGATGGAAGTGGGCCAGCAGGCCGTGGAAGT GTGGCAGGGACTGGCCCTGCTGAGCGAGGCCGTGCTGAGAGGACAGGCCCTGCT GGTGAACAGCAGCCAGCCCTGGGAGCCCCTGCAGCTGCATGTGGATAAGGCCGT GTCCGGCCTGCGGAGCCTGACCACACTGCTGAGAGCCCTGGGCGCTCAGAAAGA GGCCATCTCTCCCCCTGATGCCGCCTCTGCCGCCCCTCTGAGAACCATCACCGCCG ACACCTTCCGGAAGCTGTTCCGGGTGTACAGCAACTTCCTGCGGGGCAAGCTGAA GCTGTACACCGGCGAGGCCTGCCGGACCGGCGATAGATAAGCTGGCGCGCC (SEQ ID NO: 67).

In another embodiment, the methods of the present invention the methods of the present invention provide an EPO peptide set forth in SEQ ID NO: 68 having two CTP amino acid peptides on the N-terminus and two CTP amino acid peptides on the C-terminus:
MGVHECPAWLWLLLSLLSLPLGLPVLGSSSSKAPPPSLPSPSRLPGPSDTPILPQSSSSK APPPSLPSPSRLPGPSDTPILPQAPPRLICDSRVLERYLLEAKEAENITTGCAEHCSLNEN ITVPDTKVNLYAWKRMEVGQQAVEVWQGLALL-SEAVLRGQALLVNSSQPWEPLQL HVDKAVSGLRSLT-TLLRALGAQKEAISPPDAASAAPLRTITADTFRKL-FRVYSNFLRG
KLKLYTGEACRTGDRSSSSKAPPPSLPSPSRLPGPSDT-PILPQSSSSKAPPPSLPSPSRLP GPSDTPILPQ (SEQ ID NO: 68).

In another embodiment, the methods of the present invention provide a nucleic acid sequence, set forth in SEQ ID NO: 69, encoding an EPO peptide and two CTP amino acid peptides on the N-terminus and two CTP amino acid peptides on the C-terminus:
ATGGGCGTGCACGAGTGTCCTGCTTGGCTGTGGCT-GCTGCTGAGCCTGCTGTCCCT GCCTCTGGGCCTGC-CTGTGCTGGGCAGCAGCAGCTCTAAGGCCCCTC-CACCCAGC
CTGCCCAGCCCTTCTAGACTGCCTGGCCCCAGCGA-CACCCCCATCCTGCCTCAGA GCAGCAGCAG-CAAGGCCCCACCACCATCCCTGCCTAGCCCCA-GCAGACTGCCAG
GCCCTTCCGATACCCCAATCCTGCCCCAGGC-CCCTCCCAGACTGATCTGCGACAG CCGGGTGCTG-GAAAGATACCTGCTGGAAGCCAAAGAGGCCGA-GAACATCACCAC
CGGCTGCGCCGAGCACTGCAGCCTGAACGA-GAATATCACCGTGCCCGACACCAA AGTGAACTTC-TACGCCTGGAAGCGGATGGAAGTGGGCCAGCAG-GCCGTGGAAGT
GTGGCAGGGACTGGCCCTGCTGAGCGAGGCCGT-GCTGAGAGGACAGGCCCTGCT GGTGAACAGCA-GCCAGCCCTGGGAGCCCCTGCAGCTGCATGTGGA-TAAGGCCGT
GTCCGGCCTGCGGAGCCTGACCACACTGCT-GAGAGCCCTGGGCGCTCAGAAAGA GGC-CATCTCTCCCCCTGATGCCGCCTCTGCCGCCCTCT-GAGAACCATCACCGCCG
ACACCTTCCGGAAGCTGTTCCGGGTGTACAG-CAACTTCCTGCGGGGCAAGCTGAA GCTGTACAC-CGGCGAGGCCTGCCGGACCGGCGATAGAAGCA-GCTCCAGCAAGGC
TCCACCCCCCAGCCTGCCATCCCCAAGTAGACTGC-CCGGGCCCTCTGACACACCT ATCCTGCCACAGTC-CAGCAGCTCCAAAGCTCCCCCACCATCCCTC-CCATCCCCATC
CAGACTGCCTGGACCATCCGACACTCCAATTCTGC-CTCAGTAAGCTTGGCGCGCC (SEQ ID NO: 69).

In one embodiment, "interferon" refers to the mammalian interferon polypeptide Type I. In one embodiment, "interferon" refers to the mammalian interferon polypeptide Type II. In some embodiments, additional suitable interferon polypeptides as known to those of ordinary skill in the art are utilized. In some embodiments, the interferon is alpha-interferon. In some embodiments, the interferon is beta-interferon. In some embodiments, the interferon is gamma-interferon. In some embodiments, the interferon is omega-interferon. In some embodiments, the interferon is a subspecies interferon. In one embodiment, the subspecies interferon (IFN) is IFN-α2a. In one embodiment, the subspecies *interferon* (IFN) is IFN-α 2b. In one embodiment, the subspecies interferon (IFN) is IFN-β1a. In one embodiment, the interferon (IFN) subspecies is IFN-β1b.

In one embodiment, interferon of the present invention exhibits interferon activity, such as antiviral or antiproliferative activity. In some embodiments, GenBank accession nos. of non-limiting examples of interferons are listed in Table 1 below.

In one embodiment, an interferon of the present invention also refers to homologues. In one embodiment, an interferon amino acid sequence of the present invention is at least 50% homologous to interferon sequences listed in Table 1 as determined using BlastP software of the National Center of Biotechnology Information (NCBI) using default parameters). In one embodiment, an interferon amino acid sequence of the present invention is at least 60% homologous interferon sequences listed in Table 1 as determined using BlastP software of the National Center of Biotechnology Information (NCBI) using default parameters. In one embodiment, interferon amino acid sequence of the present invention is at least 70% homologous to interferon sequences listed in Table 1, as determined using BlastP software of the National Center of Biotechnology Information (NCBI) using default parameters. In one embodiment, an interferon amino acid sequence of the present invention is at least 80% homologous to interferon sequences listed in Table 1, as determined using BlastP software of the National Center of Biotechnology Information (NCBI) using default parameters. In one embodiment, interferon amino acid sequence of the present invention is at least 90% homologous to interferon sequences listed in Table 1, as determined using BlastP software of the National Center of Biotechnology Information (NCBI) using default parameters. In one embodiment, an interferon amino acid sequence of the present invention is at least 95% homologous to interferon sequences listed in Table 1, as determined using BlastP software of the National Center of Biotechnology Information (NCBI) using default parameters. In some embodiments, homology according to the present invention also encompasses deletions, insertions, or substitution variants, including an amino acid substitution, thereof and biologically active polypeptide fragments thereof. In one embodiment the cysteine in position 17 of interferon β is substituted by a Serine.

Table 1 below lists examples of interferons with their respective NCBI sequence numbers

TABLE 1

| Interferon name | NCBI sequence number |
| --- | --- |
| interferon, α1 | NP_076918.1 |
| interferon, α 10 | NP_002162.1 |
| interferon, α 13 | NP_008831.2 |
| interferon, α 14 | NP_002163.1 |
| interferon, α 16 | NP_002164.1 |
| interferon, α 17 | NP_067091.1 |
| interferon, α 2 | NP_000596.2 |
| interferon, α 21 | NP_002166.1 |
| interferon, α 4 | NP_066546.1 |
| interferon, α 5 | NP_002160.1 |
| interferon, α 6 | NP_066282.1 |
| interferon, α 7 | NP_066401.2 |
| interferon, α 8 | NP_002161.2 |
| interferon, beta precursor | NP_002167.1 |
| interferon, ε1 | NP_795372.1 |
| interferon, γ | NP_000610.2 |
| interferon, ε | NP_064509.1 |
| interferon, Ω1 | NP_002168.1 |

In another embodiment, the interferon (IFN) provided herein as the peptide or as a polypeptide is a type I interferon. In another embodiment, the interferon (IFN) is IFN-α In another embodiment, the interferon (IFN) is IFN-β. In another embodiment, the interferon (IFN) is IFN-γ. In another embodiment, an interferon (IFN) peptide as described herein comprises an amino acid sequence set forth in SEQ ID NO: 27. In another embodiment, SEQ ID NO: 27 comprises the following amino acid (AA) sequence: MTNKCLLQIALLLCFSTTALSMSYNLLGFLQRSSN-FQCQKLLWQLNGRLEYCLKDRM NFDIPEE-IKQLQQFQKEDAALTIYEMLQNIFAIFRQDSSSTG-WNETIVENLLANVYHQI NHLKTVLEEKLEKEDFTRGKLMSSLHLKRYYGRIL-HYLKAKEYSHCAWTIVRVEILR NFYFINRLTGYLRN (SEQ ID NO: 27, Human Interferon-β1a). In another embodiment, an interferon (IFN) peptide as described herein comprises an amino acid sequence of human interferon β1a (hIFN β1a). In another embodiment, an interferon (IFN) peptide as described herein comprises an amino acid sequence set fourth in GenBank Accession No. NP_002167.1.

In another embodiment, an interferon (IFN) peptide as described herein is encoded by a nucleotide acid sequence set forth in SEQ ID NO: 28. In another embodiment, SEQ ID NO: 28 comprises the following nucleotide acid (NA) sequence: tctagaggacatgaccaacaagtgcctgctgcagatcgccctgctgctgtgcttca-gcaccaccgccctgagcatgagctacaacctg ctgggcttcctgcagaggtcca-gcaacttccagtgccagaagctgctgtggcagctgaacggcaggctggaatact-gcctgaaggac aggatgaacttcgacatcccagaggaaatcaagcagctgcagcagttcca-gaaggaggacgccgccctgaccatctacgagatgct gcagaacatcttcgc-catcttcaggcaggacagcagcagcaccggctggaacgagaccatcgtgga-gaacctgctggccaacgtgt accaccagatcaaccacctgaaaaccgtgctggaagagaagctggaaaaggag-gacttcaccaggggcaagctgatgagcagcct gcacctgaagaggtactacg-gcagaatcctgcactacctgaaggccaaggagtacagccactgcgcctggac-catcgtgagggtgg agatcctgaggaacttctacttcatcaacaggctgaccggctacctgaggaact-gatgagtccgcggccgc (SEQ ID NO: 28, Human Interferon-β1a). In another embodiment, an interferon (IFN) peptide as described herein is encoded by a nucleotide acid (NA) molecule of human interferon β1a (hIFN β1a). In another embodiment, an interferon (IFN) peptide as described herein is encoded by a nucleotide acid (NA) molecule comprising a nucleotide acid sequence set fourth in GenBank Accession No. NM_002176.

In another embodiment, an interferon (IFN) peptide as described herein comprises an amino acid sequence set forth in SEQ ID NO: 29. In another embodiment, SEQ ID NO: 29 comprises the following amino acid (AA) sequence: TF*LQPFEAFALAQQVVGDTVRVVNMTNKCLLQIA-LLLCFSTTALSMSYNLLGFLQR SSNFQCQKLLWQLN-GRLEYCLKDRMNFDIPEEIKQLQQFQKEDAALTI-YEMLQNIFAI FRQDSSSTGWNETIVENLLANVYHQ-INHLKTVLEEKLEKEDFTRGKLMSSLHLKRYY GRILHYLKAKEYSHCAWTIVRVEILRNFYFINRLT-GYLRN (SEQ ID NO: 29).

In another embodiment, an interferon (IFN) peptide as described herein is encoded by a nucleotide acid sequence set forth in SEQ ID NO: 30. In another embodiment, SEQ ID NO: 30 comprises the following nucleotide acid (NA) sequence: acattctaactgcaaccttttcgaagcctttgctctggcacaacaggtagtaggcga-cactgttcgtgttgtcaacatgaccaacaagtgtct cctccaaattgctctcctgttgt-gatctccactacagctctttccatgagctacaacttgcttggattccta-caaagaagcagcaattttcag tgtcagaagctcctgtggcaattgaatgggaggcttgaatactgcctcaaggacag-gatgaactttgacatccctgaggagattaagc a gctgcagcagttcca-gaaggaggacgccgcattgaccatctatgagatgctccagaacatctttgct-attttcagacaagattcatcagc actggctggaatgagactattgttgagaacctcctggctaatgtctatcatcaga-taaaccatctgaagacagtcctggaagaaaaactg gagaaagaagatttcacca-ggggaaaactcatgagcagtctgcacctgaaaagatatatgggaggattctgcat-tacctgaaggcca aggagtacagtcactgtgcctggaccatagtcagagtggaaatcctaaggaacttt-tacttcattaacagacttacaggttacctccgaaa ctga (SEQ ID NO: 30).

In another embodiment, the polypeptide as described herein comprises an interferon (IFN) peptide and a CTP unit. In another embodiment, the polypeptide as described herein comprises an interferon (IFN) peptide and a CTP unit attached to the C-terminus. In another embodiment, the polypeptide as described herein comprises an interferon (IFN) peptide and at least one CTP unit attached to the C-terminus. In another embodiment, the polypeptide as described herein comprises an interferon (IFN) peptide and a CTP unit attached to the N-terminus. In another embodiment, the polypeptide as described herein comprises an interferon (IFN) peptide and at least one CTP unit attached to the N-terminus. In another embodiment, the polypeptide as described herein comprises an interferon (IFN) peptide, at least one CTP unit attached to the N-terminus, and/or at least one CTP unit attached to the C-terminus. In another embodiment, the polypeptide as described herein comprises an interferon (IFN) peptide, at least one CTP unit attached to the N-terminus, and two CTP units in tandem attached to the C-terminus. In another embodiment, the polypeptide as described herein comprises an interferon (IFN) peptide, at least one CTP unit attached to the N-terminus, and two CTP units attached to the C-terminus. In another embodiment, the polypeptide as described herein comprises an interferon (IFN) peptide, one CTP unit attached to the N-terminus, and at least two CTP units attached to the C-terminus. In another embodiment, the polypeptide as described herein comprises an interferon (IFN) peptide, one CTP unit attached to the N-terminus, and at least two CTP units in tandem attached to the C-terminus.

In another embodiment, the polypeptide as described herein comprises an interferon (IFN) peptide and at least three CTP units. In another embodiment, the polypeptide as described herein comprises an interferon (IFN) peptide and three CTP units. In another embodiment, the polypeptide as described herein comprises an interferon (IFN) peptide-CTP polypeptide encoded by an amino acid sequence comprising the amino acid sequence set forth in SEQ ID NO: 31. In another embodiment, SEQ ID NO: 31 comprises the following amino acid (AA) sequence: MTNKCLLQIALLLCFSTTALSMSYNLLGFLQRSSN-FQCQKLLWQLNGRLEYCLKDRM NFDIPEE-IKQLQQFQKEDAALTIYEMLQNIFAIFRQDSSSTG-WNETIVENLLANVYHQI NHLKTVLEEKLEKEDFTRGKLMSSLHLKRYYGRIL-HYLKAKEYSHCAWTIVRVEILR NFYFINRLTGYLRN-SSSSKAPPPSLPSPSRLPGPSDTPILPQ (SEQ ID NO: 31).

In another embodiment, the polypeptide as described herein comprising an to interferon (IFN) peptide—and CTP is encoded by a nucleic acid molecule set forth in SEQ ID NO: 32. In another embodiment, SEQ ID NO: 32 comprises the following nucleotide acid (NA) sequence: tctagaggacatgaccaacaagtgcctgctgcagatcgccctgctgctgtgcttca-gcaccaccgccctgagcatgagctacaacctg ctgggcttcctgcagaggtcca-gcaacttccagtgccagaagctgctgtggcagctgaacggcaggctggaatact-gcctgaaggac aggatgaacttcgacatcccagaggaaatcaagcagctgcagcagttcca-gaaggaggacgccgccctgaccatctacgagatgct gcagaacatcttcgc-catcttcaggcaggacagcagcagcaccggctggaacgagaccatcgtgga-gaacctgctggccaacgtgt accaccagatcaaccacctgaaaaccgtgctggaagagaagctggaaaaggag-gacttcaccaggggcaagctgatgagcagcct gcacctgaagaggtactacg-gcagaatcctgcactacctgaaggccaaggagtacagccactgcgcctggaccatcgtgagggtgg
agatcctgaggaacttctacttcatcaacaggctgaccggctacctgaggaaca-
gctccagcagcaaggcccctccaccttccctgcc cagtccaagccgactc-
cctgggccctccgatacaccaattctgccacagtgatga (SEQ ID NO: 32).

In another embodiment, the polypeptide as described herein comprises an interferon (IFN) peptide and two CTP units attached to its carboxy terminus. In another embodiment, the polypeptide as described herein comprises an interferon (IFN) peptide-CTP(×2) encoded by an amino acid sequence comprising the amino acid sequence set forth in SEQ ID NO: 33. In another embodiment, SEQ ID NO: 33 comprises the following amino acid (AA) sequence:
MTNKCLLQIALLLCFSTTALSMSYNLLGFLQRSSN-
FQCQKLLWQLNGRLEYCLKDRM NFDIPEE-
IKQLQQFQKEDAALTIYEMLQNIFAIFRQDSSSTG-
WNETIVENLLANVYHQI
NHLKTVLEEKLEKEDFTRGKLMSSLHLKRYYGRIL-
HYLKAKEYSHCAWTIVRVEILR NFYFINRLTGYLRN-
SSSSKAPPPSLPSPSRLPGPSDTPILPQSSSSKAP-
PPSLPSPSRLPGP SDTPILPQ (SEQ ID NO: 33).

In another embodiment, the polypeptide as described herein comprising an interferon (IFN) peptide—and two CTP units attached to its carboxy terminus is encoded by a nucleic acid molecule set forth in SEQ ID NO: 34. In another embodiment, SEQ ID NO: 34 comprises the following nucleotide acid (NA) sequence:
tctagaggacatgaccaacaagtgcctgctgcagatcgccctgctgctgtgcttca-
gcaccaccgccctgagcatgagctacaacctg ctgggcttcctgcagaggtcca-
gcaacttccagtgccagaagctgctgtggcagctgaacggcaggctggaatact-
gcctgaaggac
aggatgaacttcgacatcccagaggaaatcaagcagctgcagcagttcca-
gaaggaggacgccgccctgaccatctacgagatgct gcagaacatcttcgc-
catcttcaggcaggacagcagcagcaccggctggaacgagaccatcgtgga-
gaacctgctggccaacgtgt
accaccagatcaaccacctgaaaaccgtgctggaagagaagctggaaaaggag-
gacttcaccaggggcaagctgatgagcagcct gcacctgaagaggtactacg-
gcagaatcctgcactacctgaaggccaaggagtacagccactgcgcctggac-
catcgtgagggtgg
agatcctgaggaacttctacttcatcaacaggctgaccggctacctgaggaaca-
gctccagcagcaaggcccctccaccttccctgcc cagtccaagccgactc-
cctgggccctccgacacaccaatcctgccacagagcagctcctctaaggcccctc-
ctccatcctgccatcc
ccctcccggctgcctggccctctgacacccctatcctgcctcagtgat-
gaaggtctggatccgcggccgc (SEQ ID NO: 34).

In another embodiment, the polypeptide as described herein comprises an interferon (IFN) peptide, a single CTP unit attached to the IFN's amino terminus, and two CTP units attached to the IFN's carboxy terminus. In another embodiment, the polypeptide as described herein comprises an interferon (IFN) peptide, a single CTP unit attached to the IFN's amino terminus and two CTP units attached in tandem to the IFN's carboxy terminus. In another embodiment, the polypeptide as described herein comprises (from amino to carboxy termini): CTP(×1)-interferon (IFN) peptide-CTP(×2) comprising an amino acid sequence set forth in SEQ ID NO: 365. In another embodiment, SEQ ID NO: 35 comprises the following amino acid (AA) sequence:
MTNKCLLQIALLLCFSTTALSSSSSKAPPPSLPSPSR-
LPGPSDTPILPQMSYNLLGFLQRS SNFQCQKLL-
WQLNGRLEYCLKDRMNFDIPEEIKQLQQFQKE-
DAALTIYEMLQNIFAIF
RQDSSSTGWNETIVENLLANVYHQINHLKTV-
LEEKLEKEDFTRGKLMSSLHLKRYYG RIL-
HYLKAKEYSHCAWTIVRVEILRNFYFINRLTGYLRN-
SSSSKAPPPSLPSPSRLPGPS
DTPILPQSSSSKAPPPSLPSPSRLPGPSDTPILPQ (SEQ ID NO: 35).

In another embodiment, the polypeptide as described herein comprising an interferon (IFN) peptide, a single CTP unit attached to the IFN's amino terminus and two CTP units attached to the IFN's carboxy terminus is encoded by a nucleic acid molecule set forth in SEQ ID NO: 36. In another embodiment, SEQ ID NO: 36 comprises the following nucleotide acid (NA) sequence:
tctagaggacatgaccaacaagtgcctgctgcagatcgccctgctgctgtgcttca-
gcaccaccgccctgagcagcagcagctccaa ggccccacccccagcctgc-
ccagccccagcagactgccaggccccagcgacacccccatcctgccccagat-
gagctacaacctg
ctgggcttcctgcagaggtccagcaacttccagtgccagaagctgctgtggca-
gctgaacggcaggctggaatactgcctgaaggac aggatgaacttcgacatc-
ccagaggaaatcaagcagctgcagcagttccagaaggaggacgccgccctgac-
catctacgagatgct
gcagaacatcttcgccatcttcaggcaggacagcagcagcaccggctggaacga-
gaccatcgtggagaacctgctggccaacgtgt accaccagatcaaccacct-
gaaaaccgtgctggaagagaagctggaaaaggaggacttcacca-
ggggcaagctgatgagcagcct
gcacctgaagaggtactacggcagaatcctgcactacctgaaggccaaggagta-
cagccactgcgcctggaccatcgtgagggtgg agatcctgaggaacttctact-
tcatcaacaggctgaccggctacctgaggaacagctccagcagcaaggcccctc-
caccttccctgcc
cagtccaagccgactccctgggccctccgacacaccaatcctgccacagagca-
gctcctctaaggcccctcctccatccctgccatcc cctcccggctgcctggc-
ccctctgacacccctatcctgcctcagtgatgaaggtctggatccgcggccgc
(SEQ ID NO: 36).

In another embodiment, the polypeptide as described herein comprises an interferon (IFN) peptide, a single CTP attached to the IFN's amino terminus, and a single CTP located within an IFN coding sequence. In another embodiment, the polypeptide as described herein comprises (from amino to carboxy termini): CTP(×1)-interferon (IFN) peptide (fragment 1)-CTP-interferon (IFN) peptide (fragment 2) comprising an amino acid sequence set forth in SEQ ID NO: 37. In another embodiment, SEQ ID NO: 37 comprises the following amino acid (AA) sequence:
MTNKCLLQIALLLCFSTTALSSSSSKAPPPSLPSPSR-
LPGPSDTPILPQMSYNLLGFLQRS SNFQCQKLL-
WQLNGRLEYCLKDRMNFDIPEEIKQLQQFQKE-
DAALTIYEMLQNIFAIF
RQDSSSTGWNETIVENLLANVYHQINHLKTV-
LEEKLEKEDFTRGKLMSSLHLKRYYG RIL-
HYLKAKEYSHCAWTIVRVEILRNFYFINRLTGYLRN-
SSSSKAPPPSLPSPSRLPGPS
DTPILPQMSYNLLGFLQRSSNFQCQKLLWQLNGR-
LEYCLKDRMNFDIPEEIKQLQQFQ KEDAALTIYEM-
LQNIFAIFRQDSSSTGWNETIVENLLANVYHQINHLK-
TVLEEKLEKE
DFTRGKLMSSLHLKRYYGRILHYLKAKEYSHCAW-
TIVRVEILRNFYFINRLTGYLRN (SEQ ID NO: 37).

In another embodiment, the polypeptide as described herein comprising an interferon (IFN) peptide, a single CTP unit attached to the IFN's amino terminus, and a single CTP unit located within the IFN coding sequence is encoded by a nucleic acid molecule set forth in SEQ ID NO: 38. In another embodiment, SEQ ID NO: 38 comprises the following nucleotide acid (NA) sequence:
tctagaggacatgaccaacaagtgcctgctgcagatcgccctgctgctgtgcttca-
gcaccaccgccctgagcagcagcagctccaa ggccccacccccagcctgc-
ccagccccagcaggctgccaggccccagcgacacccccatcctgccccagat-
gagctacaacctg
ctgggcttcctgcagaggtccagcaacttccagtgccagaaactgctgtggca-
gctgaacggcaggctggaatactgcctgaaggac cggatgaacttcgacatc-
cccgaagagatcaagcagctgcagcagttccagaaagaggacgccgccctgac-
catctacgagatgct
cagaacatcttcgccatcttcaggcaggacagcagcagcaccggctggaacgagaccatcgtggagaacctgctggccaacgtgta ccaccagatcaaccacct-
gaaaaccgtgctggaagagaagctggaaaaagaggacttcacca-
ggggcaagctgatgagcagcctg
cacctgaagaggtactacggcagaatcctgcactacctgaaggccaaagagta-
cagccactgcgcctggaccatcgtgagggtgga gatcctgcggaacttctact-
tcatcaacaggctgaccggctacctgaggaacagctccagcagcaaggcccctc-
cacccctccctgccc
tccccaagcagactgcccggaccctccgacacaccaattctgccacagatgtc-
ctacaatctgctcggatttctgcagcgctcctccaa ctttcagtgtcagaagctc-
ctctggcagctcaatggccgcctggaatattgtctgaaagacagaatgaatttt-
gacatcccagaggaaatt
aaacagctccagcagtttcagaaagaagatgctgctctcacaatctatgaaat-
gctccagaatatctttgcaatctttcgccaggacagct cctccaccgggtggaat-
gagacaattgtcgagaatctgctcgccaatgtctatcatcagatcaatcacct-
caagacagtcctcgaagaa
aaactcgaaaaagaagatttcacacgcgggcaaactgatgtcctccctgcatct-
gaagcgctactatgggcgcatcctgcattatctgaaa gctaaagaatactccact-
gtgcttggacaattgtgcgcgtcgagatcctgagaaactttttatttcattaaccgcct-
gacaggatacctgc gcaactgatgaaggtctggatgcggccgc (SEQ ID NO: 38).

In another embodiment, the polypeptide as described herein comprises an interferon (IFN) peptide and a single CTP unit attached to its amino terminus. In another embodiment, the polypeptide as described herein comprises an interferon (IFN) peptide-CTP comprising an amino acid sequence set forth in SEQ ID NO: 39. In another embodiment, SEQ ID NO: 39 comprises the following amino acid (AA) sequence:
MTNKCLLQIALLLCFSTTALSSSSSKAPPPSLPSPSR-
LPGPSDTPILPQMSYNLLGFLQRS SNFQCQKLL-
WQLNGRLEYCLKDRMNFDIPEEIKQLQQFQKE-
DAALTIYEMLQNIFAIF
RQDSSSTGWNETIVENLLANVYHQINHLKTV-
LEEKLEKEDFTRGKLMSSLHLKRYYG RIL-
HYLKAKEYSHCAWTIVRVEILRNFYFINRLTGYLRN*
(SEQ ID NO: 39).

In another embodiment, the polypeptide as described herein comprising an interferon (IFN) peptide—and a single CTP attached to its amino terminus is encoded by a nucleic acid molecule set forth in SEQ ID NO: 40. In another embodiment, SEQ ID NO: 40 comprises the following nucleotide acid (NA) sequence:
tctagaggacatgaccaacaagtgcctgctgcagatcgccctgctgctgtgcttca-
gcaccaccgccctgagcagcagcagctccaa ggccccacccccccagcctgc-
ccagcccagcagactgccaggccccagcgacaccccatcctgccccagat-
gagctacaacctg
ctgggcttcctgcagaggtccagcaacttccagtgccagaaactgctgtggca-
gctgaacggcaggctggaatactgcctgaaggac cggatgaacttcgacatc-
cccgaagagatcaagcagctgcagcagttccagaaagaggacgccgccctgac-
catctacgagatgctg
cagaacatcttcgccatcttcaggcaggacagcagcagcaccggctggaacga-
gaccatcgtggagaacctgctggccaacgtgta ccaccagatcaaccacct-
gaaaaccgtgctggaagagaagctggaaaaagaggacttcacca-
ggggcaagctgatgagcagcct
cacctgaagaggtactacggcagaatcctgcactacctgaaggccaaagagta-
cagccactgcgcctggaccatcgtgagggtgga gatcctgaggaacttctact-
tcatcaacaggctgaccggctacctgaggaacagctccagcagcaaggcccctc-
caccttccctgcc
cagtccaagccgactccctgggccctccgatacaccaattctgccacagtgat-
gaaggtctggatgcggccgc (SEQ ID NO: 40).

In another embodiment, the polypeptide as described herein comprises an interferon (IFN) peptide, a single CTP unit attached to its amino terminus, and a single CTP unit attached to its carboxy terminus. In another embodiment, the polypeptide as described herein comprises an interferon (IFN) peptide-CTP comprising an amino acid sequence set forth in to SEQ ID NO: 41. In another embodiment, SEQ ID NO: 41 comprises the following amino acid (AA) sequence:
MTNKCLLQIALLLCFSTTALSSSSSKAPPPSLPSPSR-
LPGPSDTPILPQMSYNLLGFLQRS SNFQCQKLL-
WQLNGRLEYCLKDRMNFDIPEEIKQLQQFQKE-
DAALTIYEMLQNIFAIF
RQDSSSTGWNETIVENLLANVYHQINHLKTV-
LEEKLEKEDFTRGKLMSSLHLKRYYG RIL-
HYLKAKEYSHCAWTIVRVEILRNFYFINRLTGYLRN-
SSSSKAPPPSLPSPSRLPGPS DTPILPQ* (SEQ ID NO: 41).

In another embodiment, the polypeptide as described herein comprising an interferon (IFN) peptide, a single CTP unit attached to its amino terminus, and a single CTP unit attached to its carboxy terminus is encoded by a nucleic acid molecule set forth in SEQ ID NO: 42. In another embodiment, SEQ ID NO: 42 comprises the following nucleotide acid (NA) sequence:
tctagaggacatgaccaacaagtgcctgctgcagatcgccctgctgctgtgcttca-
gcaccaccgccctgagcagcagcagctccaa ggccccacccccccagcctgc-
ccagcccagcagactgccaggccccagcgacaccccatcctgccccagat-
gagctacaacctg
ctgggcttcctgcagaggtccagcaacttccagtgccagaagctgctgtggca-
gctgaacggcaggctggaatactgcctgaaggac aggatgaacttcgacatc-
ccagaggaaatcaagcagctgcagcagttccagaaggaggacgccgccctgac-
catctacgagatgct
gcagaacatcttcgccatcttcaggcaggacagcagcagcaccggctggaacga-
gaccatcgtggagaacctgctggccaacgtgt accaccagatcaaccacct-
gaaaaccgtgctggaagagaagctggaaaaggaggacttcacca-
ggggcaagctgatgagcagcct
gcacctgaagaggtactacggcagaatcctgcactacctgaaggccaaggagta-
cagccactgcgcctggaccatcgtgagggtgg agatcctgaggaacttctact-
tcatcaacaggctgaccggctacctgaggaacagctccagcagcaaggcccctc-
caccttccctgcc
cagtccaagccgactccctgggcctccgatacaccaattctgccacagtgat-
gaaggtctggatgcggccgc (SEQ ID NO: 42).

In another embodiment, an interferon β peptide comprises SEQ ID NO: 43 comprising the following amino acid (AA) sequence:
MSYNLLGFLQRSSNFQSQKLLWQLNGRLEY-
CLKDRMNFDIPEEIKQLQQFQKEDAAL TIYEMLQNI-
FAIFRQDSSSTGWNETIVENLLANVYHQINHLKTV-
LEEKLEKEDFTRGK
LMSSLHLKRYYGRILHYLKAKEYSHCAWTIVRVEIL-
RNFYFINRLTGYLRN (SEQ ID NO: 43).

In one embodiment, the polypeptide or fragment thereof provide herein is a glucagon-like peptide-1. In another embodiment, glucagon-like peptide-1 is utilized according to the teachings of the present invention. In another embodiment, the attachment of CTP to sequences to both the amino and carboxy termini of a "glucagon-like peptide-1" results in increased potency. In another embodiment, the attachment of CTP to both the amino and carboxy termini of a peptide results in prolonged in-vivo activity. In another embodiment, the attachment of CTP to both the amino and carboxy termini of the glucagon-like peptide-results in prolonged in-vivo activity.

In one embodiment, "glucagon-like peptide-1" (GLP-1) refers to a mammalian polypeptide. In one embodiment, "glucagon-like peptide-1" (GLP-1) refers to a human polypeptide. In another embodiment GLP-1 is cleaved from the glucagon preproprotein (Genbank ID No. NP002045) that has the ability to bind to the GLP-1 receptor and initiate a signal transduction pathway resulting in insulinotropic activity. In one embodiment, "insulinotropic activity" refers to the ability to stimulate insulin secretion in response to elevated glucose levels, thereby causing glucose uptake by cells and decreased plasma glucose levels. In some embodiments, GLP-1 polypeptides include, but are not limited to those described in U.S. Pat. No. 5,118,666; which is incorporated by reference herein.

In one embodiment, a GLP-1 of the present invention also refers to a GLP-1 homologue. In one embodiment, GLP-1 amino acid sequence of the present invention is at least 50% homologous to GLP-1 sequences set forth in Genbank ID No. NP002045 as determined using BlastP software of the National Center of Biotechnology Information (NCBI) using default parameters. In one embodiment, GLP-1 amino acid sequence of the present invention is at least 60% homologous to GLP-1 sequences set forth in Genbank ID No. NP002045 as determined using BlastP software of the National Center of Biotechnology Information (NCBI) using default parameters. In one embodiment, GLP-1 amino acid sequence of the present invention is at least 70% homologous to GLP-1 sequences set forth in Genbank ID No. NP002045 as determined using BlastP software of the National Center of Biotechnology Information (NCBI) using default parameters. In one embodiment, GLP-1 amino acid sequence of the present invention is at least 80% homologous to GLP-1 sequences set forth in Genbank ID No. NP002045 as determined using BlastP software of the National Center of Biotechnology Information (NCBI) using default parameters. In one embodiment, GLP-1 amino acid sequence of the present invention is at least 90% homologous to GLP-1 sequences set forth in Genbank ID No. NP002045 as determined using BlastP software of the National Center of Biotechnology Information (NCBI) using default parameters. In one embodiment, GLP-1 amino acid sequence of the present invention is at least 95% homologous to GLP-1 sequences set forth in Genbank ID No. NP002045 as determined using BlastP software of the National Center of Biotechnology Information (NCBI) using default parameters.

In one embodiment, the polypeptide of interest or fragment thereof provided herein is an apolipoprotein. In another embodiment, the polypeptide or fragment thereof provided herein is an apolipoprotein A1 (APO-A1). In another embodiment, the apolipoprotein is attached to at least one CTP peptide on the N- and or the C-terminus. In another embodiment, the apolipotrein is apolipoprotein AI, apolipoprotein AII, apolipoprotein AIV, or an analogue or variant thereof.

In one embodiment, the apolipoprotein constructs according to the present invention may broadly be looked upon as HDL analogues due to their ability to form complexes with cholesterol and other lipids and assist in the transportation of these compounds to the liver.

In another embodiment, functional equivalence to native apolipoprotein A-I, A-II or A-IV may conveniently be measured using a lipid binding assay. The ability of the CTP-modified apolipoprotein to elicit substantially the same physiological response in a mammal may conveniently be measured by measurement of the ability to perform reverse cholesterol transport in a test organism such as rabbits or rodents such as mice.

In one embodiment, the polypeptide comprising the CTP-modified apolipoprotein is capable of performing reverse cholesterol transport as well as or even better than native apolipoproteins in-vivo, despite the modification caused by the addition of at least one CTP. In another embodiment, in-vitro the CTP-modified apolipoprotein has lower in-vitro biological activity but it is compensated by an extended half-life. In another embodiment, the plasma half-life of the CTP-modified apolipoprotein is preferably increased compared to that of the wild-type apolipoprotein. In one embodiment, the increased half-life is due to the hydrodynamic size of the apolipoprotein construct, which may reduce the rate of filtration through the kidneys.

In one embodiment, the amino acid sequence of APO-A1 is DEPPQSPWDRVKDKATVYVDVLKDS-GRDYVSQFEGSAGKGLNLKLLDNWDSVTST FSKL-REQLGPVTQEFWDNLEKETEGLRGEM-SKDLEEVKAKVQPYLDDFQKKWQEE MELYRQKVEPLRAELQEGARQKLHELQEKLSPL-GEEMRDRARAHVDALRTHLAPYS DELRQRLAAR-LEALKENGGARLAEYHAKATEHLSTLSEKAK-PALEDLRQGLLPVLES FKVSFLSALEEYTKKLNTQ (SEQ ID NO: 44) or a homologue or variant or fragment thereof. In one embodiment, the methods of the present invention the methods of the present invention provide an amino acid sequence comprising an APO-A1 peptide having one CTP amino acid peptide on the C-terminus: MKAAVLTLAVLFLTGSQARHFWQQDEPPQSPW-DRVKDLATVYVDVLKDSGRDYVS QFEGSALG-KQLNLKLLDNWDSVTSTFSKLREQLGPVTQEFWDN-LEKETEGLRQEMS KDLEEVKAKVQPYLDDFQKKWQEEMELYRQKVE-PLRAELQEGARQKLHELQEKLS PLGEEMRDR-ARAHVDALRTHLAPYSDELRQRLAARLEALKENG-GARLAEYHAKATE HLSTLSEKAKPALEDLRQGLLPVLESFKVSFLSAL-EEYTKKLNTQSSSSKAPPPSLPSPS RLPGPSDTPILPQ (SEQ ID NO: 70).

In another embodiment, the methods of the present invention provide a nucleic acid sequence, set forth in SEQ ID NO: 71, encoding an APO-A1 peptide and one CTP amino acid peptide on the C-terminus:
ATGAAGGCCGCCGTGCTGACCCTGGCCGTGCT-GTTTCTGACCGGCTCTCAGGCCC GGCACTTCTG-GCAGCAGGACGAGCCTCCCCAGTC-CCCCTGGGACAGAGTGAAGG
ACCTGGCCACCGTGTACGTGGACGTGCT-GAAGGACTCCGGCAGAGACTACGTGTC CCAGTTC-GAGGGCTCTGCCCTGGGCAAGCAGCTGAACCT-GAAGCTGCTGGACAAC TGGGACTCCGTGACCTCCACCTTCTCCAAGCT-GCGCGAACAGCTGGGACCTGTGA CCCAGGAAT-TCTGGGACAACCTGGAAAAAGAGACAGAGGGCCT-GAGACAGGAA ATGTCCAAGGACCTGGAAGAGGTCAAAGC-CAAGGTGCAGCCCTACCTGGACGAC TTCCA-GAAGAAATGGCAGGAAGAGATGGAACTGTACCG-GCAGAAGGTGGAACCC CTGCGGGCCGAGCTGCAGGAAGGCGCTAGACA-GAAGCTGCACGAACTGCAGGAA AAGCTGTC-CCCCCTGGGCGAGGAAATGCGGGACAGAGCCA-GAGCCCACGTGGAC GCCCTGAGAACCCACCTGGCCCCTACTCTGAC-GAGCTGCGGCAGAGGCTGGCCG CCAGACTG-GAAGCCCTGAAAGAGAACGGCGGAGCCCGGCTG-GCCGAGTACCACG CTAAGGCTACCGAGCACCTGTCCACCCTGTCCGA-GAAGGCCAAGCCCGCCCTGGA AGATCTGCGGCA-GGGCCTGCTGCCCGTGCTGGAATCCTTCAAGGT-GTCCTTCCTG TCCGCTCTGGAAGAGTACACCAAGAAGCT-GAACACCCAGTCCTCCAGCTCCAAGG CCCCTC-CACCCTCCCTGCCTAGCCCTAGTAGACTGC-CTGGGCCCTCCGACACCCCC ATCCTGCCCCAGTGATGAGGATCCGCGGCCGC-GAGCTC (SEQ ID NO: 71).

In one embodiment, the methods of the present invention the methods of the present invention provide an amino acid sequence comprising an APO-A1 peptide having two CTP amino acid peptide C-terminus:
MKAAVLTLAVLFLTGSQARHFWQQDEPPQSPW-DRVKDLATVYVDVLKDSGRDYVS QFEGSALG-KQLNLKLLDNWDSVTSTFSKLREQLGPVTQEFWDN-LEKETEGLRQEMS KDLEEVKAKVQPYLDDFQKKWQEEMELYRQKVE-PLRAELQEGARQKLHELQEKLS PLGEEMRDR-ARAHVDALRTHLAPYSDELRQRLAARLEALKENG-GARLAEYHAKATE HLSTLSEKAKPALEDLRQGLLPVLESFKVSFLSAL-EEYTKKLNTQSSSSKAPPPSLPSPS RLPGPSDTPIL-PQSSSSKAPPPSLPSPSRLPGPSDTPILPQ (SEQ ID NO: 72).

In another embodiment, the methods of the present invention provide a nucleic acid sequence, set forth in SEQ ID NO: 73, encoding an APO-A1 peptide and two CTP amino acid peptide on the C-terminus:
ATGAAGGCCGCCGTGCTGACCCTGGCCGTGCT-GTTTCTGACCGGCTCTCAGGCCC GGCACTTCTG-GCAGCAGGACGAGCCTCCCCAGTC-CCCCTGGGACAGAGTGAAGG ACCTGGCCACCGTGTACGTGGACGTGCT-GAAGGACTCCGGCAGAGACTACGTGTC CCAGTTC-GAGGGCTCTGCCCTGGGCAAGCAGCTGAACCT-GAAGCTGCTGGACAAC TGGGACTCCGTGACCTCCACCTTCTCCAAGCT-GCGCGAACAGCTGGGACCTGTGA CCCAGGAAT-TCTGGGACAACCTGGAAAAAGAGACAGAGGGCCT-GAGACAGGAA ATGTCCAAGGACCTGGAAGAGGTCAAAGC-CAAGGTGCAGCCCTACCTGGACGAC TTCCA-GAAGAAATGGCAGGAAGAGATGGAACTGTACCG-GCAGAAGGTGGAACCC CTGCGGGCCGAGCTGCAGGAAGGCGCTAGACA-GAAGCTGCACGAACTGCAGGAA AAGCTGTC-CCCCCTGGGCGAGGAAATGCGGGACAGAGCCA-GAGCCCACGTGGAC GCCCTGAGAACCCACCTGGCCCCCTACTCTGAC-GAGCTGCGGCAGAGGCTGGCCG CCAGACTG-GAAGCCCTGAAAGAGAACGGCGGAGCCCGGCTG-GCCGAGTACCACG CTAAGGCTACCGAGCACCTGTCCACCCTGTCCGA-GAAGGCCAAGCCCGCCCTGGA AGATCTGCGGCA-GGGCCTGCTGCCCGTGCTGGAATCCTTCAAGGT-GTCCTTCCTG TCCGCTCTGGAAGAGTACACCAAGAAGCT-GAACACCCAGTCCTCCAGCTCCAAGG CCCCTC-CACCCTCCCTGCCTAGCCCTAGTAGACTGC-CTGGGCCCTCCGACACACC AATCCTGCCACAGAGCAGCTCCTCTAAGGCCCCTC-CTCCATCCCTGCCATCCCCCT CCCGGCTGCCTGGC-CCCTCTGACACCCCTATCCTGCCTCAGTGAT-GAAGGTCTGG ATCCGCGGCCGC (SEQ ID NO: 73).

In one embodiment, a functional equivalent of an apolipoprotein or fragments thereof may be obtained by addition, substitution or deletion of at least one amino acid. When the amino acid sequence comprises a substitution of one amino acid for another, such a substitution may be a conservative amino acid substitution. Fragments of SEQ ID NO: 44 may comprise more than one such substitution, such as, for e.g., two conservative amino acid substitutions, for example three or four conservative amino acid substitutions, such as five or six conservative amino acid substitutions, for example seven or eight conservative amino acid substitutions, such as from 10 to 15 conservative amino acid substitutions, for example from 15 to 25 conservative amino acid substitution, such as from 25 to 75 conservative amino acid substitutions, for example from 75 to 125 conservative amino acid substitutions, such as from 125 to 175 conservative amino acid substitutions. Substitutions can be made within any one or more groups of predetermined amino acids.

In another embodiment, a fragment of apolipoprotein contains the lipid binding region.

"Functional equivalency" as used in the present invention is according to one preferred embodiment established by means of reference to the corresponding functionality of a predetermined fragment of the sequences provided herein.

Functional equivalents of variants of the sequences provided herein will be understood to exhibit amino acid sequences gradually differing from the preferred predetermined sequence, as the number and scope of insertions, deletions and substitutions including conservative substitutions increases. This difference is measured as a reduction in homology between the preferred predetermined sequence and the fragment or functional equivalent.

In one embodiment, the polypeptide of interest or fragment thereof provided herein is a cytokine. In another embodiment, the cytokine is a Hematopoietin cytokine. In another embodiment, the cytokine is an Interferon cytokine. In another embodiment, the cytokine is a chemokine. In another embodiment, the cytokine is a Tumor Necrosis Factor cytokine. In another embodiment, a cytokine as used herein comprises biological activity and clinical efficacy. In another embodiment, a cytokine as used herein is a therapeutic protein.

All fragments or functional equivalents of apolipoprotein are included within the scope of this invention, regardless of the degree of homology that they show to a preferred predetermined sequence of apolipoprotein. The reason for this is that some regions of the sequence SEQ ID NO: 44 are most likely readily mutatable, or capable of being completely deleted, without any significant effect on the binding activity of the resulting fragment. Methods of generating functionally equivalent variants of SEQ ID NO:44 are described in U.S. Pat. No. 6,897,039, incorporated herein by reference.

In one embodiment, the polypeptide of interest or fragment thereof provided herein is a coagulation factor. In another embodiment, a coagulation factor of the invention is a protein. In another embodiment, a coagulation factor of the invention is a peptide. In another embodiment, a coagulation factor of the invention is a polypeptide. In another embodiment, the coagulation factor is an enzyme. In another embodiment, the coagulation factor is a serine protease. In another embodiment, the coagulation factor is a glycoprotein. In another embodiment, the coagulation factor is a transglutaminase. In another embodiment, the coagulation factor is an inactive zymogen. In another embodiment, the coagulation factor is any coagulation factor known to one of skill in the art. In another embodiment, the coagulation factor is FVIII. In another embodiment, the coagulation factor is FV. In another embodiment, the coagulation factor is Factor XIII. In another embodiment, the coagulation factor is factor X. In another embodiment, the coagulation factor is thrombin. In another embodiment, the coagulation factor is fibrin. In another embodiment, the coagulation factor is FVIIa. In another embodiment, the coagulation factor is FVII. In another embodiment, the coagulation factor is FIX. In another embodiment, the coagulation factor is FX. In another embodiment, the coagulation factor is FXIa. In another embodiment, the coagulation factor is FXII. In another embodiment, the coagulation factor is FXa. In another embodiment, the coagulation factor is FVa. In another embodiment, the coagulation factor is prothrombin. In another embodiment, the coagulation factor is thrombin. In another embodiment, the coagulation factor is FV. In another embodiment, the coagulation factor is FXI. In another embodiment, the coagulation factor is vWF. In another embodiment, the coagulation factor is FVIIIa. In another embodiment, the coagulation factor is B-deleted Domain FVIII (FVIIIBDD). In another embodiment, the coagulation factor is FIXa. In another embodiment, the coagulation factor is prekallikrein. In another embodiment, the coagulation factor is kallikrein. In another embodiment, the coagulation factor is FXIIa. In another embodiment, the coagulation factor is fibrinogen. In another embodiment, the coagulation factor is thrombomodulin. In another embodiment, the coagulation factor is FII.

In another embodiment, the coagulation factor is a glycoprotein. In another embodiment, the coagulation factor is a vitamin K dependent glycoprotein. In another embodiment, the coagulation factor is a vitamin K independent glycoprotein. In another embodiment, the coagulation factor is a recombinant protein. In another embodiment, the coagulation factor is a recombinant glycoprotein. In another embodiment, the coagulation factor is a recombinant glycoprotein FV. In another embodiment, the coagulation factor is a recombinant FVI. In another embodiment, the coagulation factor is a recombinant FVII. In another embodiment, the coagulation factor is a recombinant FVIII. In another embodiment, the coagulation factor is a recombinant FIX. In another embodiment, the coagulation factor is a recombinant FX. In another embodiment, the coagulation factor is a recombinant FXI. In another embodiment, the coagulation factor is a recombinant FXII. In another embodiment, the coagulation factor is a recombinant FvW. In another embodiment, the coagulation factor is a recombinant FII. In another embodiment, the coagulation factor is a recombinant FIXa. In another embodiment, the coagulation factor is a recombinant FXIa. In another embodiment, the coagulation factor is a recombinant fibrin. In another embodiment, the coagulation factor is a recombinant FVIIa. In another embodiment, the coagulation factor is a recombinant FXa. In another embodiment, the coagulation factor is a recombinant FVa. In another embodiment, the coagulation factor is a recombinant prothrombin. In another embodiment, the coagulation factor is a recombinant thrombin. In another embodiment, the coagulation factor is a recombinant FVIIIa. In another embodiment, the coagulation factor is a recombinant prekallikrein. In another embodiment, the coagulation factor is a recombinant kallikrein. In another embodiment, the coagulation factor is a recombinant FXIIa. In another embodiment, the coagulation factor is any known recombinant coagulation factor. In another embodiment, the coagulation factor comprising a signal peptide is any known recombinant coagulation factor. In another embodiment, a coagulation factor comprises 1-10 CTP repeats attached to the C-terminus and no CTPs attached to the N-terminus. In another embodiment, the coagulation factor comprising a signal peptide is any known recombinant coagulation factor. In another embodiment, a coagulation factor comprises at least one CTP attached to the C-terminus and no CTPs attached to the N-terminus. In another embodiment, a coagulation factor comprising 1-10 CTP repeats attached to the C-terminus and no CTPs attached to the N-terminus is an engineered coagulation factor. In another embodiment, a coagulation factor comprising at least one CTP attached to the C-terminus and no CTPs attached to the N-terminus an engineered coagulation factor. In another embodiment, a coagulation factor comprising 1-10 CTP repeats attached to the C-terminus and no CTPs attached to the N-terminus a conjugated coagulation factor. In another embodiment, a coagulation factor comprising at least one CTP attached to the C-terminus and no CTPs attached to the N-terminus a conjugated coagulation factor.

In another embodiment, the coagulation factor comprising a domain organization similar or identical to the domain organization of FIX, FVII, factor X, protein C and prothrombin. In another embodiment, the coagulation factor is synthesized as precursors with N-terminal propeptide. In another embodiment, the coagulation factor as used herein is in an inactive pro-enzyme form. In another embodiment, the coagulation factor is produces in hepatocytes. In another embodiment, the coagulation factor comprises a docking site for gammacarboxylase which converts glutamic acids (Glu) into gamma carboxy glutamic acids (Gla). In another embodiment, the coagulation factor is a commercially available coagulation factor.

In another embodiment, the amino acid sequence of factor VII comprises the following amino acid sequence:
MVSQALRLLCLLLGLQGCLAAVFVTQEEAHGV-LHRRRRANAFLEELRPGSLE RECKEEQCSFEEA-REIFKDAERTKLFWISYSDGDQCASSPCQNGGSCK-DQLQSYICFC
LPAFEGRNCETHKDDQLICVNENGGCEQYCSDHTGT-KRSCRCHEGYSLLADGVSCTP TVEYPCGKIPILE-KRNASKPQGRIVGGKYCPKGECPWQYLLLYNGAQL-CGGTLINTIW
VVSAAHCFDKIKNRRNLIAVLGEHDLSEHDGDEQSR-RVAQVIIPSTYVPGTTNHDIAL LRLHQPVVLTDHV-VPLCLPERTFSERTLAFVRFSLVSGWGQLLDRGA-TALELMVLNV
PRLMTQDCLQQSRKVGDSPNITEYMFCAGYSDG-SKDSCKGDSGGPHATHYRGTWYL TGIVSWGQGCAT-VGHFGVYTRVSQYIEWLQKLMRSEPRPGVLLRAPFP (SEQ ID NO: 45).

In another embodiment, the amino acid sequence of factor VII comprises the following amino acid sequence:
MVSQALRLLCLLLGLQGCLAAVFVTQEEAHGV-LHRRRRANAFLEELRPGSLERECKE EQCSFEEA-REIFKDAERTKLFWISYSDGDQCASSPCQNGGSCK-DQLQSYICFCLPAFEG
RNCETHKDDQLICVNENGGCEQYCSDHTGTKR-SCRCHEGYSLLADGVSCTPTVEYPC GKIPILE-KRNASKPQGRIVGGKVCPKGECPWQVLLLVNGAQL-CGGTLINTIWVVSAA
HCFDKIKNRRNLIAVLGEHDLSEHDGDEQSR-RVAQVIIPSTYVPGTTNHDIALLRLHQ PVVLTDHV-VPLCLPERTFSERTLAFVRFSLVSGWGQLLDRGA-TALELMVLNVPRLMT
QDCLQQSRKVGDSPNITEYMFCAGYSDGSKDSCK-GDSGGPHATHYRGTWYLTGIVS WGQGCATVGHF-GVYTRVSQYIEWLQKLMRSEPRP-
GVLLRAPFP*GCGR. (SEQ ID NO: 46).

In another embodiment, the nucleic acid sequence encoding factor VII comprises the nucleic acid sequence:
CTCGAGGACATGGTCTCCCAGGCCCTCAGGCTC-CTCTGCCTTCTGCTTGGGCTTCA GGGCTGCCTG-GCTGCAGTCTTCGTAACCCAGGAGGAAGCCCACG-GCGTCCTGCA
CCGGCGCCGGCGCGCCAACGCGTTCCTGGAG-GAGCTGCGGCCGGGCTCCCTGGA GAGGGAGTG-CAAGGAGGAGCAGTGCTCCTTCGAGGAGGC-CCGGGAGATCTTCAA
GGACGCGGAGAGGACGAAGCTGTTCTGGATTTCT- TACAGTGATGGGGACCAGTG TGCCTCAAGTCCATGCCAGAATGGGGGCTCCTGCAAGGACCAGCTCCAGTCCTAT
ATCTGCTTCTGCCTCCCTGCCTTCGAGGGCCGGAACTGTGAGACGCACAAGGATG ACCAGCTGATCTGTGTGAACGAGAACGGCGGCTGTGAGCAGTACTGCAGTGACC
ACACGGGCACCAAGCGCTCCTGTCGGTGCCACGAGGGGTACTCTCTGCTGGCAG ACGGGGTGTCCTGCACACCCACAGTTGAATATCCATGTGGAAAAATACCTATTCT
AGAAAAAAGAAATGCCAGCAAACCCCAAGGCCGAATTGTGGGGGGCAAGGTGT
GCCCCAAAGGGGAGTGTCCATGGCAGGTCCTGTTGTTGGTGAATGGAGCTCAGTT GTGTGGGGGGACCCTGATCAACACCATCTGGGTGGTCTCCGCGGCCCACTGTTTC
GACAAAATCAAGAACTGGAGGAACCTGATCGCGGTGCTGGGCGAGCACGACCTC AGCGAGCACGACGGGGATGAGCAGAGCCGGCGGGTGGCGCAGGTCATCATCCCC
AGCACGTACGTCCCGGGCACCACCAACCACGACATCGCGCTGCTCCGCCTGCACC AGCCCGTGGTCCTCACTGACCATGTGGTGCCCCTCTGCCTGCCCGAACGGACGTT
CTCTGAGAGGACGCTGGCCTTCGTGCGCTTCTCATTGGTCAGCGGCTGGGGCCAG CTGCTGGACCGTGGCGCCACGGCCCTGGAGCTCATGGTCCTCAACGTGCCCCGGC
TGATGACCCAGGACTGCCTGCAGCAGTCACGGAAGGTGGGAGACTCCCCAAATA TCACGGAGTACATGTTCTGTGCCGGCTACTCGGATGGCAGCAAGGACTCCTGCAA
GGGGGACAGTGGAGGCCCACATGCCACCCACTACCGGGGCACGTGGTACCTGAC GGGCATCGTCAGCTGGGGCCAGGGCTGCGCAACCGTGGGCCACTTTGGGGTGTA
CACCAGGGTCTCCCAGTACATCGAGTGGCTGCAAAAGCTCATGCGCTCAGAGCC ACGCCCAGGAGTCCTCCTGCGAGCCCCATTTCCCTGAGGATGCGGCCGC (SEQ ID NO: 47).

In another embodiment, the nucleic acid sequence encoding factor VII-CTP (attached to the carboxy terminus) comprises the following nucleic acid sequence:
CTCGAGGACATGGTCTCCCAGGCCCTCAGGCTCCTCTGCCTTCTGCTTGGGCTTCA GGGCTGCCTGGCTGCAGTCTTCGTAACCCAGGAGGAAGCCCACGGCGTCCTGCA
CCGGCGCCGGCGCGCCAACGCGTTCCTGGAGGAGCTGCGGCCGGGCTCCCTGGA GAGGGAGTGCAAGGAGGAGCAGTGCTCCTTCGAGGAGGCCCGGGAGATCTTCAA
GGACGCGGAGAGGACGAAGCTGTTCTGGATTTCTTACAGTGATGGGGACCAGTG TGCCTCAAGTCCATGCCAGAATGGGGGCTCCTGCAAGGACCAGCTCCAGTCCTAT
ATCTGCTTCTGCCTCCCTGCCTTCGAGGGCCGGAACTGTGAGACGCACAAGGATG ACCAGCTGATCTGTGTGAACGAGAACGGCGGCTGTGAGCAGTACTGCAGTGACC
ACACGGGCACCAAGCGCTCCTGTCGGTGCCACGAGGGGTACTCTCTGCTGGCAG ACGGGGTGTCCTGCACACCCACAGTTGAATATCCATGTGGAAAAATACCTATTCT
AGAAAAAAGAAATGCCAGCAAACCCCAAGGCCGAATTGTGGGGGGCAAGGTGT
GCCCCAAAGGGGAGTGTCCATGGCAGGTCCTGTTGTTGGTGAATGGAGCTCAGTT GTGTGGGGGGACCCTGATCAACACCATCTGGGTGGTCTCCGCGGCCCACTGTTTC
GACAAAATCAAGAACTGGAGGAACCTGATCGCGGTGCTGGGCGAGCACGACCTC AGCGAGCACGACGGGGATGAGCAGAGCCGGCGGGTGGCGCAGGTCATCATCCCC
AGCACGTACGTCCCGGGCACCACCAACCACGACATCGCGCTGCTCCGCCTGCACC AGCCCGTGGTCCTCACTGACCATGTGGTGCCCCTCTGCCTGCCCGAACGGACGTT
CTCTGAGAGGACGCTGGCCTTCGTGCGCTTCTCATTGGTCAGCGGCTGGGGCCAG CTGCTGGACCGTGGCGCCACGGCCCTGGAGCTCATGGTCCTCAACGTGCCCCGGC
TGATGACCCAGGACTGCCTGCAGCAGTCACGGAAGGTGGGAGACTCCCCAAATA TCACGGAGTACATGTTCTGTGCCGGCTACTCGGATGGCAGCAAGGACTCCTGCAA
GGGGGACAGTGGAGGCCCACATGCCACCCACTACCGGGGCACGTGGTACCTGAC CGGCATCGTGAGCTGGGGCCAGGGCTGCGCCACCGTGGGCCACTTCGGCGTGTAC
ACCAGGGTGTCCCAGTACATCGAGTGGCTGCAGAAACTGATGAGAAGCGAGCCC AGACCCGGCGTGCTGCTGAGAGCCCCCTTCCCCAGCAGCAGCTCCAAGGCCCCTC
CCCCTAGCCTGCCCAGCCCTAGCAGACTGCCTGGGCCCAGCGACACCCCCATCCT GCCCCAGTGAGGATCCGCGGCCGC (SEQ ID NO: 48).

In another embodiment, the amino acid sequence of factor VII-CTP (attached to the carboxy terminus) comprises the following amino acid sequence:
MVSQALRLLCLLLGLQGCLAAVFVTQEEAHGVLHRRRRANAFLEELRPGSLERECKE EQCSFEEAREIFKDAERTKLFWISYSDGDQCASSPCQNGGSCKDQLQSYICFCLPAFEG
RNCETHKDDQLICVNENGGCEQYCSDHTGTKRSCRCHEGYSLLADGVSCTPTVEYPC GKIPILEKRNASKPQGRIVGGKVCPKGECPWQVLLLVNGAQLCGGTLINTIWVVSAA
HCFDKIKNRRNLIAVLGEHDLSEHDGDEQSRRVAQVIIPSTYVPGTTNHDIALLRLHQ PVVLTDHVVPLCLPERTFSERTLAFVRFSLVSGWGQLLDRGATALELMVLNVPRLMT
QDCLQQSRKVGDSPNITEYMFCAGYSDGSKDSCKGDSGGPHATHYRGTWYLTGIVS WGQGCATVGHFGVYTRVSQYIEWLQKLMRSEPRPGVLLRAPFPSSSSKAPPPSLPSPS RLPGPSDTPILPQ* (SEQ ID NO: 49).

In another embodiment, the nucleic acid sequence encoding factor VII-CTP-CTP (attached to the carboxy terminus) comprises the following nucleic acid sequence:
CTCGAGGACATGGTCTCCCAGGCCCTCAGGCTCCTCTGCCTTCTGCTTGGGCTTCA GGGCTGCCTGGCTGCAGTCTTCGTAACCCAGGAGGAAGCCCACGGCGTCCTGCA
CCGGCGCCGGCGCGCCAACGCGTTCCTGGAGGAGCTGCGGCCGGGCTCCCTGGA GAGGGAGTGCAAGGAGGAGCAGTGCTCCTTCGAGGAGGCCCGGGAGATCTTCAA
GGACGCGGAGAGGACGAAGCTGTTCTGGATTTCTTACAGTGATGGGGACCAGTG TGCCTCAAGTCCATGCCAGAATGGGGGCTCCTGCAAGGACCAGCTCCAGTCCTAT
ATCTGCTTCTGCCTCCCTGCCTTCGAGGGCCGGAACTGTGAGACGCACAAGGATG ACCAGCT- GATCTGTGTGAACGAGAACGGCGGCTGTGAGCAGTACTGCAGTGACC
ACACGGGCACCAAGCGCTCCTGTCGGTGCCACGAGGGGTACTCTCTGCTGGCAG ACGGGGTGTCCTGCACACCCACAGTTGAATATCCATGTGGAAAAATACCTATTCT
AGAAAAAAGAAATGCCAGCAAACCCCAAGGCCGAATTGTGGGGGGCAAGGTGT
GCCCCAAAGGGGAGTGTCCATGGCAGGTCCTGTTGTTGGTGAATGGAGCTCAGTT GTGTGGGGGGACCCTGATCAACACCATCTGGGTGGTCTCCGCGGCCCACTGTTTC
GACAAAATCAAGAACTGGAGGAACCTGATCGCGGTGCTGGGCGAGCACGACCTC AGCGAGCACGACGGGGATGAGCAGAGCCGGCGGGTGGCGCAGGTCATCATCCCC
AGCACGTACGTCCCGGGCACCACCAACCACGACATCGCGCTGCTCCGCCTGCACC AGCCCGTGGTCCTCACTGACCATGTGGTGCCCCTCTGCCTGCCCGAACGGACGTT
CTCTGAGAGGACGCTGGCCTTCGTGCGCTTCTCATTGGTCAGCGGCTGGGGCCAG CTGCTGGACCGTGGCGCCACGGCCCTGGAGCTCATGGTCCTCAACGTGCCCCGGC
TGATGACCCAGGACTGCCTGCAGCAGTCACGGAAGGTGGGAGACTCCCCAAATA TCACGGAGTACATGTTCTGTGCCGGCTACTCGGATGGCAGCAAGGACTCCTGCAA
GGGGGACAGTGGAGGCCCACATGCCACCCACTACCGGGGCACGTGGTACCTGAC CGGCATCGTGAGCTGGGGCCAGGGCTGCGCCACCGTGGGCCACTTCGGCGTGTA
CACCAGGGTGTCCCAGTACATCGAGTGGCTGCAGAAACTGATGAAGCGAGCC CAGACCCGGCGTGCTGCTGAGAGCCCCCTTCCCCAGCAGCAGCTCCAAGGCCCCT
CCCCCTAGCCTGCCCAGCCCTAGCAGACTGCCTGGGCCCTCCGACACACCAATCC TGCCACAGAGCAGCTCCTCTAAGGCCCCTCCTCCATCCCTGCCATCCCCCTCCCG
GCTGCCAGGCCCCTCTGACACCCCTATCCTGCCTCAGTGATGAAGGTCTGGATCC GCGGCCGC (SEQ ID NO: 50).

In another embodiment, the amino acid sequence of factor VII-CTP-CTP (attached to the carboxy terminus) comprises the following amino acid sequence:
MVSQALRLLCLLLGLQGCLAAVFVTQEEAHGVLHRRRRANAFLEELRPGSLERECKE EQCSFEEAREIFKDAERTKLFWISYSDGDQCASSPCQNGGSCKDQLQSYICFCLPAFEG
RNCETHKDDQLICVNENGGCEQYCSDHTGTKRSCRCHEGYSLLADGVSCTPTVEYPC GKIPILEKRNASKPQGRIVGGKVCPKGECPWQVLLLVNGAQLCGGTLINTIWVVSAA
HCFDKIKNRRNLIAVLGEHDLSEHDGDEQSRRVAQVIIPSTYVPGTTNHDIALLRLHQ PVVLTDHVVPLCLPERTFSERTLAFVRFSLVSGWGQLLDRGATALELMVLNVPRLMT
QDCLQQSRKVGDSPNITEYMFCAGYSDGSKDSCKGDSGGPHATHYRGTWYLTGIVS WGQGCATVGHFGVYTRVSQYIEWLQKLMRSEPRPGVLLRAPFPSSSSKAPPPSLPSPS
RLPGPSDTPILPQSSSSKAPPPSLPSPSRLPGPSDTPILPQ** (SEQ ID NO: 51).

In another embodiment, the amino acid sequence of factor VII-CTP-CTP-CTP (three attached to the carboxy terminus) comprises the following amino acid sequence:
MVSQALRLLCLLLGLQGCLAAVFVTQEEAHGVLHRRRRANAFLEELRPGSLERECKE EQCSFEEAREIFKDAERTKLFWISYSDGDQCASSPCQNGGSCKDQLQSYICFCLPAFEG
RNCETHKDDQLICVNENGGCEQYCSDHTGTKRSCRCHEGYSLLADGVSCTPTVEYPC GKIPILEKRNASKPQGRIVGGKVCPKGECPWQVLLLVNGAQLCGGTLINTIWVVSAA
HCFDKIKNRRNLIAVLGEHDLSEHDGDEQSRRVAQVIIPSTYVPGTTNHDIALLRLHQ PVVLTDHVVPLCLPERTFSERTLAFVRFSLVSGWGQLLDRGATALELMVLNVPRLMT
QDCLQQSRKVGDSPNITEYMFCAGYSDGSKDSCKGDSGGPHATHYRGTWYLTGIVS WGQGCATVGHFGVYTRVSQYIEWLQKLMRSEPRPGVLLRAPFPSSSSKAPPPSLPSPS
RLPGPSDTPILPQSSSSKAPPPSLPSPSRLPGPSDTPILPQSSSSKAPPPSLPSPSRLPGPSD TPILPQ (SEQ ID NO: 52).

In another embodiment, the amino acid sequence of factor VII-CTP(×4) (four to attached to the carboxy terminus) comprises the following amino acid sequence:
MVSQALRLLCLLLGLQGCLAAVFVTQEEAHGVLHRRRRANAFLEELRPGSLERECKE EQCSFEEAREIFKDAERTKLFWISYSDGDQCASSPCQNGGSCKDQLQSYICFCLPAFEG
RNCETHKDDQLICVNENGGCEQYCSDHTGTKRSCRCHEGYSLLADGVSCTPTVEYPC GKIPILEKRNASKPQGRIVGGKVCPKGECPWQVLLLVNGAQLCGGTLINTIWVVSAA
HCFDKIKNRRNLIAVLGEHDLSEHDGDEQSRRVAQVIIPSTYVPGTTNHDIALLRLHQ PVVLTDHVVPLCLPERTFSERTLAFVRFSLVSGWGQLLDRGATALELMVLNVPRLMT
QDCLQQSRKVGDSPNITEYMFCAGYSDGSKDSCKGDSGGPHATHYRGTWYLTGIVS WGQGCATVGHFGVYTRVSQYIEWLQKLMRSEPRPGVLLRAPFPSSSSKAPPPSLPSPS
RLPGPSDTPILPQSSSSKAPPPSLPSPSRLPGPSDTPILPQSSSSKAPPPSLPSPSRLPGPSD TPILPQSSSSKAPPPSLPSPSRLPGPSDTPILPQ (SEQ ID NO: 53).

In another embodiment, the amino acid sequence of factor VII-CTP(×5) (five attached to the carboxy terminus) comprises the following amino acid sequence:
MVSQALRLLCLLLGLQGCLAAVFVTQEEAHGVLHRRRRANAFLEELRPGSLERECKE EQCSFEEAREIFKDAERTKLFWISYSDGDQCASSPCQNGGSCKDQLQSYICFCLPAFEG
RNCETHKDDQLICVNENGGCEQYCSDHTGTKRSCRCHEGYSLLADGVSCTPTVEYPC GKIPILEKRNASKPQGRIVGGKVCPKGECPWQVLLLVNGAQLCGGTLINTIWVVSAA
HCFDKIKNRRNLIAVLGEHDLSEHDGDEQSRRVAQVIIPSTYVPGTTNHDIALLRLHQ PVVLTDHVVPLCLPERTFSERTLAFVRFSLVSGWGQLLDRGATALELMVLNVPRLMT
QDCLQQSRKVGDSPNITEYMFCAGYSDGSKDSCKGDSGGPHATHYRGTWYLTGIVS WGQGCATVGHFGVYTRVSQYIEWLQKLMRSEPRPGVLLRAPFPSSSSKAPPPSLPSPS
RLPGPSDTPILPQSSSSKAPPPSLPSPSRLPGPSDTPILPQSSSSKAPPPSLPSPSRLPGPSD TPILPQSSSSKAPPPSLPSPSRLPGPSDTPILPQSSSSKAPPPSLPSPSRLPGPSDTPILPQ (SEQ ID NO: 54).

In another embodiment, the nucleic acid sequence encoding factor IX comprises the following nucleic acid sequence:

GCGATCGCCATGCAGCGCGTGAACATGATCATG-
GCAGAATCACCAGGCCTCATC ACCATTGCCTTT-
TAGGATATCTACTCAGTGCTGAATGTACA-
GTTTTTCTTGATCAT
GAAAACGCCAACAAAATTCTGAATCGGC-
CAAAGAGGTATAATTCAGGTAAATTG GAAGAGTTT-
GTTCAAGGGAACCTTGAGAGAGAATGTATG-
GAAGAAAAGTGTAGT
TTTGAAGAAGCACGAGAAGTTTTTGAAAACACT-
GAAAGAACAACTGAATTTTGG AAGCAGTATGTT-
GATGGAGATCAGTGTGAGTCCAATCCATGTT-
TAAATGGCGGCA
GTTGCAAGGATGACATTAATTCCTATGAATGTTGGT-
GTCCCTTTGGATTTGAAGG AAAGAACTGT-
GAATTAGATGTAACATGTAACATTAAGAATGGCA-
GATGCGAGCA
GTTTTGTAAAAATAGTGCTGATAACAAGGTGGTTT-
GCTCCTGTACTGAGGGATAT CGACTTGCA-
GAAAACCAGAAGTCCTGTGAACCAGCAGTGC-
CATTTCCATGTGGA
AGAGTTTCTGTTTCACAAACTTCTAAGCTCAC-
CCGTGCTGAGACTGTTTTCCTGA TGTGGACTATG-
TAAATTCTACTGAAGCTGAAACCATTTTGGA-
TAACATCACTCAA
AGCACCCAATCATTTAATGACTTCACTCGAGTTGT-
TGGTGGAGAAGATGCCAAAC CAGGTCAATTCCCT-
TGGCAGGTTGTTTTGAATGGTAAAGTTGATGCAT-
TCTGTGG
AGGCTCTATCGTTAATGAAAAATGGATTGTAACT-
GCTGCCCACTGTGTTGAAACT GGTGTTAAAATTA-
CAGTTGTCGCAGGTGAACATAATATTGAGGAGACA-
GAACAT
ACAGAGCAAAAGCGAAATGTGATTCGAATTATTC-
CTCACCACAACTACAATGCA GCTATTAATAAGTA-
CAACCATGACATTGCCCTTCTGGAACTGGACGAAC-
CCTTAG
TGCTAAACAGCTACGTTACACCTATTTGCATTGCT-
GACAAGGAATACACGAACAT CTTCCTCAAATTTG-
GATCTGGCTATGTAAGTGGCTGGGGAAGAGTCTTC-
CACAAA
GGGAGATCAGCTTTAGTTCTCCAGTACCTTAGAGT-
TCCACTTGTTGACCGAGCCA CATGTCTTCGATCTA-
CAAAGTTCACCATCTATAACAACATGTTCTGT-
GCTGGCTTC
CATGAAGGAGGTAGAGATTCATGTCAAGGAGA-
TAGTGGGGGACCCCATGTTACT GAAGTG-
GAAGGGACCAGTTTCTTAACTGGAATTATT-
AGCTGGGGTGAAGAGTGT
GCAATGAAAGGCAAATATGGAATATATACCAAGG-
TATCCCGGTATGTCAACTGG
ATTAAGGAAAAAACAAAGCTCACTTGAACGCGGC-
CGC (SEQ ID NO: 55).

In another embodiment, the amino acid sequence of factor IX comprises the following amino acid sequence:
MQRVNMIMAESPGLITICLLGYLLSAECTVFLD-
HENANKILNRPKRYNSGKLEEFVQG NLEREC-
MEEKCSFEEAREVFENTERTTEF-
WKQYVDGDQCESNPCLNGGSCKDDINSY
ECWCPFGFEGKNCELDVTCNIKNGRCEQFCKN-
SADNKVVCSCTEGYRLAENQKSCE PAVPFPCGRVS-
VSQTSKLTRAETVFPDVDYVNSTEAETILD-
NITQSTQSFNDFTRVVG
GEDAKPGQFPWQVVLNGKVDAFCGGSIVNEK-
WIVTAAHCVETGVKITVVAGEHNIE ETEHTEQKRN-
VIRIIPHHNYNAAINKYNHDIALLELDEPLVLNSYVT-
PICIADKEYTNIF
LKFGSGYVSGWGRVFHKGRSALVLQYLRV-
PLVDRATCLRSTKFTIYNNMFCAGFHE GGRDSC-
QGDSGGPHVTEVEGTSFLTGIISWGEECAMKGKYGI-
YTKVSRYVNWIKEKT KLT* (SEQ ID NO: 56).

In another embodiment, the nucleic acid sequence encoding factor IX-CTP (attached to the carboxy terminus) comprises the following nucleic acid sequence:
GCGATCGCCATGCAGCGCGTGAACATGATCATG-
GCAGAATCACCAGGCCTCATC ACCATCTGCCTTT-
TAGGATATCTACTCAGTGCTGAATGTACA-
GTTTTTCTTGATCA
TGAAAACGCCAACAAAATTCTGAATCGGC-
CAAAGAGGTATAATTCAGGTAAATT GGAAGAGTTT-
GTTCAAGGGAACCTTGAGAGAGAATGTATG-
GAAGAAAAGTGTAG
TTTTGAAGAAGCACGAGAAGTTTTTGAAAACACT-
GAAAGAACAACTGAATTTTG GAAGCAGTATGTT-
GATGGAGATCAGTGTGAGTCCAATCCATGTT-
TAAATGGCGGC
AGTTGCAAGGATGACATTAATTCCTATGAATGTTG-
GTGTCCCTTTGGATTTGAAG GAAAGAACTGT-
GAATTAGATGTAACATGTAACATTAAGAATGGCA-
GATGCGAGC
AGTTTTGTAAAAATAGTGCTGATAACAAGGTG-
GTTTGCTCCTGTACTGAGGGATA TCGACTTGCA-
GAAAACCAGAAGTCCTGTGAACCAGCAGTGC-
CATTTCCATGTGGA
AGAGTTTCTGTTTCACAAACTTCTAAGCTCAC-
CCGTGCTGAGACTGTTTTCCTGA TGTGGACTATG-
TAAATTCTACTGAAGCTGAAACCATTTTGGA-
TAACATCACTCAA
AGCACCCAATCATTTAATGACTTCACTCGAGTTGT-
TGGTGGAGAAGATGCCAAAC CAGGTCAATTCCCT-
TGGCAGGTTGTTTTGAATGGTAAAGTTGATGCAT-
TCTGTGG
AGGCTCTATCGTTAATGAAAAATGGATTGTAACT-
GCTGCCCACTGTGTTGAAACT GGTGTTAAAATTA-
CAGTTGTCGCAGGTGAACATAATATTGAGGAGACA-
GAACAT
ACAGAGCAAAAGCGAAATGTGATTCGAATTATTC-
CTCACCACAACTACAATGCA GCTATTAATAAGTA-
CAACCATGACATTGCCCTTCTGGAACTGGACGAAC-
CCTTAG
TGCTAAACAGCTACGTTACACCTATTTGCATTGCT-
GACAAGGAATACACGAACAT CTTCCTCAAATTTG-
GATCTGGCTATGTAAGTGGCTGGGGAAGAGTCTTC-
CACAAA
GGGAGATCAGCTTTAGTTCTTCAGTACCTTAGAGT-
TCCACTTGTTGACCGAGCCA CATGTCTTCGATCTA-
CAAAGTTCACCATCTATAACAACATGTTCTGT-
GCTGGCTTC
CATGAAGGAGGTAGAGATTCATGTCAAGGAGA-
TAGTGGGGGACCCCATGTTACT GAAGTG-
GAAGGGACCAGTTTCTTAACTGGAATTATT-
AGCTGGGGTGAAGAGTGT
GCAATGAAAGGCAAATATGGAATATATACCAAGG-
TATCCCGGTATGTCAACTGG
ATTAAGGAAAAAACAAAGCTCACTAGCTCCAGCA-
GCAAGGCCCCTCCCCCGAGC CTGCCCTC-
CCCAAGCAGGCTGCCTGGGCCCTCCGACACAC-
CAATCCTGCCACAGT
GATGAAGGTCTGGATCCGCGGCCGC (SEQ ID NO: 57).

In another embodiment, the amino acid sequence of factor IX-CTP (attached to the carboxy terminus) comprises the following amino acid sequence:
MQRVNMIMAESPGLITICLLGYLLSAECTVFLD-
HENANKILNRPKRYNSGKLEEFVQG NLEREC- MEEKCSFEEAREVFENTERTTEF-
WKQYVDGDQCESNPCLNGGSCKDDINSY
ECWCPFGFEGKNCELDVTCNIKNGRCEQFCKN-
SADNKVVCSCTEGYRLAENQKSCE PAVPFPCGRVS-
VSQTSKLTRAETVFPDVDYVNSTEAETILD-
NITQSTQSFNDFTRVVG
GEDAKPGQFPWQVVLNGKVDAFCGGSIVNEK-
WIVTAAHCVETGVKITVVAGEHNIE ETEHTEQKRN-
VIRIIPHHNYNAAINKYNHDIALLELDEPLVLNSYVT-
PICIADKEYTNIF
LKFGSGYVSGWGRVFHKGRSALVLQYLRV-
PLVDRATCLRSTKFTIYNNMFCAGFHE GGRDSC-
QGDSGGPHVTEVEGTSFLTGIISWGEECAMKGKYGI-
YTKVSRYVNWIKEKT
KLTSSSSKAPPPSLPSPSRLPGPSDTPILPQ** (SEQ ID NO: 58).

In another embodiment, the nucleic acid sequence encoding factor IX-CTP-CTP (attached to the carboxy terminus) comprises the following nucleic acid sequence:
GCGATCGCCATGCAGCGCGTGAACATGATCATG-
GCAGAATCACCAGGCCTCATC ACCATCTGCCTTT-
TAGGATATCTACTCAGTGCTGAATGTACA-
GTTTTTCTTGATCA
TGAAAACGCCAACAAAATTCTGAATCGGC-
CAAAGAGGTATAATTCAGGTAAATT GGAAGAGTTT-
GTTCAAGGGAACCTTGAGAGAGAATGTATG-
GAAGAAAAGTGTAG
TTTTGAAGAAGCACGAGAAGTTTTTGAAAACACT-
GAAAGAACAACTGAATTTTG GAAGCAGTATGTT-
GATGGAGATCAGTGTGAGTCCAATCCATGTT-
TAAATGGCAGC
AGTTGCAAGGATGACATTAATTCCTATGAATGTTG-
GTGTCCCTTTGGATTTGAAG GAAAGAACTGT-
GAATTAGATGTAACATGTAACATTAAGAATGGCA-
GATGCGAGC
AGTTTTGTAAAAATAGTGCTGATAACAAGGTG-
GTTTGCTCCTGTACTGAGGGATA TCGACTTGCA-
GAAAACCAGAAGTCCTGTGAACCAGCAGTGC-
CATTTCCATGTGGA
AGAGTTTCTGTTTCACAAACTTCTAAGCTCAC-
CCGTGCTGAGACTGTTTTTCCTGA TGTGGACTATG-
TAAATTCTACTGAAGCTGAAACCATTTTGGA-
TAACATCACTCAA
AGCACCCAATCATTTAATGACTTCACTCGAGTTGT-
TGGTGGAGAAGATGCCAAAC CAGGTCAATTCCCT-
TGGCAGGTTGTTTTGAATGGTAAAGTTGATGCAT-
TCTGTGG
AGGCTCTATCGTTAATGAAAAATGGATTGTAACT-
GCTGCCCACTGTGTTGAAACT GGTGTTAAAATTA-
CAGTTGTCGCAGGTGAACATAATATTGAGGAGACA-
GAACAT
ACAGAGCAAAAGCGAAATGTGATTCGAATTATTC-
CTCACCACAACTACAATGCA GCTATTAATAAGTA-
CAACCATGACATTGCCCTTCTGGAACTGGACGAAC-
CCTTAG
TGCTAAACAGCTACGTTACACCTATTTGCATTGCTA-
CAAGGAATACACGAACATC TTCCTCAAATTTG-
GATCTGGCTATGTAAGTGGCTGGGGAAGAGTCTTC-
CACAAAG
GGAGATCAGCTTTAGTTCTTCAGTACCTTAGAGT-
TCCACTTGTTGACCGAGCCAC ATGTCTTCGATCTA-
CAAAGTTCACCATCTATAACAACATGTTCTGT-
GCTGGCTTCC
ATGAAGGAGGTAGAGATTCATGTCAAGGAGA-
TAGTGGGGGACCCCATGTTACTG AAGTG-
GAAGGGACCAGTTTCTTAACTGGAATTATT-
AGCTGGGGTGAAGAGTGTG CAAT-
GAAAGGCAAATATGGAATATATACCAAGGTATC-
CCGGTATGTCAACTGGA
TTAAGGAAAAAACAAAGCTCACTAGCTCCAGCAG-
CAAGGCCCCTCCCCCGAGCC TGCCCTC-
CCCAAGCAGGCTGCCTGGGCCCTCCGACACAC-
CAATCCTGCCACAGAG
CAGCTCCTCTAAGGCCCCTCCTCCATCCCTGC-
CATCCCCCTCCCGGCTGCCTGGCC CCTCTGACAC-
CCCTATCCTGCCTCAGTGATGAAGGTCTGGATC-
CGCGGCCGC (SEQ ID NO: 59).

In another embodiment, the amino acid sequence of factor IX-CTP-CTP (attached the carboxy terminus) comprises the following amino acid sequence:
MQRVNMIMAESPGLITICLLGYLLSAECTVFLD-
HENANKILNRPKRYNSGKLEEFVQG NLEREC-
MEEKCSFEEAREVFENTERTTEF-
WKQYVDGDQCESNPCLNGGSCKDDINSY
ECWCPFGFEGKNCELDVTCNIKNGRCEQFCKN-
SADNKVVCSCTEGYRLAENQKSCE PAVPFPCGRVS-
VSQTSKLTRAETVFPDVDYVNSTEAETILD-
NITQSTQSFNDFTRVVG
GEDAKPGQFPWQVVLNGKVDAFCGGSIVNEK-
WIVTAAHCVETGVKITVVAGEHNIE ETEHTEQKRN-
VIRIIPHHNYNAAINKYNHDIALLELDEPLVLNSYVT-
PICIADKEYTNIF
LKFGSGYVSGWGRVFHKGRSALVLQYLRV-
PLVDRATCLRSTKFTIYNNMFCAGFHE GGRDSC-
QGDSGGPHVTEVEGTSFLTGIISWGEECAMKGKYGI-
YTKVSRYVNWIKEKT
KLTSSSSKAPPPSLPSPSRLPGPSDTPILPQSSSSKAP-
PPSLPSPSRLPGPSDTPILPQ** (SEQ ID NO: 60).

In another embodiment, the amino acid sequence of factor IX-CTP(×3) (three attached to the carboxy terminus) comprises the following amino acid sequence:
MQRVNMIMAESPGLITICLLGYLLSAECTVFLD-
HENANKILNRPKRYNSGKLEEFVQG NLEREC-
MEEKCSFEEAREVFENTERTTEF-
WKQYVDGDQCESNPCLNGGSCKDDINSY
ECWCPFGFEGKNCELDVTCNIKNGRCEQFCKN-
SADNKVVCSCTEGYRLAENQKSCE PAVPFPCGRVS-
VSQTSKLTRAETVFPDVDYVNSTEAETILD-
NITQSTQSFNDFTRVVG
GEDAKPGQFPWQVVLNGKVDAFCGGSIVNEK-
WIVTAAHCVETGVKITVVAGEHNIE ETEHTEQKRN-
VIRIIPHHNYNAAINKYNHDIALLELDEPLVLNSYVT-
PICIADKEYTNIF
LKFGSGYVSGWGRVFHKGRSALVLQYLRV-
PLVDRATCLRSTKFTIYNNMFCAGFHE GGRDSC-
QGDSGGPHVTEVEGTSFLTGIISWGEECAMKGKYGI-
YTKVSRYVNWIKEKT
KLTSSSSKAPPPSLPSPSRLPGPSDTPILPQSSSSKAP-
PPSLPSPSRLPGPSDTPILPQSSSS KAPPPSLPSPSR-
LPGPSDTPILPQ (SEQ ID NO: 61).

In another embodiment, the amino acid sequence of factor IX-CTP(×4) (four attached to the carboxy terminus) comprises the following amino acid sequence:
MQRVNMIMAESPGLITICLLGYLLSAECTVFLD-
HENANKILNRPKRYNSGKLEEFVQG NLEREC-
MEEKCSFEEAREVFENTERTTEF-
WKQYVDGDQCESNPCLNGGSCKDDINSY
ECWCPFGFEGKNCELDVTCNIKNGRCEQFCKN-
SADNKVVCSCTEGYRLAENQKSCE PAVPFPCGRVS-
VSQTSKLTRAETVFPDVDYVNSTEAETILD-
NITQSTQSFNDFTRVVG
GEDAKPGQFPWQVVLNGKVDAFCGGSIVNEK-
WIVTAAHCVETGVKITVVAGEHNIE ETEHTEQKRN-
VIRIIPHHNYNAAINKYNHDIALLELDEPLVLNSYVT- PICIADKEYTNIF LKFGSGYVSGWGRVFHKGRSALVLQYLRV-PLVDRATCLRSTKFTIYNNMFCAGFHE GGRDSC-QGDSGGPHVTEVEGTSFLTGIISWGEECAMKGKYGI-YTKVSRYVNWIKEKT KLTSSSSKAPPPSLPSPSRLPGPSDTPILPQSSSSKAP-PPSLPSPSRLPGPSDTPILPQSSSS KAPPPSLPSPSR-LPGPSDTPILPQSSSSKAPPPSLPSPSRLPGPSDTPILPQ (SEQ ID NO: 62).

In another embodiment, the amino acid sequence of factor IX-CTP(×5) (five attached to the carboxy terminus) comprises the following amino acid sequence:
MQRVNMIMAESPGLITICLLGYLLSAECTVFLD-HENANKILNRPKRYNSGKLEEFVQG NLEREC-MEEKCSFEEAREVFENTERTTEF-WKQYVDGDQCESNPCLNGGSCKDDINSY ECWCPFGFEGKNCELDVTCNIKNGRCEQFCKN-SADNKVVCSCTEGYRLAENQKSCE PAVPFPCGRVS-VSQTSKLTRAETVFPDVDYVNSTEAETILD-NITQSTQSFNDFTRVVG GEDAKPGQFPWQVVLNGKVDAFCGGSIVNEK-WIVTAAHCVETGVKITVVAGEHNIE ETEHTEQKRN-VIRIIPHHNYNAAINKYNHDIALLELDEPLVLNSYVT-PICIADKEYTNIF LKFGSGYVSGWGRVFHKGRSALVLQYLRV-PLVDRATCLRSTKFTIYNNMFCAGFHE GGRDSC-QGDSGGPHVTEVEGTSFLTGIISWGEECAMKGKYGI-YTKVSRYVNWIKEKT KLTSSSSKAPPPSLPSPSRLPGPSDTPILPQSSSSKAP-PPSLPSPSRLPGPSDTPILPQSSSS KAPPPSLPSPSR-LPGPSDTPILPQSSSSKAPPPSLPSPSRLPGPSDTPIL-PQSSSSKAPPPSL PSPSRLPGPSDTPILPQ (SEQ ID NO: 63).

In another embodiment, furin is added to a cell expressing the coagulation factor-CTP of the invention. In another embodiment, furin increases the production efficiency of a coagulation factor-CTP of the invention in a cell. In another embodiment, furin is co-transfected with the vector comprising the coding sequence of the coagulation factor-CTP of the invention. In another embodiment, furin is encoded by a separate vector. In another embodiment, furin and a coagulation factor-CTP are encoded by one vector. In another embodiment, the coding sequence of furin is inserted into pCI-DHFR. In another embodiment, the coding sequence of furin is engineered in pCI-dhfr/smaI+NotI, Furin/AsisI F.I.+ NotI.

In another embodiment, the nucleic acid sequence encoding furin comprises the following nucleic acid sequence:
tctagagtcgacccCGCCATGGAGCTGAGGCCCTGGTTGC-TATGGGTGGTAGCAGCAACA GGAACCTTGGTCCT-GCTAGCAGCTGATGCTCAGGGCCAGAAGGTCT-TCACCAACA CGTGGGCTGTGCGCATCCCTGGAGGCCCAGCG-GTGGCCAACAGTGTGGCACGGA AGCATGGGTTC-CTCAACCTGGGCCAGATCTTCGGGGACTATTAC-CACTTCTGGCA TCGAGGAGTGACGAAGCGGTCCCTGTCGCCTCAC-CGCCCGCGGCACAGCCGGCT GCAGAGGGAGCCT-CAAGTACAGTGGCTGGAACAGCAGGTGGCAAAGC-GACGGA CTAAACGGGACGTGTACCAGGAGCCCACAGAC-CCCAAGTTTCCTCAGCAGTGGT ACCTGTCTGGTGT-CACTCAGCGGGACCTGAATGTGAAGGCGGC-CTGGGCGCAGG GCTACACAGGGCACGGCATTGTGGTCTCCATTCTG-GACGATGGCATCGAGAAGA ACCACCCGGACTTG-GCAGGCAATTATGATCCTGGGGCCAGTTTTGATGT-CAATGA CCAGGACCCTGACCCCCAGCCTCGGTACACACA-GATGAATGACAACAGGCACGG CACACGGTGT-GCGGGGGAAGTGGCTGCGGTGGCCAACAACGGT-GTCTGTGGTGT AGGTGTGGCCTACAACGCCCGCATTGGAGGGGT-GCGCATGCTGGATGGCGAGGT GACAGATGCAGTG-GAGGCACGCTCGCTGGGCCTGAACCCCAACCA-CATCCACAT CTACAGTGCCAGCTGGGGCCCCGAGGATGACG-GCAAGACAGTGGATGGGCCAGC CCGCCTCGC-CGAGGAGGCCTTCTTCCGTGGGGTTAGCCAGGGC-CGAGGGGGCT GGGCTCCATCTTTGTCTGGGC-CTCGGGGAACGGGGGCCGGGAACATGACAGCTG CAACTGCGACGGCTACACCAACAGTATCTA-CACGCTGTCCATCAGCAGCGCCAC GCAGTTTG-GCAACGTGCCGTGGTACAGCGAGGCCTGCTCGTC-CACACTGGCCACG ACCTACAGCAGTGGCAACCAGAATGAGAAGCA-GATCGTGACGACTGACTTGCGG CAGAAGTGCACG-GAGTCTCACACGGGCACCTCAGCCTCTGCCCCCT-TAGCAGCCG GCATCATTGCTCTCACCCTGGAGGCCAATAAGAAC-CTCACATGGCGGGACATGC AACACCTGGTGGTA-CAGACCTCGAAGCCAGCCCACCTCAATGCCAAC-GACTGGG CCACCAATGGTGTGGGCCGGAAAGTGAGCCACT-CATATGGCTACGGGCTTTTGG ACGCAGGCGCCATG-GTGGCCCTGGCCCAGAATTGGACCACAGTGGC-CCCCCAGC GGAAGTGCATCATCGACATCCTCACCGAGC-CCAAAGACATCGGGAAACGGCTCG AGGTGCG-GAAGACCGTGACCGCGTGCCTGGGCGAGCCCAAC-CACATCACTCGGC TGGAGCACGCTCAGGCGCGGCTCACCCTGTC-CTATAATCGCCGTGGCGACCTGGC CATCCACCTG-GTCAGCCCCATGGGCACCCGCTCCACCCTGCTG-GCAGCCAGGCCA CATGACTACTCCGCAGATGGGTTTAATGACTGGGC-CTTCATGACAACTCATTCCT GGGATGAGGATC-CCTCTGGCGAGTGGGTCCTAGAGATTGAAAACAC-CAGCGAAG CCAACAACTATGGGACGCTGACCAAGTTCAC-CCTCGTACTCTATGGCACCGCCCC TGAGGGGCTGC-CCGTACCTCCAGAAAGCAGTGGCTGCAAGACCCT-CACGTCCAG TCAGGCCTGTGTGGTGTGCGAGGAAGGCTTCTC-CCTGCACCAGAAGAGCTGTGTC CAGCACTGC-CCTCCAGGCTTCGCCCCCCAAGTCCTCGATACG-CACTATAGCACCG AGAATGACGTGGAGACCATCCGGGCCAGCGTCT-GCGCCCCCTGCCACGCCTCAT GTGCCACATGCCA-GGGGCCGGCCCTGACAGACTGCCTCAGCTGC-CCCAGCCACG CCTCCTTGGACCCTGTGGAGCAGACTTGCTCCCG-GCAAAGCCAGAGCAGCCGAG AGTCCCCGCCACA-GCAGCAGCCACCTCGGCTGCCCCCGGAGGTGGAG-GCGGGGC AACGGCTGCGGGCAGGGCTGCTGCCCTCACACCT-GCCTGAGGTGGTGGCCGGCC TCAGCTGCGCCT-TCATCGTGCTGGTCTTCGTCACTGTCTTCCTGGTC-CTGCAGCTG CGCTCTGGCTTTAGTTTTCGGGGGGTGAAGGTGTA-CACCATGGACCGTGGCCTCA TCTCCTA-CAAGGGGCTGCCCCCTGAAGCCTGGCAGGAG-GAGTGCCCGTCTGACTC AGAAGAGGACGAGGGCCGGGGCGAGAGGACCGC-CTTTATCAAAGACCAGAGCG CCCTCTGAACGCG-GCCGC (SEQ ID NO: 64).

In another embodiment, the amino acid sequence of furin comprises the following amino acid sequence:
MELRPWLLWVVAATGTLVLLAADAQGQKVFTNT-WAVRIPGGPAVANSVARKHGFL NLGQIFGDYYHF-WHRGVTKRSLSPHRPRHSRLQREPQVQWLEQQ-VAKRRTKRDVYQ EPTDPKFPQQWYLSGVTQRDLNVKAAWAQGYTGH-GIVVSILDDGIEKNHPDLAGNY DPGASFDVNDQDPD-PQPRYTQMNDNRHGTRCA-GEVAAVANNGVCGVGVAYNARI GGVRMLDGEVTDAVEARSLGLNPNHIHIYSASWG-PEDDGKTVDGPARLAEEAFFRG VSQGRGGLG-SIFVWASGNGGREHDSCNCDGYTNSIYTLSISSATQF-GNVPWYSEACSS TLATTYSSGNQNEKQIVTTDLRQKCTESHTGT-SASAPLAAGIIALTLEANKNLTWRD MQHLV-VQTSKPAHLNANDWATNGVGRKVSHSYGYGLL-DAGAMVALAQNWTTVA PQRKCIIDILTEPKDIGKRLEVRKTVTACLGEPN-HITRLEHAQARLTLSYNRRGDLAIH LVSPMGTRSTL-LAARPHDYSADGFNDWAFMTTHSWDEDPSGEWV-LEIENTSEANNY GTLTKFTLVLYGTAPEGLPVPPESSGCKTLTSSQACV-VCEEGFSLHQKSCVQHCPPGF APQVLDTHYSTEND-VETIRASVCAPCHASCATCQGPALTDCLSCPSHASLD-PVEQTCS RQSQSSRESPPQQQPPRLPPEVEAGQRLRAGLLP-SHLPEVVAGLSCAFIVLVFVTVFLV LQLRS-GFSFRGVKVYTMDRGLISYKGLPPEAWQEECPSD-SEEDEGRGERTAFIKDQSA L* (SEQ ID NO: 65).

In some embodiments, the term coagulation factor further includes homologues of known coagulation factors which have a coagulating activity. In some embodiments, homology according to the present invention also encompasses deletions, insertions, or substitution variants, including an amino acid substitution, thereof and biologically active polypeptide fragments thereof.

In another embodiment, the invention includes homologues of a coagulation factor having a coagulation activity. In another embodiment, the invention includes homologues of a coagulation factor as described herein having a coagulation activity. In another embodiment, homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 99% homologous to a coagulation factor as determined using BlastP software of the National Center of Biotechnology Information (NCBI) using default parameters.

In another embodiment, the invention includes homologues of furin. In another embodiment, homologues e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 99% homologous to a furin as determined using BlastP software of the National Center of Biotechnology Information (NCBI) using default parameters.

In one embodiment, the homologues of polypeptides or fragments thereof provided herein also refer to deletion, insertion, or substitution variants, including amino acid substitution, thereof and biologically active polypeptide fragments thereof.

In another embodiment, three chorionic gonadotrophin carboxy terminal peptides are attached to the C-terminus of the peptide or polypeptide provided herein. In another embodiment, four chorionic gonadotrophin carboxy terminal peptides are attached to the C-terminus of the polypeptide or fragment thereof provided herein. In another embodiment, five chorionic gonadotrophin carboxy terminal peptides are attached to the C-terminus of the polypeptide or fragment thereof provided herein. In another embodiment, 1-10 CTP are attached to the amino or C-terminus of polypeptide or fragment thereof provided herein. In another embodiment, 1-10 CTP are attached to the N-terminus of polypeptide or fragment thereof provided herein. In another embodiment, 1-10 CTP are attached to the C-terminus of polypeptide or fragment thereof provided herein.

It is to be understood that the compositions and methods of the present invention comprising the elements or steps as described herein may, in another embodiment, consist of those elements or steps, or in another embodiment, consist essentially of those elements or steps. In another embodiment, the term "comprise" refers to the inclusion of the indicated active agent, such as the CTP-modified polypeptide or fragment thereof, as well as inclusion of other active agents, and pharmaceutically or physiologically acceptable carriers, excipients, emollients, stabilizers, etc., as are known in the pharmaceutical industry. In another embodiment, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In another embodiment, the term "consisting essentially of" may refer to components which facilitate the release of the active ingredient. In another embodiment, the term "consisting" refers to a composition, which contains the active ingredient and a pharmaceutically acceptable carrier or excipient.

In one embodiment, the methods provided herein comprise a polypeptide or a fragment thereof attached to at least one gonadotrophin carboxy terminal peptides (CTPs) attached at the N- or C-terminus of the polypeptide or fragments thereof.

In another embodiment, the methods provided herein comprise a polypeptide or a fragment thereof attached to 1 to 3 gonadotrophin carboxy terminal peptides (CTPs) attached at the N- and/or C-terminus of the polypeptide or fragments thereof. In another embodiment, the methods provided herein comprise a polypeptide or a fragment thereof attached to 1 to 5 gonadotrophin carboxy terminal peptides (CTPs) attached at the N- and/or C-terminus of the polypeptide or fragments thereof. In another embodiment, the methods provided herein comprise a polypeptide or a fragment thereof attached to 1 to 10 gonadotrophin carboxy terminal peptides (CTPs) attached at the N- and/or C-terminus of the polypeptide or fragments thereof. In another embodiment, the methods provided herein comprise a polypeptide or a fragment thereof attached to 2 to 3 gonadotrophin carboxy terminal peptides (CTPs) attached at the N- and/or C-terminus of the polypeptide or fragments thereof. In another embodiment, the methods provided herein comprise a polypeptide or a fragment thereof attached to 2 to 5 gonadotrophin carboxy terminal peptides (CTPs) attached at the N- and/or C-terminus of the polypeptide or fragments thereof. In another embodiment, the methods provided herein comprise a polypeptide or a fragment thereof attached to 2 to 10 gonadotrophin carboxy terminal peptides (CTPs) attached at the N- and/or C-terminus of the polypeptide or fragments thereof. In another embodiment, the methods provided herein comprise a polypeptide or a fragment thereof attached to 3 to 5 gonadotrophin carboxy terminal peptides (CTPs) attached at the N- and/or C-terminus of the polypeptide or fragments thereof. In another embodiment, the methods provided herein comprise a polypeptide or a fragment thereof attached to 3 to 8 gonadotrophin carboxy terminal peptides (CTPs) attached at the N- and/or C-terminus of the polypeptide or fragments thereof. In another embodiment, the methods provided herein comprise a polypeptide or a fragment thereof attached to 3 to 10 gonadotrophin carboxy terminal peptides (CTPs) attached at the N- and/or C-terminus of the polypeptide or fragments thereof. In another embodiment, the methods provided herein comprise a polypeptide or fragments thereof attached to 6 to 10 gonadotrophin carboxy terminal peptides (CTPs) attached at the N- and/or C-terminus of the polypeptide or fragments thereof. In another embodiment, the methods provided herein comprise a polypeptide or fragments thereof attached to 1 gonadotrophin carboxy terminal peptides (CTPs) attached at the N- and/or C-terminus of the polypeptide or fragments thereof. In another embodiment, the methods provided herein comprise a polypeptide or fragments thereof attached to 2, 3, 4, 5, 6, 7, 8, 9, or 10 gonadotrophin carboxy terminal peptides (CTPs) attached at the N- and/or C-terminus of the polypeptide or fragments thereof. In another embodiment, the CTP peptides are tandemly attached on either side (N-terminus or C-terminus) of the polypeptide or fragments thereof.

In one embodiment, provided herein is an expression vector comprising the polynucleotide provided herein. In another embodiment, provided herein is a cell comprising the expression vector. In another embodiment, provided herein is a composition comprising the expression vector.

In another embodiment, the invention provides a composition comprising the cell as described herein. In another embodiment, the cell is a eukaryotic cell. In another embodiment, the cell is a prokaryotic cell.

In one embodiment, a CTP sequence at the C-terminal end of a polypeptide or fragments thereof provides enhanced protection against degradation of the polypeptide or fragments thereof. In another embodiment, a CTP sequence at the C-terminal end of the polypeptide or fragments thereof provides enhanced protection against clearance. In another embodiment, a CTP sequence at the C-terminal end of the polypeptide or fragments thereof provides prolonged clearance time. In another embodiment, a CTP sequence at the C-terminal end of the polypeptide or fragments thereof enhances its Cmax. In another embodiment, a CTP sequence at the C-terminal end of the polypeptide or fragments thereof enhances its Tmax. In another embodiment, a CTP sequence at the C-terminal end of the polypeptide or fragments thereof prolongs its T½. In another embodiment, aCTP sequence at the C-terminal end of the polypeptide or fragments thereof prolongs its AUC.

In another embodiment, a conjugated polypeptide or fragment thereof of the invention is used in the same manner as an unmodified polypeptide or fragment thereof. In another embodiment, a polypeptide or fragment thereof of the invention is used in the same manner as an unmodified polypeptide or fragment thereof. In another embodiment, a polypeptide or fragment thereof of this invention has an increased circulating half-life and plasma residence time, decreased clearance, and increased clinical activity in vivo. In another embodiment, due to the improved properties of the polypeptide or fragment thereof provided herein, this conjugate is administered less frequently than the polypeptide or fragment thereof.

In another embodiment, decreased frequency of administration results in improved treatment strategy, which in one embodiment, leads to improved patient compliance leading to improved treatment outcomes, as well as improved patient quality of life. In another embodiment, compared to conventional conjugates, the conjugates provided herein having the hydrodynamic volume further provided herein have an improved in vivo potency, improved stability, elevated AUC levels, and enhanced circulating half-life.

In another embodiment, the present invention further provides a pharmaceutical composition comprising a CTP-modified polypeptide comprising of one glycosylated gonadotropin carboxy terminal peptides (CTPs) attached to the N-terminus and two glycosylated CTP attached to the C-terminus of the polypeptide or fragments thereof.

In another embodiment, it is to be understood that combinations of glycosylated and non-glycosylated CTPs can be used in modifying the polypeptides of interest or fragments thereof, further provided herein. Such combinations can include, for example, at least one non-glycosylated CTP attached to the N-terminus of the polypeptide or fragments thereof, and at least one glycosylated CTP attached to the C-terminus of the same, and vice versa. Moreover, and in another embodiment, combinations of at least one glycosylated CTP and at least one non-glycosylated CTP attached to the same terminus (N- or C-terminus) are also envisioned. These combinations may also include truncations of the glycosylated and/or non-glycosylated CTP. Such combinations can be determined by a skilled artisan guided by the invention provided herein so as to arrive at an optimal hydrodynamic volume or hydrodynamic size for the polypeptides of interest or fragments thereof. As a result the polypeptides of interest or fragments thereof having an optimal hydrodynamic volume can possess the optimally desired characteristics, i.e., improved potency, improved stability, elevated AUC levels, enhanced bioavailability and enhanced circulating half-life.

In one embodiment, provided herein is a pharmaceutical composition comprising a therapeutically effective amount of the CTP-modified polypeptide of interest or fragment thereof provided herein. In another embodiment, a therapeutically effective amount of CTP-modified polypeptides or fragments thereof is determined according to factors such as the specific condition being treated, the condition of the patient being treated, as well as the other ingredients in the composition. In another embodiment, the therapeutic efficacy of the CTP-modified polypeptide or fragment thereof is optimally adjusted by adding or removing glycosylated and/or non-glycosylated CTP peptides in order to arrive at the optimal hydrodynamic volume. It is to be understood that in doing so, a skilled artisan can arrive at a CTP-modified polypeptide or fragment thereof that possesses the optimal therapeutic efficacy.

In one embodiment, the CTP-modified polypeptide or fragment thereof provided herein has therapeutic uses. In another embodiment, the CTP-modified polypeptide or fragment thereof provided herein has prophylactic uses.

In one embodiment, the terms "reducing, reduction, lowering, etc." when used in relation to the methods provided herein refer to 100% reduction from a previously measured or determined level or from a normal level. In another embodiment, the reduction is by 89-99% from a previously determined level. In another embodiment, the reduction is by 79-88% from a previously determined level. In another embodiment, the reduction is by 69-78% from a previously determined level. In another embodiment, the reduction is by 59-68% from a previously determined level. In another embodiment, the reduction is by 49-58% from a previously determined level. In another embodiment, the reduction is by 39-48% from a previously determined level. In another embodiment, the reduction is by 29-38% from a previously determined level. In another embodiment, the reduction is by 19-28% from a previously determined level. In another embodiment, the reduction is by 9-18% from a previously determined level. In another embodiment, the reduction is by 5-8% from a previously determined level. In another embodiment, the reduction is by 1-4% from a previously determined level.

In one embodiment, tissue-specific promoters suitable for use with the present invention include sequences which are functional in one or more specific cell populations. Examples include, but are not limited to, promoters such as albumin that is liver-specific [Pinkert et al., (1987) Genes Dev. 1:268-277], lymphoid-specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). Inducible promoters suitable for use with the present invention include, for example, the tetracycline-inducible promoter (Srour, M. A., et al., 2003. Thromb. Haemost. 90: 398-405).

In one embodiment, the phrase "a polynucleotide molecule" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, a "complementary polynucleotide sequence" refers to a sequence, which results from reverse transcription of messenger RNA using a reverse transcriptase or any other RNA-dependent DNA polymerase. In one embodiment, the sequence can be subsequently amplified in vivo or in vitro using a DNA polymerase.

In one embodiment, a "genomic polynucleotide sequence" refers to a sequence derived (isolated) from a chromosome and thus it represents a contiguous portion of a chromosome.

In one embodiment, a "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing therebetween. In one embodiment, the intronic sequences can be of any source, including of other genes, and typically includes conserved splicing signal sequences. In one embodiment, intronic sequences include cis-acting expression regulatory elements.

In one embodiment, polynucleotides of the present invention are prepared using PCR techniques, or any other method or procedure known to one skilled in the art. In another embodiment, the procedure involves the ligation of two different DNA sequences (See, for example, "Current Protocols in Molecular Biology", eds. Ausubel et al., John Wiley & Sons, 1992).

In one embodiment, polynucleotides of the present invention which encode the engineered polypeptides of interest or fragments thereof provided herein are inserted into expression vectors (i.e., a nucleic acid construct) to enable expression of the recombinant peptide/polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In another embodiment, the expression vector of the present invention includes a shuttle vector which renders this vector suitable for replication and integration in both prokaryotes and eukaryotes. In another embodiment, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the CTP-modified polypeptides or fragments thereof provided herein. In another embodiment, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In one embodiment, non-bacterial expression systems are used (e.g., mammalian expression systems such as CHO cells) to express the polypeptide or fragment thereof provided herein. In another embodiment, the expression vector used to express polynucleotides of the present invention in mammalian cells is pCI-dhfrr vector. Construction of the pCI-dhfrr vector is described, according to one embodiment, in Example's Materials and Methods, below.

In one embodiment, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion proteins are engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447, which is incorporated by reference herein in its entirety. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In one embodiment, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In one embodiment, expression vectors containing regulatory elements from eukaryotic viruses such as retroviruses are used in the present invention. SV40 vectors include pSVT7 and pMT2. In another embodiment, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In one embodiment, recombinant viral vectors are useful for in vivo expression of the peptides/polypeptides of the present invention since they offer advantages such as lateral infection and targeting specificity. In one embodiment, lateral infection is inherent in the life cycle of, for example, a retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992, incorporated herein by reference, for positive-negative selection methods.

In one embodiment, introduction of nucleic acid by viral infection offers several advantages over other methods such as lipofection and electroporation, since higher transfection efficiency can be obtained due to the infectious nature of viruses.

It will be appreciated that the engineered polypeptides or fragments thereof of provided herein can also be expressed from a nucleic acid construct administered to the individual employing any suitable mode of administration (e.g., subcutaneous administration, oral administration, intra-nasal administration, intra-venal administration, or in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In one embodiment, plant expression vectors are used. In one embodiment, the expression of a polypeptide coding sequence is driven by a number of promoters. In another embodiment, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

t will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In one embodiment, transformed cells are cultured under effective conditions, which allow for the expression of high amounts of recombinant engineered oxyntomodulin peptides. In another embodiment, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In another embodiment, a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. In another embodiment, culturing is carried out at a temperature, pH and oxygen content appropriate for a recombinant cell. In another embodiment, the determination of culturing conditions are within the expertise of one of ordinary skill in the art.

In one embodiment, depending on the vector and host system used for production, the resultant polypeptide or fragment thereof or, in another embodiment, the resultant CTP-modified polypeptide or fragment thereof provided herein are expressed within a recombinant cell for glycosylation of the CTP to take place, are secreted into the fermentation medium, or are retained on the outer surface of a mammalian cell.

In one embodiment, following a predetermined time in culture, recovery of the recombinant polypeptide or fragment thereof is effected.

In one embodiment, the phrase "recovering the recombinant engineered polypeptide or fragment thereof" refers to collecting the whole fermentation medium containing the polypeptide or fragment thereof and need not imply additional steps of separation or purification. In another embodiment, additional steps of separation or purification well known in the art are carried out in order to recover the recombinant engineered polypeptide or fragment thereof.

In one embodiment, engineered polypeptides or fragments thereof or variants thereof provided herein are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide or fragment thereof provided herein and fused cleavable moiety. Further, a fusion protein can be designed so that the polypeptide can be readily isolated by affinity chromatography; e.g., by immobilization on a column specific for the cleavable moiety. A cleavage site is engineered between the engineered polypeptides or fragments thereof and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the engineered peptide or polypeptide provided herein is retrieved in "substantially pure" form.

In one embodiment, the phrase "substantially pure" refers to a purity that allows for the effective use of the protein in the applications described herein.

The engineered polypeptide or fragment thereof provided herein can also be synthesized using in vitro expression systems. In another embodiment, in vitro synthesis methods are well known in the art and the components of the system are commercially available.

In one embodiment, the recombinant engineered polypeptides or fragments thereof are synthesized and purified; their therapeutic efficacy can be assayed either in vivo or in vitro. The binding activities of the recombinant engineered polypeptides or fragments thereof of the present invention can be ascertained using various assays as known to one of skill in the art.

In another embodiment, the polypeptides or fragments thereof of the present invention can be provided to the individual per se. In one embodiment, the engineered polypeptides or fragments thereof provided herein can be provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the polypeptide sequence of interest, which is accountable for the biological effect.

In another embodiment, the phrases "physiologically acceptable carrier" and "pharmaceutically acceptable carrier" which are interchangeably used herein refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979)).

In another embodiment, the term "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

Various embodiments of dosage ranges are contemplated by this invention. The dosage of the CTP-modified polypeptide or fragments thereof provided herein, in one embodiment, is in the range of 0.005-100 mg/day. In another embodiment, the dosage is in the range of 0.005-5 mg/day. In another embodiment, the dosage is in the range of 0.01-50 mg/day. In another embodiment, the dosage is in the range of 0.1-20 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-5 mg/day. In another embodiment, the dosage is in the range of 0.5-50 mg/day. In another embodiment, the dosage is in the range of 0.2-15 mg/day. In another embodiment, the dosage is in the range of 0.8-65 mg/day. In another embodiment, the dosage is in the range of 1-50 mg/day. In another embodiment, the dosage is in the range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in a range of 60-120 mg/day. In another embodiment, the dosage is in the range of 12-40 mg/day. In another embodiment, the dosage is in the range of 40-60 mg/day. In another embodiment, the dosage is in a range of 50-100 mg/day. In another embodiment, the dosage is in a range of 1-60 mg/day. In another embodiment, the dosage is in the range of 15-25 mg/day. In another embodiment, the dosage is in the range of 5-10 mg/day. In another embodiment, the dosage is in the range of 55-65 mg/day.

In another embodiment, the dosage is in a range of 50-500 mg/day. In another embodiment, the dosage is in a range of 50-150 mg/day. In another embodiment, the dosage is in a range of 100-200 mg/day. In another embodiment, the dosage is in a range of 150-250 mg/day. In another embodiment, the dosage is in a range of 200-300 mg/day. In another embodiment, the dosage is in a range of 250-400 mg/day. In another embodiment, the dosage is in a range of 300-500 mg/day. In another embodiment, the dosage is in a range of 350-500 mg/day.

In one embodiment, the dosage is 20 mg/day. In one embodiment, the dosage is 30 mg/day. In one embodiment, the dosage is 40 mg/day. In one embodiment, the dosage is 50 mg/day. In one embodiment, the dosage is 0.01 mg/day. In another embodiment, the dosage is 0.1 mg/day. In another embodiment, the dosage is 1 mg/day. In another embodiment, the dosage is 0.530 mg/day. In another embodiment, the dosage is 0.05 mg/day. In another embodiment, the dosage is 50 mg/day. In another embodiment, the dosage is 10 mg/day. In another embodiment, the dosage is 20-70 mg/day. In another embodiment, the dosage is 5 mg/day.

In one embodiment, the dosage of the CTP-modified polypeptides or fragments thereof is 1-5 mg/day. In one embodiment, the dosage of the CTP-modified polypeptides or fragments thereof is 1-3 mg/day. In another embodiment, the dosage of the CTP-modified polypeptides or fragments thereof is 2 mg/day.

In another embodiment, the dosage is 1-90 mg/day. In another embodiment, the dosage is 1-90 mg/2 days. In another embodiment, the dosage is 1-90 mg/3 days. In another embodiment, the dosage is 1-90 mg/4 days. In another embodiment, the dosage is 1-90 mg/5 days. In another embodiment, the dosage is 1-90 mg/6 days. In another embodiment, the dosage is 1-90 mg/week. In another embodiment, the dosage is 1-90 mg/9 days. In another embodiment, the dosage is 1-90 mg/11 days. In another embodiment, the dosage is 1-90 mg/14 days.

In another embodiment, the CTP-modified polypeptide or fragment thereof dosage is 10-50 mg/day. In another embodiment, the dosage is 10-50 mg/2 days. In another embodiment, the dosage is 10-50 mg/3 days. In another embodiment, the dosage is 10-50 mg/4 days. In another embodiment, the dosage is 10-50 micrograms mg/5 days. In another embodiment, the dosage is 10-50 mg/6 days. In another embodiment, the dosage is 10-50 mg/week. In another embodiment, the dosage is 10-50 mg/9 days. In another embodiment, the dosage is 10-50 mg/11 days. In another embodiment, the dosage is 10-50 mg/14 days.

In another embodiment, the doses can be given as mg/kg or units/kg. In another embodiment, dosage of the CTP-modified polypeptide or fragments thereof provided herein, in one embodiment, is in the range of 0.005-100 mg/kg or units/kg. In another embodiment, the dosage is in the range of 0.005-5 mg/kg or units/kg. In another embodiment, the dosage is in the range of 0.01-50 mg/kg or units/kg. In another embodiment, the dosage is in the range of 0.1-20 mg/kg or units/kg. In another embodiment, the dosage is in the range of 0.1-10 mg/kg or units/kg. In another embodiment, the dosage is in the range of 0.01-5 mg/kg or units/kg. In another embodiment, the dosage is in the range of 0.001-0.01 mg/kg or units/kg. In another embodiment, the dosage is in the range of 0.001-0.1 mg/kg or units/kg. In another embodiment, the dosage is in the range of 0.1-5 mg/kg or units/kg. In another embodiment, the dosage is in the range of 0.5-50 mg/kg or units/kg. In another embodiment, the dosage is in the range of 0.2-15 mg/kg or units/kg. In another embodiment, the dosage is in the range of 0.8-65 mg/kg or units/kg. In another embodiment, the dosage is in the range of 1-50 mg/kg or units/kg. In another embodiment, the dosage is in the range of 5-10 mg/kg or units/kg. In another embodiment, the dosage is in the range of 8-15 mg/kg or units/kg. In another embodiment, the dosage is in a range of 10-20 mg/kg or units/kg. In another embodiment, the dosage is in the range of 20-40 mg/kg or units/kg. In another embodiment, the dosage is in a range of 60-120 mg/kg or units/kg. In another embodiment, the dosage is in the range of 12-40 mg/kg or units/kg. In another embodiment, the dosage is in the range of 40-60 mg/kg or units/kg. In another embodiment, the dosage is in a range of 50-100 mg/kg or units/kg. In another embodiment, the dosage is in a range of 1-60 mg/kg or units/kg. In another embodiment, the dosage is in the range of 15-25 mg/kg or units/kg. In another embodiment, the dosage is in the range of 5-10 mg/kg or units/kg. In another embodiment, the dosage is in the range of 55-65 mg/kg or units/kg.

In another embodiment, a polypeptide comprising polypeptides or fragments thereof provided herein and at least one CTP unit is formulated in an intranasal dosage form. In another embodiment, a polypeptide comprising polypeptides or fragments thereof provided herein and at least one CTP unit is formulated in an injectable dosage form. In another embodiment, a polypeptide comprising polypeptides or fragments thereof provided herein and at least one CTP unit is administered to a subject in a dose ranging from 0.0001 mg to 0.6 mg. In another embodiment, a polypeptide comprising polypeptides or fragments thereof provided herein and at least one CTP unit is administered to a subject in a dose ranging from 0.001 mg to 0.005 mg. In another embodiment, a polypeptide comprising polypeptides or fragments thereof provided herein and at least one CTP unit is administered to a subject in a dose ranging from 0.005 mg to 0.01 mg. In another embodiment, a polypeptide comprising polypeptides or fragments thereof provided herein and at least one CTP unit is administered to a subject in a dose ranging from 0.01 mg to 0.3 mg. In another embodiment, a polypeptide comprising polypeptides or fragments thereof provided herein and at least one CTP unit is administered to a subject in a dose in a dose ranging from 0.2 mg to 0.6 mg. In another embodiment, the polypeptides or fragments thereof provided herein is free of CTPs on its amino terminus.

In another embodiment, a polypeptide comprising a polypeptide or fragment thereof provided herein and at least one CTP unit is administered to a subject in a dose ranging from 0.2 mg to 2 mg. In another embodiment, a polypeptide comprising a polypeptide or fragment thereof provided herein and at least one CTP unit is administered to a subject in a dose ranging from 2 mg to 6 mg. In another embodiment, a polypeptide comprising a polypeptide or fragment thereof provided herein and at least one CTP unit is administered to a subject in a dose ranging from 4 mg to 10 mg. In another embodiment, a polypeptide comprising a polypeptide or fragment thereof provided herein and at least one CTP unit is administered to a subject in a dose ranging from 5 mg and 15 mg.

In another embodiment, a polypeptide comprising a polypeptide or fragment thereof provided herein and at least one CTP unit is administered to a subject in a dose ranging from 0.2 mg to 2 mg. In another embodiment, a polypeptide comprising a polypeptide or fragment thereof provided herein and at least one CTP unit is administered to a subject in a dose ranging from 2 mg to 6 mg. In another embodiment, a polypeptide comprising a polypeptide or fragment thereof provided herein and at least one CTP unit is administered to a subject in a dose ranging from 4 mg to 10 mg. In another embodiment, a polypeptide comprising a polypeptide or fragment thereof provided herein and at least one CTP unit is administered to a subject in a dose ranging from 5 mg and 15 mg.

In another embodiment, the dosage of CTP-modified polypeptides or fragments thereof provided herein is such that it contains 65% of the amount of the agonist than that administered using the non-CTP-modified polypeptides or fragments thereof. In another embodiment, the dosage of CTP-modified polypeptides or fragments thereof provided herein is such that it contains 55% of the amount of the agonist than that administered using the non-CTP-modified polypeptides or fragments thereof. In another embodiment, the dosage of CTP-modified polypeptides or fragments thereof provided herein is such that it contains 45% of the amount of the agonist than that administered using the non-CTP-modified polypeptides or fragments thereof. In another embodiment, the dosage of CTP-modified polypeptides or fragments thereof provided herein is such that it contains 10% of the amount of the agonist than that administered using the non-CTP-modified polypeptides or fragments thereof. In another embodiment, the dosage of CTP-modified polypeptides or fragments thereof provided herein is such that it contains 25% of the amount of the agonist than that administered using the non-CTP-modified polypeptides or fragments thereof. In another embodiment, the dosage of CTP-modified polypeptides or fragments thereof provided herein is such that it contains 35% of the amount of the agonist than that administered using the non-CTP-modified polypeptides or fragments thereof. In another embodiment, the dosage of CTP-modified polypeptides or fragments thereof provided herein is such that it contains 75% of the amount of the agonist than that administered using the non-CTP-modified polypeptides or fragments thereof. In another embodiment, the dosage of CTP-modified polypeptides or fragments thereof provided herein is such that it contains 100% of the amount of the agonist than that administered using the non-CTP-modified agonist. However, even if the dosage contains the same amount of agonist as non-CTP-modified polypeptides or fragments thereof, it is still advantageous to subjects in that it will be administered less frequently because of its increased half-life compared to normal agonist.

In another embodiment, a therapeutically effective amount of a conjugated polypeptide or fragments thereof provided herein is between 50-500 IU per kg body weight administered once a day. In another embodiment, a therapeutically effective amount of a conjugated polypeptide or fragment thereof is 150-250 IU per kg body weight, administered once a day. In another embodiment, a pharmaceutical composition comprising a conjugated polypeptide or fragment thereof is formulated at a strength effective for administration by various means to a human patient.

In one embodiment, the CTP-modified polypeptide comprising polypeptides or fragments thereof provided herein is administered in an amount effective to bring circulating polypeptides or fragments thereof's activity to 20-30 IU/dL in a subject. In another embodiment, the CTP-modified polypeptide comprising polypeptides or fragments thereof provided herein is administered in an amount effective to bring circulating polypeptides or fragments thereof's activity to 25-50 IU/dL in a subject. In another embodiment, the CTP-modified polypeptide comprising polypeptides or fragments thereof provided herein is is administered in an amount effective to bring circulating polypeptides or fragments thereof's activity to 50-100 IU/dL in a subject. In another embodiment, the CTP-modified polypeptide comprising polypeptides or fragments thereof provided herein is administered in an amount effective to bring circulating polypeptides' or fragments thereof's activity to 100-200 IU/dL in a subject. In another embodiment, the CTP-modified polypeptide comprising polypeptides or fragments thereof provided herein is administered in an amount effective to bring circulating polypeptides or fragments thereof's activity to 10-50 IU/dL in a subject. In another embodiment, the CTP-modified polypeptide comprising polypeptides or fragments thereof provided herein is administered in an amount effective to bring circulating polypeptides or fragments thereof's activity to 20-100 IU/dL in a subject.

In one embodiment, the CTP-modified polypeptides or fragments thereof provided herein are administered to a subject on a weekly basis. In another embodiment, the CTP-modified polypeptides or fragments thereof provided herein are administered to a subject twice a week. In another embodiment, the CTP-modified polypeptides or fragments thereof provided herein are administered to a subject on a fortnightly (once every two weeks) basis. In another embodiment, the CTP-modified polypeptides or fragments thereof provided herein are administered to a subject twice a month. In another embodiment, the CTP-modified polypeptides or fragments thereof provided herein are administered to a subject once a month. In another embodiment, the CTP-modified polypeptides or fragments thereof provided herein are administered to a subject on a daily basis. In another embodiment, the CTP-modified polypeptides or fragments thereof provided herein are administered to a subject every two days. In another embodiment, a polypeptide comprising a polypeptide or fragment thereof provided herein and at least one CTP unit is administered to a subject once every three days.

In another embodiment, a polypeptide comprising a polypeptide or fragment thereof and at least one CTP unit is administered to a subject once every four days. In another embodiment, a polypeptide comprising a polypeptide or fragment thereof provided herein and at least one CTP unit is administered to a subject once every five days. In another embodiment, a polypeptide comprising a polypeptide or fragment thereof provided herein and at least one CTP unit is administered to a subject once every six days. In another embodiment, a polypeptide comprising a polypeptide or fragment thereof provided herein and at least one CTP unit is administered to a subject once every 7-14 days. In another embodiment, a polypeptide comprising a polypeptide or fragment thereof provided herein and at least one CTP unit is administered to a subject once every 10-20 days. In another embodiment, a polypeptide comprising a polypeptide or fragment thereof provided herein and at least one CTP unit is administered to a subject once every 5-15 days. In another embodiment, a polypeptide comprising a polypeptide or fragment thereof provided herein and at least one CTP unit is administered to a subject once every 15-30 days.

In another embodiment, the methods of the invention include increasing the compliance of patients afflicted with chronic illnesses that are in need of a polypeptide or fragments thereof provided herein therapy. In another embodiment, by increasing the hydrodynamic size of a CTP-modified polypeptide or fragment thereof by a factorprovided herein. In another embodiment, the methods of the invention enable reduction in the dosing frequency of the polypeptide or fragment thereof.

In another embodiment, the term compliance comprises adherence. In another embodiment, the methods of the invention include increasing the compliance of patients in need of a therapy by increasing the hydrodynamic size of a polypeptide or fragment thereof by a factor or increment provided herein which results in reducing the frequency of administration of the polypeptide or fragment thereof. In another embodiment, reduction in the frequency of administration of the polypeptide or fragment thereof provided herein is achieved due to the CTP modifications and a subsequent increase hydrodynamic size by a factor or increment provided herein, which renders the polypeptide or fragments thereof more stable. In another embodiment, reduction in the frequency of administration of the polypeptide or fragment thereof provided herein is achieved due to the CTP modifications and subsequent increase in hydrodynamic size by a factor or increment provided herein, which increase the half-life (T½) of the polypeptide or fragments thereof. In another embodiment, reduction in the frequency of administration of the polypeptide or fragments thereof provided herein is achieved by increasing the hydrodynamic size of a polypeptide or fragment thereof by a factor or incrementprovided herein which results in increasing the clearance time or reducing the clearance rate of the polypeptide or fragment thereof provided herein.

In another embodiment, reduction in the frequency of administration of a polypeptide or fragment thereof provided herein is achieved by increasing the hydrodynamic size of a polypeptide or fragment thereof by a factor or increment provided herein which results in increasing the AUC measure of the polypeptide or fragments thereof.

Oral administration, in one embodiment, comprises a unit dosage form comprising tablets, capsules, lozenges, chewable tablets, suspensions, emulsions and the like. Such unit dosage forms comprise a safe and effective amount of the desired polypeptides or fragments thereof provided herein, each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In another embodiment, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In another embodiment, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in another embodiment, comprise liquid solutions, emulsions, to suspensions, and the like. In another embodiment, pharmaceutically-acceptable carriers suitable for preparation of such compositions are well known in the art. In another embodiment, liquid oral compositions comprise from about 0.001% to about 0.933% of the desired compound or compounds, or in another embodiment, from about 0.01% to about 10%.

In one embodiment, compositions for use in the methods of this invention comprise solutions or emulsions, which in another embodiment are aqueous solutions or emulsions comprising a safe and effective amount of the compounds of the present invention and optionally, other compounds, intended for topical intranasal administration. In another embodiment, the compositions comprise from about 0.001% to about 10.0% w/v of a subject compound, more preferably from about 00.1% to about 2.0, which is used for systemic delivery of the compounds by the intranasal route.

In another embodiment, a polypeptide comprising a polypeptide or fragment thereof and at least one CTP unit is injected into the muscle (intramuscular injection). In another embodiment, a polypeptide comprising a polypeptide or fragment thereof and at least one CTP unit is injected below the skin (subcutaneous injection). In another embodiment, a polypeptide comprising a polypeptide or fragment thereof provided herein and at least one CTP unit is injected into the muscle. In another embodiment, a polypeptide comprising a polypeptide or fragment thereof provided herein and at least one CTP unit is injected into the skin. In another embodiment, a polypeptide or fragment thereof provided herein as described herein is administered via systemic administration. In another embodiment, a polypeptide or fragment thereof provided herein as described herein is administered by intravenous injection. In another embodiment, administration can be parenteral, pulmonary, oral, topical, intradermal, intramuscular, intraperitoneal, intravenous, subcutaneous, intranasal, transnasal, intraocular, ophthalmic, epidural, buccal, rectal, transmucosal, intestinal or parenteral delivery, including intramedullary injections as well as intrathecal or direct intraventricular administration.

In another embodiment, the preparation is administered in a local rather than systemic manner, for example, via injection of the preparation directly into a specific region of a patient's body.

In one embodiment, the route of administration may be enteral. In another embodiment, the route may be conjunctival, transdermal, intradermal, intra-arterial, vaginal, rectal, intratumoral, parcanceral, transmucosal, intramuscular, intravascular, intraventricular, intracranial, intra-nasal, sublingual, or a combination thereof.

In another embodiment, the pharmaceutical compositions are administered by intravenous, intra-arterial, or intramuscular injection of a liquid preparation. In another embodiment, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, and in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, for e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in a conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables of the invention are formulated in aqueous solutions. In one embodiment, injectables of the invention are formulated in physiologically compatible buffers such as Hank's solution, Ringer's solution, or physiological salt buffer. In another embodiment, for transmucosal administration, penetrants appropriate to the barrier to be permeated are used in the formulation. Such penetrants are generally known in the art.

In one embodiment, the preparations described herein are formulated for parenteral administration, for e.g., by bolus injection or continuous infusion. In another embodiment, formulations for injection are presented in unit dosage form, for e.g., in ampoules or in multidose containers with optionally, an added preservative. In another embodiment, compositions are suspensions, solutions or emulsions in oily or aqueous vehicles, and contain formulatory agents such as suspending, stabilizing and/or dispersing agents.

The compositions also comprise, in another embodiment, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in another embodiment, local anesthetics or other actives. The compositions can be used as sprays, mists, drops, and the like.

In one embodiment, pharmaceutical compositions for parenteral administration include aqueous solutions of the active preparation in water-soluble form. Additionally, suspensions of the active ingredients can be prepared as appropriate oil or water based injection suspensions. Suitable lipophilic solvents or vehicles include, in another embodiment, fatty oils such as sesame oil, or synthetic fatty acid esters such as ethyl oleate, triglycerides or liposomes. Aqueous injection suspensions contain, in another embodiment, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; J. E. Diederichs and al., Pharm./nd. 56 (1994) 267-275).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, for e.g., Goodson, in Medical Applications of Controlled Release, supra, vol. 2, pp. 115-138 (1984). Other controlled release systems are discussed in the review by Langer (Science 249:1527-1533 (1990).

In another embodiment, the active ingredient is in powder form for constitution with a suitable vehicle, for e.g., sterile, pyrogen-free water based solution, before use. Compositions are formulated, in another embodiment, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In one embodiment, pharmaceutical compositions suitable for use in context of the present invention include compositions wherein the active ingredients are contained in an amount effective to achieve the intended purpose. In another embodiment, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g.

colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compounds solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

Preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also prepared, placed in an appropriate container, and labeled for treatment of an indicated condition.

In another embodiment, a polypeptide or fragment thereof or a variant (CTP-modified) form thereof, as described herein, is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized polypeptide or fragment thereof provided herein, prepared in sterile water for injection. In another embodiment, a pharmaceutical composition comprises a lyophilized polypeptide or fragments thereof provided herein, is prepared in sterile PBS for injection. In another embodiment, a pharmaceutical composition comprises a lyophilized polypeptide or fragment thereof provided herein, prepared in sterile 0.9% NaCl for injection.

In another embodiment, the pharmaceutical composition comprises a CTP-modified polypeptide or fragment thereof as described herein and complex carriers such as human serum albumin, polyols, sugars, and anionic surface active stabilizing agents. In another embodiment, the pharmaceutical composition comprises a CTP-polypeptide or fragment thereof and lactobionic acid and an acetate/glycine buffer. In another embodiment, the pharmaceutical composition comprises a CTP-modified polypeptide or fragment thereof as described herein and amino acids, such as arginine or glutamate that increase the solubility of interferon compositions in water. In another embodiment, the pharmaceutical composition comprises a lyophilized CTP-modified polypeptide or fragments thereof as described herein and glycine or human serum albumin (HSA), a buffer (e.g. acetate) and an isotonic agent (e.g. NaCl). In another embodiment, the pharmaceutical composition comprises a lyophilized CTP-modified polypeptide or fragments thereof, as described herein and phosphate buffer, glycine and HSA.

In another embodiment, the pharmaceutical composition comprising a CTP-modified polypeptide or fragments thereof, as described herein is stabilized when placed in buffered solutions having a pH between about 4 and 7.2. In another embodiment, the pharmaceutical composition comprising a CTP-modified polypeptide or fragments thereof is in a buffered solution having a pH between about 4 and 8.5. In another embodiment, the pharmaceutical composition comprising a CTP-modified polypeptide or fragments thereof is in a buffered solution having a pH between about 6 and 7. In another embodiment, the pharmaceutical composition comprising a CTP-modified polypeptide or fragments thereof is in a buffered solution having a pH of about 6.5. In another embodiment, the pharmaceutical composition comprising a CTP-modified polypeptide or fragments thereof as described herein is stabilized with an amino acid as a stabilizing agent and in some cases a salt (if the amino acid does not contain a charged side chain).

In another embodiment, the pharmaceutical composition comprising a CTP-modified polypeptide or fragments thereof as described herein is a liquid composition comprising a stabilizing agent at between about 0.3% and 5% by weight which is an amino acid.

In another embodiment, the pharmaceutical composition comprising a CTP-modified polypeptide or fragments thereof as described herein provides dosing accuracy and product safety. In another embodiment, the pharmaceutical composition comprising a CTP-modified polypeptide or fragments thereof as described herein provides a biologically active, stable liquid formulation for use in injectable applications. In another embodiment, the pharmaceutical composition comprises a non-lyophilized CTP-modified polypeptide or fragments thereof as described herein.

In another embodiment, the pharmaceutical composition comprising a CTP-modified polypeptide or fragment thereof provided herein provides a liquid formulation permitting storage for a long period of time in a liquid state facilitating storage and shipping prior to administration.

In another embodiment, the pharmaceutical composition comprising a CTP-modified polypeptide or fragments thereof, provided herein comprises solid lipids as matrix material. In another embodiment, the injectable pharmaceutical composition comprising a CTP-modified polypeptide or fragments thereof, as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser E P 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a CTP-modified polypeptide or fragment thereof, as described herein comprises polymeric microparticles. In another embodiment, the pharmaceutical composition comprising a CTP-modified polypeptide or fragment thereof, as described herein comprises nanoparticles. In another embodiment, the pharmaceutical composition comprising a CTP-modified polypeptide or fragment thereof, as described herein comprises liposomes. In another embodiment, the pharmaceutical composition comprising a CTP-modified polypeptide or fragment thereof, as described herein comprises lipid emulsion. In another embodiment, the pharmaceutical composition comprising a CTP-modified polypeptide or fragment thereof, as described herein comprises microspheres. In another embodiment, the pharmaceutical composition comprising a CTP-modified polypeptide or fragment thereof, as described herein comprises lipid nanoparticles. In another embodiment, the pharmaceutical composition comprising a CTP-modified polypeptide or fragment thereof, as described herein comprises lipid nanoparticles comprising amphiphilic lipids. In another embodiment, the pharmaceutical composition comprising a CTP-modified polypeptide or fragments thereof, as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the polypeptides or fragments thereof provided herein can be provided to the individual with additional active agents to achieve an improved therapeutic effect as compared to treatment with each agent by itself. In another embodiment, measures (e.g., dosing and selection of the complementary agent) are taken to avoid adverse side effects which are associated with combination therapies.

In one embodiment, the term "about," means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

Production of Different CTP-Modified Proteins

The DNA coding region of human growth hormone (hGH), erythropoietin (EPO), APO-A1, Factor IX and Factor VII were ligated to the DNA sequence of CTP peptide. The CTP peptide was fused to the N-terminus and/or C-terminus in single copy or in tandem, as detailed in Table 2. The engineered plasmids were transfected and expressed in CHO cell line that enable proper structuring of the O-glycans, which play a critical role in increasing the hydrodynamic volume of the proteins (see Table 5). The different proteins were purified according to custom processes that were developed uniquely for each protein, as detailed below:

CTP-EPO-CTP-CTP: The clarified harvest was loaded on a Blue Sepharose column. The eluted product was diluted and loaded on a Q Sepharose column. The eluted fraction from the Q Sepharose column was processed by ultrafiltration using an Amicon centrifugal device (30 kDa cut-off) and was dialyzed. The concentrated and dialyzed fraction was loaded on a Phenyl Sepharose column. The eluted fraction from Phenyl Sepharose was processed by ultrafiltration with an Amicon centrifugal device (30 kDa cut-off) and dialyzed against PBS pH 7.

CTP-CTP-EPO and CTP-CTP-EPO-CTP-CTP: Clarified harvest was loaded onto a DEAE Sepharose column and eluted. The eluted fraction was conditioned with Ammonium Sulfate and was loaded on a Phenyl Sepharose HS column Elution Phenyl was concentrated and dialyzed. The next two columns are in a flow-through mode: Hydroxyapatite type I 40μ and SP Sepharose. The final product was concentrated, dialyzed and stored at −20° C.

APO-CTP and APO-CTP-CTP: These two versions of APO proteins were purified with an affinity column (Capture Select Apo, Bac). The clarified harvest was diluted 1:1 with PBS and eluted from the column. The elution was concentrated and dialyzed against PBS and stored at −80° C.

CTP-hGH-CTP-CTP: The clarified harvest is filtered using UFDF1. Virus inactivation is accomplished. The first chromatography is an anion exchange chromatography, DEAE Sepharose FF. The resin of the second chromatography is Phenyl Sepharose. The eluate pool of the second chromatography is diafiltrated and concentrated in UFDF-2. The UFDF-2 step is followed by two more chromatographies, Ceramic Hydroxyapatite Type I 40 μM and SP Sepharose FF, in a flow-through mode. Nanofiltration was performed. The product solution is concentrated to 41±1 mg/mL and dialyzed.

FIX-CTP-CTP-CTP: Tris-HCl, pH 9 was added to clarified harvest. The first chromatography column was carried out using an anion exchange, Q column. The next column was Heparin Hyper D. The eluted fraction was adjusted to final concentration of 10 mM Sodium Phosphate with a final pH of 6.8. The last chromatography step was performed on CHT resin. The eluted fraction was concentrated and dialyzed againt TBS pH 7.5.

FIX-CTP-CTP-CTP-CTP: The clarified harvest is concentrated and dialyzed. The only chromatography step is an affinity chromatography, immobilized Jacalin. The eluted product was concentrated and dialyzed against TBS pH 7.5.

FIX-CTP-CTP-CTP-CTP-CTP: The clarified harvest is concentrated and dialyzed. The only chromatography step is an affinity chromatography, immobilized Jacalin The eluted product was concentrated and dialyzed against TBS pH 7.5.

APOA1-CTP-CTP: The clarified harvest was concentrated and dialyzed. The first chromatography was carried out using an anion exchange chromatography, DEAE Sepharose FF column. The second chromatography step was performed on Immobilized Jacalin resin The eluate was diafiltrated and concentrated in UFDF-2 against TBS pH 7.4.

APOA1-CTP: The first chromatography was carried out using an affinity chromatography, Capture-Select APO-AI column. The second chromatography step was performed on Immobilized Jacalin resin The eluate was diafiltrated and concentrated in UFDF-2 against TBS pH 7.4.

APOA1: The diluted harvest was loaded on affinity chromatography, Capture-Select APO-AI. The eluate was diafiltrated and concentrated in UFDF-2 against TBS pH 7.4.

FVIIa-CTP-CTP-CTP: The clarified harvest was concentrated and dialyzed. Virus inactivation was accomplished The first chromatography was carried out usig an affinity column, VII Select. The eluted fraction was diluted before loading on the next column-Ceramic Hydroxyapatite (CHT). The CHT eluate was loaded on Phenyl Sepharose column. The eluate was diafiltrated and was activated on an anion exchange chromatography Column. The column is than washed and the product was eluted. Nanofiltration was performed.

FVIIa-CTP-CTP-CTP-CTP-CTP: The clarified harvest was concentrated and dialyzed. The first chromatography was carried out using an affinity column, VII Select. The eluted fraction was loaded on the next column—Ceramic Hydroxyapatite (CHT). The column was washed and the product was eluted. The CHT eluate was loaded on Phenyl Sepharose column. The eluate is diafiltrated and concentrated. Factor VII was activated on an anion exchange chromatography. The column was then washed and the product was eluted.

Table 2: Schematic Description of CTP-Modified Protein

TABLE 2

Schematic description of
CTP-modified protein
Plasmid schematic description

| |
| --- |
| CTP-hGH-CTP-CTP (MOD-4023) |
| CTP-CTP-EPO |
| CTP-EPO-CTP-CTP |
| CTP-CTP-EPO-CTP-CTP |
| APO-CTP |
| APO-CTP-CTP |
| FIX-CTP-CTP-CTP |
| FIX-CTP-CTP-CTP-CTP |
| FIX CTP-CTP CTP CTP-CTP |
| FVIIa-CTP-CTP-CTP |
| FVIIa-CTP-CTP-CTP-CTP-CTP |

Deglycosylation of CTP-Modified Proteins

Deglycosylation of CTP-modified proteins was performed using Glyko Sialidase A (cat. no. PZ PZGK80040, Prozyme), O-glycanase (cat. no. PZ PZGK80090, Prozyme) and N-glycanase (cat. no. PZGKE-5006A, Prozyme). Proteins were digested for 2 h (at 37° C.) with sialidasa A, followed by digestion with O-glycanase and if needed with N-glycanase for overnight.

Molecular Weight Determination by MALDI-TOF

Molecular weights (Mw) of the CTP-modified proteins were measured by MALDI-TOF technology using the REFLEX-IV model (Bruker Daltonics, Bremen, Germany). Matrix-assisted laser desorption/ionisation-time of flight mass spectrometry (MALDI-TOF MS) is a technique in which a co-precipitate of an UV-light absorbing matrix and a biomolecule like proteins or peptide is irradiated by a laser pulse. The ionized biomolecules are accelerated in an electric field and enter the flight tube. During the flight in this tube, different molecules are separated according to their mass to charge ratio and reach the detector at different times. In this way each molecule yields a distinct signal that can be converted to molecular weight. The method is used for characterization of different proteins and peptide with molecular masses between 400 and 350,000 Da. It is a very sensitive method, which allows the detection of low (10-15 to 10-18 mole) quantities of sample with an accuracy of 0.1-0.01%. The measurements were performed at the Analytical Research Services Unit (Ben-Gurion University, Beer-Sheva, Israel).

Analysis of Hydrodynamic Size by HPLC Using SEC Column

The hydrodynamic size of the proteins were measured by HPLC (Dionex UltiMate 3000) using TSKgel G2000SW SEC column (cat. no. 08540, TosoHaas) for hGH, Epo and Apo native and related CTP-modified proteins or a TSKgel G3000WXL SEC column (cat. no. 08541, TosoHaas) for Factor IX and Factor VII native and related CTP-modified proteins. The H Mw calibration kit (Cat. No. 151-1901, BioRad) was used for measuring proteins size The results were fitted to a logarithmic fit (y=a*ln X+b) and the hydrodynamic sizes of the different proteins were calculated.

Results

Example 1: Production of Different CTP-Modified Proteins

Figure 2:
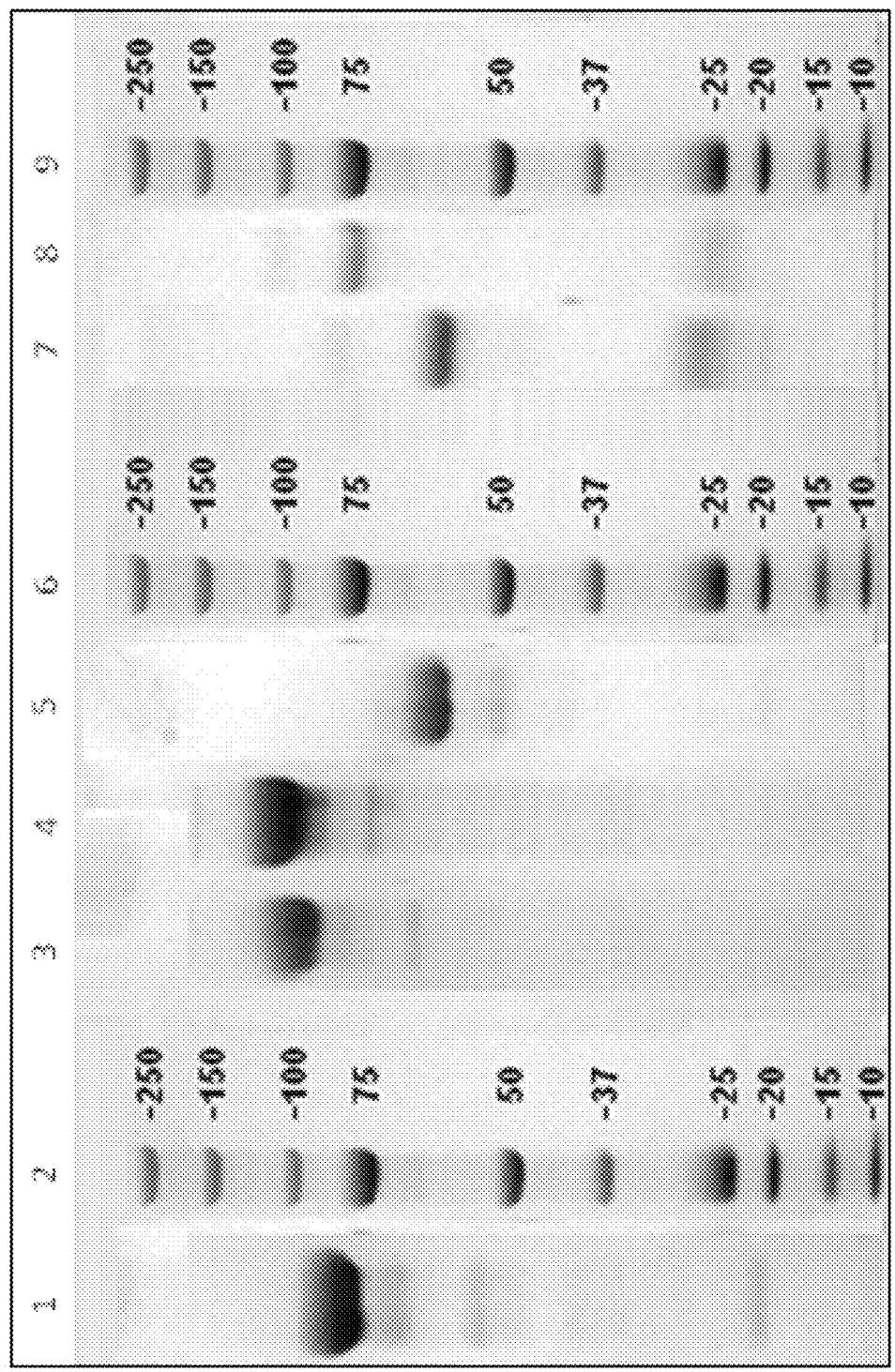
FIG. 2 shows an SDS-PAGE analysis of five different purified CTP-modified proteins and their corresponding native proteins. 1. FIX-CTP-CTP-CTP 2. size marker 3. FIX-CTP-CTP-CTP-CTP 4. FIX-CTP-CTP-CTP-CTP-CTP 5. Mononine® (rFIX) 6. size marker 7. FVIIa-CTP-CTP-CTP 8. FVIIa-CTP-CTP-CTP-CTP-CTP 9. size marker.

Eleven different CTP-modified proteins were transfected and expressed in a CHO cell line. The various harvests were purified according to the methods described above. The purified proteins are shown in FIGS. 1 & 2.

Example 2: Analysis of Molecular Weight by MALDI-TOF Method

Figure 3A:
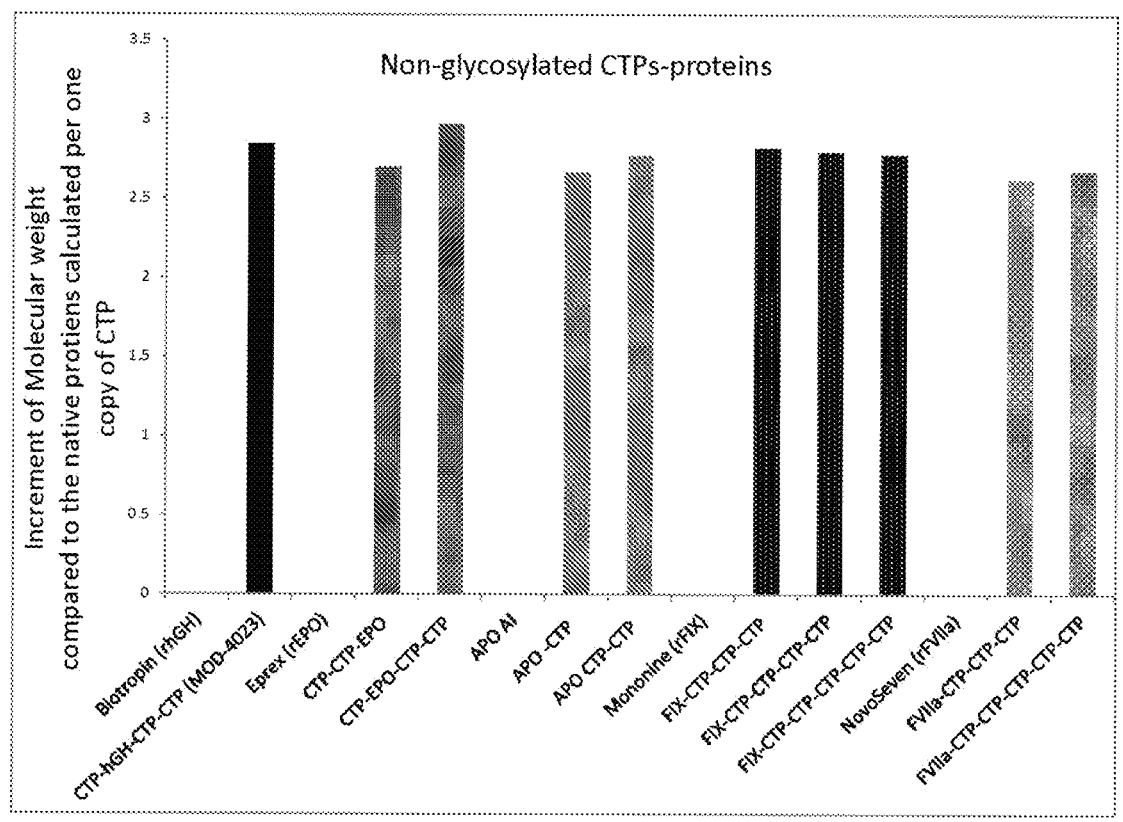
FIG. 3 shows increment of molecular weight (kDa) of one copy of CTP of both non-glycosylated (A) and glycosylated (B) CTP-modified proteins as was measured by MALDI-TOF.
Figure 3B:
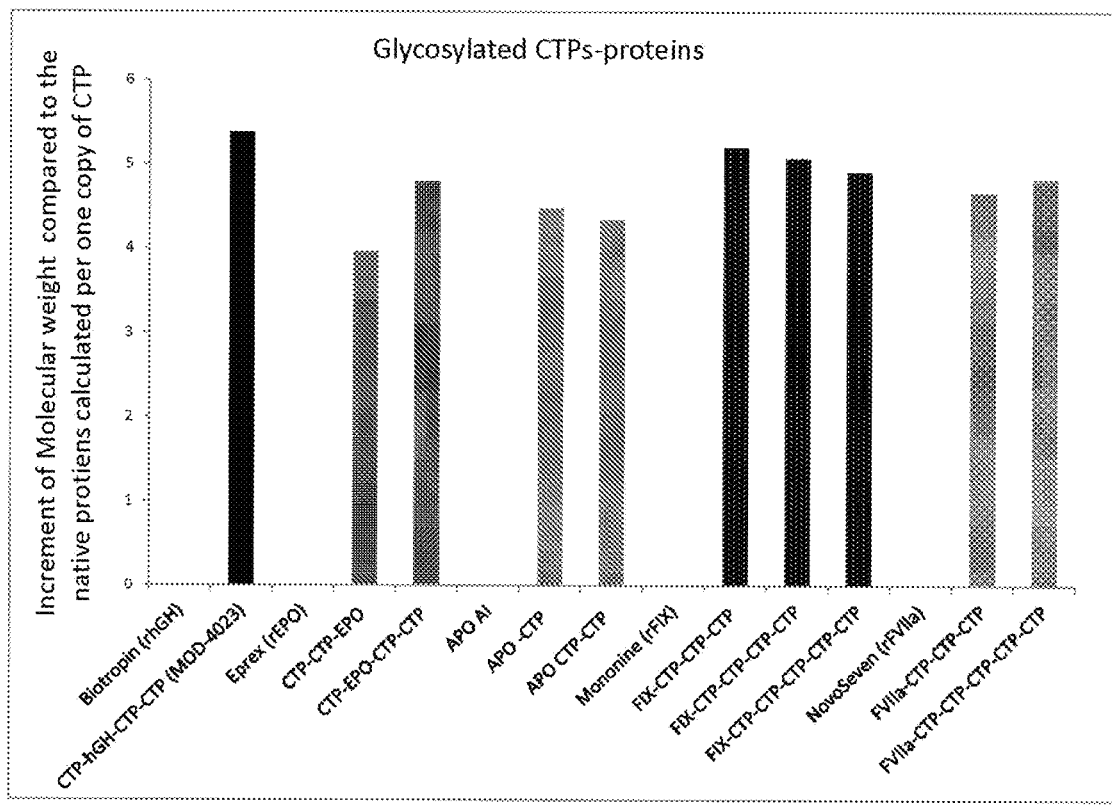

The molecular weight of different glycosylated and non-glycosylated CTP-modified proteins was determined using MALDI-TOF technology and was compared to their corresponding native proteins' (intact proteins which are not fused to CTP, namely, Biotropin for hGH, EPREX® for Epo, ApoAI, Mononine® for Factor IX and Novoseven® for FVIIa) molecular weight Table 3). The measured Mw for all native and non-glycosylated proteins was in good agreement with the theoretical Mw, which is based on the proteins' amino acid sequences. The increments in the molecular weights per one copy of non-glycosylated and glycosylated CTP were calculated and are depicted in FIGS. 3A and 3B, respectively. The contribution of one copy of CTP to the molecular weight was calculated as follows: First, the increment in the molecular weight was calculated by subtracting the measured, or the theoretical—in the case of native hGH—, molecular weight of the native proteins from the measured molecular weight of their corresponding CTP-modified proteins. Then, the calculated increment was divided by the number of CTP copies for each protein. For example, MOD-4023 (hGH that was fused to one copy of CTP at the N-terminus and to 2 copies of CTP in tandem at the C-terminus) has molecular weight of 38,128, while the native hGH has a theoretical molecular weight of 22,000. The difference between those two proteins is 16.13 kDa which means that the contribution of each glycosylated CTP is 5.4 kDa (16.13 divided by 3 copies of CTP). The average contribution of one copy of non-glycosylated CTP in all measured proteins is 2.76 kDa±0.103 (FIG. 3A, Table 3). This result is aligned with the theoretical Mw of a single CTP, which is 2.78 kDa. The glycosylated CTP contributes an average of 4.76 kDa±0.422 to the Mw (FIG. 3B, Table 3), without significant differences between the various measured proteins.

Example 3: Analysis of Hydrodynamic Size by HPLC Method

Hydrodynamic volume is the major parameter influencing the retention time (RT) of proteins when passed through size exclusion column. Therefore, protein sizes were calculated by SEC column using HMw Gel filtration calibration kit (cat. no. 151-1901, BioRad). The retention time of the standards were measured in both SEC TSK 2000 and TSK 3000 columns and the % relative error (% RE) for each column was calculated in order to determine the precision of the analytical methods. The % RE of the obsereved Mw of the calibration proteins were calculated and compared to the known and expected Mw of the calibration proteins. The results of the calculated Mw for the calibration curve and the % RE are presented in Table 4a for TSK 2000 SEC column and in Table 4b for TSK 3000 SEC column. The results show that the % RE was below or equal to 20% (<20%), indicating high precision for a broad range of a protein's determined molecular weight.

TABLE 4a

H Mw calibration curve results and calculated % RE using TSK 2000. The expected molecular weight of the calibration curve proteins were provided by the commercial kit (H Mw calibration kit BioRad Cat. No. 151-1901) that was used.

| Standard proteins | Expected M.W. | R.T. | Observed M.W. | % RE |
|---|---|---|---|---|
| Gamma-globulin | 158,000 | 15.535 | 155279.16 | −1.72 |
| Ovalbumin | 44,000 | 18.535 | 52924.39 | 20.28 |
| Myoglobulin | 17,000 | 22.315 | 13635.14 | −19.79 |
| Vitamin B12 | 1,350 | 28.61 | 1424.88 | 5.55 |

TABLE 3

MALDI-TOF results of non-glycosylated and glycosylated CTP-modified proteins and their corresponding native proteins.

| Proteins Description | Theoretical Mw (based on protein backbone excluding glycan contribution) | Non-glycosylated proteins. MALDI-TOF results (Da) | Glycosylated proteins. MALDI-TOF results (Da) | Increment of molecular size per one copy of non-glycosylated CTP | Increment of molecular size per one copy of glycosylated CTP |
|---|---|---|---|---|---|
| Biotropin(rhGH) | 22000 | ND | ND | ND | ND |
| CTP-hGH-CTP-CTP (MOD-4023) | 30469.4 | 30525 | 38128 | 2.8 | 5.4 |
| EPREX ®(rEPO) | 18396 | 18246 | 29160 | 0.0 | 0.0 |
| CTP-CTP-EPO | 23956 | 23690 | 37074 | 2.7 | 4.0 |
| CTP-EPO-CTP-CTP | 26736 | 27300 | 43547.8 | 3.0 | 4.8 |
| APO AI | 28078 | 28021.5 | 28024.5 | 0.0 | 0.0 |
| APO -CTP | 30858 | 30686.5 | 32505 | 2.7 | 4.5 |
| APO CTP-CTP | 33638 | 33569 | 36710 | 2.8 | 4.3 |
| Mononine ® (rFIX) | 48695.6 | 47172 | 53270 | 0.0 | 0.0 |
| FIX-CTP-CTP-CTP | 57036 | 55626.5 | 68876 | 2.8 | 5.2 |
| FIX-CTP-CTP-CTP-CTP | 59816.2 | 58346.5 | 73552.5 | 2.8 | 5.1 |
| FIX-CTP-CTP-CTP-CTP-CTP | 62596.2 | 61051.5 | 77797 | 2.8 | 4.9 |
| Novoseven ® (rFVIIa) | 47222.6 | 45899 | 50310.4 | 0.0 | |
| FVIIa-CTP-CTP-CTP | 58343.1 | 53755.5 | 64302 | 2.6 | 4.7 |
| FVIIa-CTP-CTP-CTP-CTP-CTP | 61123.2 | 59266 | 74431 | 2.7 | 4.8 |
| | | | Ave. | 2.76 | 4.76 |
| | | | SD | 0.103 | 0.422 |
| | | | % CV | 3.72 | 8.87 |

ND—Not determined

TABLE 4b

H Mw calibration curve results and calculated % RE using TSK 3000 column. The expected Mw of the calibration curve proteins were provided by the commercial kit that was used (H Mw calibration kit BioRad Cat. No. 151-1901).

| Standard proteins | Expected M.W. | R.T. | Observed M.W. | % RE |
|---|---|---|---|---|
| Tyroglobulin | 670,000 | 11.925 | 753,500 | 12.46 |
| Gamma-globulin | 158,000 | 16.250 | 126,808 | −19.74 |
| Ovalbumin | 44,000 | 18.702 | 46,172 | 4.94 |
| Myoglobulin | 17,000 | 21.012 | 17,824 | 4.85 |

Figure 4A:
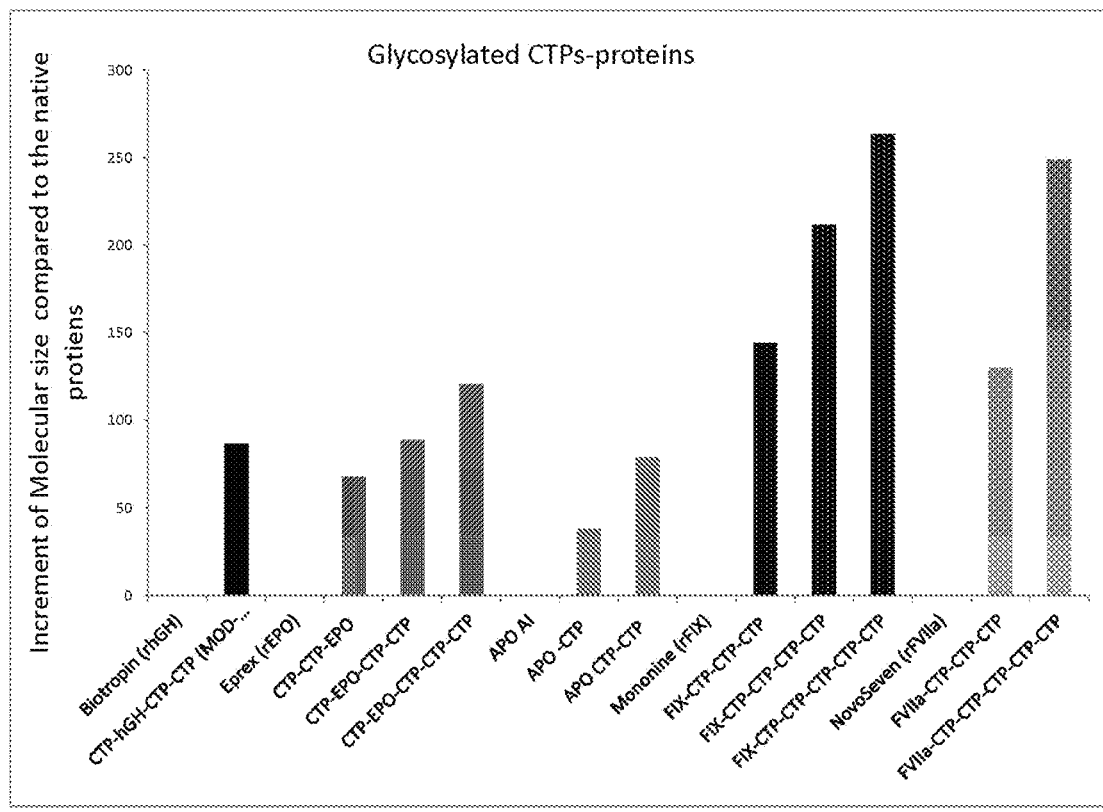
FIG. 4 shows increment of hydrodynamic size of glycosylated CTP-modified proteins compared to their corresponding native proteins, measured by SEC-HPLC. (A) exhibits the total increment of hydrodynamic size, while (B) exhibits the calculated increment per one copy of glycosylated CTP.
Figure 4B:
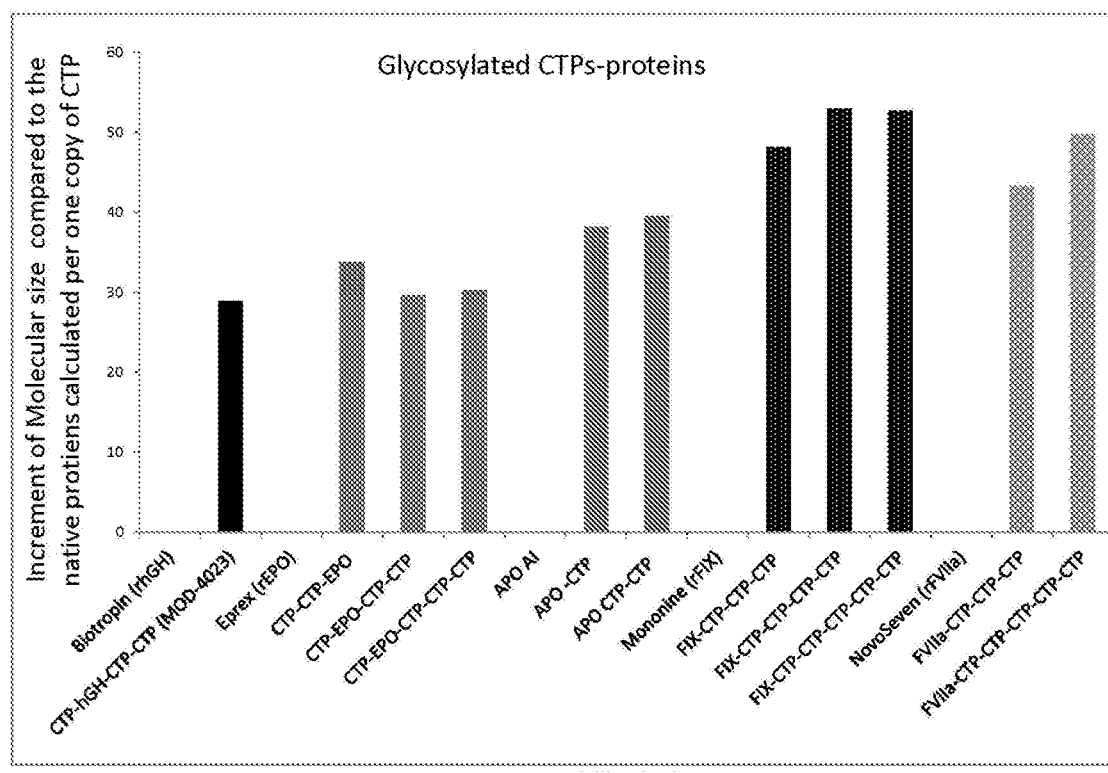

In order to determine the contribution of glycosylated CTP to the hydrodynamic volume of CTP-modified proteins, various CTP-modified proteins were analyzed by SEC column and their hydrodynamic sizes were calculated. The corresponding recombinant proteins: Biotropin (rhGH), EPREX® (rEPO), ApoAI, Mononine® (rFIX) and Novoseven® (rFVIIa) were analyzed in parallel to their CTP-modified corresponding proteins in order to calculate the contribution of glycosylated CTP to the protein (Table 5, FIG. 4). FIG. 4A presents the total increment of hydrodynamic size of CTP-modified proteins to the native proteins as was measured by SEC column

TABLE 5

SEC-HPLC results and calculated increament of one copy of CTP of CTP-modified proteins and their corresponding native proteins.

| Glycosylated proteins | SEC-HPLC Mw (Da) | Increase in kDa per glycosylated CTP |
|---|---|---|
| Biotropin (rhGH) | 21116 | NA |
| CTP-hGH-CTP-CTP (MOD-4023) | 107750 | 28.9 |
| EPREX ® (rEPO) | 79014 | NA |
| CTP-CTP-EPO | 146616 | 33.8 |
| CTP-EPO-CTP-CTP | 168032 | 29.7 |
| CTP-CTP-EPO-CTP-CTP | 199970 | 30.2 |
| APO | 62086 | NA |
| APO -CTP | 100233 | 38.1 |
| APO CTP-CTP | 141094 | 39.5 |
| Mononine ® (rFIX) | 117553 | NA |
| FIX-CTP-CTP-CTP | 261982 | 48.1 |
| FIX-CTP-CTP-CTP-CTP | 329362 | 53.0 |
| FIX-CTP-CTP-CTP-CTP-CTP | 381095 | 52.7 |
| Novoseven ® (rFVIIa) | 76706 | NA |
| FVIIa -CTP-CTP-CTP | 206645 | 43.3 |
| FVIIa -CTP-CTP-CTP-CTP-CTP | 325602 | 49.8 |

The increment in the molecular weight of one copy of glycosylated CTP was calculated by subtracting the measured hydrodynamic size of the native proteins from the measured hydrodynamic size of their corresponding CTP-modified proteins. Then, the calculated increment was divided by the number of CTP copies for each protein. The calculated contributions of one copy of glycosylated CTPs to the molecular weight of various proteins are presented in FIG. 4B. The various proteins exhibit increments that range between 29 kDa to 53 kDa per one copy of glycosyted CTP.

Interestingly and unexpectedly, the contribution of one copy of glycosylated CTP of the FIX and FVIIa was markedly higher with a contribution of 43-53 kDa (per one copy of CTP) compared to other measured proteins (Table 5). The increment in the hydrodynamic size per one copy of glycosylated CTP is much higher than the calculated contribution of 4.76 kDa per one copy of glycosylated CTP to the molecular weight, as measured by MALDI-TOF. The differences in the calculated Mw between the methods results from the fact that is while MALDI-TOF is measuring the actual Mw of the protein, the SEC-HPLC measurement is affected by the protein's hydrodynamic volume, suggesting that glycosylated CTP is substantially increasing the hydrodynamic volume of proteins to which it is attached. The magnitude in the hydrodynamic volume is about 6-11 fold higher compared to the calculated contribution per CTP measured by MALDI-TOF. Of note, the contribution of CTP to the hydrodynamic size of the protein being modified was lower for hGH and CTP-modified EPO variants (around 30 kDa) but slightly higher for FIX and FVII-CTP modified variants, and was surprisingly not affected by the number of CTPs being added to the particular protein.

Figure 5A:
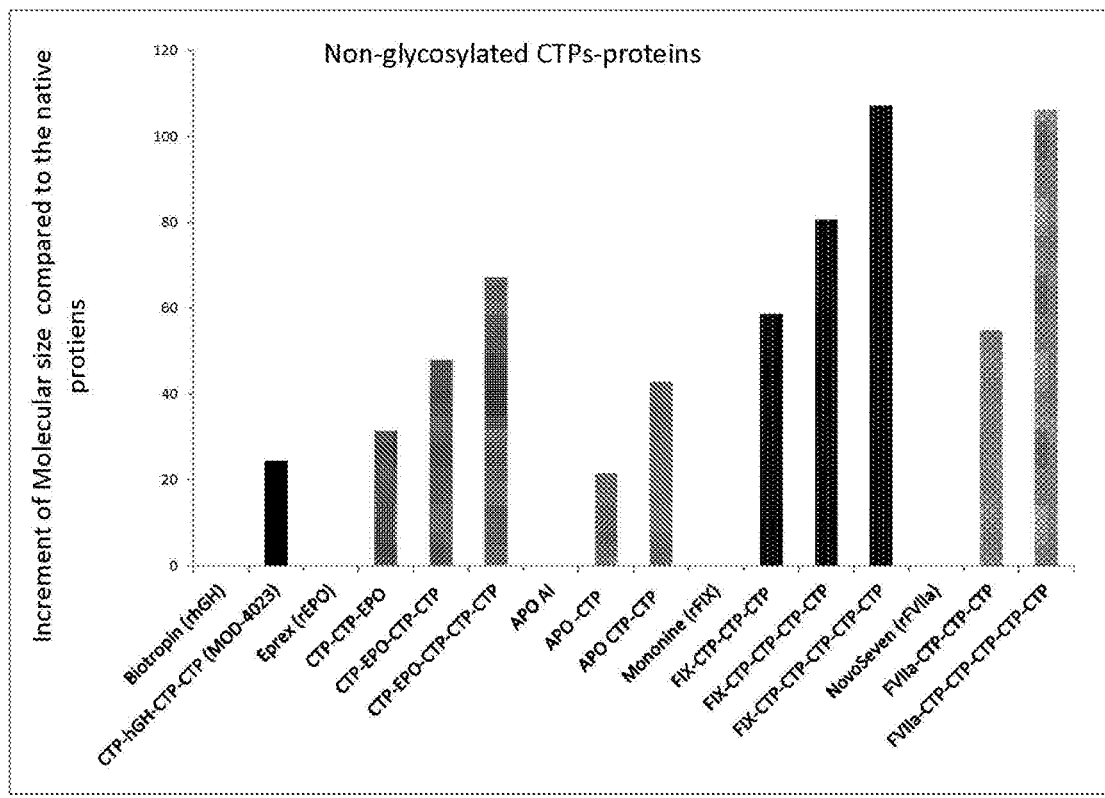
FIG. 5 shows increment of hydrodynamic size of non-glycosylated CTP-modified proteins compared to their corresponding native proteins, measured by SEC-HPLC column (A) exhibits the total increment of hydrodynamic size, while (B) exhibits the calculated increment per one copy of non-glycosylated CTP.
Figure 5B:
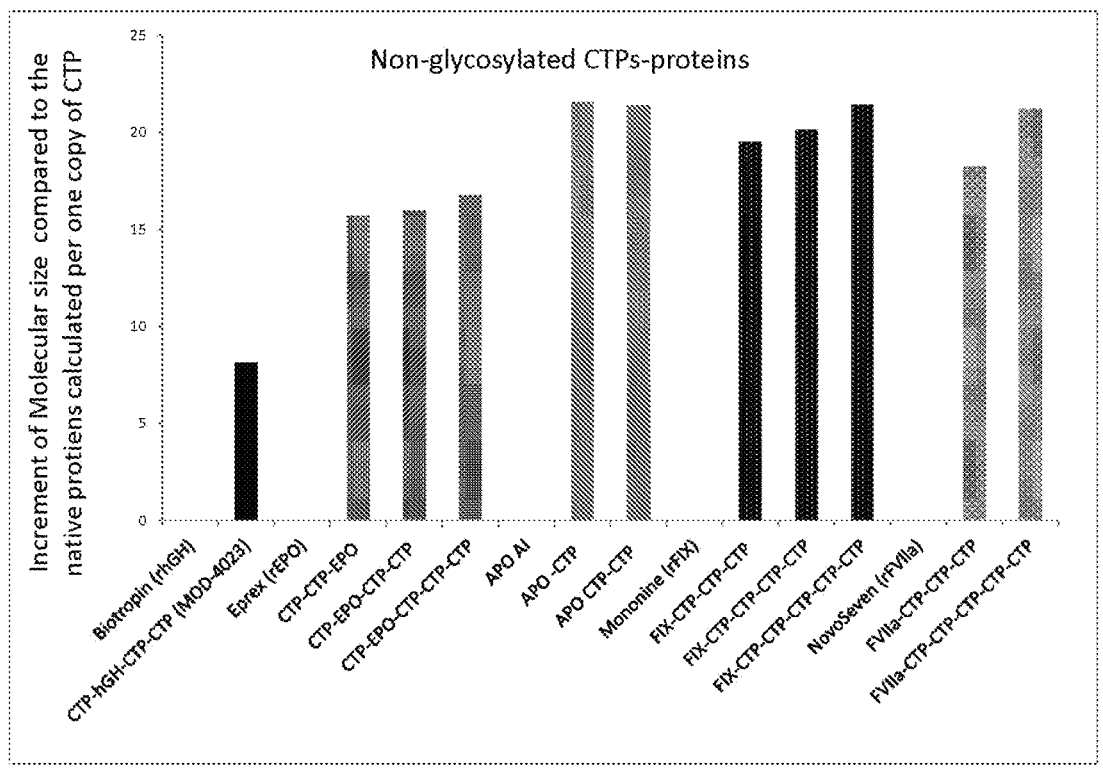

In addition, the contribution of non-glycosylated CTP to the protein's Mw was determined by SEC-HPLC (Table 6, FIGS. 5A & 5B). The de-glycosylation was performed by incubating the proteins with Sialidase A (remove sialic acid) for 2 h at 37° C. followed by adding O-glycanase (to remove O-glycans). In the case of EPREX® (rEPO), Mononine® (rFIX), NovoSeven® (rFVII) and their corresponding CTP-modified proteins, which contain N-glycans, N-glycanase was added for an over-night digestion to remove N-glycans. The contribution of non-glycosylated CTP to the hydrodynamic size or volume of various proteins was calculated and compared to their corresponding native proteins, i.e., the contribution of non-glycosylated CTP-modified polypeptides to the hydrodynamic volume were calculated by comparing the hydrodynamic volume of the non-glycosylated CTP-modified polypeptides to that of the non-glycosylated corresponding native protein. For example, for EPO, the N- and O-glycans were removed from Eprex®, and the increase in hydrodynamic volume of the CTP-modified Epo variants were calculated and compared to their molecular weight).

FIG. 5A depicts the increment in the hydrodynamic size of the intact proteins, while FIG. 5B depicts the contribution of one copy of non-glycosylated CTP-modified proteins. Remarkably, non-glycosylated CTP increases the hydrodynamic size of the CTP-modified proteins when compared to the corresponding native proteins. The calculated contribution of one copy of non-glycosylated CTP was different between the various proteins, ranging between 8 kDa to 21 kDa per one copy of non glycosylated CTP (Table 6). Considering that the theoretical molecular weight of CTP, which consists of 28 amino acids, is 2.78 kDa and the measured molecular weight (by MALDI-TOF) was also about 2.76 kDa, these results suggest that the contribution of non-glycosylated CTP to the molecular weight is higher than expected. Further, and as similarly observed for glycosylated CTP, the hydrodynamic volume was also observed to be much higher than the expected for non-glycolysated CTP. Overall, attaching CTP to a protein results in an increase in hydrodynamic volume that is attributable to both the CTP backbone and the CTP glycans.

It was also observed that number of CTPs added to a particular protein did not affect the contribution to the hydrodynamic size of the same. The most significant increment of non-glycosylated CTP was observed for Apo, FIX and FVII that have copies of CTP in the C-terminus of the protein. This finding that adding CTP at the C-terminus leads to a higher contribution to hydrodynamic volume was unexpected. Interestingly and unexpectedly the contribution of one copy of non-glycosylated CTP of Apo, FIX and FVIIa CTP-modified proteins was very similar and measured ~20 kDa (Table 6) but the contribution of glycosylated CTP of the coagulation factors was significantly higher compared to Apo glycosylated CTP (Table 5).

TABLE 6

SEC-HPLC results and calculated increament of one copy of CTP of non-glycosylated CTP-modified proteins and their corresponding native proteins.

| Non-glycosylated proteins | SEC-HPLC Mw (Da) | Increase in kDa per non-glycosylated CTP |
|---|---|---|
| Biotropin(rhGH) | 21116 | NA |
| CTP-hGH-CTP-CTP (MOD-4023) | 45480 | 8.1 |
| EPREX ® (rEPO) | 18083 | NA |
| CTP-CTP-EPO | 49472 | 15.7 |
| CTP-EPO-CTP-CTP | 65991 | 16.0 |
| CTP-CTP-EPO-CTP-CTP | 85228 | 16.8 |
| APO | 61267 | NA |
| APO -CTP | 82846 | 21.6 |
| APO CTP-CTP | 104007 | 21.4 |
| Mononine ® (rFIX) | 79539 | NA |
| FIX-CTP-CTP-CTP | 138132 | 19.5 |
| FIX-CTP-CTP-CTP-CTP | 160115 | 20.1 |
| FIX-CTP-CTP-CTP-CTP-CTP | 186677 | 21.4 |
| Novoseven ® (rFVIIa) | 52570 | NA |
| FVIIa-CTP-CTP-CTP | 107321 | 18.3 |
| FVIIa-CTP-CTP-CTP-CTP-CTP | 158706 | 21.2 |

This study showed that one copy of glycosylated CTP contributes at least 28 (kDa) to the hydrodynamic volume while the increment of Mw is 4.76 (kDa) 0.422, as determined using SEC-HPLC and MALDI-TOF, respectively. This unexpected magnitude in the hydrodynamic volume of CTP-modified proteins is likely the reason for the observed extended serum half-life and enhancement of biological activity of CTP-modified proteins. The non-glycosylated CTP contributes at least 8 (kDa) to the hydrodynamic volume, while the molecular weight increment was 2.76 (kDa) 0.103. Interestingly, the Mw of non-glycosylated and glycosylated CTP peptide as was measured by MALDI-TOF was similar between all of the proteins. Further, the hydrodynamic volume of glycosylated and non-glycosylated CTP peptide-modified proteins as measured by SEC-HPLC were different. These findings suggest that although the Mw of the CTP peptide is similar when fused to different proteins in different position, it causes an unexpected increase of the hydrodynamic volume of different proteins to which it is attached, as evidence by the SEC column measurements.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of incrementally increasing the hydrodynamic size of a recombinant polypeptide of interest wherein said recombinant polypeptide of interest is selected from the group consisting of a coagulation factor IX (FIX) and a coagulation factor VIIa (FVIIa),
said method comprising a step of recombinantly fusing
(a) three chorionic gonadotrophin carboxy terminal peptide CTP units to the carboxy terminus of said coagulation factor IX (FIX) and no CTPs attached to the N-terminus; or
(b) three CTP units to the carboxy terminus of said coagulation factor VIIa (FVIIa) and no CTPs attached to the N-terminus;
followed by a step of expressing the recombinant CTP-modified polypeptides in a Chinese hamster ovary (CHO) host cell, wherein expression comprises glycosylating said CTP-units and the glycosylation comprises O-glycosylation;
wherein said glycosylated CTP units incrementally increase the hydrodynamic size of the FIX by an increment of about 48-53 kDA per each of said glycosylated CTP units, and,
wherein said glycoslyated CTP units incrementally increase the hydrodynamic size of the FVIIa by an increment of about 43-50 kDA per each of said glycosylated CTP units,
thereby incrementally increasing the hydrodynamic size of said recombinant polypeptide of interest.

2. The method of claim 1, wherein said O-glycosylation is a GalNAc attachment to serine (Ser) or threonine (Thr) in the polypeptide chain by an α-glycosidic linkage or a core 1 glycosylation, O-fucosylation, O-mannosylation, or O-glycosylation.

3. The method of claim 2, wherein said O-glycosylation is followed by the addition of one to sixty galactose molecules or by the addition of one to 120 sialic acid molecules.

4. The method of claim 1, wherein increasing said hydrodynamic size increases the bioavailability of said polypeptide.

5. The method of claim 1, wherein the amino acid sequence of at least one of said CTP units is selected from the group consisting of SEQ ID NO: 1 and SEQ ID NO: 2.

6. The method of claim 1, wherein at least one of said CTP units is truncated.

7. The method of claim 1, wherein at least one of said CTP units is attached to said polypeptide via a linker.

8. The method of claim 7, wherein said linker is a peptide bond.

* * * * *

SEQUENCE LISTING

```
<160> NUMBER OF SEQ ID NOS: 73

<210> SEQ ID NO 1
<211> LENGTH: 32
<212> TYPE: PRT
<213> ORGANISM: Artificial Sequence
<220> FEATURE:
<223> OTHER INFORMATION: CTP sequence

<400> SEQUENCE: 1

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 2
<211> LENGTH: 28
<212> TYPE: PRT
<213> ORGANISM: Artificial Sequence
<220> FEATURE:
<223> OTHER INFORMATION: CTP sequence

<400> SEQUENCE: 2

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 3
<211> LENGTH: 12
<212> TYPE: PRT
<213> ORGANISM: Artificial Sequence
<220> FEATURE:
<223> OTHER INFORMATION: Truncated CTP sequence

<400> SEQUENCE: 3

Ser Ser Ser Ser Lys Ala Pro Pro Pro Ser Leu Pro
1               5                   10
```

```
<210> SEQ ID NO 4
<211> LENGTH: 26
<212> TYPE: PRT
<213> ORGANISM: Artificial Sequence
<220> FEATURE:
<223> OTHER INFORMATION: hGH signal peptide

<400> SEQUENCE: 4

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 5
<211> LENGTH: 217
<212> TYPE: PRT
<213> ORGANISM: Homo sapiens

<400> SEQUENCE: 5

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 6
<211> LENGTH: 192
<212> TYPE: PRT
<213> ORGANISM: Artificial Sequence
<220> FEATURE:
<223> OTHER INFORMATION: hGH sequence

<400> SEQUENCE: 6

Met Phe Pro Thr Ile Pro Leu Ser Arg Leu Phe Asp Asn Ala Met Leu
1               5                   10                  15
```

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 7
<211> LENGTH: 25
<212> TYPE: PRT
<213> ORGANISM: Artificial Sequence
<220> FEATURE:
<223> OTHER INFORMATION: hGH sequence

<400> SEQUENCE: 7

Met Phe Pro Thr Ile Pro Leu Ser Arg Leu Phe Asp Asn Ala Met Leu
1               5                   10                  15

Arg Ala His Arg Leu His Gln Leu Ala
            20                  25

<210> SEQ ID NO 8
<211> LENGTH: 217
<212> TYPE: PRT
<213> ORGANISM: Homo sapiens

<400> SEQUENCE: 8

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Val Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
        130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
        210                 215

<210> SEQ ID NO 9
<211> LENGTH: 245
<212> TYPE: PRT
<213> ORGANISM: Artificial Sequence
<220> FEATURE:
<223> OTHER INFORMATION: hGH-CTP

<400> SEQUENCE: 9

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
    210                 215                 220

Pro Pro Ser Leu Pro Ser Pro Ser Arg Leu Pro Gly Pro Ser Asp Thr
225                 230                 235                 240

Pro Ile Leu Pro Gln
            245

```
<210> SEQ ID NO 10
<211> LENGTH: 273
<212> TYPE: PRT
<213> ORGANISM: Artificial Sequence
<220> FEATURE:
<223> OTHER INFORMATION: hGH-CTP-CTP

<400> SEQUENCE: 10

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
    210                 215                 220

Pro Pro Ser Leu Pro Ser Pro Ser Arg Leu Pro Gly Pro Ser Asp Thr
225                 230                 235                 240

Pro Ile Leu Pro Gln Ser Ser Ser Lys Ala Pro Pro Pro Ser Leu
                245                 250                 255

Pro Ser Pro Ser Arg Leu Pro Gly Pro Ser Asp Thr Pro Ile Leu Pro
            260                 265                 270

Gln

<210> SEQ ID NO 11
<211> LENGTH: 301
<212> TYPE: PRT
<213> ORGANISM: Artificial Sequence
<220> FEATURE:
<223> OTHER INFORMATION: CTP-hGH-CTP-CTP

<400> SEQUENCE: 11

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30
```

```
Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
 50                  55                  60

Asp Asn Ala Met Leu Arg Ala His Arg Leu His Gln Leu Ala Phe Asp
 65                  70                  75                  80

Thr Tyr Gln Glu Phe Glu Ala Tyr Ile Pro Lys Glu Gln Lys Tyr
                 85                  90                  95

Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
            195                 200                 205

Ala Leu Leu Lys Asn Tyr Gly Leu Leu Tyr Cys Phe Arg Lys Asp Met
210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Pro Ser Leu
                245                 250                 255

Pro Ser Pro Ser Arg Leu Pro Gly Pro Ser Asp Thr Pro Ile Leu Pro
            260                 265                 270

Gln Ser Ser Ser Ser Lys Ala Pro Pro Pro Ser Leu Pro Ser Pro Ser
            275                 280                 285

Arg Leu Pro Gly Pro Ser Asp Thr Pro Ile Leu Pro Gln
            290                 295                 300

<210> SEQ ID NO 12
<211> LENGTH: 285
<212> TYPE: PRT
<213> ORGANISM: Artificial Sequence
<220> FEATURE:
<223> OTHER INFORMATION: Truncated-CTP-hGH-CTP-CTP

<400> SEQUENCE: 12

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Ser Ser Ser Ser Lys Ala
             20                  25                  30

Pro Pro Pro Ser Leu Pro Phe Pro Thr Ile Pro Leu Ser Arg Leu Phe
            35                  40                  45

Asp Asn Ala Met Leu Arg Ala His Arg Leu His Gln Leu Ala Phe Asp
 50                  55                  60

Thr Tyr Gln Glu Phe Glu Ala Tyr Ile Pro Lys Glu Gln Lys Tyr
 65                  70                  75                  80

Ser Phe Leu Gln Asn Pro Gln Thr Ser Leu Cys Phe Ser Glu Ser Ile
                 85                  90                  95
```

```
Pro Thr Pro Ser Asn Arg Glu Glu Thr Gln Gln Lys Ser Asn Leu Glu
            100                 105                 110

Leu Leu Arg Ile Ser Leu Leu Leu Ile Gln Ser Trp Leu Glu Pro Val
        115                 120                 125

Gln Phe Leu Arg Ser Val Phe Ala Asn Ser Leu Val Tyr Gly Ala Ser
    130                 135                 140

Asp Ser Asn Val Tyr Asp Leu Leu Lys Asp Leu Glu Glu Gly Ile Gln
145                 150                 155                 160

Thr Leu Met Gly Arg Leu Glu Asp Gly Ser Pro Arg Thr Gly Gln Ile
                165                 170                 175

Phe Lys Gln Thr Tyr Ser Lys Phe Asp Thr Asn Ser His Asn Asp Asp
            180                 185                 190

Ala Leu Leu Lys Asn Tyr Gly Leu Leu Tyr Cys Phe Arg Lys Asp Met
        195                 200                 205

Asp Lys Val Glu Thr Phe Leu Arg Ile Val Gln Cys Arg Ser Val Glu
210                 215                 220

Gly Ser Cys Gly Phe Ser Ser Ser Lys Ala Pro Pro Pro Ser Leu
225                 230                 235                 240

Pro Ser Pro Ser Arg Leu Pro Gly Pro Ser Asp Thr Pro Ile Leu Pro
                245                 250                 255

Gln Ser Ser Ser Lys Ala Pro Pro Pro Ser Leu Pro Ser Pro Ser
            260                 265                 270

Arg Leu Pro Gly Pro Ser Asp Thr Pro Ile Leu Pro Gln
                275                 280                 285

<210> SEQ ID NO 13
<211> LENGTH: 273
<212> TYPE: PRT
<213> ORGANISM: Artificial Sequence
<220> FEATURE:
<223> OTHER INFORMATION: CTP-hGH-CTP

<400> SEQUENCE: 13

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
        35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
        115                 120                 125

Leu Leu Arg Ile Ser Leu Leu Leu Ile Gln Ser Trp Leu Glu Pro Val
    130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175
```

```
Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Ser Leu
                245                 250                 255

Pro Ser Pro Ser Arg Leu Pro Gly Pro Ser Asp Thr Pro Ile Leu Pro
            260                 265                 270

Gln

<210> SEQ ID NO 14
<211> LENGTH: 245
<212> TYPE: PRT
<213> ORGANISM: Artificial Sequence
<220> FEATURE:
<223> OTHER INFORMATION: GH-CTP

<400> SEQUENCE: 14

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
                20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
        115                 120                 125

Leu Leu Arg Ile Ser Leu Leu Leu Ile Gln Ser Trp Leu Glu Pro Val
130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225                 230                 235                 240

Gly Ser Cys Gly Phe
                245
```

```
<210> SEQ ID NO 15
<211> LENGTH: 853
<212> TYPE: DNA
<213> ORGANISM: Artificial Sequence
<220> FEATURE:
<223> OTHER INFORMATION: CTP-hGH-CTP

<400> SEQUENCE: 15
tctagaggac atggccaccg gcagcaggac cagcctgctg ctggccttcg gcctgctgtg    60
cctgccatgg ctgcaggagg gcagcgccag ctcttcttct aaggctccac ccccatctct   120
gcccagcccc agcagactgc cgggcccag cgacacaccc attctgcccc agttccccac    180
catcccctg agcaggctgt tcgacaacgc catgctgagg gctcacaggc tgcaccagct   240
ggcctttgac acctaccagg agttcgagga agcctacatc cccaaggagc agaagtacag   300
cttcctgcag aaccccagag cctccctgtg cttcagcgag agcatcccca ccccagcaa    360
cagagaggag acccagcaga gagcaacct ggagctgctg aggatctccc tgctgctgat    420
ccagagctgg ctggagcccg tgcagttcct gagaagcgtg ttcgccaaca gcctggtgta   480
cggcgccagc gacagcaacg tgtacgacct gctgaaggac ctggaggagg gcatccagac   540
cctgatgggc cggctggagg acggcagccc caggaccggc cagatcttca gcagaccta    600
cagcaagttc gacaccaaca gccacaacga cgacgccctg ctgaagaact acgggctgct   660
gtactgcttc agaaaggaca tggacaaggt ggagaccttc ctgaggatcg tgcagtgcag   720
aagcgtggag ggcagctgcg gcttcagctc agcagcaag gccctcccc cgagcctgcc    780
ctccccaagc aggctgcctg ggcctccga cacaccaatc ctgcctcagt gatgaaggtc   840
tggatgcggc cgc                                                       853

<210> SEQ ID NO 16
<211> LENGTH: 937
<212> TYPE: DNA
<213> ORGANISM: Artificial Sequence
<220> FEATURE:
<223> OTHER INFORMATION: CTP-hGH-CTP-CTP

<400> SEQUENCE: 16
tctagaggac atggccaccg gcagcaggac cagcctgctg ctggccttcg gcctgctgtg    60
cctgccatgg ctgcaggagg gcagcgccag ctcttcttct aaggctccac ccccatctct   120
gcccagcccc agcagactgc cgggcccag cgacacaccc attctgcccc agttccccac    180
catcccctg agcaggctgt tcgacaacgc catgctgagg gctcacaggc tgcaccagct   240
ggcctttgac acctaccagg agttcgagga agcctacatc cccaaggagc agaagtacag   300
cttcctgcag aaccccagag cctccctgtg cttcagcgag agcatcccca ccccagcaa    360
cagagaggag acccagcaga gagcaacct ggagctgctg aggatctccc tgctgctgat    420
ccagagctgg ctggagcccg tgcagttcct gagaagcgtg ttcgccaaca gcctggtgta   480
cggcgccagc gacagcaacg tgtacgacct gctgaaggac ctggaggagg gcatccagac   540
cctgatgggc cggctggagg acggcagccc caggaccggc cagatcttca gcagaccta    600
cagcaagttc gacaccaaca gccacaacga cgacgccctg ctgaagaact acgggctgct   660
gtactgcttc agaaaggaca tggacaaggt ggagaccttc ctgaggatcg tgcagtgcag   720
aagcgtggag ggcagctgcg gcttcagctc agcagcaag gccctcccc cgagcctgcc    780
ctccccaagc aggctgcctg ggcctccga cacaccaatc ctgccacaga gcagctcctc   840
taaggcccct cctccatccc tgccatcccc ctccggctg cctggccct ctgacacccc    900
```
tatcctgcct cagtgatgaa ggtctggatg cggccgc                                937

<210> SEQ ID NO 17
<211> LENGTH: 889
<212> TYPE: DNA
<213> ORGANISM: Artificial Sequence
<220> FEATURE:
<223> OTHER INFORMATION: CTP-hGH-CTP-CTP

<400> SEQUENCE: 17
tctagaggac atggccaccg gcagcaggac cagcctgctg ctggccttcg gcctgctgtg     60
cctgccatgg ctgcaggagg gcagcgccag ctcttcttct aaggctccac ccccgagcct    120
gccccttccc accatccccc tgagcaggct gttcgacaac gccatgctga gggctcacag    180
gctgcaccag ctggcctttg acacctacca ggagttcgag gaagcctaca tccccaagga    240
gcagaagtac agcttcctgc agaaccccca gacctccctg tgcttcagcg agagcatccc    300
caccccagc aacagagagg agacccagca gaagagcaac ctggagctgc tgaggatctc    360
cctgctgctg atccagagct ggctggagcc cgtgcagttc ctgagaagcg tgttcgccaa    420
cagcctggtg tacggcgcca gcgacagcaa cgtgtacgac ctgctgaagg acctggagga    480
gggcatccag accctgatgg gccggctgga ggacggcagc cccaggaccg ccagatctc    540
caagcagacc tacagcaagt tcgacaccaa cagccacaac gacgacgccc tgctgaagaa    600
ctacgggctg ctgtactgct tcagaaagga catggacaag gtggagacct tcctgaggat    660
cgtgcagtgc agaagcgtgg agggcagctg cggcttcagc tccagcagca aggcccctcc    720
cccgagcctg ccctccccaa gcaggctgcc tgggccctcc gacacaccaa tcctgccaca    780
gagcagctcc tctaaggccc tcctccatc cctgccatcc cctcccggc tgcctggccc    840
ctctgacacc cctatcctgc ctcagtgatg aaggtctgga tgcggccgc                 889

<210> SEQ ID NO 18
<211> LENGTH: 37
<212> TYPE: PRT
<213> ORGANISM: Artificial Sequence
<220> FEATURE:
<223> OTHER INFORMATION: Oxyntomodulin

<400> SEQUENCE: 18

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 19
<211> LENGTH: 221
<212> TYPE: PRT
<213> ORGANISM: Artificial Sequence
<220> FEATURE:
<223> OTHER INFORMATION: EPO peptide

<400> SEQUENCE: 19

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

```
Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg Ser Ser Ser Lys Ala Pro Pro Pro Ser Leu Pro Ser Pro Ser
            195                 200                 205

Arg Leu Pro Gly Pro Ser Asp Thr Pro Ile Leu Pro Gln
210                 215                 220

<210> SEQ ID NO 20
<211> LENGTH: 249
<212> TYPE: PRT
<213> ORGANISM: Artificial Sequence
<220> FEATURE:
<223> OTHER INFORMATION: EPO-CTP-CTP

<400> SEQUENCE: 20

Met Gly Val His Glu Cys Pro Ala Trp Leu Trp Leu Leu Leu Ser Leu
 1               5                  10                  15

Leu Ser Leu Pro Leu Gly Leu Pro Val Leu Gly Ala Pro Pro Arg Leu
                 20                  25                  30

Ile Cys Asp Ser Arg Val Leu Glu Arg Tyr Leu Leu Glu Ala Lys Glu
             35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190
```

-continued

```
Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln Ser Ser Ser
    210                 215                 220

Ser Lys Ala Pro Pro Pro Ser Leu Pro Ser Pro Ser Arg Leu Pro Gly
225                 230                 235                 240

Pro Ser Asp Thr Pro Ile Leu Pro Gln
                245

<210> SEQ ID NO 21
<211> LENGTH: 277
<212> TYPE: PRT
<213> ORGANISM: Artificial Sequence
<220> FEATURE:
<223> OTHER INFORMATION: CTP-EPO-CTP-CTP

<400> SEQUENCE: 21

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Ser Lys
                20                  25                  30

Ala Pro Pro Pro Ser Leu Pro Ser Pro Ser Arg Leu Pro Gly Pro Ser
            35                  40                  45

Asp Thr Pro Ile Leu Pro Gln Ala Pro Pro Arg Leu Ile Cys Asp Ser
        50                  55                  60

Arg Val Leu Glu Arg Tyr Leu Leu Glu Ala Lys Glu Ala Glu Asn Ile
65                  70                  75                  80

Thr Thr Gly Cys Ala Glu His Cys Ser Leu Asn Glu Asn Ile Thr Val
                85                  90                  95

Pro Asp Thr Lys Val Asn Phe Tyr Ala Trp Lys Arg Met Glu Val Gly
            100                 105                 110

Gln Gln Ala Val Glu Val Trp Gln Gly Leu Ala Leu Leu Ser Glu Ala
        115                 120                 125

Val Leu Arg Gly Gln Ala Leu Leu Val Asn Ser Ser Gln Pro Trp Glu
    130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
        195                 200                 205

Lys Leu Tyr Thr Gly Glu Ala Cys Arg Thr Gly Asp Arg Ser Ser Ser
    210                 215                 220

Ser Lys Ala Pro Pro Pro Ser Leu Pro Ser Pro Ser Arg Leu Pro Gly
225                 230                 235                 240

Pro Ser Asp Thr Pro Ile Leu Pro Gln Ser Ser Ser Ser Lys Ala Pro
                245                 250                 255

Pro Pro Ser Leu Pro Ser Pro Ser Arg Leu Pro Gly Pro Ser Asp Thr
            260                 265                 270

Pro Ile Leu Pro Gln
        275

<210> SEQ ID NO 22
```

<211> LENGTH: 387
<212> TYPE: PRT
<213> ORGANISM: Artificial Sequence
<220> FEATURE:
<223> OTHER INFORMATION: EPO-CTP

<400> SEQUENCE: 22

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Pro Ser Leu Pro Ser Pro Ser Arg
        195                 200                 205

Leu Pro Gly Pro Ser Asp Thr Pro Ile Leu Pro Gln Ala Pro Pro Arg
    210                 215                 220

Leu Ile Cys Asp Ser Arg Val Leu Glu Arg Tyr Leu Leu Glu Ala Lys
225                 230                 235                 240

Glu Ala Glu Asn Ile Thr Thr Gly Cys Ala Glu His Cys Ser Leu Asn
                245                 250                 255

Glu Asn Ile Thr Val Pro Asp Thr Lys Val Asn Phe Tyr Ala Trp Lys
            260                 265                 270

Arg Met Glu Val Gly Gln Gln Ala Val Glu Val Trp Gln Gly Leu Ala
        275                 280                 285

Leu Leu Ser Glu Ala Val Leu Arg Gly Gln Ala Leu Leu Val Asn Ser
    290                 295                 300

Ser Gln Pro Trp Glu Pro Leu Gln Leu His Val Asp Lys Ala Val Ser
305                 310                 315                 320

Gly Leu Arg Ser Leu Thr Thr Leu Leu Arg Ala Leu Gly Ala Gln Lys
                325                 330                 335

Glu Ala Ile Ser Pro Pro Asp Ala Ala Ser Ala Ala Pro Leu Arg Thr
            340                 345                 350

Ile Thr Ala Asp Thr Phe Arg Lys Leu Phe Arg Val Tyr Ser Asn Phe
        355                 360                 365

Leu Arg Gly Lys Leu Lys Leu Tyr Thr Gly Glu Ala Cys Arg Thr
    370                 375                 380
```

```
Gly Asp Arg
385

<210> SEQ ID NO 23
<211> LENGTH: 221
<212> TYPE: PRT
<213> ORGANISM: Artificial Sequence
<220> FEATURE:
<223> OTHER INFORMATION: CTP-EPO

<400> SEQUENCE: 23

Met Gly Val His Glu Cys Pro Ala Trp Leu Trp Leu Leu Ser Leu
 1               5                  10                  15

Leu Ser Leu Pro Leu Gly Leu Pro Val Leu Gly Ser Ser Ser Lys
                20                  25                  30

Ala Pro Pro Pro Ser Leu Pro Ser Pro Ser Arg Leu Pro Gly Pro Ser
                35                  40                      45

Asp Thr Pro Ile Leu Pro Gln Ala Pro Pro Arg Leu Ile Cys Asp Ser
                50                  55                      60

Arg Val Leu Glu Arg Tyr Leu Leu Glu Ala Lys Glu Ala Glu Asn Ile
65                  70                  75                  80

Thr Thr Gly Cys Ala Glu His Cys Ser Leu Asn Glu Asn Ile Thr Val
                    85                  90                  95

Pro Asp Thr Lys Val Asn Phe Tyr Ala Trp Lys Arg Met Glu Val Gly
                100                 105                 110

Gln Gln Ala Val Glu Val Trp Gln Gly Leu Ala Leu Leu Ser Glu Ala
                115                 120                 125

Val Leu Arg Gly Gln Ala Leu Leu Val Asn Ser Ser Gln Pro Trp Glu
    130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
                180                 185                 190

Phe Arg Lys Leu Phe Arg Val Tyr Ser Asn Phe Leu Arg Gly Lys Leu
                195                 200                 205

Lys Leu Tyr Thr Gly Glu Ala Cys Arg Thr Gly Asp Arg
    210                 215                 220

<210> SEQ ID NO 24
<211> LENGTH: 249
<212> TYPE: PRT
<213> ORGANISM: Artificial Sequence
<220> FEATURE:
<223> OTHER INFORMATION: CTP-EPO-CTP

<400> SEQUENCE: 24

Met Gly Val His Glu Cys Pro Ala Trp Leu Trp Leu Leu Ser Leu
 1               5                  10                  15

Leu Ser Leu Pro Leu Gly Leu Pro Val Leu Gly Ser Ser Ser Lys
                20                  25                  30

Ala Pro Pro Pro Ser Leu Pro Ser Pro Ser Arg Leu Pro Gly Pro Ser
                35                  40                      45

Asp Thr Pro Ile Leu Pro Gln Ala Pro Pro Arg Leu Ile Cys Asp Ser
                50                  55                      60

Arg Val Leu Glu Arg Tyr Leu Leu Glu Ala Lys Glu Ala Glu Asn Ile
```

```
                65                  70                  75                  80
Thr Thr Gly Cys Ala Glu His Cys Ser Leu Asn Glu Asn Ile Thr Val
                85                  90                  95

Pro Asp Thr Lys Val Asn Phe Tyr Ala Trp Lys Arg Met Glu Val Gly
            100                 105                 110

Gln Gln Ala Val Glu Val Trp Gln Gly Leu Ala Leu Leu Ser Glu Ala
        115                 120                 125

Val Leu Arg Gly Gln Ala Leu Leu Val Asn Ser Ser Gln Pro Trp Glu
    130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
        195                 200                 205

Lys Leu Tyr Thr Gly Glu Ala Cys Arg Thr Gly Asp Arg Ser Ser Ser
    210                 215                 220

Ser Lys Ala Pro Pro Pro Ser Leu Pro Ser Pro Ser Arg Leu Pro Gly
225                 230                 235                 240

Pro Ser Asp Thr Pro Ile Leu Pro Gln
                245

<210> SEQ ID NO 25
<211> LENGTH: 193
<212> TYPE: PRT
<213> ORGANISM: Artificial Sequence
<220> FEATURE:
<223> OTHER INFORMATION: EPO

<400> SEQUENCE: 25

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
```

180                 185                 190

Arg

<210> SEQ ID NO 26
<211> LENGTH: 873
<212> TYPE: DNA
<213> ORGANISM: Artificial Sequence
<220> FEATURE:
<223> OTHER INFORMATION: EPO-CTP-CTP

<400> SEQUENCE: 26

```
tctagaggtc atcatggggg tgcacgaatg tcctgcctgg ctgtggcttc tcctgtccct      60
tctgtcgctc cctctgggcc tcccagtcct gggctcctct tcctcaaagg ccctcccccc     120
gagccttcca gtccatccc gactcccggg ccctcggac accccaatat taccacaagc      180
cccaccacgc tcatctgtg acagccgagt cctggagagg tacctcttgg aggccaagga     240
ggccgagaat atcacgacgg ctgtgctga acactgcagc ttgaatgaga atatcactgt      300
cccagacacc aaagttaatt tctatgcctg aagaggatg gaggtcgggc agcaggccgt      360
agaagtctgg cagggcctgg ccctgctgtc ggaagctgtc ctgcggggcc aggccctgtt     420
ggtcaactct tcccagccgt gggagcccct gcagctgcat gtggataaag ccgtcagtgg     480
ccttcgcagc ctcaccactc tgcttcgggc tctgggagcc agaaggaag ccatctcccc      540
tccagatgcg gcctcagctg ctccactccg aacaatcact gctgacactt ccgcaaact      600
cttccgagtc tactccaatt tcctccgggg aaagctgaag ctgtacacag gggaggcctg     660
caggacaggg gacagatcct cttcctcaaa ggcccctccc ccgagccttc caagtccatc     720
ccgactcccg ggccctccg acacaccaat cctgccacag agcagctcct ctaaggcccc      780
tcctccatcc ctgccatccc cctcccggct gcctggcccc tctgacaccc ctatcctgcc     840
tcagtgatga aggtcttctg gatccgcggc cgc                                  873
```

<210> SEQ ID NO 27
<211> LENGTH: 187
<212> TYPE: PRT
<213> ORGANISM: Homo sapiens

<400> SEQUENCE: 27

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

```
Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 28
<211> LENGTH: 589
<212> TYPE: DNA
<213> ORGANISM: Homo sapiens

<400> SEQUENCE: 28
tctagaggac atgaccaaca agtgcctgct gcagatcgcc ctgctgctgt gcttcagcac      60
caccgccctg agcatgagct acaacctgct gggcttcctg cagaggtcca gcaacttcca     120
gtgccagaag ctgctgtggc agctgaacgg caggctggaa tactgcctga aggacaggat     180
gaacttcgac atcccagagg aaatcaagca gctgcagcag ttccagaagg aggacgccgc     240
cctgaccatc tacgagatgc tgcagaacat cttcgccatc ttcaggcagg acagcagcag     300
caccggctgg aacgagacca tcgtggagaa cctgctggcc aacgtgtacc accagatcaa     360
ccacctgaaa accgtgctgg aagagaagct ggaaaaggag gacttcacca ggggcaagct     420
gatgagcagc ctgcacctga agaggtacta cggcagaatc ctgcactacc tgaaggccaa     480
ggagtacagc cactgcgcct ggaccatcgt gagggtggag atcctgagga acttctactt     540
catcaacagg ctgaccggct acctgaggaa ctgatgagtc cgcggccgc                 589

<210> SEQ ID NO 29
<211> LENGTH: 211
<212> TYPE: PRT
<213> ORGANISM: Artificial Sequence
<220> FEATURE:
<223> OTHER INFORMATION: Interferon

<400> SEQUENCE: 29

Thr Phe Leu Gln Pro Phe Glu Ala Phe Ala Leu Ala Gln Gln Val Val
1               5                   10                  15

Gly Asp Thr Val Arg Val Val Asn Met Thr Asn Lys Cys Leu Leu Gln
                20                  25                  30

Ile Ala Leu Leu Leu Cys Phe Ser Thr Thr Ala Leu Ser Met Ser Tyr
            35                  40                  45

Asn Leu Leu Gly Phe Leu Gln Arg Ser Ser Asn Phe Gln Cys Gln Lys
50                  55                  60

Leu Leu Trp Gln Leu Asn Gly Arg Leu Glu Tyr Cys Leu Lys Asp Arg
65                  70                  75                  80

Met Asn Phe Asp Ile Pro Glu Glu Ile Lys Gln Leu Gln Gln Phe Gln
                85                  90                  95

Lys Glu Asp Ala Ala Leu Thr Ile Tyr Glu Met Leu Gln Asn Ile Phe
                100                 105                 110

Ala Ile Phe Arg Gln Asp Ser Ser Ser Thr Gly Trp Asn Glu Thr Ile
            115                 120                 125

Val Glu Asn Leu Leu Ala Asn Val Tyr His Gln Ile Asn His Leu Lys
        130                 135                 140

Thr Val Leu Glu Glu Lys Leu Glu Lys Glu Asp Phe Thr Arg Gly Lys
145                 150                 155                 160

Leu Met Ser Ser Leu His Leu Lys Arg Tyr Tyr Gly Arg Ile Leu His
                165                 170                 175
```

Tyr Leu Lys Ala Lys Glu Tyr Ser His Cys Ala Trp Thr Ile Val Arg
            180                 185                 190

Val Glu Ile Leu Arg Asn Phe Tyr Phe Ile Asn Arg Leu Thr Gly Tyr
        195                 200                 205

Leu Arg Asn
    210

<210> SEQ ID NO 30
<211> LENGTH: 639
<212> TYPE: DNA
<213> ORGANISM: Artificial Sequence
<220> FEATURE:
<223> OTHER INFORMATION: Interferon

<400> SEQUENCE: 30

```
acattctaac tgcaaccttt cgaagccttt gctctggcac aacaggtagt aggcgacact      60
gttcgtgttg tcaacatgac caacaagtgt ctcctccaaa ttgctctcct gttgtgcttc     120
tccactcag ctctttccat gagctacaac ttgcttggat tcctacaaag aagcagcaat      180
tttcagtgtc agaagctcct gtggcaattg aatgggaggc ttgaatactg cctcaaggac     240
aggatgaact tgacatccc tgaggagatt aagcagctgc agcagttcca gaaggaggac      300
gccgcattga ccatctatga gatgctccag aacatctttg ctattttcag acaagattca     360
tctagcactg gctggaatga gactattgtt gagaacctcc tggctaatgt ctatcatcag     420
ataaaccatc tgaagacagt cctggaagaa aaactggaga agaagatttt caccagggga     480
aaactcatga gcagtctgca cctgaaaaga tattatggga ggattctgca ttacctgaag     540
gccaaggagt acagtcactg tgcctggacc atagtcagag tggaaatcct aaggaacttt     600
tacttcatta acagacttac aggttacctc cgaaactga                            639
```

<210> SEQ ID NO 31
<211> LENGTH: 215
<212> TYPE: PRT
<213> ORGANISM: Artificial Sequence
<220> FEATURE:
<223> OTHER INFORMATION: IFN-CTP

<400> SEQUENCE: 31

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

```
Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Ser Ser Ser Ser Lys
            180                 185                 190

Ala Pro Pro Pro Ser Leu Pro Ser Pro Ser Arg Leu Pro Gly Pro Ser
        195                 200                 205

Asp Thr Pro Ile Leu Pro Gln
    210                 215
```

<210> SEQ ID NO 32
<211> LENGTH: 661
<212> TYPE: DNA
<213> ORGANISM: Artificial Sequence
<220> FEATURE:
<223> OTHER INFORMATION: IFN-CTP

<400> SEQUENCE: 32

```
tctagaggac atgaccaaca agtgcctgct gcagatcgcc ctgctgctgt gcttcagcac      60
caccgccctg agcatgagct acaacctgct gggcttcctg cagaggtcca gcaacttcca     120
gtgccagaag ctgctgtggc agctgaacgg caggctggaa tactgcctga aggacaggat     180
gaacttcgac atcccagagg aaatcaagca gctgcagcag ttccagaagg aggacgccgc     240
cctgaccatc tacgagatgc tgcagaacat cttcgccatc ttcaggcagg acagcagcag     300
caccggctgg aacgagacca tcgtggagaa cctgctggcc aacgtgtacc accagatcaa     360
ccacctgaaa accgtgctgg aagagaagct ggaaaaggag gacttcacca ggggcaagct     420
gatgagcagc ctgcacctga agaggtacta cggcagaatc ctgcactacc tgaaggccaa     480
ggagtacagc cactgcgcct ggaccatcgt gagggtggag atcctgagga acttctactt     540
catcaacagg ctgaccggct acctgaggaa cagctccagc agcaaggccc ctccaccttc     600
cctgccaagt ccaagccgac tccctgggcc ctccgataca ccaattctgc cacagtgatg     660
a                                                                     661
```

<210> SEQ ID NO 33
<211> LENGTH: 243
<212> TYPE: PRT
<213> ORGANISM: Artificial Sequence
<220> FEATURE:
<223> OTHER INFORMATION: IFN-CTP-CTP

<400> SEQUENCE: 33

```
Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110
```

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
        130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Ser Ser Ser Ser Lys
            180                 185                 190

Ala Pro Pro Ser Leu Pro Ser Pro Ser Arg Leu Pro Gly Pro Ser
        195                 200                 205

Asp Thr Pro Ile Leu Pro Gln Ser Ser Ser Lys Ala Pro Pro Pro
    210                 215                 220

Ser Leu Pro Ser Pro Ser Arg Leu Pro Gly Pro Ser Asp Thr Pro Ile
225                 230                 235                 240

Leu Pro Gln

<210> SEQ ID NO 34
<211> LENGTH: 765
<212> TYPE: DNA
<213> ORGANISM: Artificial Sequence
<220> FEATURE:
<223> OTHER INFORMATION: IFN-CTP-CTP

<400> SEQUENCE: 34

```
tctagaggac atgaccaaca agtgcctgct gcagatcgcc ctgctgctgt gcttcagcac      60
caccgccctg agcatgagct acaacctgct gggcttcctg cagaggtcca gcaacttcca    120
gtgccagaag ctgctgtggc agctgaacgg caggctggaa tactgcctga aggacaggat    180
gaacttcgac atcccagagg aaatcaagca gctgcagcag ttccagaagg aggacgccgc    240
cctgaccatc tacgagatgc tgcagaacat cttcgccatc ttcaggcagg acagcagcag    300
caccggctgg aacgagacca tcgtggagaa cctgctggcc aacgtgtacc accagatcaa    360
ccacctgaaa accgtgctgg aagagaagct ggaaaaggag gacttcacca ggggcaagct    420
gatgagcagc ctgcacctga gaggtacta cggcagaatc ctgcactacc tgaaggccaa    480
ggagtacagc cactgcgcct ggaccatcgt gagggtggaa atcctgagga acttctactt    540
catcaacagg ctgaccggct acctgaggaa cagctccagc agcaaggccc ctccaccttc    600
cctgccaagt ccaagccgac tccctgggcc tccgacaca ccaatcctgc acagagcag    660
ctcctctaag gcccctcctc catccctgcc atcccctcc cggctgcctg gcccctctga    720
caccctatc ctgcctcagt gatgaaggtc tggatccgcg ccgc                     765
```

<210> SEQ ID NO 35
<211> LENGTH: 271
<212> TYPE: PRT
<213> ORGANISM: Artificial Sequence
<220> FEATURE:
<223> OTHER INFORMATION: CTP-IFN-CTP-CTP

<400> SEQUENCE: 35

Met Thr Asn Lys Cys Leu Leu Gln Ile Ala Leu Leu Cys Phe Ser
1               5                   10                  15

Thr Thr Ala Leu Ser Ser Ser Ser Ser Lys Ala Pro Pro Pro Ser Leu
            20                  25                  30

```
Pro Ser Pro Ser Arg Leu Pro Gly Pro Ser Asp Thr Pro Ile Leu Pro
            35                  40                  45
Gln Met Ser Tyr Asn Leu Leu Gly Phe Leu Gln Arg Ser Ser Asn Phe
 50                  55                  60
Gln Cys Gln Lys Leu Leu Trp Gln Leu Asn Gly Arg Leu Glu Tyr Cys
 65                  70                  75                  80
Leu Lys Asp Arg Met Asn Phe Asp Ile Pro Glu Glu Ile Lys Gln Leu
                 85                  90                  95
Gln Gln Phe Gln Lys Glu Asp Ala Ala Leu Thr Ile Tyr Glu Met Leu
                100                 105                 110
Gln Asn Ile Phe Ala Ile Phe Arg Gln Asp Ser Ser Ser Thr Gly Trp
                115                 120                 125
Asn Glu Thr Ile Val Glu Asn Leu Leu Ala Asn Val Tyr His Gln Ile
            130                 135                 140
Asn His Leu Lys Thr Val Leu Glu Glu Lys Leu Glu Lys Glu Asp Phe
145                 150                 155                 160
Thr Arg Gly Lys Leu Met Ser Ser Leu His Leu Lys Arg Tyr Tyr Gly
                165                 170                 175
Arg Ile Leu His Tyr Leu Lys Ala Lys Glu Tyr Ser His Cys Ala Trp
            180                 185                 190
Thr Ile Val Arg Val Glu Ile Leu Arg Asn Phe Tyr Phe Ile Asn Arg
            195                 200                 205
Leu Thr Gly Tyr Leu Arg Asn Ser Ser Ser Ser Lys Ala Pro Pro Pro
            210                 215                 220
Ser Leu Pro Ser Pro Ser Arg Leu Pro Gly Pro Ser Asp Thr Pro Ile
225                 230                 235                 240
Leu Pro Gln Ser Ser Ser Ser Lys Ala Pro Pro Pro Ser Leu Pro Ser
                245                 250                 255
Pro Ser Arg Leu Pro Gly Pro Ser Asp Thr Pro Ile Leu Pro Gln
                260                 265                 270

<210> SEQ ID NO 36
<211> LENGTH: 849
<212> TYPE: DNA
<213> ORGANISM: Artificial Sequence
<220> FEATURE:
<223> OTHER INFORMATION: CTP-IFN-CTP-CTP

<400> SEQUENCE: 36
tctagaggac atgaccaaca agtgcctgct gcagatcgcc ctgctgctgt gcttcagcac      60
caccgccctg agcagcagca gctccaaggc cccacccccc agcctgccca gcccagcag     120
actgccaggc cccagcgaca ccccatcct gccccagatg agctacaacc tgctgggctt     180
cctgcagagg tccagcaact tccagtgcca gaagctgctg tggcagctga cggcaggct     240
ggaatactgc ctgaaggaca ggatgaactt cgacatccca gaggaaatca agcagctgca     300
gcagttccag aaggaggacg ccgccctgac catctacgag atgctgcaga acatcttcgc     360
catcttcagg caggacagca gcagcaccgg ctggaacgag accatcgtgg agaacctgct     420
ggccaacgtg taccaccaga tcaaccacct gaaaaccgtg ctggaagaga gctggaaaaa     480
ggaggacttc accaggggca agctgatgag cagcctgcac ctgaagaggt actacggcag     540
aatcctgcac tacctgaagg ccaaggagta cagccactgc gcctggacca tcgtgagggt     600
ggagatcctg aggaacttct acttcatcaa caggctgacc ggctacctga ggaacagctc     660
cagcagcaag gcccctccac cttccctgcc cagtccaagc cgactccctg ggcctccga     720
```

```
cacaccaatc ctgccacaga gcagctcctc taaggcccct cctccatccc tgccatcccc      780
ctcccggctg cctggcccct ctgacacccc tatcctgcct cagtgatgaa ggtctggatc      840
cgcggccgc                                                              849
```

<210> SEQ ID NO 37
<211> LENGTH: 409
<212> TYPE: PRT
<213> ORGANISM: Artificial Sequence
<220> FEATURE:
<223> OTHER INFORMATION: CTP-IFN(CTP)

<400> SEQUENCE: 37

```
Met Thr Asn Lys Cys Leu Leu Gln Ile Ala Leu Leu Cys Phe Ser
1               5                   10                  15

Thr Thr Ala Leu Ser Ser Ser Ser Lys Ala Pro Pro Ser Leu
            20                  25                  30

Pro Ser Pro Ser Arg Leu Pro Gly Pro Ser Asp Thr Pro Ile Leu Pro
            35                  40                  45

Gln Met Ser Tyr Asn Leu Leu Gly Phe Leu Gln Arg Ser Ser Asn Phe
        50                  55                  60

Gln Cys Gln Lys Leu Leu Trp Gln Leu Asn Gly Arg Leu Glu Tyr Cys
65                  70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
            100                 105                 110

Gln Asn Ile Phe Ala Ile Phe Arg Gln Asp Ser Ser Ser Thr Gly Trp
        115                 120                 125

Asn Glu Thr Ile Val Glu Asn Leu Leu Ala Asn Val Tyr His Gln Ile
130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
        195                 200                 205

Leu Thr Gly Tyr Leu Arg Asn Ser Ser Ser Lys Ala Pro Pro Pro
    210                 215                 220

Ser Leu Pro Ser Pro Ser Arg Leu Pro Gly Pro Ser Asp Thr Pro Ile
225                 230                 235                 240

Leu Pro Gln Met Ser Tyr Asn Leu Leu Gly Phe Leu Gln Arg Ser Ser
                245                 250                 255

Asn Phe Gln Cys Gln Lys Leu Leu Trp Gln Leu Asn Gly Arg Leu Glu
            260                 265                 270

Tyr Cys Leu Lys Asp Arg Met Asn Phe Asp Ile Pro Glu Glu Ile Lys
        275                 280                 285

Gln Leu Gln Gln Phe Gln Lys Glu Asp Ala Ala Leu Thr Ile Tyr Glu
    290                 295                 300

Met Leu Gln Asn Ile Phe Ala Ile Phe Arg Gln Asp Ser Ser Ser Thr
305                 310                 315                 320

Gly Trp Asn Glu Thr Ile Val Glu Asn Leu Leu Ala Asn Val Tyr His
                325                 330                 335
```

```
Gln Ile Asn His Leu Lys Thr Val Leu Glu Glu Lys Leu Glu Lys Glu
                340                 345                 350

Asp Phe Thr Arg Gly Lys Leu Met Ser Ser Leu His Leu Lys Arg Tyr
            355                 360                 365

Tyr Gly Arg Ile Leu His Tyr Leu Lys Ala Lys Glu Tyr Ser His Cys
        370                 375                 380

Ala Trp Thr Ile Val Arg Val Glu Ile Leu Arg Asn Phe Tyr Phe Ile
385                 390                 395                 400

Asn Arg Leu Thr Gly Tyr Leu Arg Asn
                405

<210> SEQ ID NO 38
<211> LENGTH: 1261
<212> TYPE: DNA
<213> ORGANISM: Artificial Sequence
<220> FEATURE:
<223> OTHER INFORMATION: CTP-IFN(CTP)

<400> SEQUENCE: 38
tctagaggac atgaccaaca agtgcctgct gcagatcgcc ctgctgctgt gcttcagcac      60
caccgccctg agcagcagca gctccaaggc cccacccccc agcctgccca gccccagcag     120
gctgccaggc cccagcgaca cccccatcct gccccagatg agctacaacc tgctgggctt     180
cctgcagagg tccagcaact tccagtgcca gaaactgctg tggcagctga acggcaggct     240
ggaatactgc ctgaaggacc ggatgaactt cgacatcccc gaagagatca gcagctgca      300 gcagttccag aaagaggacg ccgccctgac catctacgag atgctgcaga acatcttcgc     360
catcttcagg caggacagca gcagcaccgg ctggaacgag accatcgtgg agaacctgct     420
ggccaacgtg taccaccaga tcaaccacct gaaaaccgtg ctggaagaga gctggaaaa      480 agaggacttc accaggggca gctgatgag cagcctgcac ctgaagaggt actacggcag     540
aatcctgcac tacctgaagg ccaaagagta cagccactgc gcctggacca tcgtgagggt     600
ggagatcctg cggaacttct acttcatcaa caggctgacc ggctacctga ggaacagctc     660
cagcagcaag gccccccac cctccctgcc ctccccaagc agactgcccg gaccctccga     720
cacaccaatt ctgccacaga tgtcctacaa tctgctcgga tttctgcagc gctcctccaa     780
cttttcagtg tcagaagctcc tctggcagct caatggccgc tggaatatt gtctgaaaga     840 cagaatgaat tttgacatcc agagggaaat taaacagctc cagcagtttc agaaagaaga     900
tgctgctctc acaatctatg aaatgctcca gaatatcttt gcaatctttc gccaggacag     960
ctcctccacc gggtggaatg agacaattgt cgagaatctg ctcgccaatg tctatcatca    1020
gatcaatcac ctcaagacag tcctcgaaga aaaactcgaa aagaagatt cacacgcgg     1080 caaactgatg tcctccctgc atctgaagcg ctactatggg cgcatcctgc attatctgaa    1140
agctaaagaa tactcccact gtgcttggac aattgtgcgc gtcgagatcc tgagaaactt    1200
ttatttcatt aaccgcctga caggatacct gcgcaactga tgaaggtctg gatgcggccg    1260
c                                                                   1261

<210> SEQ ID NO 39
<211> LENGTH: 215
<212> TYPE: PRT
<213> ORGANISM: Artificial Sequence
<220> FEATURE:
<223> OTHER INFORMATION: CTP-IFN

<400> SEQUENCE: 39
```

```
Met Thr Asn Lys Cys Leu Leu Gln Ile Ala Leu Leu Leu Cys Phe Ser
1               5                   10                  15

Thr Thr Ala Leu Ser Ser Ser Ser Lys Ala Pro Pro Pro Ser Leu
            20              25                  30

Pro Ser Pro Ser Arg Leu Pro Gly Pro Ser Asp Thr Pro Ile Leu Pro
                35              40                  45

Gln Met Ser Tyr Asn Leu Leu Gly Phe Leu Gln Arg Ser Ser Asn Phe
    50              55                  60

Gln Cys Gln Lys Leu Leu Trp Gln Leu Asn Gly Arg Leu Glu Tyr Cys
65                  70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
                100                 105                 110

Gln Asn Ile Phe Ala Ile Phe Arg Gln Asp Ser Ser Ser Thr Gly Trp
            115                 120                 125

Asn Glu Thr Ile Val Glu Asn Leu Leu Ala Asn Val Tyr His Gln Ile
            130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
            195                 200                 205

Leu Thr Gly Tyr Leu Arg Asn
    210                 215

<210> SEQ ID NO 40
<211> LENGTH: 673
<212> TYPE: DNA
<213> ORGANISM: Artificial Sequence
<220> FEATURE:
<223> OTHER INFORMATION: CTP-IFN

<400> SEQUENCE: 40
tctagaggac atgaccaaca agtgcctgct gcagatcgcc ctgctgctgt gcttcagcac    60
caccgccctg agcagcagca gctccaaggc cccaccccca gcctgcccca gcccagcag   120 gctgccaggc cccagcgaca cccccatcct gccccagatg agctacaacc tgctgggctt   180
cctgcagagg tccagcaact tccagtgcca gaaactgctg tggcagctga acggcaggct   240
ggaatactgc ctgaaggacc ggatgaactt cgacatcccc gaagagatca agcagctgca   300
gcagttccag aaagaggacg ccgccctgac catctacgag atgctgcaga acatcttcgc   360
catcttcagg caggacagca gcagcaccgg ctggaacgag accatcgtgg agaacctgct   420
ggccaacgtg taccaccaga tcaaccacct gaaaaccgtg ctggaagaga gctggaaaa   480 agaggacttc accaggggca agctgatgag cagcctgcac ctgaagaggt actacggcag   540
aatcctgcac tacctgaagg ccaaagagta cagccactgc gcctggacca tcgtgagggt   600
ggagatcctg cggaacttct acttcatcaa caggctgacc ggctacctga ggaactgatg   660
agtccgcggc cgc                                                     673

<210> SEQ ID NO 41
<211> LENGTH: 243
```

```
<212> TYPE: PRT
<213> ORGANISM: Artificial Sequence
<220> FEATURE:
<223> OTHER INFORMATION: CTP-IFN-CTP

<400> SEQUENCE: 41
```

| | | | | | | | | | | | | | | | |
|---|---|---|---|---|---|---|---|---|---|---|---|---|---|---|---|
| Met | Thr | Asn | Lys | Cys | Leu | Leu | Gln | Ile | Ala | Leu | Leu | Leu | Cys | Phe | Ser |
| 1 | | | | 5 | | | | | 10 | | | | | 15 | |
| Thr | Thr | Ala | Leu | Ser | Ser | Ser | Ser | Lys | Ala | Pro | Pro | Pro | Ser | Leu | |
| | | | 20 | | | | | 25 | | | | | 30 | | |
| Pro | Ser | Pro | Ser | Arg | Leu | Pro | Gly | Pro | Ser | Asp | Thr | Pro | Ile | Leu | Pro |
| | | | 35 | | | | 40 | | | | | 45 | | | |
| Gln | Met | Ser | Tyr | Asn | Leu | Leu | Gly | Phe | Leu | Gln | Arg | Ser | Ser | Asn | Phe |
| | 50 | | | | | 55 | | | | | 60 | | | | |
| Gln | Cys | Gln | Lys | Leu | Leu | Trp | Gln | Leu | Asn | Gly | Arg | Leu | Glu | Tyr | Cys |
| 65 | | | | | 70 | | | | | 75 | | | | | 80 |
| Leu | Lys | Asp | Arg | Met | Asn | Phe | Asp | Ile | Pro | Glu | Glu | Ile | Lys | Gln | Leu |
| | | | | 85 | | | | | 90 | | | | | 95 | |
| Gln | Gln | Phe | Gln | Lys | Glu | Asp | Ala | Ala | Leu | Thr | Ile | Tyr | Glu | Met | Leu |
| | | | 100 | | | | | 105 | | | | | 110 | | |
| Gln | Asn | Ile | Phe | Ala | Ile | Phe | Arg | Gln | Asp | Ser | Ser | Ser | Thr | Gly | Trp |
| | | | 115 | | | | | 120 | | | | | 125 | | |
| Asn | Glu | Thr | Ile | Val | Glu | Asn | Leu | Leu | Ala | Asn | Val | Tyr | His | Gln | Ile |
| | 130 | | | | | 135 | | | | | 140 | | | | |
| Asn | His | Leu | Lys | Thr | Val | Leu | Glu | Glu | Lys | Leu | Glu | Lys | Glu | Asp | Phe |
| 145 | | | | | 150 | | | | | 155 | | | | | 160 |
| Thr | Arg | Gly | Lys | Leu | Met | Ser | Ser | Leu | His | Leu | Lys | Arg | Tyr | Tyr | Gly |
| | | | | 165 | | | | | 170 | | | | | 175 | |
| Arg | Ile | Leu | His | Tyr | Leu | Lys | Ala | Lys | Glu | Tyr | Ser | His | Cys | Ala | Trp |
| | | | 180 | | | | | 185 | | | | | 190 | | |
| Thr | Ile | Val | Arg | Val | Glu | Ile | Leu | Arg | Asn | Phe | Tyr | Phe | Ile | Asn | Arg |
| | | | 195 | | | | | 200 | | | | | 205 | | |
| Leu | Thr | Gly | Tyr | Leu | Arg | Asn | Ser | Ser | Ser | Ser | Lys | Ala | Pro | Pro | Pro |
| | 210 | | | | | 215 | | | | | 220 | | | | |
| Ser | Leu | Pro | Ser | Pro | Ser | Arg | Leu | Pro | Gly | Pro | Ser | Asp | Thr | Pro | Ile |
| 225 | | | | | 230 | | | | | 235 | | | | | 240 |
| Leu | Pro | Gln | | | | | | | | | | | | | |

```
<210> SEQ ID NO 42
<211> LENGTH: 763
<212> TYPE: DNA
<213> ORGANISM: Artificial Sequence
<220> FEATURE:
<223> OTHER INFORMATION: CTP-IFN-CTP

<400> SEQUENCE: 42
tctagaggac atgaccaaca agtgcctgct gcagatcgcc ctgctgctgt gcttcagcac    60
caccgccctg agcagcagca gctccaaggc cccacccccc agcctgccca gcccagcag   120 actgccaggc cccagcgaca cccccatcct gccccagatg agctacaacc tgctgggctt   180
cctgcagagg tccagcaact tccagtgcca gaagctgctg tggcagctga acggcaggct   240
ggaatactgc ctgaaggaca ggatgaactt cgacatccca gaggaaatca agcagctgca   300
gcagttccag aaggaggacg ccgccctgac catctacgag atgctgcaga acatcttcgc   360
catcttcagg caggacagca gcagcaccgg ctggaacgag accatcgtgg agaacctgct   420
ggccaacgtg taccaccaga tcaaccacct gaaaaccgtg ctggaagaga gctggaaaa   480
```

```
ggaggacttc accaggggca agctgatgag cagcctgcac ctgaagaggt actacggcag    540
aatcctgcac tacctgaagg ccaaggagta cagccactgc gcctggacca tcgtgagggt    600
ggagatcctg aggaacttct acttcatcaa caggctgacc ggctacctga ggaacagctc    660
cagcagcaag gccctccac cttccctgcc cagtccaagc cgactccctg ggccctccga    720
tacaccaatt ctgccacagt gatgaaggtc tggatgcggc cgc                      763
```

```
<210> SEQ ID NO 43
<211> LENGTH: 166
<212> TYPE: PRT
<213> ORGANISM: Artificial
<220> FEATURE:
<223> OTHER INFORMATION: IFN-beta

<400> SEQUENCE: 43
```

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

```
<210> SEQ ID NO 44
<211> LENGTH: 242
<212> TYPE: PRT
<213> ORGANISM: Artificial
<220> FEATURE:
<223> OTHER INFORMATION: APO-A1

<400> SEQUENCE: 44
```

Asp Glu Pro Pro Gln Ser Pro Trp Asp Arg Val Lys Asp Lys Ala Thr
1               5                   10                  15

Val Tyr Val Asp Val Leu Lys Asp Ser Gly Arg Asp Tyr Val Ser Gln
            20                  25                  30

Phe Glu Gly Ser Ala Gly Lys Gly Leu Asn Leu Lys Leu Leu Asp Asn
        35                  40                  45

Trp Asp Ser Val Thr Ser Thr Phe Ser Lys Leu Arg Glu Gln Leu Gly
    50                  55                  60

Pro Val Thr Gln Glu Phe Trp Asp Asn Leu Glu Lys Glu Thr Glu Gly
65                  70                  75                  80

```
Leu Arg Gly Glu Met Ser Lys Asp Leu Glu Val Lys Ala Lys Val
                85                  90                  95

Gln Pro Tyr Leu Asp Asp Phe Gln Lys Lys Trp Gln Glu Glu Met Glu
            100                 105                 110

Leu Tyr Arg Gln Lys Val Glu Pro Leu Arg Ala Glu Leu Gln Glu Gly
            115                 120                 125

Ala Arg Gln Lys Leu His Glu Leu Gln Glu Lys Leu Ser Pro Leu Gly
130                 135                 140

Glu Glu Met Arg Asp Arg Ala Arg Ala His Val Asp Ala Leu Arg Thr
145                 150                 155                 160

His Leu Ala Pro Tyr Ser Asp Glu Leu Arg Gln Arg Leu Ala Ala Arg
                165                 170                 175

Leu Glu Ala Leu Lys Glu Asn Gly Gly Ala Arg Leu Ala Glu Tyr His
            180                 185                 190

Ala Lys Ala Thr Glu His Leu Ser Thr Leu Ser Glu Lys Ala Lys Pro
            195                 200                 205

Ala Leu Glu Asp Leu Arg Gln Gly Leu Leu Pro Val Leu Glu Ser Phe
            210                 215                 220

Lys Val Ser Phe Leu Ser Ala Leu Glu Glu Tyr Thr Lys Lys Leu Asn
225                 230                 235                 240

Thr Gln

<210> SEQ ID NO 45
<211> LENGTH: 444
<212> TYPE: PRT
<213> ORGANISM: Homo sapiens

<400> SEQUENCE: 45

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
            115                 120                 125

Cys Val Asn Glu Asn Gly Gly Cys Glu Gln Tyr Cys Ser Asp His Thr
130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
            195                 200                 205
```

```
Leu Val Asn Gly Ala Gln Leu Cys Gly Gly Thr Leu Ile Asn Thr Ile
210                 215                 220

Trp Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
                275                 280                 285

Pro Val Val Leu Thr Asp His Val Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
                340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro
            435                 440

<210> SEQ ID NO 46
<211> LENGTH: 448
<212> TYPE: PRT
<213> ORGANISM: Homo sapiens

<400> SEQUENCE: 46

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
                20                  25                  30

Leu His Arg Arg Arg Arg Ala Asn Ala Phe Leu Glu Glu Leu Arg Pro
            35                  40                  45

Gly Ser Leu Glu Arg Glu Cys Lys Glu Glu Gln Cys Ser Phe Glu Glu
        50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
130                 135                 140
```

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
            165                 170                 175

Pro Ile Leu Glu Lys Arg Asn Ala Ser Lys Pro Gln Gly Arg Ile Val
        180                 185                 190

Gly Gly Lys Val Cys Pro Lys Gly Glu Cys Pro Trp Gln Val Leu Leu
    195                 200                 205

Leu Val Asn Gly Ala Gln Leu Cys Gly Gly Thr Leu Ile Asn Thr Ile
210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Gly Cys Gly Arg
        435                 440                 445

<210> SEQ ID NO 47
<211> LENGTH: 1356
<212> TYPE: DNA
<213> ORGANISM: Homo sapiens

<400> SEQUENCE: 47
ctcgaggaca tggtctccca ggccctcagg ctcctctgcc ttctgcttgg gcttcagggc    60
tgcctggctg cagtcttcgt aacccaggag gaagcccacg gcgtcctgca ccggcgccgg   120
cgcgccaacg cgttcctgga ggagctgcgg ccgggctccc tggagaggga gtgcaaggag   180
gagcagtgct ccttcgagga ggcccgggag atcttcaagg acgcggagag gacgaagctg   240
ttctggattt cttacagtga tgggaccag tgtgcctcaa gtccatgcca gaatgggggc   300
tcctgcaaga ccagctcca gtcctatatc tgcttctgcc tccctgcctt cgagggccgg   360
aactgtgaga cgcacaagga tgaccagctg atctgtgtga cgagaacgg cggctgtgag   420

| | |
|---|---|
| cagtactgca gtgaccacac gggcaccaag cgctcctgtc ggtgccacga ggggtactct | 480 |
| ctgctggcag acggggtgtc ctgcacaccc acagttgaat atccatgtgg aaaaatacct | 540 |
| attctagaaa aaagaaatgc cagcaaaccc caaggccgaa ttgtgggggg caaggtgtgc | 600 |
| cccaaagggg agtgtccatg gcaggtcctg ttgttggtga atggagctca gttgtgtggg | 660 |
| gggaccctga tcaacaccat ctgggtggtc tccgcggccc actgtttcga caaaatcaag | 720 |
| aactggagga acctgatcgc ggtgctgggc gagcacgacc tcagcgagca cgacggggat | 780 |
| gagcagagcc ggcgggtggc gcaggtcatc atccccagca cgtacgtccc gggcaccacc | 840 |
| aaccacgaca tcgcgctgct ccgcctgcac cagcccgtgg tcctcactga ccatgtggtg | 900 |
| cccctctgcc tgcccgaacg gacgttctct gagaggacgc tggccttcgt gcgcttctca | 960 |
| ttggtcagcg gctggggcca gctgctggac cgtggcgcca cggccctgga gctcatggtc | 1020 |
| ctcaacgtgc cccggctgat gacccaggac tgcctgcagc agtcacggaa ggtgggagac | 1080 |
| tccccaaata tcacggagta catgttctgt gccggctact cggatggcag caaggactcc | 1140 |
| tgcaaggggg acagtggagg cccacatgcc acccactacc ggggcacgtg gtacctgacg | 1200 |
| ggcatcgtca gctggggcca gggctgcgca accgtgggcc actttgggt gtacaccagg | 1260 |
| gtctcccagt acatcgagtg gctgcaaaag ctcatgcgct cagagccacg cccaggagtc | 1320 |
| ctcctgcgag ccccatttcc ctgaggatgc ggccgc | 1356 |

<210> SEQ ID NO 48
<211> LENGTH: 1442
<212> TYPE: DNA
<213> ORGANISM: Artificial Sequence
<220> FEATURE:
<223> OTHER INFORMATION: Factor VII-CTP

<400> SEQUENCE: 48

| | |
|---|---|
| ctcgaggaca tggtctccca ggccctcagg ctcctctgcc ttctgcttgg gcttcagggc | 60 |
| tgcctggctg cagtcttcgt aacccaggag gaagcccacg gcgtcctgca ccggcgccgg | 120 |
| cgcgccaacg cgttcctgga ggagctgcgg ccgggctccc tggagaggga gtgcaaggag | 180 |
| gagcagtgct ccttcgagga ggcccgggag atcttcaagg acgcggagag gacgaagctg | 240 |
| ttctggattt cttacagtga tgggaccag tgtgcctcaa gtccatgcca gaatgggggc | 300 |
| tcctgcaagg accagctcca gtcctatatc tgcttctgcc tccctgcctt cgagggccgg | 360 |
| aactgtgaga cgcacaagga tgaccagctg atctgtgtga acgagaacgg cggctgtgag | 420 |
| cagtactgca gtgaccacac gggcaccaag cgctcctgtc ggtgccacga ggggtactct | 480 |
| ctgctggcag acggggtgtc ctgcacaccc acagttgaat atccatgtgg aaaaatacct | 540 |
| attctagaaa aaagaaatgc cagcaaaccc caaggccgaa ttgtgggggg caaggtgtgc | 600 |
| cccaaagggg agtgtccatg gcaggtcctg ttgttggtga atggagctca gttgtgtggg | 660 |
| gggaccctga tcaacaccat ctgggtggtc tccgcggccc actgtttcga caaaatcaag | 720 |
| aactggagga acctgatcgc ggtgctgggc gagcacgacc tcagcgagca cgacggggat | 780 |
| gagcagagcc ggcgggtggc gcaggtcatc atccccagca cgtacgtccc gggcaccacc | 840 |
| aaccacgaca tcgcgctgct ccgcctgcac cagcccgtgg tcctcactga ccatgtggtg | 900 |
| cccctctgcc tgcccgaacg gacgttctct gagaggacgc tggccttcgt gcgcttctca | 960 |
| ttggtcagcg gctggggcca gctgctggac cgtggcgcca cggccctgga gctcatggtc | 1020 |
| ctcaacgtgc cccggctgat gacccaggac tgcctgcagc agtcacggaa ggtgggagac | 1080 |

```
tccccaaata tcacggagta catgttctgt gccggctact cggatggcag caaggactcc    1140 tgcaagggg  acagtggagg cccacatgcc acccactacc ggggcacgtg gtacctgacc    1200
ggcatcgtga gctggggcca gggctgcgcc accgtgggcc acttcggcgt gtacaccagg    1260
gtgtcccagt acatcgagtg gctgcagaaa ctgatgagaa gcgagcccag acccggcgtg    1320
ctgctgagag ccccttccc cagcagcagc tccaaggccc tcccccctag cctgcccagc    1380
cctagcagac tgcctgggcc cagcgacacc cccatcctgc cccagtgagg atccgcggcc    1440
gc                                                                  1442
```

<210> SEQ ID NO 49
<211> LENGTH: 472
<212> TYPE: PRT
<213> ORGANISM: Artificial Sequence
<220> FEATURE:
<223> OTHER INFORMATION: Factor VII-CTP

<400> SEQUENCE: 49

```
Met Val Ser Gln Ala Leu Arg Leu Leu Cys Leu Leu Leu Gly Leu Gln
 1               5                  10                  15

Gly Cys Leu Ala Ala Val Phe Val Thr Gln Glu Glu Ala His Gly Val
             20                  25                  30

Leu His Arg Arg Arg Arg Ala Asn Ala Phe Leu Glu Glu Leu Arg Pro
         35                  40                  45

Gly Ser Leu Glu Arg Glu Cys Lys Glu Glu Gln Cys Ser Phe Glu Glu
     50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Ser Pro Cys Gln Asn Gly
                 85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
```

```
                290                   295                   300
Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ser Ser Ser Ser
        435                 440                 445

Lys Ala Pro Pro Pro Ser Leu Pro Ser Pro Ser Arg Leu Pro Gly Pro
    450                 455                 460

Ser Asp Thr Pro Ile Leu Pro Gln
465                 470

<210> SEQ ID NO 50
<211> LENGTH: 1535
<212> TYPE: DNA
<213> ORGANISM: Artificial Sequence
<220> FEATURE:
<223> OTHER INFORMATION: Factor VII-CTP-CTP

<400> SEQUENCE: 50
ctcgaggaca tggtctccca ggccctcagg ctcctctgcc ttctgcttgg gcttcagggc      60
tgcctggctg cagtcttcgt aacccaggag gaagcccacg gcgtcctgca ccggcgccgg     120
cgcgccaacg cgttcctgga ggagctgcgg ccgggctccc tggagaggga gtgcaaggag     180
gagcagtgct ccttcgagga ggcccgggag atcttcaagg acgcggagag gacgaagctg     240
ttctggattt cttacagtga tggggaccag tgtgcctcaa gtccatgcca gaatggggggc    300
tcctgcaagg accagctcca gtcctatatc tgcttctgcc tccctgcctt cgagggccgg     360
aactgtgaga gcacaagga tgaccagctg atctgtgtga cgagaacgg cggctgtgag       420
cagtactgca gtgaccacac gggcaccaag cgctcctgtc ggtgccacga ggggtactct     480
ctgctggcag acgggtgtc ctgcacaccc acagttgaat atccatgtgg aaaaatacct     540
attctagaaa aagaaatgc cagcaaaccc caaggccgaa ttgtgggggg caaggtgtgc     600
cccaaagggg agtgtccatg gcaggtcctg ttgttggtga atggagctca gttgtgtggg     660
gggaccctga tcaacaccat ctgggtggtc tccgcggccc actgtttcga caaaatcaag     720
aactggagga acctgatcgc ggtgctgggc gagcacgacc tcagcgagca cgacggggat     780
gagcagagcc ggcgggtggc gcaggtcatc atccccagcc gtacgtccc gggcaccacc     840
aaccacgaca tcgcgctgct ccgcctgcac cagcccgtgg tcctcactga ccatgtggtg     900
cccctctgcc tgcccgaacg acgttctct gagaggacgc tggccttcgt gcgcttctca     960
ttggtcagcg gctggggcca gctgctggac cgtggcgcca cggccctgga gctcatggtc    1020
```

-continued

```
ctcaacgtgc cccggctgat gacccaggac tgcctgcagc agtcacggaa ggtgggagac    1080
tccccaaata tcacggagta catgttctgt gccggctact cggatggcag caaggactcc    1140 tgcaagggg acagtggagg cccacatgcc acccactacc ggggcacgtg gtacctgacc     1200
ggcatcgtga gctggggcca gggctgcgcc accgtgggcc acttcggcgt gtacaccagg    1260
gtgtcccagt acatcgagtg gctgcagaaa ctgatgagaa gcgagcccag accggcgtg    1320 ctgctgagag ccccttccc cagcagcagc tccaaggccc ctcccctag cctgcccagc      1380 cctagcagac tgcctgggcc ctccgacaca ccaatcctgc cacagagcag ctcctctaag    1440
gcccctcctc catccctgcc atccccctcc cggctgccag cccctctga caccctatc     1500 ctgcctcagt gatgaaggtc tggatccgcg ccgc                                1535
```

<210> SEQ ID NO 51
<211> LENGTH: 500
<212> TYPE: PRT
<213> ORGANISM: Artificial Sequence
<220> FEATURE:
<223> OTHER INFORMATION: factor VII-CTP-CTP

<400> SEQUENCE: 51

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270
```

-continued

```
Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
        290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro Ser Ser Ser Ser
        435                 440                 445

Lys Ala Pro Pro Pro Ser Leu Pro Ser Pro Ser Arg Leu Pro Gly Pro
    450                 455                 460

Ser Asp Thr Pro Ile Leu Pro Gln Ser Ser Ser Lys Ala Pro Pro
465                 470                 475                 480

Pro Ser Leu Pro Ser Pro Ser Arg Leu Pro Gly Pro Ser Asp Thr Pro
                485                 490                 495

Ile Leu Pro Gln
            500

<210> SEQ ID NO 52
<211> LENGTH: 528
<212> TYPE: PRT
<213> ORGANISM: Artificial Sequence
<220> FEATURE:
<223> OTHER INFORMATION: factor VII-CTP-CTP-CTP

<400> SEQUENCE: 52

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125
```

```
Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
                180                 185                 190

Gly Gly Lys Val Cys Pro Lys Gly Glu Cys Pro Trp Gln Val Leu Leu
            195                 200                 205

Leu Val Asn Gly Ala Gln Leu Cys Gly Gly Thr Leu Ile Asn Thr Ile
210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
                260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
                340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Ser Ser Ser Ser
            435                 440                 445

Lys Ala Pro Pro Pro Ser Leu Pro Ser Pro Ser Arg Leu Pro Gly Pro
450                 455                 460

Ser Asp Thr Pro Ile Leu Pro Gln Ser Ser Ser Lys Ala Pro Pro Pro
465                 470                 475                 480

Pro Ser Leu Pro Ser Pro Ser Arg Leu Pro Gly Pro Ser Asp Thr Pro
                485                 490                 495

Ile Leu Pro Gln Ser Ser Ser Lys Ala Pro Pro Pro Ser Leu Pro
                500                 505                 510

Ser Pro Ser Arg Leu Pro Gly Pro Ser Asp Thr Pro Ile Leu Pro Gln
            515                 520                 525

<210> SEQ ID NO 53
<211> LENGTH: 556
<212> TYPE: PRT
```

-continued

<213> ORGANISM: Artificial Sequence
<220> FEATURE:
<223> OTHER INFORMATION: factor VII-CTP-CTP-CTP-CTP

<400> SEQUENCE: 53

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
    370                 375                 380

Pro His Ala Thr His Tyr Arg Gly Thr Trp Tyr Leu Thr Gly Ile Val
```

```
385                 390                 395                 400
Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Ser Ser Ser Ser
                435                 440                 445

Lys Ala Pro Pro Pro Ser Leu Pro Ser Pro Ser Arg Leu Pro Gly Pro
450                 455                 460

Ser Asp Thr Pro Ile Leu Pro Gln Ser Ser Ser Lys Ala Pro Pro Pro
465                 470                 475                 480

Pro Ser Leu Pro Ser Pro Ser Arg Leu Pro Gly Pro Ser Asp Thr Pro
                485                 490                 495

Ile Leu Pro Gln Ser Ser Ser Lys Ala Pro Pro Pro Ser Leu Pro
                500                 505                 510

Ser Pro Ser Arg Leu Pro Gly Pro Ser Asp Thr Pro Ile Leu Pro Gln
                515                 520                 525

Ser Ser Ser Ser Lys Ala Pro Pro Pro Ser Leu Pro Ser Pro Ser Arg
                530                 535                 540

Leu Pro Gly Pro Ser Asp Thr Pro Ile Leu Pro Gln
545                 550                 555

<210> SEQ ID NO 54
<211> LENGTH: 584
<212> TYPE: PRT
<213> ORGANISM: Artificial Sequence
<220> FEATURE:
<223> OTHER INFORMATION: factor VII-CTP-CTP-CTP-CTP

<400> SEQUENCE: 54

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
                20                  25                  30

Leu His Arg Arg Arg Arg Ala Asn Ala Phe Leu Glu Glu Leu Arg Pro
                35                  40                  45

Gly Ser Leu Glu Arg Glu Cys Lys Glu Glu Gln Cys Ser Phe Glu Glu
                50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
                100                 105                 110

Ala Phe Glu Gly Arg Asn Cys Glu Thr His Lys Asp Asp Gln Leu Ile
                115                 120                 125

Cys Val Asn Glu Asn Gly Gly Cys Glu Gln Tyr Cys Ser Asp His Thr
                130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
                180                 185                 190

Gly Gly Lys Val Cys Pro Lys Gly Glu Cys Pro Trp Gln Val Leu Leu
```

```
            195                 200                 205
Leu Val Asn Gly Ala Gln Leu Cys Gly Gly Thr Leu Ile Asn Thr Ile
210                 215                 220

Trp Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
                260                 265                 270

Val Pro Gly Thr Thr Asn His Asp Ile Ala Leu Leu Arg Leu His Gln
                275                 280                 285

Pro Val Val Leu Thr Asp His Val Val Pro Leu Cys Leu Pro Glu Arg
                290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
                340                 345                 350

Arg Lys Val Gly Asp Ser Pro Asn Ile Thr Glu Tyr Met Phe Cys Ala
                355                 360                 365

Gly Tyr Ser Asp Gly Ser Lys Asp Ser Cys Lys Gly Asp Ser Gly Gly
                370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro Ser Ser Ser Ser
                435                 440                 445

Lys Ala Pro Pro Pro Ser Leu Pro Ser Pro Ser Arg Leu Pro Gly Pro
450                 455                 460

Ser Asp Thr Pro Ile Leu Pro Gln Ser Ser Ser Lys Ala Pro Pro
465                 470                 475                 480

Pro Ser Leu Pro Ser Pro Ser Arg Leu Pro Gly Pro Ser Asp Thr Pro
                485                 490                 495

Ile Leu Pro Gln Ser Ser Ser Lys Ala Pro Pro Pro Ser Leu Pro
                500                 505                 510

Ser Pro Ser Arg Leu Pro Gly Pro Ser Asp Thr Pro Ile Leu Pro Gln
                515                 520                 525

Ser Ser Ser Lys Ala Pro Pro Pro Ser Leu Pro Ser Pro Ser Arg
                530                 535                 540

Leu Pro Gly Pro Ser Asp Thr Pro Ile Leu Pro Gln Ser Ser Ser Ser
545                 550                 555                 560

Lys Ala Pro Pro Pro Ser Leu Pro Ser Pro Ser Arg Leu Pro Gly Pro
                565                 570                 575

Ser Asp Thr Pro Ile Leu Pro Gln
                580

<210> SEQ ID NO 55
<211> LENGTH: 1404
<212> TYPE: DNA
<213> ORGANISM: Homo sapiens
```

<400> SEQUENCE: 55

```
gcgatcgcca tgcagcgcgt gaacatgatc atggcagaat caccaggcct catcaccatt      60
gccttttagg atatctactc agtgctgaat gtacagtttt tcttgatcat gaaaacgcca     120
acaaaattct gaatcggcca aagaggtata attcaggtaa attggaagag tttgttcaag     180
ggaaccttga gagagaatgt atggaagaaa agtgtagttt tgaagaagca cgagaagttt     240
ttgaaaacac tgaagaaca actgaatttt ggaagcagta tgttgatgga gatcagtgtg      300
agtccaatcc atgtttaaat ggcggcagtt gcaaggatga cattaattcc tatgaatgtt     360
ggtgtccctt tggatttgaa ggaagaact gtgaattaga tgtaacatgt aacattaaga      420
atggcagatg cgagcagttt tgtaaaaata gtgctgataa caaggtggtt gctcctgta      480
ctgagggata tcgacttgca gaaaaccaga agtcctgtga accagcagtg ccatttccat     540
gtggaagagt ttctgtttca caacttcta agctcacccg tgctgagact gttttcctg      600
atgtggacta tgtaaattct actgaagctg aaaccatttt ggataacatc actcaaagca     660
cccaatcatt taatgacttc actcgagttg ttggtggaga agatgccaaa ccaggtcaat     720
tcccttggca ggttgttttg aatggtaaag ttgatgcatt ctgtggaggc tctatcgtta     780
atgaaaaatg gattgtaact gctgcccact gtgttgaaac tggtgttaaa attacagttg     840
tcgcaggtga acataatatt gaggagacag aacatacaga gcaaaagcga atgtgattc      900
gaattattcc tcaccacaac tacaatgcag ctattaataa gtacaaccat gacattgccc     960
ttctggaact ggacgaaccc ttagtgctaa acagctacgt tacacctatt tgcattgctg    1020
acaaggaata cacgaacatc ttcctcaaat ttggatctgg ctatgtaagt ggctggggaa    1080
gagtcttcca caagggaga tcagctttag ttctccagta ccttagagtt ccacttgttg     1140
accgagccac atgtcttcga tctacaaagt tcaccatcta taacaacatg ttctgtgctg    1200
gcttccatga aggaggtaga gattcatgtc aaggagatag tggggaccc catgttactg     1260
aagtggaagg gaccagtttc ttaactggaa ttattagctg gggtgaagag tgtgcaatga    1320
aaggcaaata tggaatatat accaaggtat cccggtatgt caactggatt aaggaaaaaa    1380
caaagctcac ttgaacgcgg ccgc                                            1404
```

<210> SEQ ID NO 56
<211> LENGTH: 461
<212> TYPE: PRT
<213> ORGANISM: Homo sapiens

<400> SEQUENCE: 56

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110
```

```
Asn Ser Tyr Glu Cys Trp Cys Pro Phe Gly Phe Glu Gly Lys Asn Cys
    115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
    435                 440                 445

Arg Tyr Val Asn Trp Ile Lys Glu Lys Thr Lys Leu Thr
450                 455                 460

<210> SEQ ID NO 57
<211> LENGTH: 1502
<212> TYPE: DNA
<213> ORGANISM: Artificial Sequence
<220> FEATURE:
<223> OTHER INFORMATION: factor IX-CTP

<400> SEQUENCE: 57
gcgatcgcca tgcagcgcgt gaacatgatc atggcagaat caccaggcct catcaccatc    60
```

```
tgccttttag gatatctact cagtgctgaa tgtacagttt ttcttgatca tgaaaacgcc      120
aacaaaattc tgaatcggcc aaagaggtat aattcaggta aattggaaga gtttgttcaa      180
gggaaccttg agagagaatg tatggaagaa aagtgtagtt ttgaagaagc acgagaagtt      240
tttgaaaaca ctgaaagaac aactgaattt tggaagcagt atgttgatgg agatcagtgt      300
gagtccaatc catgttttaaa tggcggcagt tgcaaggatg acattaattc ctatgaatgt      360
tggtgtccct ttggatttga aggaaagaac tgtgaattag atgtaacatg taacattaag      420
aatggcagat gcgagcagtt ttgtaaaaat agtgctgata caaggtggt ttgctcctgt       480 actgagggat atcgacttgc agaaaaccag aagtcctgtg aaccagcagt gccatttcca      540
tgtggaagag tttctgtttc acaaacttct aagctcaccc gtgctgagac tgttttttcct     600 gatgtggact atgtaaattc tactgaagct gaaaccattt tggataacat cactcaaagc      660
acccaatcat ttaatgactt cactcgagtt gttggtggag aagatgccaa accaggtcaa      720
ttcccttggc aggttgtttt gaatggtaaa gttgatgcat tctgtggagg ctctatcgtt      780
aatgaaaaat ggattgtaac tgctgcccac tgtgttgaaa ctggtgttaa aattacagtt      840
gtcgcaggtg aacataatat tgaggagaca gaacatacag agcaaaagcg aaatgtgatt      900
cgaattattc ctcaccacaa ctacaatgca gctattaata agtacaacca tgacattgcc      960
cttctggaac tggacgaacc cttagtgcta acagctacg ttacacctat ttgcattgct       1020
gacaaggaat acacgaacat cttcctcaaa tttggatctg gctatgtaag tggctgggga     1080
agagtcttcc acaaagggag atcagcttta gttcttcagt accttagagt tccacttgtt      1140
gaccgagcca catgtcttcg atctacaaag ttcaccatct ataacaacat gttctgtgct      1200
ggcttccatg aaggaggtag agattcatgt caaggagata gtgggggacc ccatgttact      1260
gaagtggaag ggaccagttt cttaactgga attattagct ggggtgaaga gtgtgcaatg      1320
aaaggcaaat atggaatata taccaaggta tcccggtatg tcaactggat taaggaaaaa     1380
acaaagctca ctagctccag cagcaaggcc cctcccccga gcctgccctc cccaagcagg     1440
ctgcctgggc cctccgacac accaatcctg ccacagtgat gaaggtctgg atccgcggcc     1500
gc                                                                    1502
```

<210> SEQ ID NO 58
<211> LENGTH: 489
<212> TYPE: PRT
<213> ORGANISM: Artificial Sequence
<220> FEATURE:
<223> OTHER INFORMATION: factor IX-CTP

<400> SEQUENCE: 58

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
```

```
                100             105             110
Asn Ser Tyr Glu Cys Trp Cys Pro Phe Gly Phe Glu Gly Lys Asn Cys
            115                 120                 125
Glu Leu Asp Val Thr Cys Asn Ile Lys Asn Gly Arg Cys Glu Gln Phe
            130                 135             140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
                180                 185                 190
Glu Thr Val Phe Pro Asp Val Asp Tyr Val Asn Ser Thr Glu Ala Glu
                195                 200                 205
Thr Ile Leu Asp Asn Ile Thr Gln Ser Thr Gln Ser Phe Asn Asp Phe
            210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
                260                 265                 270
Val Lys Ile Thr Val Val Ala Gly Glu His Asn Ile Glu Glu Thr Glu
                275                 280                 285
His Thr Glu Gln Lys Arg Asn Val Ile Arg Ile Ile Pro His His Asn
            290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
                340                 345                 350
Val Ser Gly Trp Gly Arg Val Phe His Lys Gly Arg Ser Ala Leu Val
                355                 360                 365
Leu Gln Tyr Leu Arg Val Pro Leu Val Asp Arg Ala Thr Cys Leu Arg
            370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
                420                 425                 430
Glu Glu Cys Ala Met Lys Gly Lys Tyr Gly Ile Tyr Thr Lys Val Ser
                435                 440                 445
Arg Tyr Val Asn Trp Ile Lys Glu Lys Thr Lys Leu Thr Ser Ser Ser
            450                 455                 460
Ser Lys Ala Pro Pro Pro Ser Leu Pro Ser Pro Ser Arg Leu Pro Gly
465                 470                 475                 480
Pro Ser Asp Thr Pro Ile Leu Pro Gln
                485

<210> SEQ ID NO 59
<211> LENGTH: 1585
<212> TYPE: DNA
<213> ORGANISM: Artificial Sequence
```

<220> FEATURE:
<223> OTHER INFORMATION: factor IX-CTP-CTP

<400> SEQUENCE: 59

```
gcgatcgcca tgcagcgcgt gaacatgatc atggcagaat caccaggcct catcaccatc      60
tgccttttag atatctact  cagtgctgaa tgtacagttt ttcttgatca tgaaaacgcc     120
aacaaaattc tgaatcggcc aaagaggtat aattcaggta aattggaaga gtttgttcaa     180
gggaaccttg agagagaatg tatggaagaa agtgtagtt  tgaagaagc  acgagaagtt    240
tttgaaaaca ctgaaagaac aactgaattt tggaagcagt atgttgatgg agatcagtgt     300
gagtccaatc catgtttaaa tggcggcagt tgcaaggatg acattaattc ctatgaatgt     360
tggtgtccct ttggatttga aggaaagaac tgtgaattag atgtaacatg taacattaag     420
aatggcagat gcgagcagtt ttgtaaaaat agtgctgata caaggtggt  ttgctcctgt    480
actgagggat atcgacttgc agaaaaccag aagtcctgtg aaccagcagt gccatttcca     540
tgtggaagag tttctgtttc acaaacttct aagctcaccc gtgctgagac tgttttccct     600
gatgtggact atgtaaattc tactgaagct gaaaccattt tggataacat cactcaaagc     660
acccaatcat ttaatgactt cactcgagtt gttggtggag aagatgccaa accaggtcaa     720
ttcccttggc aggttgtttt gaatggtaaa gttgatgcat tctgtggagg ctctatcgtt     780
aatgaaaaat ggattgtaac tgctgcccac tgtgttgaaa ctggtgttaa aattacagtt     840
gtcgcaggtg aacataatat tgaggagaca gaacatacag agcaaaagcg aaatgtgatt     900
cgaattattc ctcaccacaa ctacaatgca gctattaata agtacaacca tgacattgcc     960
cttctggaac tggacgaacc cttagtgcta aacagctacg ttacacctat ttgcattgct    1020
acaaggaata cacgaacatc ttcctcaaat ttggatctgg ctatgtaagt ggctggggaa    1080
gagtcttcca caagggaga  tcagctttag ttcttcagta ccttagagtt ccacttgttg    1140
accgagccac atgtcttcga tctacaaagt tcaccatcta taacaacatg ttctgtgctg    1200
gcttccatga aggaggtaga gattcatgtc aaggagatag tggggaccc  catgttactg    1260
aagtggaagg gaccagtttc ttaactgaa  ttattagctg gggtgaagag tgtgcaatga    1320
aaggcaaata tggaatatat accaaggtat cccggtatgt caactggatt aaggaaaaaa    1380
caaagctcac tagctccagc agcaaggccc ctcccccgag cctgcccctcc ccaagcaggc    1440
tgcctgggcc ctccgacaca ccaatcctgc cacagagcag ctcctctaag gccccctcctc   1500
catccctgcc atcccctcc  cggctgcctg gcccctctga cacccctatc ctgcctcagt    1560
gatgaaggtc tggatccgcg gccgc                                           1585
```

<210> SEQ ID NO 60
<211> LENGTH: 517
<212> TYPE: PRT
<213> ORGANISM: Artificial Sequence
<220> FEATURE:
<223> OTHER INFORMATION: factor IX-CTP-CTP

<400> SEQUENCE: 60

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
```

```
                50            55            60
Met Glu Glu Lys Cys Ser Phe Glu Ala Arg Glu Val Phe Glu Asn
65                  70                  75                  80

Thr Glu Arg Thr Thr Glu Phe Trp Lys Gln Tyr Val Asp Gly Asp Gln
                        85                  90                  95

Cys Glu Ser Asn Pro Cys Leu Asn Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Ser Ser Ser
    450                 455                 460

Ser Lys Ala Pro Pro Ser Leu Pro Ser Pro Ser Arg Leu Pro Gly
465                 470                 475                 480
```

```
Pro Ser Asp Thr Pro Ile Leu Pro Gln Ser Ser Ser Lys Ala Pro
            485                 490                 495

Pro Pro Ser Leu Pro Ser Pro Ser Arg Leu Pro Gly Pro Ser Asp Thr
        500                 505                 510

Pro Ile Leu Pro Gln
        515

<210> SEQ ID NO 61
<211> LENGTH: 545
<212> TYPE: PRT
<213> ORGANISM: Artificial Sequence
<220> FEATURE:
<223> OTHER INFORMATION: factor IX-CTP-CTP-CTP

<400> SEQUENCE: 61

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320
```

```
Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr Ser Ser Ser
        450                 455                 460

Ser Lys Ala Pro Pro Pro Ser Leu Pro Ser Pro Ser Arg Leu Pro Gly
465                 470                 475                 480

Pro Ser Asp Thr Pro Ile Leu Pro Gln Ser Ser Ser Ser Lys Ala Pro
                485                 490                 495

Pro Pro Ser Leu Pro Ser Pro Ser Arg Leu Pro Gly Pro Ser Asp Thr
            500                 505                 510

Pro Ile Leu Pro Gln Ser Ser Ser Ser Lys Ala Pro Pro Pro Ser Leu
        515                 520                 525

Pro Ser Pro Ser Arg Leu Pro Gly Pro Ser Asp Thr Pro Ile Leu Pro
    530                 535                 540

Gln
545
```

<210> SEQ ID NO 62
<211> LENGTH: 573
<212> TYPE: PRT
<213> ORGANISM: Artificial Sequence
<220> FEATURE:
<223> OTHER INFORMATION: factor IX-CTP-CTP-CTP-CTP

<400> SEQUENCE: 62

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125
```

```
Glu Leu Asp Val Thr Cys Asn Ile Lys Asn Gly Arg Cys Glu Gln Phe
    130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
    210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
    290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
    370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr Ser Ser Ser
450                 455                 460
Ser Lys Ala Pro Pro Pro Ser Leu Pro Ser Pro Ser Arg Leu Pro Gly
465                 470                 475                 480
Pro Ser Asp Thr Pro Ile Leu Pro Gln Ser Ser Ser Lys Ala Pro
                485                 490                 495
Pro Pro Ser Leu Pro Ser Pro Ser Arg Leu Pro Gly Pro Ser Asp Thr
            500                 505                 510
Pro Ile Leu Pro Gln Ser Ser Ser Lys Ala Pro Pro Ser Leu
        515                 520                 525
Pro Ser Pro Ser Arg Leu Pro Gly Pro Ser Asp Thr Pro Ile Leu Pro
    530                 535                 540
```

Gln Ser Ser Ser Ser Lys Ala Pro Pro Ser Leu Pro Ser Pro Ser
545                 550                 555                 560

Arg Leu Pro Gly Pro Ser Asp Thr Pro Ile Leu Pro Gln
                565                 570

<210> SEQ ID NO 63
<211> LENGTH: 601
<212> TYPE: PRT
<213> ORGANISM: Artificial Sequence
<220> FEATURE:
<223> OTHER INFORMATION: factor IX-CTP-CTP-CTP-CTP-CTP

<400> SEQUENCE: 63

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

```
Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Ser Ser Ser
    450                 455                 460

Ser Lys Ala Pro Pro Pro Ser Leu Pro Ser Pro Ser Arg Leu Pro Gly
465                 470                 475                 480

Pro Ser Asp Thr Pro Ile Leu Pro Gln Ser Ser Ser Lys Ala Pro
                485                 490                 495

Pro Pro Ser Leu Pro Ser Pro Ser Arg Leu Pro Gly Pro Ser Asp Thr
                500                 505                 510

Pro Ile Leu Pro Gln Ser Ser Ser Lys Ala Pro Pro Pro Ser Leu
            515                 520                 525

Pro Ser Pro Ser Arg Leu Pro Gly Pro Ser Asp Thr Pro Ile Leu Pro
    530                 535                 540

Gln Ser Ser Ser Lys Ala Pro Pro Ser Leu Pro Ser Pro Ser
545                 550                 555                 560

Arg Leu Pro Gly Pro Ser Asp Thr Pro Ile Leu Pro Gln Ser Ser Ser
                565                 570                 575

Ser Lys Ala Pro Pro Pro Ser Leu Pro Ser Pro Ser Arg Leu Pro Gly
            580                 585                 590

Pro Ser Asp Thr Pro Ile Leu Pro Gln
    595                 600
```

<210> SEQ ID NO 64
<211> LENGTH: 2413
<212> TYPE: DNA
<213> ORGANISM: Homo sapiens

<400> SEQUENCE: 64

```
tctagagtcg accccgccat ggagctgagg ccctggttgc tatgggtggt agcagcaaca      60
ggaaccttgg tcctgctagc agctgatgct cagggccaga aggtcttcac caacacgtgg      120
gctgtgcgca tccctggagg cccagcggtg gccaacagtg tggcacggaa gcatgggttc     180
ctcaacctgg gccagatctt cggggactat taccacttct ggcatcgagg agtgacgaag     240
cggtccctgt cgcctcaccg cccgcggcac agccggctgc agagggagcc tcaagtacag     300
tggctggaac agcaggtggc aaagcgacgg actaaacggg acgtgtacca ggagcccaca     360
gaccccaagt ttcctcagca gtggtacctg tctggtgtca ctcagcggga cctgaatgtg     420
aaggcggcct gggcgcaggg ctacacaggg cacggcattg tggtctccat tctggacgat    480
ggcatcgaga gaaccaccc ggacttggca gcaattatg atcctggggc cagttttgat     540
gtcaatgacc aggaccctga ccccagcct cggtacacac agatgaatga caacaggcac     600
```

```
ggcacacggt gtgcggggga agtggctgcg gtggccaaca acggtgtctg tggtgtaggt    660
gtggcctaca acgcccgcat tggaggggtg cgcatgctgg atggcgaggt gacagatgca    720
gtggaggcac gctcgctggg cctgaacccc aaccacatcc acatctacag tgccagctgg    780
ggccccgagg atgacggcaa gacagtggat gggccagccc gcctcgccga ggaggccttc    840
ttccgtgggg ttagccaggg ccgaggggggg ctgggctcca tctttgtctg ggcctcgggg    900
aacgggggcc gggaacatga cagctgcaac tgcgacggct acaccaacag tatctacacg    960
ctgtccatca gcagcgccac gcagtttggc aacgtgccgt ggtacagcga ggcctgctcg   1020
tccacactgg ccacgaccta cagcagtggc aaccagaatg agaagcagat cgtgacgact   1080
gacttgcggc agaagtgcac ggagtctcac acgggcacct cagcctctgc cccttagca    1140
gccggcatca ttgctctcac cctggaggcc aataagaacc tcacatgcgc ggacatgcaa   1200
cacctggtgg tacagacctc gaagccagcc cacctcaatg ccaacgactg ggccaccaat   1260
ggtgtgggcc ggaaagtgag ccactcatat ggctacgggc ttttggacgc aggcgccatg   1320
gtggccctgg cccagaattg gaccacagtg ccccccagc ggaagtgcat catcgacatc   1380
ctcaccgagc ccaaagacat cgggaaacgg ctcgaggtgc ggaagaccgt gaccgcgtgc   1440
ctgggcgagc ccaaccacat cactcggctg gagcacgctc aggcgcggct caccctgtcc   1500
tataatcgcc gtggcgacct ggccatccac ctggtcagcc ccatgggcac ccgctccacc   1560
ctgctggcag ccaggccaca tgactactcc gcagatgggg ttaatgactg gccttcatg    1620
acaactcatt cctgggatga ggatccctct ggcgagtggg tcctagagat tgaaaacacc   1680
agcgaagcca acaactatgg gacgctgacc aagttcaccc tcgtactcta tggcaccgcc   1740
cctgagggc tgcccgtacc tccagaaagc agtggctgca agaccctcac gtccagtcag   1800
gcctgtgtgg tgtgcgagga aggcttctcc ctgcaccaga agagctgtgt ccagcactgc   1860
cctccaggct tcgccccccca gtcctcgat acgcactata gcaccgagaa tgacgtggag   1920
accatccggg ccagcgtctg cgcccccgtgc cacgcctcat gtgccacatg ccaggggccg   1980
gccctgacag actgcctcag ctgccccagc cacgcctcct ggaccctgt ggagcagact   2040
tgctccggc aaagccagag cagccgagag tccccgccac agcagcagcc acctcggctg   2100
ccccggagg tggaggcggg gcaacggctg cgggcagggc tgctgccctc acacctgcct   2160
gaggtggtgg ccgccctcag ctgcgccttc atcgtgctgg tcttcgtcac tgtcttcctg   2220
gtcctgcagc tgcgctctgg ctttagtttt cgggggggtga aggtgtacac catggaccgt   2280
ggcctcatct cctacaaggg gctgccccct gaagcctggc aggaggagtg cccgtctgac   2340
tcagaagagg acgagggccg gggcgagagg accgccttta tcaaagacca gagcgccctc   2400
tgaacgcggc cgc                                                     2413
```

<210> SEQ ID NO 65
<211> LENGTH: 794
<212> TYPE: PRT
<213> ORGANISM: Homo sapiens

<400> SEQUENCE: 65

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45
```

```
Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Thr Lys Arg Asp Val Tyr Gln Glu
            100                 105                 110

Pro Thr Asp Pro Lys Phe Pro Gln Gln Trp Tyr Leu Ser Gly Val Thr
            115                 120                 125

Gln Arg Asp Leu Asn Val Lys Ala Ala Trp Ala Gln Gly Tyr Thr Gly
        130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
```

```
              465                 470                 475                 480
         Ile Thr Arg Leu Glu His Ala Gln Ala Arg Leu Thr Leu Ser Tyr Asn
                         485                 490                 495

Arg Arg Gly Asp Leu Ala Ile His Leu Val Ser Pro Met Gly Thr Arg
                         500                 505                 510

Ser Thr Leu Leu Ala Ala Arg Pro His Asp Tyr Ser Ala Asp Gly Phe
                         515                 520                 525

Asn Asp Trp Ala Phe Met Thr Thr His Ser Trp Asp Glu Asp Pro Ser
                         530                 535                 540

Gly Glu Trp Val Leu Glu Ile Glu Asn Thr Ser Glu Ala Asn Asn Tyr
         545                 550                 555                 560

Gly Thr Leu Thr Lys Phe Thr Leu Val Leu Tyr Gly Thr Ala Pro Glu
                         565                 570                 575

Gly Leu Pro Val Pro Pro Glu Ser Ser Gly Cys Lys Thr Leu Thr Ser
                         580                 585                 590

Ser Gln Ala Cys Val Val Cys Glu Glu Gly Phe Ser Leu His Gln Lys
                         595                 600                 605

Ser Cys Val Gln His Cys Pro Pro Gly Phe Ala Pro Gln Val Leu Asp
                         610                 615                 620

Thr His Tyr Ser Thr Glu Asn Asp Val Glu Thr Ile Arg Ala Ser Val
         625                 630                 635                 640

Cys Ala Pro Cys His Ala Ser Cys Ala Thr Cys Gln Gly Pro Ala Leu
                         645                 650                 655

Thr Asp Cys Leu Ser Cys Pro Ser His Ala Ser Leu Asp Pro Val Glu
                         660                 665                 670

Gln Thr Cys Ser Arg Gln Ser Gln Ser Ser Arg Glu Ser Pro Pro Gln
                         675                 680                 685

Gln Gln Pro Pro Arg Leu Pro Pro Glu Val Glu Ala Gly Gln Arg Leu
                         690                 695                 700

Arg Ala Gly Leu Leu Pro Ser His Leu Pro Glu Val Val Ala Gly Leu
         705                 710                 715                 720

Ser Cys Ala Phe Ile Val Leu Val Phe Val Thr Val Phe Leu Val Leu
                         725                 730                 735

Gln Leu Arg Ser Gly Phe Ser Phe Arg Gly Val Lys Val Tyr Thr Met
                         740                 745                 750

Asp Arg Gly Leu Ile Ser Tyr Lys Gly Leu Pro Pro Glu Ala Trp Gln
                         755                 760                 765

Glu Glu Cys Pro Ser Asp Ser Glu Asp Glu Gly Arg Gly Glu Arg
                         770                 775                 780

Thr Ala Phe Ile Lys Asp Gln Ser Ala Leu
         785                 790

<210> SEQ ID NO 66
<211> LENGTH: 249
<212> TYPE: PRT
<213> ORGANISM: Artificial Sequence
<220> FEATURE:
<223> OTHER INFORMATION: CTP-CTP-EPO

<400> SEQUENCE: 66

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Ser Lys
                20                  25                  30

Ala Pro Pro Pro Ser Leu Pro Ser Pro Ser Arg Leu Pro Gly Pro Ser
```

|  | 35 |  |  |  |  | 40 |  |  |  |  | 45 |  |  |
|---|---|---|---|---|---|---|---|---|---|---|---|---|---|

Asp Thr Pro Ile Leu Pro Gln Ser Ser Ser Lys Ala Pro Pro
 50                     55                      60

Ser Leu Pro Ser Pro Ser Arg Leu Pro Gly Pro Ser Asp Thr Pro Ile
65                  70                  75                  80

Leu Pro Gln Ala Pro Pro Arg Leu Ile Cys Asp Ser Arg Val Leu Glu
                85                  90                  95

Arg Tyr Leu Leu Glu Ala Lys Glu Ala Glu Asn Ile Thr Thr Gly Cys
                100                 105                 110

Ala Glu His Cys Ser Leu Asn Glu Asn Ile Thr Val Pro Asp Thr Lys
                115                 120                 125

Val Asn Phe Tyr Ala Trp Lys Arg Met Glu Val Gly Gln Gln Ala Val
                130                 135                 140

Glu Val Trp Gln Gly Leu Ala Leu Leu Ser Glu Ala Val Leu Arg Gly
145                 150                 155                 160

Gln Ala Leu Leu Val Asn Ser Ser Gln Pro Trp Glu Pro Leu Gln Leu
                165                 170                 175

His Val Asp Lys Ala Val Ser Gly Leu Arg Ser Leu Thr Thr Leu Leu
                180                 185                 190

Arg Ala Leu Gly Ala Gln Lys Glu Ala Ile Ser Pro Pro Asp Ala Ala
                195                 200                 205

Ser Ala Ala Pro Leu Arg Thr Ile Thr Ala Asp Thr Phe Arg Lys Leu
210                 215                 220

Phe Arg Val Tyr Ser Asn Phe Leu Arg Gly Lys Leu Lys Leu Tyr Thr
225                 230                 235                 240

Gly Glu Ala Cys Arg Thr Gly Asp Arg
                245

```
<210> SEQ ID NO 67
<211> LENGTH: 762
<212> TYPE: DNA
<213> ORGANISM: Artificial Sequence
<220> FEATURE:
<223> OTHER INFORMATION: CTP-CTP-EPO

<400> SEQUENCE: 67
atgggcgtgc acgagtgtcc tgcttggctg tggctgctgc tgagcctgct gtccctgcct      60
ctgggcctgc tgtgctgggc agcagcagc tctaaggccc ctccacccag cctgcccagc     120
ccttctagac tgcctggccc cagcgacacc cccatcctgc ctcagagcag cagcagcaag     180
gccccaccac catccctgcc tagccccagc agactgccag ccttccga tacccaatc      240 ctgccccagg ccctcccag actgatctgc gacagccggg tgctggaaag atacctgctg     300
gaagccaaag aggccgagaa catcaccacc ggctgcgccg agcactgcag cctgaacgag     360
aatatcaccg tgcccgacac caaagtgaac ttctacgcct ggaagcggat ggaagtgggc     420
cagcaggccg tggaagtgtg gcagggactg gccctgctga gcgaggccgt gctgagagga     480
caggccctgc tggtgaacag cagccagccc tgggagcccc tgcagctgca tgtggataag     540
gccgtgtccg gcctgcggag cctgaccaca ctgctgagag ccctgggcgc tcagaaagag     600
gccatctctc cccctgatgc cgcctctgcc ggccctctga accatcac cgccgacacc      660 ttccggaagc tgttccgggt gtacagcaac ttcctgcggg gcaagctgaa gctgtacacc     720
ggcgaggcct gccggaccgg cgatagataa gcttggcgcg cc                       762

<210> SEQ ID NO 68
```

<211> LENGTH: 305
<212> TYPE: PRT
<213> ORGANISM: Artificial Sequence
<220> FEATURE:
<223> OTHER INFORMATION: CTP-CTP-EPO-CTP-CTP

<400> SEQUENCE: 68

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ser Ser Ser Ser Lys
            20                  25                  30

Ala Pro Pro Pro Ser Leu Pro Ser Pro Ser Arg Leu Pro Gly Pro Ser
        35                  40                  45

Asp Thr Pro Ile Leu Pro Gln Ser Ser Ser Ser Lys Ala Pro Pro Pro
    50                  55                  60

Ser Leu Pro Ser Pro Ser Arg Leu Pro Gly Pro Ser Asp Thr Pro Ile
65                  70                  75                  80

Leu Pro Gln Ala Pro Pro Arg Leu Ile Cys Asp Ser Arg Val Leu Glu
                85                  90                  95

Arg Tyr Leu Leu Glu Ala Lys Glu Ala Glu Asn Ile Thr Thr Gly Cys
            100                 105                 110

Ala Glu His Cys Ser Leu Asn Glu Asn Ile Thr Val Pro Asp Thr Lys
        115                 120                 125

Val Asn Phe Tyr Ala Trp Lys Arg Met Glu Val Gly Gln Gln Ala Val
    130                 135                 140

Glu Val Trp Gln Gly Leu Ala Leu Leu Ser Glu Ala Val Leu Arg Gly
145                 150                 155                 160

Gln Ala Leu Leu Val Asn Ser Ser Gln Pro Trp Glu Pro Leu Gln Leu
                165                 170                 175

His Val Asp Lys Ala Val Ser Gly Leu Arg Ser Leu Thr Thr Leu Leu
            180                 185                 190

Arg Ala Leu Gly Ala Gln Lys Glu Ala Ile Ser Pro Pro Asp Ala Ala
        195                 200                 205

Ser Ala Ala Pro Leu Arg Thr Ile Thr Ala Asp Thr Phe Arg Lys Leu
    210                 215                 220

Phe Arg Val Tyr Ser Asn Phe Leu Arg Gly Lys Leu Lys Leu Tyr Thr
225                 230                 235                 240

Gly Glu Ala Cys Arg Thr Gly Asp Arg Ser Ser Ser Lys Ala Pro
                245                 250                 255

Pro Pro Ser Leu Pro Ser Pro Ser Arg Leu Pro Gly Pro Ser Asp Thr
            260                 265                 270

Pro Ile Leu Pro Gln Ser Ser Ser Ser Lys Ala Pro Pro Pro Ser Leu
        275                 280                 285

Pro Ser Pro Ser Arg Leu Pro Gly Pro Ser Asp Thr Pro Ile Leu Pro
    290                 295                 300

Gln
305
```

<210> SEQ ID NO 69
<211> LENGTH: 930
<212> TYPE: DNA
<213> ORGANISM: Artificial Sequence
<220> FEATURE:
<223> OTHER INFORMATION: CTP-CTP-EPO-CTP-CTP

<400> SEQUENCE: 69
atgggcgtgc acgagtgtcc tgcttggctg tggctgctgc tgagcctgct gtccctgcct    60

```
ctgggcctgc ctgtgctggg cagcagcagc tctaaggccc ctccacccag cctgcccagc    120
ccttctagac tgcctggccc cagcgacacc cccatcctgc ctcagagcag cagcagcaag    180
gccccaccac catccctgcc tagccccagc agactgccag gcccttccga tacccccaatc   240 ctgccccagg cccctcccag actgatctgc gacagccggg tgctggaaag atacctgctg    300
gaagccaaag aggccgagaa catcaccacc ggctgcgccg agcactgcag cctgaacgag    360
aatatcaccg tgcccgacac caaagtgaac ttctacgcct ggaagcggat ggaagtgggc    420
cagcaggccg tggaagtgtg cagggactg ccctgctga gcgaggccgt gctgagagga    480
caggccctgc tggtgaacag cagccagccc tgggagcccc tgcagctgca tgtggataag    540
gccgtgtccg gcctgcggag cctgaccaca ctgctgagag ccctgggcgc tcagaaagag    600
gccatctctc ccctgatgc cgcctctgcc gcccctctga aaccatcac cgccgacacc     660 ttccggaagc tgttccgggt gtacagcaac ttcctgcggg gcaagctgaa gctgtacacc    720
ggcgaggcct gccggaccgg cgatagaagc agctccagca aggctccacc ccccagcctg    780
ccatccccaa gtagactgcc cgggccctct gacacaccta tcctgccaca gtccagcagc    840
tccaaagctc ccccaccatc cctcccatcc ccatccagac tgcctggacc atccgacact    900
ccaattctgc ctcagtaagc ttggcgcgcc                                    930
```

```
<210> SEQ ID NO 70
<211> LENGTH: 295
<212> TYPE: PRT
<213> ORGANISM: Artificial Sequence
<220> FEATURE:
<223> OTHER INFORMATION: APO-A1-CTP

<400> SEQUENCE: 70

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205
```

```
Gly Gly Ala Arg Leu Ala Glu Tyr His Ala Lys Ala Thr Glu His Leu
        210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Ser Ser Ser Ser Lys
            260                 265                 270

Ala Pro Pro Pro Ser Leu Pro Ser Pro Ser Arg Leu Pro Gly Pro Ser
        275                 280                 285

Asp Thr Pro Ile Leu Pro Gln
        290                 295

<210> SEQ ID NO 71
<211> LENGTH: 911
<212> TYPE: DNA
<213> ORGANISM: Artificial Sequence
<220> FEATURE:
<223> OTHER INFORMATION: APO-A1-CTP

<400> SEQUENCE: 71
atgaaggccg ccgtgctgac cctggccgtg ctgtttctga ccggctctca ggcccggcac      60
ttctggcagc aggacgagcc tccccagtcc ccctgggaca gagtgaagga cctgccacc     120 gtgtacgtgg acgtgctgaa ggactccggc agagactacg tgtcccagtt cgagggctct    180
gccctgggca gcagctgaa cctgaagctg ctggacaact gggactccgt gacctccacc     240
ttctccaagc tgcgcgaaca gctgggacct gtgacccagg aattctggga caacctggaa    300
aaagagacag agggcctgag acaggaaatg tccaaggacc tggaagaggt caaagccaag    360
gtgcagccct acctggacga cttccagaag aaatggcagg aagagatgga actgtaccgg    420
cagaaggtgg aacccctgcg ggccgagctg caggaaggcg ctagacagaa gctgcacgaa    480
ctgcaggaaa agctgtcccc cctgggcgag gaaatgcggg acagagccag agcccacgtg    540
gacgccctga gaacccacct ggccccctac tctgacgagc tgcggcagag gctggccgcc    600
agactggaag ccctgaaaga aacggcggga gcccggctgg ccgagtacca cgctaaggct    660
accgagcacc tgtccaccct gtccgagaag gccaagcccg ccctggaaga tctgcggcag    720
ggcctgctgc ccgtgctgga atccttcaag gtgtccttcc tgtccgctct ggaagagtac    780
accaagaagc tgaacaccca gtcctccagc tccaaggccc ctccaccctc cctgcctagc    840
cctagtagac tgcctgggcc ctccgacacc cccatcctgc cccagtgatg aggatccgcg    900
gccgcgagct c                                                         911

<210> SEQ ID NO 72
<211> LENGTH: 323
<212> TYPE: PRT
<213> ORGANISM: Artificial Sequence
<220> FEATURE:
<223> OTHER INFORMATION: APO-A1-CTP-CTP

<400> SEQUENCE: 72

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45
```

```
Ser Gly Arg Asp Tyr Val Ser Gln Phe Glu Gly Ser Ala Leu Gly Lys
 50                  55                  60

Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Met Glu Leu Tyr Arg Gln Lys Val Glu
130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln Ser Ser Ser Ser Lys
            260                 265                 270

Ala Pro Pro Pro Ser Leu Pro Ser Pro Ser Arg Leu Pro Gly Pro Ser
        275                 280                 285

Asp Thr Pro Ile Leu Pro Gln Ser Ser Ser Ser Lys Ala Pro Pro Pro
290                 295                 300

Ser Leu Pro Ser Pro Ser Arg Leu Pro Gly Pro Ser Asp Thr Pro Ile
305                 310                 315                 320

Leu Pro Gln

<210> SEQ ID NO 73
<211> LENGTH: 995
<212> TYPE: DNA
<213> ORGANISM: Artificial Sequence
<220> FEATURE:
<223> OTHER INFORMATION: APO-A1-CTP-CTP

<400> SEQUENCE: 73
atgaaggccg ccgtgctgac cctggccgtg ctgtttctga ccggctctca ggcccggcac        60
ttctggcagc aggacgagcc tccccagtcc ccctgggaca gagtgaagga cctggccacc       120
gtgtacgtgg acgtgctgaa ggactccggc agagactacg tgtcccagtt cgagggctct       180
gccctgggca gcagctgaa cctgaagctg ctggacaact gggactccgt gacctccacc       240
ttctccaagc tgcgcgaaca gctgggacct gtgacccagg aattctggga caacctggaa       300
aaagagacag agggcctgag acaggaaatg tccaaggacc tggaagaggt caaagccaag       360
gtgcagccct acctggacga cttccagaag aaatggcagg aagagatgga actgtaccgg       420
cagaaggtgg aacccctgcg ggccgagctg caggaaggcg ctagacagaa gctgcacgaa       480
```

```
ctgcaggaaa agctgtcccc cctgggcgag gaaatgcggg acagagccag agcccacgtg      540
gacgccctga gaacccacct ggcccccatc tctgacgagc tgcggcagag gctggccgcc      600
agactggaag ccctgaaaga gaacggcgga gcccggctgg ccgagtacca cgctaaggct      660
accgagcacc tgtccaccct gtccgagaag gccaagcccg ccctggaaga tctgcggcag      720
ggcctgctgc ccgtgctgga atccttcaag gtgtccttcc tgtccgctct ggaagagtac      780
accaagaagc tgaacaccca gtcctccagc tccaaggccc ctccaccctc cctgcctagc      840
cctagtagac tgcctgggcc ctccgacaca ccaatcctgc cacagagcag ctcctctaag      900
gcccctcctc catccctgcc atcccctcc cggctgcctg gcccctctga caccccatc       960 ctgcctcagt gatgaaggtc tggatccgcg gccgc                                 995
```